US010000755B2

(12) United States Patent
Sadovsky et al.

(10) Patent No.: US 10,000,755 B2
(45) Date of Patent: *Jun. 19, 2018

(54) USE OF THE CHROMOSOME 19 MICRORNA CLUSTER (C19MC) FOR TREATING MICROBIAL DISEASE AND PROMOTING AUTHOPHAGY

(71) Applicant: University of Pittsburgh—Of the Commonwealth System of Higher Education, Pittsburgh, PA (US)

(72) Inventors: Yoel Sadovsky, Pittsburgh, PA (US); Carolyn Coyne Candrilli, Jefferson Hills, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/417,717

(22) Filed: Jan. 27, 2017

(65) Prior Publication Data

US 2017/0211069 A1 Jul. 27, 2017

Related U.S. Application Data

(62) Division of application No. 14/383,222, filed as application No. PCT/US2013/029420 on Mar. 6, 2013, now Pat. No. 9,593,334.

(60) Provisional application No. 61/607,899, filed on Mar. 7, 2012.

(51) Int. Cl.
*C07H 21/02* (2006.01)
*C07H 21/04* (2006.01)
*A61K 48/00* (2006.01)
*C12N 15/113* (2010.01)

(52) U.S. Cl.
CPC ...... *C12N 15/1131* (2013.01); *C12N 15/1132* (2013.01); *C12N 15/1133* (2013.01); *C12N 2310/141* (2013.01)

(58) Field of Classification Search
CPC .. A61K 48/00; A61K 31/713; C12N 2310/11; C12N 15/113
See application file for complete search history.

(56) References Cited

U.S. PATENT DOCUMENTS 7,795,419 B2 9/2010 Bentwich et al.

FOREIGN PATENT DOCUMENTS

WO WO 2011/023413 3/2011

OTHER PUBLICATIONS

Bayer et al., "Human trophoblasts confer resistance to viruses implicated in perinatal infection," *Am J Obstet Gynecol* 212(1):71. e1-8, 2015.
Bortolin-Cavaille et al., "C19MC microRNAs are Processed from Introns of Large Pol-II, Non-Protein-Coding Transcripts," *Nucl. Acids Res*., vol. 37:3464-3473, 2009.
Chen et al., "Inhibition of c-FLIP Expression by miR-512-3p Contributes to Taxol-Induced Apoptosis in Hepatocellular Carcinoma Cells," *Oncology Reports*, vol. 23:1457-1462, 2010.
Delorme-Axford et al., "Human placental trophoblasts confer viral resistance to recipient cells," *Proc Natl Acad Sci USA* 110(29):12048-12053, 2013.
Delorme-Axford et al., "Autophagy as a mechanism of antiviral defense at the maternal-fetal interface," *Autophagy* 9(12):2173-2174, 2013.
Mouillet et al., "The role of trophoblastic microRNAs in placental viral infection," *Int J Dev Biol* 58:281-289, 2014.
Noguer-Dance et al., "The Primate-Specific microRNA Gene Cluster (C19MC) is Imprinted in the Placenta," *Human Mol. Genetics*, vol. 19:3566-3582, 2010.
Saito et al., "Chromatin Remodeling at Alu Repeats by Epigenetic Treatment Activates Silenced microRNA-512-5p with Downregulation of Mcl-1 in Human Gastric Cancer Cells," *Oncogene*, vol. 28:2738-2744, 2009.
Santhakumar et al., "Combined Agonist-Antagonist Genome-Wide Functional Screening Identifies Broadly Reactive Antiviral microRNAs," *Proc. Natl. Acad. Sci*., vol. 107:13830-13835, 2010.

*Primary Examiner* — Amy H Bowman
(74) *Attorney, Agent, or Firm* — Klarquist Sparkman, LLP

(57) ABSTRACT

It is disclosed herein that cultured primary placental human trophoblast (PHT) cells are highly resistant to infection by a number of disparate viruses, and confer this resistance to non-placental recipient cells by exosome-mediated delivery of microRNAs (miRs). PHT cells express high levels of unique, primate-specific miRNAs, expressed from the chromosome 19 miRNA cluster (C19MC). It is further disclosed herein that C19MC miRNAs are packaged within PHT-derived exosomes and attenuate viral replication in recipient cells by inducing autophagy. Thus, provided herein are methods of inhibiting, treating or preventing microbial infections by administering one or more miRs of the C19MC. Also provided are methods of inducing autophagy in a cell by contacting the cell with one or more miRs of the C19MC.

10 Claims, 13 Drawing Sheets

FIG. 2E
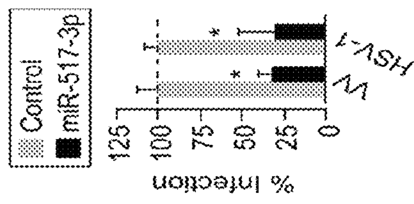
FIG. 2D
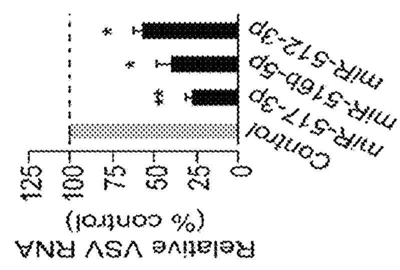
FIG. 2C
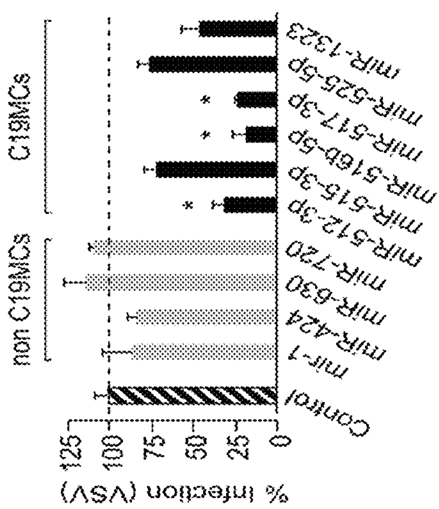
FIG. 2B
FIG. 2A
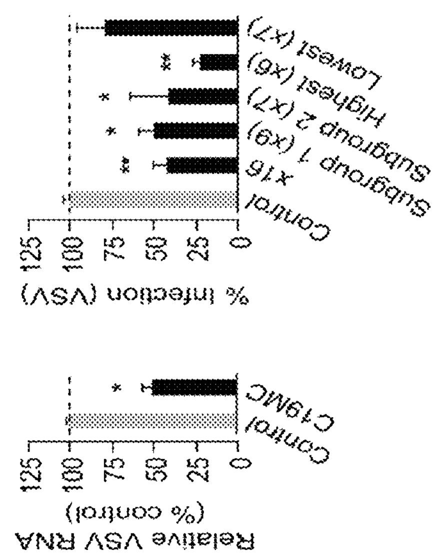

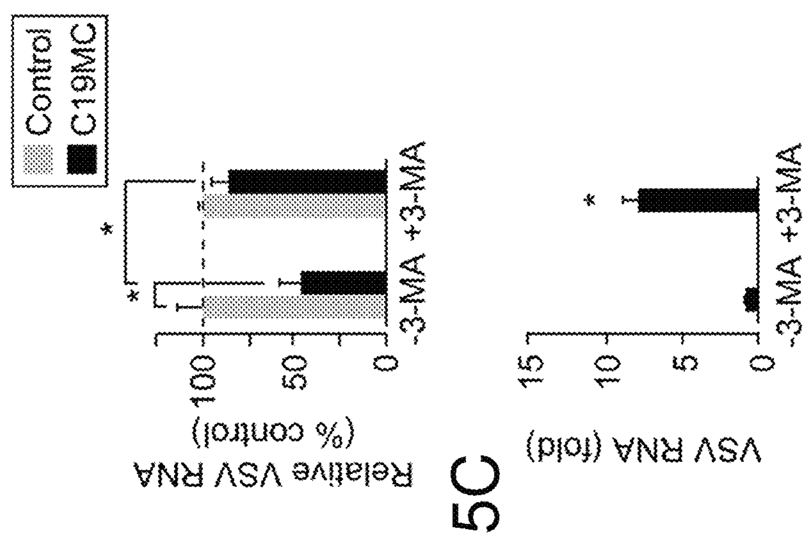
FIG. 5A
FIG. 5C
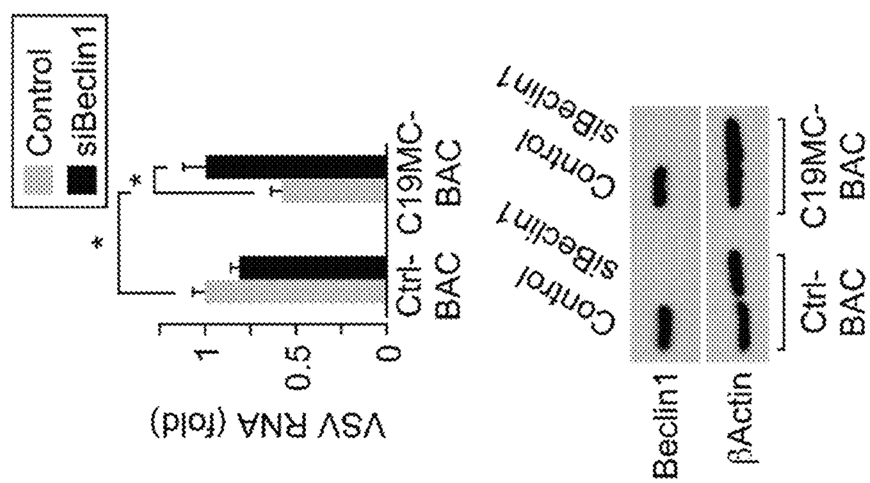
FIG. 5B

FIG. 6H
Fold (CMV)
10 8 6 4 2 0
Control C19MC
*
FIG. 6G
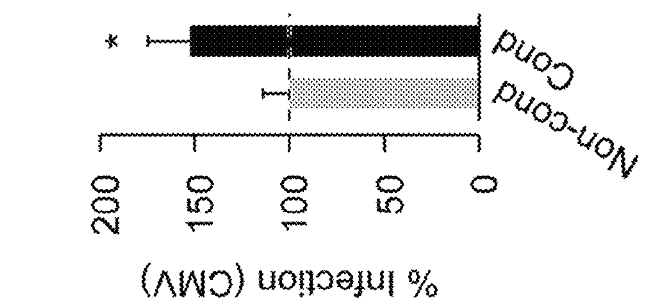
FIG. 6F
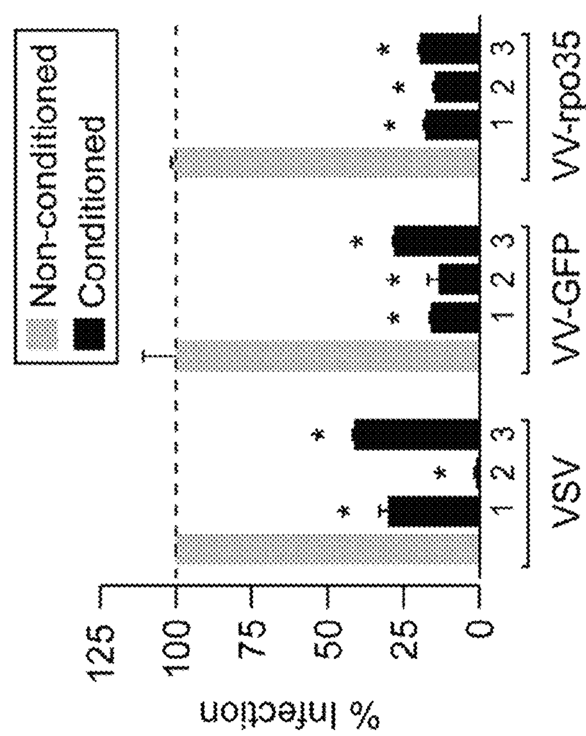

USE OF THE CHROMOSOME 19 MICRORNA CLUSTER (C19MC) FOR TREATING MICROBIAL DISEASE AND PROMOTING AUTHOPHAGY

CROSS REFERENCE TO RELATED APPLICATIONS

This is a divisional of U.S. application Ser. No. 14/383,222, filed Sep. 5, 2014, issued as U.S. Pat. No. 9,593,334 on Mar. 14, 2017, which is the U.S. National Stage of International Application No. PCT/US2013/029420, filed Mar. 6, 2013, published in English under PCT Article 21(2), which claims the benefit of U.S. Provisional Application No. 61/607,899, filed Mar. 7, 2012. The above-listed applications are herein incorporated by reference in their entirety.

ACKNOWLEDGMENT OF GOVERNMENT SUPPORT

This invention was made with government support under grant numbers AI081759 and HD065893 awarded by the National Institutes of Health. The government has certain rights in the invention.

FIELD

This disclosure concerns the use of microRNAs encoded by the primate-specific chromosome 19 miRNA cluster (C19MC) for the prophylaxis and/or treatment of microbial infection and diseases associated with autophagy.

BACKGROUND

Strategies to reduce the risk of fetal infection are of critical importance during pregnancy, where maternal to fetal transmission of microbes can have devastating consequences to the developing embryo, ranging from fetal infection, induced preterm delivery, structural or functional congenital anomalies, miscarriages and stillbirths (Ornoy and Tenenbaum, *Reprod Toxicol* 21, 446-457, 2006; Silingardi et al., *Am J Forensic Med Pathol* 30, 394-397, 2009; Euscher et al., *Obstet Gynecol* 98, 1019-1026, 2001). Additionally, pathogenic infections can compromise maternal health and jeopardize the pregnancy even in the absence of fetal transmission. The physical barrier interfacing the maternal and fetal blood systems within human hemochorial placenta villi include the trophoblast bilayer, basement membrane, stromal cells and fetal capillary endothelial cells. The multinucleated, terminally differentiated villous syncytiotrophoblasts are bathed directly in the maternal blood, and mediate the crucial exchange of gases, nutrients, and waste products between the mother and fetus, produce crucial hormones, and immunologically guard the developing fetus. These cells, along with the less differentiated cytotrophoblasts, constitute the first line of feto-placental defense against invading microbes.

Intrauterine transmission of viruses is likely to occur by at least four potential routes: (a) transmission across the placental villous trophoblasts by hematogenous spread or ascending infection, (b) placental transfer of infected macrophages from the maternal blood, (c) transfer of viruses via paracellular routes and/or (d) transmission of viruses from the infected maternal endothelial microvasculature to endovascular extravillous cytotrophoblasts. In general, little is known regarding the defense mechanisms employed by placental trophoblasts to defend against viral infections.

Additionally, as antiviral therapeutics are generally ineffective in preventing intrauterine viral infections, elucidating the nature of these mechanism(s), as well as the underpinnings of viral counter-measures, is critical for designing therapeutic strategies aimed at preventing fetal and maternal viral disease.

Mammalian cells utilize diverse defense mechanisms to combat microbial pathogens. One crucial mechanism is the induction of autophagy, an evolutionarily conserved lysosomal degradation pathway that has been associated with an array of cellular functions, including cell death (Beaulation and Lockshin, *J Morphol* 154:39-57, 1977; Liang et al., *Nature* 402:672-676, 1999), tumorigenesis (Qu et al., *J Clin Invest* 112:1809-1820, 2003), and neurodegeneration (Hara et al., *Nature* 441:885-889, 2006; Komatsu et al., *Nature* 441:880-884, 2006). Autophagy also degrades intracellular foreign microbial invaders (a process sometimes referred to as xenophagy or virophagy). The cascade of events that culminate in autophagy begin with the formation of a double membrane organelle, the autophagosome, and ends in the degradation of engulfed material via the fusion of autophagosomes with late endosomes and/or lysosomes. The degradation of microbes via the fusion of autophagosomes with lysosomes is a key component in the antimicrobial effects of autophagy, yet the sequestration of viruses into autophagosomes can also direct MHC class II presentation (English et al., *Nat Immunol* 10:480-487, 2009), the production of antiviral type I interferons downstream of toll-like receptor 7 engagement (Lee et al., *Science* 315:1398-1401, 2007), and even altered T-cell signaling (Nedjic et al., *Nature* 455:396-400, 2008). It is becoming clear that autophagy functions at the crossroads of many aspects of cell survival, and is likely a fundamental component of antiviral signaling.

SUMMARY

It is disclosed herein that microRNAs (miRs) of the C19MC cluster promote viral resistance and induce autophagy of recipient cells.

Provided herein is a method of inhibiting or treating a microbial infection in a subject by selecting a subject with a microbial infection or at risk for contracting a microbial infection; and administering to the subject a therapeutically effective amount of one or more miRs encoded by the C19MC, thereby inhibiting or treating the microbial infection. In some embodiments, the one or more miRs are administered by administering a nucleic acid molecule encoding the entire C19MC or a biologically active portion thereof, for example a portion that encodes one or more miRs that promote viral resistance and induce autophagy. In non-limiting examples, the one or more miRs include miR-517-3p, miR-1323, miR-516b-5p, miR-525-5p, miR-512-3p, or miR-515-3p, or any combination thereof.

Also provided herein is a method of inducing autophagy in a cell by contacting the cell with an effective amount of one or more miRs encoded by the C19MC, thereby inducing autophagy in the cell. In some embodiments, the method is an in vitro method. In other embodiments, the method is an in vivo method that includes administering to a subject an effective amount of one or more miRs encoded by the C19MC, or a nucleic acid molecule encoding the C19MC or a biologically active portion thereof. In non-limiting examples, the subject suffers from a disease associated with a deficiency in autophagy and/or a disease that may be ameliorated by enhancing autophagy.

The foregoing and other objects, features, and advantages of the invention will become more apparent from the following detailed description, which proceeds with reference to the accompanying figures.

BRIEF DESCRIPTION OF THE DRAWINGS

(FIG. 1A) PHT or non-PHT cells were infected with a panel of viruses, including coxsackievirus B (CVB), poliovirus (PV), vesicular stomatitis virus (VSV), vaccinia virus (VV), herpes simplex virus-1 (HSV-1), or cytomegalovirus (CMV). Non-PHT cells were as follows: HeLa (CVB, PV), U2OS (VSV, HSV-1, and VV), and human foreskin fibroblasts (HFF, CMV). Shown are the percent infected cells (assessed by immunofluorescence (IF); *p<0.0001). (FIG. 1B) Non-PHT recipient cells were exposed for 24 h to non-conditioned or conditioned PHT medium, and then infected with CVB, VSV, HCV, or VV. Non-PHT cells were as follows: HFF (CVB), U2OS (VSV, VV), and Huh 7.5 (HCV). Shown are the percent of infected cells, assessed by IF (CVB, VSV), luciferase assay (HCV), or RT-qPCR (VV); *p<0.05, **p<0.005. (FIG. 1C, left) Cells were exposed to non-conditioned or conditioned PHT medium for 24 h, then infected with VSV or CVB. (FIG. 1C, right) Primary cells were infected with VSV following exposure to non-conditioned or conditioned PHT medium (*p<0.05, **p<0.005). (FIG. 1D) Conditioned PHT medium was subjected to heat inactivation or sonication prior to 24 h exposure to Vero cells, then infected with VSV. Percent infection assessed as in (A); (*p<0.0001). (FIG. 1E) U2OS cells were exposed for 24 h to non-conditioned, conditioned, exosome-depleted conditioned medium, exosomes purified from PHT, JEG-3, or from three preparations of murine dendritic cell (DC), and then infected with VSV. Percent infection assessed as in (A); (*p<0.0005), each PHT exosome preparation was derived from a different placental preparation.

FIGS. 2A-2E: PHT and exosomal C19MC miRNAs confer viral resistance to recipient cells. (FIG. 2A) U2OS cells stably expressing control- or C19MC-bacterial artificial chromosome (BAC) were infected with VSV (infection levels assessed by RT-qPCR, *p<0.0001). (FIG. 2B) U2OS cells were transfected with C19MC miRNA mimics that represent the miRNA sub-groups detailed in Table 2 or control mimics, and then infected with VSV (shown as percent infected cells, assessed by IF; *p<0.05, **p<0.001). (FIG. 2C) U2OS cells, transfected with mimics of the six highest expressed C19MC miRNAs, scrambled control, or non-C19MC (miR-1, -424, -630, -720) miRNA mimics, were infected with VSV (infection level assessed by IF or qPCR; *p<0.0005). (FIG. 2D) U2OS cells, transfected with mimics of the top three antiviral C19MC miRNAs or with scrambled control mimics, were infected with VSV (infection assessed by RT-qPCR; *p<0.05, **p<0.0001). (FIG. 2E) U2OS cells, transfected with scrambled control or miR-517-3p mimic, were infected with VV or HSV-1; infection assessed as in (D) (*p<0.0001).

(FIG. 3A) U2OS cells transfected with mRFP-LC3b were exposed to non-conditioned-, PHT conditioned-, exosome-depleted conditioned PHT medium, or purified PHT exosomes for 24 h, and LC3b punctae formation was assessed by confocal microscopy. Shown are confocal micrographs (top) and quantification of mRFP-LC3b punctae per cell (bottom) (*p<0.0001). (FIG. 3B, top) Electron micrographs of cells exposed to non-conditioned or conditioned PHT medium (Vero), exosome-depleted conditioned PHT medium (Vero), or purified PHT exosomes (U2OS). Arrows denote autophagosomes. Bar=500 nm. (FIG. 3B, bottom) Quantification of electron micrographs of cells exposed to non-conditioned (Vero and U2OS), conditioned PHT media samples (Vero and U2OS), exosome-depleted conditioned medium (Vero), or purified PHT exosomes (U20S) (*p<0.0001). (FIG. 3C) U2OS cells transfected with mRFP-LC3b were exposed to non-conditioned or conditioned PHT medium in the absence or presence of 3-methyladenine (3-MA) for 8 h, and LC3b punctae formation was assessed by confocal microscopy. Shown are confocal micrographs (top) and quantification of mRFP-LC3b punctae (bottom) (*p<0.0005). (FIG. 3D, top) Immunofluorescence images of VSV entry into U2OS cells transiently transfected with mRFP-LC3b exposed to non-conditioned (left) or conditioned (right) PHT medium (inset, 5× magnification). (FIG. 3D, bottom) Quantification of the extent of colocalization between VSV particles and mRFP-LC3B positive punctae (*p<0.0001).

(FIG. 4A, top) Electron micrographs of U2OS cells transfected with scrambled control or the six highest expressed C19MC miRNA mimics (Table 2). Black arrows denote autophagosomes and/or autolysosomes. Bar=500 nm. (FIG. 4A, bottom) Quantification of electron micrographs shown at top (*p<0.005), or in PHT cells. (FIG. 4B) U2OS cells were transfected with mRFP-LC3b and either scrambled control or the six highest expressed C19MC miRNA mimics. Shown are confocal micrographs (top) and quantification of mRFP-LC3b punctae per cell (bottom) (*p=0.0005). (FIG. 4C, left) Electron micrographs of U2OS cells transfected with scrambled control or the most potent antiviral miRNA mimics. Black arrows denote autophagosomes and/or autolysosomes. Bar=500 nm. (FIG. 4C, right) Quantification of adjacent electron micrographs (*p<0.005). (FIG. 4D, top) A representative immunoblot for p62 or GAPDH in U2OS cells stably transfected with either control Del- or C19MC-BAC. (FIG. 4D, bottom) Densitometry of p62 levels (normalized to GAPDH) from three independent immunoblots as described above (*p<0.05).

FIGS. 5A-5C: Suppression of autophagy restores C19MC-medated antiviral effects. (FIG. 5A) U2OS cells transfected with scrambled control or miRNA mimics of the six most prevalent C19MC miRNA mimics. Cells were exposed to 3-MA before and during VSV infection. Relative VSV RNA was analyzed by RT-qPCR (*p<0.0005). (FIG. 5B, top) U2OS cells stably expressing control- or C19MC-BAC transfected with scrambled control siRNA or beclin-1 siRNA for 72 h were infected with VSV, and relative infection was determined by RT-qPCR (*p<0.05, determined using ANOVA with Bonferroni correction). (FIG. 5B, bottom) Immunoblots for beclin-1 or actin in cells transfected as described above. (FIG. 5C) PHT cells were treated with 3-MA for 60 min prior to infection with green fluorescent protein (GFP)-VSV (in the presence of 3-MA). Relative VSV RNA was analyzed by RT-qPCR (*p<0.005). Data are representative of four independent experiments.

FIGS. 6A-6H: Medium from different preparations of PHT cells confers an antiviral effect on recipient cells. (FIG. 6A) Tissue culture infectious dose 50 (TCID50) assays for VSV in Vero cells pretreated for 24 h with non-conditioned medium (top, in triplicate) or three independent preparations of conditioned PHT medium (bottom). Cells were infected in the indicated dilution of virus in the presence of non-conditioned or conditioned medium for approximately 40-45 h and then stained with crystal violet. (FIG. 6B) Vero cells were exposed to non-conditioned (Non-cond) or conditioned (Cond) medium isolated from BeWo cells for 24 h and then infected with VSV. Shown is the percent of infected cells (as assessed by IF). (FIG. 6C) VSV was incubated in non-conditioned or conditioned PHT medium (in the absence of cells) for 1 h at 37° C. then a plaque assays performed. Shown are VSV titers (in pfu/mL). (FIG. 6D, left) U2OS cells were exposed to non-conditioned (Non-cond) or conditioned media (Cond) from two independent PHT preparations and infected with VSV. Relative VSV RNA was assessed by RT-qPCR (*p<0.0001). (FIG. 6D, right) Caco-2 or Vero cells were exposed to conditioned (Cond) medium isolated from four independent preparations of PHT cells for 24 h prior to infection with VSV. Shown is the percent of infected cells (as assessed by IF; *p<0.0005). (FIG. 6E) Huh7.5 cells were exposed to non-conditioned or conditioned medium isolated from four independent preparations of PHT cells for 24 h prior to infection with HCV. Shown is percent infection as assessed by luciferase assay (*p<0.005, **p<0.0005). (FIG. 6F) U2OS cells exposed to non-conditioned or conditioned PHT medium were infected with VSV or VV for approximately 6 h. Relative VSV or VV (early gene rpo35 or early gene GFP) RNA was assessed by RT-qPCR (*p<0.0001). (FIG. 6G) HFF cells were exposed to non-conditioned (Non-cond) or conditioned (Cond) PHT media for 24 h before and during infection with CMV. Shown is the percent of infected cells (assessed by IF; *p<0.05). (FIG. 6H) U2OS cells stably expressing control- or C19MC-BAC were infected with CMV, and infection levels assessed by RT-qPCR. Data are shown as fold-change over control (*p<0.0001). In all panels, data are displayed as mean±SD, and are representative of experiments performed a minimum of three times.

(FIG. 7A) Vero cells were transfected with mRFP-LC3b and at 24 h post-transfection were exposed for 24 h to either non-conditioned (Non-cond) or conditioned medium isolated from four independent PHT preparations. Cells were exposed to rapamycin (Rap) as a positive control. Shown are the levels of autophagic induction as determined by quantification of mRFP-LC3b positive punctae by confocal microscopy (*p<0.0001). (FIG. 7B) Vero and U2OS cells were transfected with mRFP-LC3b and then exposed to non-conditioned (Non-cond) or conditioned PHT medium (Cond) 24 h post-transfection. Cells were exposed to rapamycin (Rap) as a positive control. Shown are the levels of autophagic induction as determined by quantification of mRFP-LC3b positive punctae by confocal microscopy (*p<0.0001). (FIG. 7C) Relative mRNA levels in U2OS cells exposed to non-conditioned or conditioned PHT medium for 24 h, and analyzed using autophagy or toll-like receptor (TLR)-targeted RT-qPCR arrays. (FIG. 7D) U2OS cells stably expressing a control- or C19MC-BAC were transfected with mRFP-LC3b, fixed after 48 h, and analyzed for mRFP-LC3b punctae by confocal microscopy (*p<0.0001).

SEQUENCE LISTING

Figure 1E:
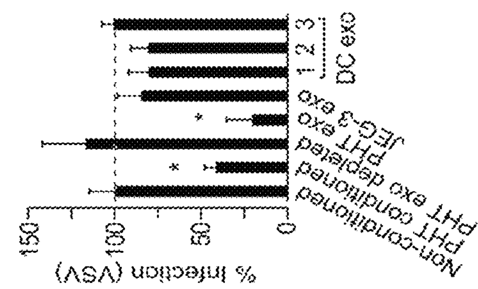
FIGS. 1A-1E: Conditioned primary human trophoblast (PHT) medium and exosomes confer viral resistance to recipient cells.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 23, 2017, 217 KB, which is incorporated by reference herein. In the accompanying sequence listing:

SEQ ID NOs: 1-59 are nucleotide sequences of miRNAs found in the C19MC.

SEQ ID NO: 60 is the nucleotide sequence of the human genomic DNA insert in the BAC RP11-1055017 clone containing region q13-42 of chromosome 19.

SEQ ID NOs: 61-82 are qPCR primers.

DETAILED DESCRIPTION

I. Abbreviations

BAC bacterial artificial chromosome
C19MC chromosome 19 microRNA cluster
CMV cytomegalovirus
Ct cycle threshold
CTB cholera toxin B
CVB coxsackievirus B
DAPI 4',6-diamidino-2-phenylindole
DC dendritic cell
ELISA enzyme-linked immunosorbent assay
EM electron microscopy
FBS fetal bovine serum
GFP green fluorescent protein
hCG human chorionic gonadotropin
HCV hepatitis C virus
HFF human foreskin fibroblast
HIV human immunodeficiency virus
HSV herpes simplex virus
IF immunofluorescence
IFN interferon
ISRE interferon stimulated responsive element
3-MA 3-methyladenine
miR microRNA
miRNA microRNA
MOI multiplicity of infection
PEI polyethylenimine
PHT primary human trophoblasts
PV poliovirus
RNAi RNA interference
RT-qPCR reverse transcriptase quantitative polymerase chain reaction
TCID50 tissue culture infectious dose 50
TLR toll-like receptor
VSV vesicular stomatitis virus
VV vaccinia virus
YFP yellow fluorescent protein II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a nucleic acid molecule or a microRNA), by any effective route. Exemplary routes of administration include, but are not limited to, injection (such as subcutaneous, intramuscular, intradermal, intraperitoneal, intrathecal and intravenous), oral, intraductal, sublingual, rectal, transdermal, intranasal, vaginal and inhalation routes.

Autophagy: A lysosomal degradation pathway that is one of the primary mechanisms for maintaining cellular homeostasis. Autophagy, which means "to eat oneself," is a self-cannibalization pathway that is known to be anti-microbial, functioning as a key innate immune pathway to degrade intracellular foreign microbial pathogens by a process termed antimicrobial autophagy or xenophagy. A diverse group of RNA and DNA viruses, bacteria and protozoa are sensitive to autophagy. Autophagy is also known to be deficient in a number of human diseases, such as inflammatory bowel disease, Crohn's disease, alcoholic liver disease, Parkinson's disease, Alzheimer's disease, heart disease, diabetes and obesity.

Figure 8:
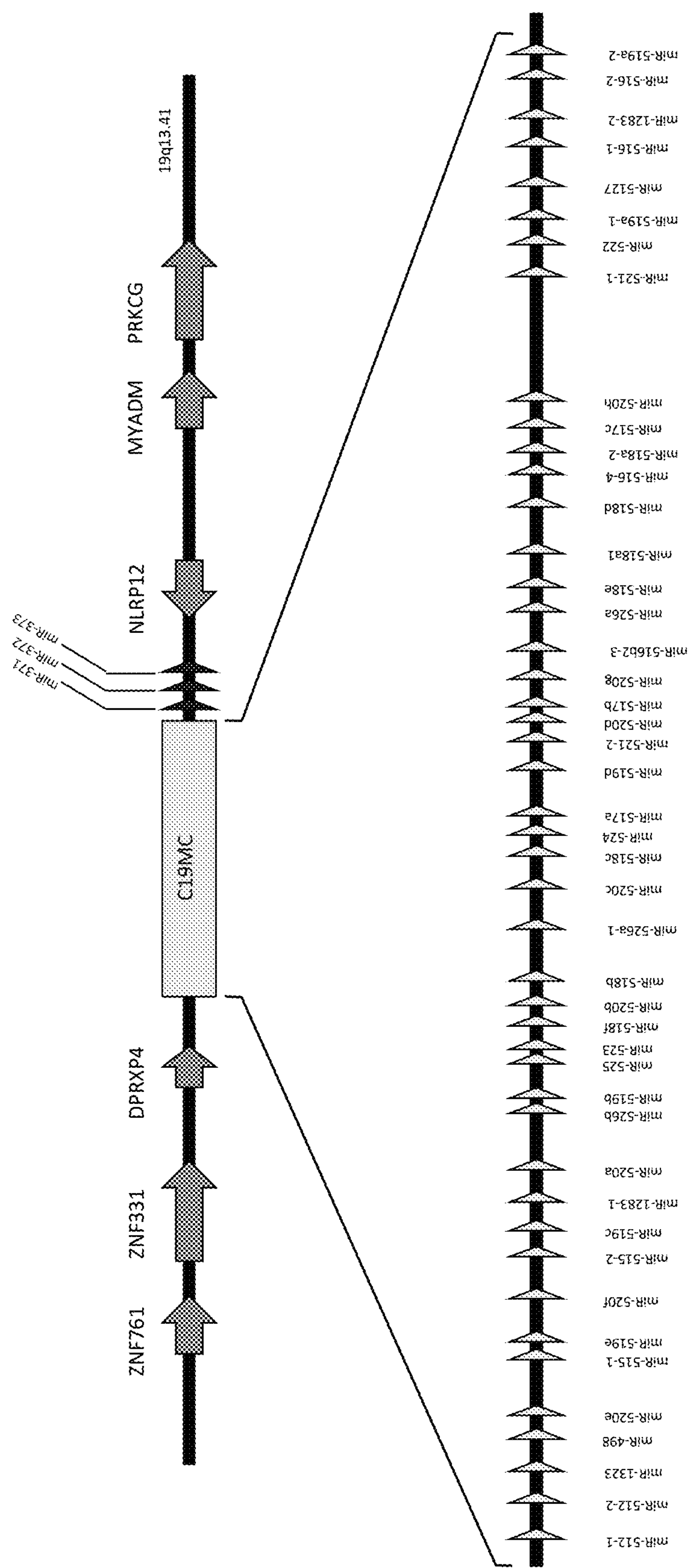
FIG. 8 is a schematic of the genomic organization of the primate-specific C19MC.

Chromosome 19 miRNA cluster (C19MC): A unique cluster of 46 primate-specific miRNA genes encoded by an approximately 100 kb region on chromosome 19 (19q13.41). The genomic organization of C19MC is shown in FIG. 8. A list of the mature miRNAs (miRs) encoded by the genes in the cluster, as well as their sequences, is provided in section V below. In the context of the present disclosure, a "biologically active portion" of the C19MC refers to any portion of the cluster (or any single miR or combination of multiple miRs encoded by the C19MC) that confers increased viral resistance and/or autophagy in a cell. In the context of the present disclosure, an "inhibitory miR" is a miR encoded by the C19MC with anti-microbial activity (and/or the ability to induce autophagy in a cell). Thus, in some examples, an inhibitory miR is a miR that increases viral resistance and/or induces autophagy in a cell. In some embodiments, the inhibitory miR does not inhibit CMV (or does not increase viral resistance to CMV).

Contacting: Placement in direct physical association; includes both in solid and liquid form. As used herein, "contacting" is used interchangeably with "exposed." In some cases, "contacting" includes transfecting, such as transfecting a nucleic acid molecule into a cell.

Exosomes: Small (30-120 nm) endosome-derived membrane vesicles. Exosomes are enriched in miRNAs.

Isolated: An "isolated" biological component (such as a nucleic acid molecule, miRNA, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Microbial infection: Infection by any type of microorganism, including viral, bacterial, fungal and protozoan infections. In some embodiments disclosed herein, the microbial infection is caused by any one of the following viruses, bacteria, fungi or protozoans:

Examples of viruses include, but are not limited to those in the following virus families: Retroviridae (for example, human immunodeficiency virus (HIV), human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus, rubella viruses); Flaviridae (for example, hepatitis C virus, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses or agents (for example, the etiological agents of spongiform encephalopathies, the agent of delta hepatitis (thought to be a defective satellite of hepatitis B virus).

Examples of bacterial pathogens include, but are not limited to: *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae, pathogenic Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis,*

*Treponema pallidium, Treponema pertenue, Leptospira, Bordetella pertussis, Shigella flexnerii, Shigella dysenteriae* and *Actinomyces israelli.*

Examples of fungal pathogens include, but are not limited to: *Cryptococcus neoformans, Histoplasma capsulatum, Coccidioides immitis, Blastomyces dermatitidis, Chlamydia trachomatis* and *Candida albicans.*

Other pathogens (such as parasitic pathogens) include, but are not limited to: *Plasmodium falciparum, Plasmodium vivax, Trypanosoma cruzi* and *Toxoplasma gondii.*

MicroRNA: MicroRNAs (also known as miRNAs and miRs) are short RNA sequences expressed from longer transcripts found in the genomes of animals, plants and viruses and at least one single-celled eukaryote (Molnár et al., *Nature* 447:1126-1129, 2007; Zhao et al., *Genes Dev.* 21:1190-1203, 2007). MicroRNAs regulate the expression of target genes by binding to complementary sites in the target gene transcripts to cause translational repression or transcript degradation (Pillai et al., *Trends Cell Biol.* 17:118-126, 2007). These small RNA molecules have been implicated in a number of biological processes related to development, cell proliferation, apoptosis, metabolism, morphogenesis and diseases (Kloosterman and Plasterk, *Dev. Cell* 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 19-24 nucleotides in length and are partially complementary to the 3'UTR (or other regions such as introns, exons or 5'UTR) of one or more target messenger RNAs (mRNAs).

A nomenclature scheme has been well established for microRNAs (Griffiths-Jones et al., *Nucleic Acids Res.* 34:D140-D144, 2006; Ambros et al., *RNA* 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "150," resulting in a complete name of "hsa-miR-150." Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-181a and miR-181b). In some cases, mature miRNAs from both the 5' and 3' arms of the hairpin precursor are identified, which are designated "3p" or "5p" (such as miR-768-3p and miR-768-5p).

MicroRNA gene product sequences are well described throughout the scientific and patent literature and are available online through miRBase (world wide web at mirbase.org), provided by the University of Manchester (previously provided by the Sanger Institute). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR**, which are sometimes identified by their "3p" or "5p" annotation, as described above.

In the context of the present disclosure, administering a "miR" to a subject or contacting a cell with a "miR" encompasses administration or contacting with a pri-miRNA, pre-miRNA or mature miRNA, or a nucleic acid molecule encoding a pri-miRNA, pre-miRNA or mature miRNA.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (such as a miR or vector encoding a miR).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Subject: Living multi-cellular vertebrate organisms, a category that includes human and non-human mammals.

Therapeutically effective amount: A quantity of a specified composition, pharmaceutical or therapeutic agent (such as a miR or nucleic acid molecule encoding a miR) sufficient to achieve a desired effect in a subject, or in a cell, being treated with the agent. The effective amount of the agent will be dependent on several factors, including, but not limited to the subject being treated, the disease or condition being treated, and the manner of administration of the therapeutic composition. In some embodiments of the present disclosure, the therapeutically effective amount (or effective amount) of a miR is the amount required to increase viral resistance or induce autophagy.

Transduce, transform or transfect: To introduce a nucleic acid molecule into a cell, such as a miR or a vector encoding a miR. These terms encompass all techniques by which a nucleic acid molecule can be introduced into a cell, including but not limited to, transduction with viral vectors, transfection with plasmid vectors, liposomal-mediated transfection and introduction of naked DNA by electroporation and particle gun acceleration. A transfected or transformed cell is a cell into which has been introduced a nucleic acid molecule by molecular biology techniques. In some examples, the nucleic acid molecule becomes stably replicated by the cell, for example by incorporation of the nucleic acid molecule into the cellular genome, or by episomal replication. In other examples, the nucleic acid molecule is transiently expressed in the cell.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Described herein is the finding that cultured primary human trophoblasts (PHT) are highly resistant to infection by diverse and unrelated viruses. The studies disclosed herein also determined that conditioned PHT culture medium confers resistance to viral infections in permissive non-placental cells, indicating that trophoblast-associated viral resistance is transmissible, and is transferred to recipient cells. It was found that a unique cluster of primate-specific microRNAs (miRNAs), which are highly expressed in human trophoblasts from the human chromosome 19 miRNA cluster (C19MC) (Noguer-Dance et al., *Hum Mol Genet* 19, 3566-3582, 2010), are packaged within PHT-derived exosomes and confer this viral resistance to recipient cells. It is further shown herein that PHT cells exhibit high rates of resting autophagy, a process involved in the maintenance of cellular homeostasis and an effective cellular countermeasure to suppress viral infections. PHT-derived exosomes and several C19MC miRNAs robustly induce autophagy in non-placental recipient cells, which is required for their resistance to viral infection. Unlike the other viruses that were tested, CMV infection is greatly enhanced by C19MC miRNAs. These findings illuminate a previously unknown pathway employed by human trophoblasts to suppress viral infections and confer viral resistance to non-placental recipient cells, suggesting a novel mechanism for shielding the placenta and maternal-derived recipient cells against viral infections during pregnancy.

IV. Overview of Several Embodiments

Provided herein is a method of inhibiting or treating a microbial infection in a subject. In some embodiments, the method includes selecting a subject with a microbial infection, or at risk for contracting a microbial infection, and administering to the subject a therapeutically effective amount of one or more microRNAs (miRs) encoded by the chromosome 19 miRNA cluster (C19MC). In some embodiments, the method includes direct administration of the one or more miRs encoded by the C19MC. In other embodiments, administering the one or more miRs encoded by the C19MC comprises administering a nucleic acid molecule encoding the C19MC or a biologically active portion thereof. In some examples, the nucleic acid molecule comprises a vector, such as a plasmid vector or a viral vector.

In some embodiments, the microbial infection is a viral infection. The viral infection can be an infection caused by any type of virus. In some examples, the virus is an RNA virus. RNA viruses include, for example, coxsackieviruses (e.g. coxsackievirus A and coxsackievirus B), poliovirus, vesicular stomatitis virus, human immunodeficiency virus, hepatitis C virus, rubella virus and morbilliviruses (such as measles virus). In particular examples, the RNA virus is a coxsackievirus, poliovirus, vesicular stomatitis virus, human immunodeficiency virus or hepatitis C virus. In other examples, the virus is a DNA virus. DNA viruses include, for example, vaccinia virus, herpes simplex viruses (HSV-1 and -2), Epstein-Barr virus, hepatitis B virus, parvovirus and varicella zoster. In particular examples, the DNA virus is a vaccinia virus or a herpes simplex virus. In some embodiments, the virus is not cytomegalovirus (CMV).

In some embodiments, the microbial infection is a bacterial infection. In some examples, the bacteria is *Staphylococcus aureus*, Group A *Streptococcus, Listeria monocytogenes, Bacillus anthracis, Burkholderia pseudomallei, Helicobacter pylori, Salmonella enterica* or *Vibrio cholerae*.

In some embodiments, the microbial infection is a parasitic infection. In some examples, the parasite is the protozoan parasite *Toxoplasma gondii*.

In some embodiments, inhibiting the microbial infection comprises preventing the microbial infection.

In some embodiments, the method comprises inhibiting or preventing intrauterine transmission of the microbial infection.

In some embodiments of the disclosed methods, administration is extrauterine. In other embodiments, administration is intrauterine.

In some examples, the one or more miRs, or nucleic acid molecule encoding the C19MC or biologically active portion thereof, is administered prophylactically to prevent infection. In other examples, the one or more miRs, or nucleic acid molecule encoding the C19MC or biologically active portion thereof, is administered to treat an existing infection.

The one or more miRs administered to the subject can be any single miR or any combination of two or more miRs that are encoded by the C19MC. Similarly, if the subject is administered a nucleic acid molecule comprising the C19MC or biologically active portion thereof, the subject can be administered the entire C19MC or a portion that encodes a single or multiple miRs. The miR genes included in the C19MC are shown in FIG. 8 and listed in Table 1. Table 1 also lists 58 unique mature miR sequences encoded by the miR genes.

In some embodiments, the subject is administered a single miR. In other embodiments, the subject is administered at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50, or at least 55 miRs. In another embodiment, the subject is administered all miRs encoded by the cluster. In particular examples, the miRs are mature miRs.

In other embodiments, the subject is administered a nucleic acid molecule comprising all miR genes of the C19MC (see Table 1). In another embodiment, the subject is administered a nucleic acid molecule encoding a single miR encoded by the C19MC. In yet other embodiments, the subject is administered a nucleic acid molecule encoding at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50, or at least 55 miRs of the C19MC. In particular examples, the miRs are mature miRs.

In some embodiments, the subject is administered the entire C19MC or a nucleic acid molecule encoding the entire C19MC.

In some embodiments, the biologically active portion of the C19MC, or the one or more miRs, comprises miR-517-3p, miR-516b-5p or miR-512-3p. In particular examples, the biologically active portion of the C19MC, or the one or more miRs comprises miR-517-3p, miR-516b-5p, and miR-512-3p. In other particular examples, the biologically active portion of the C19MC, or the one or more miRs comprises miR-517-3p, miR-1323, miR-516b-5p, miR-525-5p, miR-512-3p and miR-515-3p.

In some examples, the biologically active portion of the C19MC, or the one or more miRs, comprises miR-512-3p, miR-516b, miR-517-3p, or any combination of two or more thereof. In particular examples, the biologically active portion of the C19MC, or the one or more miRs, comprises miR-512-3p, miR-516b, miR- and 517-3p. In further examples, a single miR selected from miR-512-3p, miR-516b, miR- and 517-3p is administered to the subject.

In other examples, the biologically active portion of the C19MC, or the one or more miRs, comprises miR-512-3p, miR-515-3p, miR-516b, miR-517-3p, miR-525-5p and miR-1323. In yet other examples, the biologically active portion of the C19MC, or the one or more miRs, comprises miR-1323, miR-512-3p, miR-512-5p, miR-515-3p, miR-515-5p, miR-516b, miR-517-3p, miR-517c, miR-518a-5p, miR-518b, miR-518e, miR-519c-3p, miR-519d, miR-520c-3p, miR-520h and miR-525-5p.

In some examples, the nucleotide sequence of the one or more miRs is at least 95%, at least 96%, at least 97%, at least 98% or at least 99% identical to one or more of SEQ ID NOs: 1-59. In non-limiting examples, the nucleotide sequence of the one or more miRs comprises or consists of one or more of SEQ ID NOs: 1-59.

Further provided herein is a method of inducing autophagy in a cell. In some embodiments, the method includes contacting the cell with an effective amount of one or more miRs encoded by the C19MC. In some embodiments, the method includes directly contacting the cell with the one or more miR molecules. In other embodiments, contacting the cell with the one or more miRs encoded by the C19MC comprises contacting the cell with a nucleic acid molecule encoding the C19MC or a biologically active portion thereof. In some examples, the nucleic acid molecule comprises a vector, such as a plasmid vector a viral vector.

In some embodiments, the method is an in vitro method. In some examples of the in vitro method, the cell is a primary cell. In other examples, the cell is an immortalized cell.

In other embodiments, the method is an in vivo method and contacting the cell comprises administering to a subject an effective amount of one or more miRs encoded by the C19MC, or a nucleic acid molecule encoding the C19MC or a biologically active portion thereof. In some embodiments, the subject suffers from a disease associated with a deficiency in autophagy and/or a disease that can be ameliorated by stimulating autophagy. In particular examples, the disease is inflammatory bowel disease, Crohn's disease, alcoholic liver disease, Parkinson's disease, Alzheimer's disease, heart disease, diabetes or obesity.

The one or more miRs contacted with the cell (in vitro or in vivo) can be any single miR or any combination of two or more miRs that are encoded by the C19MC. Similarly, if the cell is contacted with a nucleic acid molecule encoding the C19MC or biologically active portion thereof, the cell can be contacted with the entire C19MC or a portion that encodes a single or multiple miRs. In some embodiments, the cell is contacted with a single miR. In other embodiments, the cell is contacted with at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50 or at least 55 miRs. In another embodiment, the cell is contacted with all miRs encoded by the C19MC. In particular examples, the miRs are mature miRs.

In other embodiments, the cell is contacted with a nucleic acid molecule comprising all miR genes of the C19MC (see Table 1). In another embodiment, the cell is contacted with a nucleic acid molecule encoding a single miR of the C19MC. In yet other embodiments, the cell is contacted with a nucleic acid molecule encoding at least 2, at least 3, at least 4, at least 5, at least 6, at least 7, at least 8, at least 9, at least 10, at least 11, at least 12, at least 13, at least 14, at least 15, at least 16, at least 17, at least 20, at least 25, at least 30, at least 35, at least 40, at least 45, at least 50 or at least 55 miRs of the C19MC. In particular examples, the miRs are mature miRs.

In some embodiments of the methods of inducing autophagy, the subject is administered the entire C19MC or a nucleic acid molecule encoding the entire C19MC.

In some embodiments of the methods of inducing autophagy, the biologically active portion of the C19MC, or the one or more miRs, comprises miR-517-3p, miR-516b-5p or miR-512-3p. In particular examples, the biologically active portion of the C19MC, or the one or more miRs comprises miR-517-3p, miR-516b-5p, and miR-512-3p. In other particular examples, the biologically active portion of the C19MC, or the one or more miRs comprises miR-517-3p, miR-1323, miR-516b-5p, miR-525-5p, miR-512-3p and miR-515-3p.

In some examples, the biologically active portion of the C19MC, or the one or more miRs, comprises miR-512-3p, miR-516b, miR-517-3p, or any combination of two or more thereof. In particular examples, the biologically active portion of the C19MC, or the one or more miRs, comprises miR-512-3p, miR-516b, and miR-517-3p. In further examples, a single miR selected from miR-512-3p, miR-516b, and miR-517-3p is contacted with the cell.

In other examples of the methods of inducing autophagy, the biologically active portion of the C19MC, or the one or more miRs, comprises miR-512-3p, miR-515-3p, miR-516b, miR-517-3p, miR-525-5p and miR-1323. In yet other examples, the biologically active portion of the C19MC, or the one or more miRs, comprises miR-1323, miR-512-3p, miR-512-5p, miR-515-3p, miR-515-5p, miR-516b, miR-517-3p, miR-517c, miR-518a-5p, miR-518b, miR-518e, miR-519c-3p, miR-519d, miR-520c-3p, miR-520h and miR-525-5p.

In some examples of the methods of inducing autophagy, the nucleotide sequence of the one or more miRs is at least 95%, at least 96%, at least 97%, at least 98% or at least 99% identical to one or more of SEQ ID NOs: 1-59. In non-limiting examples, the nucleotide sequence of the one or more miRs comprises or consists of one or more of SEQ ID NOs: 1-59.

In some embodiments of the methods disclosed herein, the one or more miRs, or the nucleic acid molecule encoding the C19MC or biologically active portion thereof, is administered to the subject or contacted with the cell using a liposomal formulation, a cationic lipid or a polypeptide carrier.

In some embodiments of the disclosed methods, the nucleic acid molecule encoding the C19MC or biologically active portion thereof comprises a vector. In some examples, the vector is a plasmid vector. In other examples, the vector is a viral vector. Viral vectors can be of, for example, adenovirus, adeno-associated virus, retrovirus, herpes virus or vaccinia virus origin. Viral vectors can include modified versions of the viruses, such as replication deficient viruses. Suitable vectors, such as gene therapy vectors, are well known in the art. In some examples, the miR is expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the present disclosure can also comprise inducible or regulatable promoters for expression of the miR.

In some embodiments, such as when the miR is administered as a naked nucleic acid molecule, the miR includes modifications, such as nucleotide modifications to increase nuclease resistance, or other modifications to enhance delivery and/or activity of the miR.

The disclosed methods comprise administering a therapeutically effective amount, or contacting a cell with an effective amount, of at least one miR encoded by the C19MC. In some embodiments, the miR is a variant or biologically-active fragment of the miR encoded by the C19MC. Thus, the miR that is administered to a subject or contacted with a cell can be identical to an endogenous (wild-type) miR (including a pri-miRNA, pre-miRNA or mature miRNA) that is encoded by the C19MC, or it can be a variant or biologically-active fragment thereof. As defined herein, a "variant" of a miR refers to a miRNA that has less than 100% identity to a corresponding wild-type miR and possesses one or more biological activities of the corresponding miR. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule), promoting viral resistance or inducing autophagy. The miR variants include species variants and variants that are the consequence of one or more mutations (e.g., a substitution, a deletion, an insertion) in a miR gene. In certain embodiments, the variant is at least about 80%, at least about 85%, at least about 90%, at least about 95%, at least about 96%, at least about 97%, at least about 98%, or at about 99% identical to a corresponding wild-type miR (such as one of the miRs listed in Table 1 or set forth herein as SEQ ID NOs: 1-59).

As used herein, a "biologically-active fragment" of a miR refers to an RNA fragment of a miR that possesses one or more biological activities of a corresponding wild-type miR. As described above, examples of such biological activities include, but are not limited to, inhibition of expression of a target RNA molecule, repressing protein translation, promoting viral resistance or inducing autophagy. In certain embodiments, the biologically-active fragment is at least about 9, at least about 11, at least about 13, at least about 15, at least about 17 or at least about 19 nucleotides in length.

V. Placental miRNAs from Chromosome 19 miRNA Cluster (C19MC)

Akin to other tissues, trophoblast differentiated functions are controlled by transcription factors, epigenetic modifiers and post-transcriptional influences that ultimately shape mRNA and protein expression. These pathways include small modulatory RNAs that interact with target gene 3'UTRs (or other regions of the genes) and promote RNA degradation and translational repression (Ghildiyal et al., *Nat Rev Genet* 10:94-108, 2009; Huntzinger and Izaurralde, *Nat Rev Genet* 12:99-110, 2011; Krol et al., *Nat Rev Genet* 11:597-610, 2010; Friedman et al., *Genome Res* 19:92-105, 2009; Thomas and Lieberman, *Nat Struct Mol Biol* 17:1169-1174, 2010; Vickers et al., *Nat Cell Biol* 13:423-433, 2011; Herranz and Cohen, *Genes Dev* 24:1339-1344, 2010; Bartel, *Cell* 136:215-233, 2009; Carthew and Sontheimer, *Cell* 136:642-655, 2009). Among all small RNAs, previous studies have shown that human trophoblasts produce primarily miRNAs throughout pregnancy, as well as other small RNAs (piRNAs, snRNAs, and snoRNAs) (Mouillet et al., *Placenta* 31:781-784, 2010; Luo et al., *Biol Reprod* 81:717-729, 2009; Mouillet et al., *Birth Defects Res A Clin Mol Teratol* 91:737-743, 2011; Barad et al., *Genome Res* 14:2486-2494, 2004; Pineles et al., *Am J Obstet Gynecol* 196:261, 2007). Many of these miRNAs are stably released into the maternal circulation, suggesting a miRNA-based mechanism for fetal-maternal communication (Mouillet et al., *Placenta* 31:781-784, 2010; Chim et al., *Clin Chem* 54:482-190, 2008).

Approximately 30-40% of placental miRNA species are expressed from defined miRNA clusters (Luo et al., *Biol Reprod* 81:717-729, 2009; Liang et al., *Genomics* 8:166, 2007; Bortolin-Cavaille et al., *Nucleic Acids Res* 37:3464-3473, 2009). Unique among these clusters is a primate-specific, large miRNA cluster (~100 kb, 46 highly-related miRNA genes), expressed from chromosomal region 19q13.41 (Bentwich et al., *Nat Genet* 37:766-770, 2005). MiRNA members of this chromosome 19 miRNA cluster (C19MC) are expressed throughout human pregnancy, and nearly exclusively in the placenta (Luo et al., *Biol Reprod* 81:717-729, 2009; Liang et al., *Genomics* 8:166, 2007; Bortolin-Cavaille et al., *Nucleic Acids Res* 37:3464-3473, 2009; Chiu et al., *Clin Chem* 52:313-316, 2006). Although the C19MC genomic sequence contains many primate-specific Alu repeats, which may mediate gene rearrangement (Zhang et al., *Mol Biol Evol* 25:1493-1502, 2008; Lehnert et al., *PLoS One* 4:e4456, 2009), secondary structure conservation and low SNP frequency of C19MC suggests that this cluster is evolutionarily stable. Selected placenta-specific miRNA species are found in the maternal blood throughout pregnancy. Their levels are not uniform, and rapidly decline in the first 24 h postpartum (Ng et al., *Proc Natl Acad Sci USA* 100:4748-4753, 2003; Gilad et al., *PLoS One* 3:e3148, 2008).

A schematic of the genomic organization of C19MC is shown in FIG. 8. A list of the specific miRNA genes included in this cluster is provided in the table below. The names and sequences of the mature forms of each miRNA gene are also shown. Many miR genes encode more than one mature product (the "5p" and "3p" products from the 5' and 3' arms, respectively, of the hairpin precursor). In some instances, two different miR genes encode a mature product with the same sequence (for example, see hsa-miR-512-1 and hsa-miR-512-2). All sequences shown in Table 1 were obtained from miRBase (world wide web at mirbase.org) on Feb. 27, 2012. The present disclosure contemplates the use of any microRNA product (a pri-mRNA, pre-miRNA or mature RNA) encoded by any of the genes listed in Table 1.

TABLE 1 miRNAs of the chromosome 19 miRNA cluster

| Gene | Mature miRNA | Sequence of Mature miRNA | SEQ ID NO: |
|---|---|---|---|
| hsa-mir-512-1 | hsa-miR-512-5p | CACUCAGCCUUGAGGGCACUUUC | 1 |
| | hsa-miR-512-3p | AAGUGCUGUCAUAGCUGAGGUC | 2 |
| hsa-mir-512-2 | hsa-miR-512-5p | CACUCAGCCUUGAGGGCACUUUC | 1 |
| | hsa-miR-512-3p | AAGUGCUGUCAUAGCUGAGGUC | 2 |
| hsa-mir-1323 | hsa-miR-1323 | UCAAAACUGAGGGGCAUUUUCU | 3 |
| hsa-mir-498 | hsa-miR-498 | UUUCAAGCCAGGGGGCGUUUUUC | 4 |
| hsa-mir-520e | hsa-miR-520e | AAAGUGCUUCCUUUUUGAGGG | 5 |
| hsa-mir-515-1 | hsa-miR-515-5p | UUCUCCAAAAGAAAGCACUUUCUG | 6 |
| | hsa-miR-515-3p | GAGUGCCUUCUUUUGGAGCGUU | 7 |
| hsa-mir-519e | hsa-miR-519e-5p | UUCUCCAAAAGGGAGCACUUUC | 8 |
| | hsa-miR-519e-3p | AAGUGCCUCCUUUUAGAGUGUU | 9 |
| hsa-mir-520f | hsa-miR-520f | AAGUGCUUCCUUUUAGAGGGUU | 10 |
| hsa-mir-515-2 | hsa-miR-515-5p | UUCUCCAAAAGAAAGCACUUUCUG | 6 |
| | hsa-miR-515-3p | GAGUGCCUUCUUUUGGAGCGUU | 7 |

TABLE 1-continued

| miRNAs of the chromosome 19 miRNA cluster | | | |
|---|---|---|---|
| Gene | Mature miRNA | Sequence of Mature miRNA | SEQ ID NO: |
| hsa-mir-519c | hsa-miR-519c-5p | CUCUAGAGGGAAGCGCUUUCUG | 11 |
| | hsa-miR-519c-3p | AAAGUGCAUCUUUUUAGAGGAU | 12 |
| hsa-mir-1283-1 | hsa-miR-1283 | UCUACAAAGGAAAGCGCUUUCU | 13 |
| hsa-mir-520a | hsa-miR-520a-5p | CUCCAGAGGGAAGUACUUUCU | 14 |
| | hsa-miR-520a-3p | AAAGUGCUUCCCUUUGGACUGU | 15 |
| hsa-mir-526b | hsa-miR-526b-5p | CUCUUGAGGGAAGCACUUUCUGU | 16 |
| | hsa-miR-526b-3p | GAAAGUGCUUCCUUUUAGAGGC | 17 |
| hsa-mir-519b | hsa-miR-519b-5p | CUCUAGAGGGAAGCGCUUUCUG | 18 |
| | hsa-miR-519b-3p | AAAGUGCAUCCUUUUAGAGGUU | 19 |
| hsa-mir-525 | hsa-miR-525-5p | CUCCAGAGGGAUGCACUUUCU | 20 |
| | hsa-miR-525-3p | GAAGGCGCUUCCCUUUAGAGCG | 21 |
| hsa-mir-523 | hsa-miR-523-5p | CUCUAGAGGGAAGCGCUUUCUG | 22 |
| | hsa-miR-523-3p | GAACGCGCUUCCCUAUAGAGGGU | 23 |
| hsa-mir-518f | hsa-miR-518f-5p | CUCUAGAGGGAAGCACUUUCUC | 24 |
| | hsa-miR-518f-3p | GAAAGCGCUUCUCUUUAGAGG | 25 |
| hsa-mir-520b | hsa-miR-520b | AAAGUGCUUCCUUUUAGAGGG | 26 |
| hsa-mir-518b | hsa-miR-518b | CAAAGCGCUCCCCUUUAGAGGU | 27 |
| hsa-mir-526a-1 | hsa-miR-526a | CUCUAGAGGGAAGCACUUUCUG | 28 |
| hsa-mir-520c | hsa-miR-520c-5p | CUCUAGAGGGAAGCACUUUCUG | 29 |
| | hsa-miR-520c-3p | AAAGUGCUUCCUUUUAGAGGGU | 30 |
| hsa-mir-518c | hsa-miR-518c-5p | UCUCUGGAGGGAAGCACUUUCUG | 31 |
| | hsa-miR-518c-3p | CAAAGCGCUUCUCUUUAGAGUGU | 32 |
| hsa-mir-524 | hsa-miR-524-5p | CUACAAAGGGAAGCACUUUCUC | 33 |
| | hsa-miR-524-3p | GAAGGCGCUUCCCUUUGGAGU | 34 |
| hsa-mir-517-3p | hsa-miR-517-5p | CCUCUAGAUGGAAGCACUGUCU | 35 |
| | hsa-miR-517-3p | AUCGUGCAUCCCUUUAGAGUGU | 36 |
| hsa-mir-519d | hsa-miR-519d | CAAAGUGCCUCCCUUUAGAGUG | 37 |
| hsa-mir-521-2 | hsa-miR-521 | AACGCACUUCCCUUUAGAGUGU | 38 |
| hsa-mir-520d | hsa-miR-520d-5p | CUACAAAGGGAAGCCCUUUC | 39 |
| | hsa-miR-520d-3p | AAAGUGCUUCUCUUUGGUGGGU | 40 |
| hsa-mir-520g | hsa-miR-520g | ACAAAGUGCUUCCCUUUAGAGUGU | 42 |
| hsa-mir-516b-2 | hsa-miR-516b-5p | AUCUGGAGGUAAGAAGCACUUU | 43 |
| | hsa-miR-516b-3p | UGCUUCCUUUCAGAGGGU | 44 |
| hsa-mir-526a-2 | hsa-miR-526a | CUCUAGAGGGAAGCACUUUCUG | 28 |
| hsa-mir-518e | hsa-miR-518e-5p | CUCUAGAGGGAAGCGCUUUCUG | 45 |
| | hsa-miR-518e-3p | AAAGCGCUUCCCUUCAGAGUG | 46 |
| hsa-mir-518a-1 | hsa-miR-518a-5p | CUGCAAAGGGAAGCCCUUUC | 47 |
| | hsa-miR-518a-3p | GAAAGCGCUUCCCUUUGCUGGA | 48 |

TABLE 1-continued

| miRNAs of the chromosome 19 miRNA cluster | | | |
|---|---|---|---|
| Gene | Mature miRNA | Sequence of Mature miRNA | SEQ ID NO: |
| hsa-mir-518d | hsa-miR-518d-5p | CUCUAGAGGGAAGCACUUUCUG | 49 |
| | hsa-miR-518d-3p | CAAAGCGCUUCCCUUUGGAGC | 50 |
| hsa-mir-516b-1 | hsa-miR-516b-5p | AUCUGGAGGUAAGAAGCACUUU | 43 |
| | hsa-miR-516b-3p | UGCUUCCUUUCAGAGGGU | 44 |
| hsa-mir-518a-2 | hsa-miR-518a-5p | CUGCAAAGGGAAGCCCUUUC | 47 |
| | hsa-miR-518a-3p | GAAAGCGCUUCCCUUUGCUGGA | 48 |
| hsa-mir-517c | hsa-miR-517-5p | CCUCUAGAUGGAAGCACUGUCU | 35 |
| | hsa-miR-517c-3p | AUCGUGCAUCCUUUUAGAGUGU | 51 |
| hsa-mir-520h | hsa-miR-520h | ACAAAGUGCUUCCCUUUAGAGU | 52 |
| hsa-mir-521-1 | hsa-miR-521 | AACGCACUUCCCUUUAGAGUGU | 38 |
| hsa-mir-522 | hsa-miR-522-5p | CUCUAGAGGGAAGCGCUUUCUG | 53 |
| | hsa-miR-522-3p | AAAAUGGUUCCCUUUAGAGUGU | 54 |
| hsa-mir-519a-1 | hsa-miR-519a-5p | CUCUAGAGGGAAGCGCUUUCUG | 55 |
| | hsa-miR-519a-3p | AAAGUGCAUCCUUUUAGAGUGU | 56 |
| hsa-mir-527 | hsa-miR-527 | CUGCAAAGGGAAGCCCUUUC | 57 |
| hsa-mir-516a-1 | hsa-miR-516a-5p | UUCUCGAGGAAAGAAGCACUUUC | 58 |
| | hsa-miR-516a-3p | UGCUUCCUUUCAGAGGGU | 59 |
| hsa-mir-1283-2 | hsa-miR-1283 | UCUACAAAGGAAAGCGCUUUCU | 13 |
| hsa-mir-516a-2 | hsa-miR-516a-5p | UUCUCGAGGAAAGAAGCACUUUC | 58 |
| | hsa-miR-516a-3p | UGCUUCCUUUCAGAGGGU | 59 |
| hsa-mir-519a-2 | hsa-miR-519a-3p | AAAGUGCAUCCUUUUAGAGUGU | 56 |

Placental Exosomes

A significant fraction of plasma miRNA is packaged in exosomes. These nanoparticles function as "cargo vehicles" (Valadi et al., *Nat Cell Biol* 9:654-659, 2007; Simpson et al., *Proteomics* 8:4083-4099, 2008; Skog et al., *Nat Cell Biol* 10:1470-1476, 2008) to transfer nucleic acids, proteins, lipids and other biomolecules to proximal and distant tissues (Thery et al., *Nat Rev Immunol* 9:581-593, 2009; Raposo et al., *J Exp Med* 183:1161-1172, 1996; Alvarez-Erviti et al., *Nat Biotechnol* 29:341-345, 2011). Exosomes belong to a large family of intracellular and extracellular microvesicular bodies, ranging in size between >100 nm (apoptotic blebs and microparticles) to approximately 30-120 nm (exosomes). Exosomes can fuse intracellularly with lysosomes to destroy content or fuse with plasma membranes to release exosomal content via exocytosis or ectocytosis (Thery et al., *Nat Rev Immunol* 2:569-579, 2002; Pan and Johnstone, *Cell* 33:967-978, 1983; Keller et al., *Immunol Lett* 107:102-108, 2006). Exosomes are defined by size, cup-shaped form, sucrose gradient buoyancy (1.13-1.19 g/mL), and a detergent-resistant, lipid raft-rich membrane bilayer of proteins, cholesterol, and sphingolipids. Some of the membrane proteins are common, such as cytoskeletal proteins, chaperones, and tetraspanins, including CD9, CD63, CD81, and others specific to the exosome's cell of origin (Simpson et al., *Proteomics* 8:4083-4099, 2008; Thery et al., *Nat Rev Immunol* 2:569-579, 2002). Surface proteins may determine exosome specificity to target cells, which they enter via endocytosis-based internalization (Morelli et al., *Blood* 104:3257-3266, 2004), cell membrane fusion (Denzer et al., *J Immunol* 165:1259-1265, 2000), or receptor-ligand interactions (Admyre et al., *Eur J Immunol* 36:1772-1781, 2006).

Thus, exosomes act as a form of communication among different cell types, with potentially striking consequences to recipient cells (e.g., induction of apoptosis, mediated by the FAS ligand binding to FAS receptors). Relevant to the present disclosure, exosomes were recently found to be enriched for miRNAs (Valadi et al., *Nat Cell Biol* 9:654-659, 2007; Eldh et al., *PLoS One* 5:e15353, 2010), akin to virally-mediated intercellular transfer of genetic material, with potential beneficial or harmful consequences (Eldh et al., *PLoS One* 5:e15353, 2010). The human placenta is known to express microvesicular bodies of diverse sizes, mainly shed as syncytiotrophoblast microparticles, implicated in preeclampsia-related placental apoptosis. Production of exosomes has been studied in first trimester trophoblasts, where exosomes likely contribute to the establishment of maternal immune tolerance, possibly via impaired T-cell signaling, down-regulation of NK cell receptor NKG2D, and enhanced apoptotic pathways through FasL, TRAIL, and PD-L (Luo et al., *Biol Reprod* 81:717-729, 2009; Taylor et al., *J Immunol* 176:1534-1542, 2006; Hedlund et al., *J Immunol* 183:340-351, 2009; Mincheva-Nilsson and Baranov, *Am J Reprod Immunol* 63:520-533, 2010). The production and function of placental exosomes after the first trimester of human pregnancy, and the role of miRNAs packaged in these exosomes, has not been previously studied.

VI. Administration of miRNAs

A nucleic acid molecule encoding C19MC, or a biologically active portion thereof (including a single miR or multiple miRs), can be administered to a subject in need of treatment using any suitable means known in the art. Nucleic acid-based therapeutic agents can be administered to a subject by any suitable route. In some examples, the nucleic acid molecules are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. In some cases, suitable administration routes are injection, infusion and direct injection into a target tissue.

In the context of the present disclosure, a miR or a nucleic acid molecule encoding C19MC, or a biologically active portion thereof, can be administered to the subject either as naked RNA or DNA in combination with a delivery reagent, or can be encoded by a recombinant plasmid or viral vector. Recombinant plasmids and viral vectors including sequences that express the C19MC or biologically active portion thereof, and techniques for delivering such plasmids and vectors to target cells, are well known in the art.

In some embodiments, liposomes are used to deliver the nucleic acid molecule to a subject. Liposomes can also increase the blood half-life of nucleic acids. Suitable liposomes for use with the present disclosure can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a nucleic acid molecule to a subject. Cationic lipids and polymers that can be used to deliver therapeutic nucleic acid molecules have been described (see, for example, Zhang et al., *J Control Release.* 123(1):1-10, 2007; Vorhies et al., *Methods Mol Biol.* 480:11-29, 2009; and U.S. Patent Application Publication No. 2009/0306194). Polypeptide carriers can also be used to administer nucleic acid molecules, such as miRs, to a subject (see, for example, Rahbek et al., *J. Gene Med.* 10:81-93, 2008).

Nucleic acid molecules can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils.

Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Administration can be accomplished by single or multiple doses. The dose required will vary from subject to subject depending on the species, age, weight and general condition of the subject, the particular nucleic acid molecule being used and its mode of administration. An appropriate dose can be determined by one of ordinary skill in the art using only routine experimentation.

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Cells and PHT Exosome Purification

Primary human trophoblasts (PHT cells) were isolated from normal singleton term placentas using the trypsin-deoxyribonuclease-dispase/Percoll method as described by Kliman et al., with previously published modifications (Kliman et al., *Endocrinology* 118, 1567-1582, 1986; Nelson et al., *Am J Obstet Gynecol* 180, 896-902, 1999). Cells were maintained in DMEM (Sigma) containing 10% fetal bovine serum (FBS, Hyclone, Logan, Utah, USA) and antibiotics at 37° C. in a 5% carbon dioxide ($CO_2$)-air atmosphere. Cells were maintained 72 h after plating, with cell quality monitored both morphologically (by microscopy) and by medium human chorionic gonadotropin (hCG) levels, determined by enzyme-linked immunosorbent assay (ELISA, DRG International, Mountainside, N.J.), showing a characteristic increase in medium hCG as cytotrophoblasts differentiate into syncytiotrophoblasts (Nelson et al., *Am J Obstet Gynecol* 180, 896-902, 1999; Chen et al., *J Biol Chem* 281, 2764-2772, 2006).

For isolation of PHT exosomes, PHT cells were maintained for 48 h in DMEM containing 10% FBS that was ultracentrifuged at 108,000×g for 10 h to deplete pre-existing FBS exosomes. Exosomes were isolated as described previously (Montecalvo et al., *J Immunol* 180, 3081-3090, 2008). Briefly, supernatants from 200 million PHT cells were combined and subsequently centrifuged at 300×g for 5 min, 1,200×g for 10 min, and 10,000×g for 30 min. Exosomes were concentrated by centrifugation at 2,500×g for 25 min using a Vivacell 100 filter (BioExpress, Kaysville, Utah, USA; F-2820-100C), then ultracentrifuged at 108,000×g for 1 h, and the exosome pellet was subsequently ultracentrifuged on top of a 30% sucrose density cushion at 108,000×g for 1 h (Lamparski et al., *J Immunol Methods* 270, 211-226, 2002). The exosomal phase was collected and resuspended in PBS, before ultracentrifugation at 108,000×g for 1 h. The total amount of exosomes was determined by total protein spectrophotometry. Exosome-depleted PHT supernatant was produced by subsequently centrifugation at 300×g for 5 min, 1,200×g for 10 min, 10,000×g for 30 min and 108,000×g for 1.5 h. Exosomes were reconstituted in FBS-exosome depleted complete medium at a ten-fold concentration over conditioned medium.

Human osteosarcoma U2OS, human foreskin fibroblast (HFF), and Huh7.5 cells were cultured in DMEM-H supplemented with 10% FBS and penicillin/streptomycin. Vero African green monkey kidney cells were maintained in DMEM-H supplemented with 5% FBS and penicillin/streptomycin. Caco-2 (ATCC clone) human intestinal epithelial cells were cultured in MEM supplemented with 10% FBS, non-essential amino acids, sodium pyruvate, and penicillin/streptomycin. Immortalized human first trimester extravillous trophoblast cells, provided by CH Graham, Kingston, Ontario, Canada (Graham et al., *Exp Cell Res* 206, 204-211, 1993) were cultured in RPMI-1640 (Cellgro, Manassas, Va., USA), supplemented with 5% bovine growth serum (HyClone) and antibiotics.

Conditioned media from PHT or other cells were harvested between 48-72 h post plating. Conditioned medium was subjected to sonication or heat-inactivation for 30 min at 65° C. Recipient cells were exposed to conditioned medium for ~24 h prior to assay.

Viruses

Experiments were performed with vesicular stomatitis virus (VSV), green fluorescent protein (GFP)-tagged VSV, recombinant yellow fluorescent protein (YFP)-tagged vaccinia virus as described (VV) (Moser et al., *PLoS Pathog* 6, e1000954, 2010), coxsackievirus B3-RD isolate (CVB3-RD) as described (Coyne and Bergelson, *Cell* 124, 119-131, 2006), poliovirus (PV) as described (Coyne et al., *EMBO J* 26, 4016-4028, 2007), cytomegalovirus (hCMV Towne strain), cell culture grown hepatitis C virus (HCV) expressing firefly luciferase (HCVcc-luc), or GFP-tagged herpes simplex virus-1 (HSV1, strain KOS) as described (Desai and Person, *J Virol* 72, 7563-7568, 1998). VSV was expanded by growth on Vero cells and media was harvested. Viral titers were determined by plaque assays as previously described (Bozym et al., *Cell Host Microbe.* 11:153-166, 2012). Plaque assays were conducted on Vero (VSV and GFP-VSV) or HeLa (CVB) cells. Confluent monolayers were treated with serial dilutions of virus for one hour at 37° C. (VSV) or at room temperature (CVB). Cells were then overlayed with agarose and incubated for 48 h. Plaques were visualized by crystal violet staining and plaques enumerated. HCVcc-luc propagation was performed as described (Liu et al., *J. Virol.* 83:2011-2014, 2009).

Experiments assessing productive virus infection were performed as follows. PHT cells were infected with CVB, PV, VSV, VV, or HSV-1 for 14-15 h (multiplicity of infection (MOI)=5), or CMV for 24 h. Infections were performed with three individual PHT preparations in duplicate. hCMV infections were performed with two individual PHT preparations in triplicate. For 3-MA experiments assessed by RT-qPCR, PHT cells were infected with GFP-VSV for 15 h at MOI=5. For experiments analyzing immediate early viral gene expression measured by RT-qPCR, PHT cells were infected with CVB, VSV, VV, or HSV-1 for 6-7 h at MOI=1. HeLa cells were infected with CVB or PV at an MOI=5 for 8 h. HFF cells were infected with CMV for 24 h, VSV or CVB (MOI=5) for 15 h. Vero cells were infected with VSV for 6 h (MOI=5). Caco-2 cells were infected with VSV or CVB for 7 h (MOI=5). RL-95 cells were infected with CVB for 15 h (MOI=5). For immunofluorescence, U2OS cells were infected with CVB for 7 h (MOI=5), VSV (MOI=5), VV, or HSV-1 (MOI=1) for 15 h. For RT-qPCR, U2OS cells were infected with CMV, VSV, HSV-1 or VV for 5-6 h (MOI=1). Huh7.5 cells were infected with HCVcc as described previously (Liu et al., *J. Virol.* 83:2011-2014, 2009).

miRNA Mimics, Plasmids, and Transfections

Mimics for C19MC miRNAs (miRIDIAN) as well as a non-targeting control miRNA mimic were obtained from Thermo-Fisher (Dharmacon, Lafayette, Colo.) as described (Donker et al., *Mol. Hum. Reprod.* 18(8):417-424, 2012). U2OS cells or other cell lines were transfected with one or multiple miRNA mimics or miRNA mimic negative control (final concentration 6 nM for each miRNA mimic) using DharmaFECT-1 transfection reagent (Thermo Fisher Scientific) or HiPerFect™ (Qiagen) according to manufacturer's instructions. Cells were assayed 48 h post-transfection.

The total concentration of non-targeting control miRNA mimics was adjusted to that of all active miRNA mimics. For siRNA transfections, U2OS cells were reverse transfected using HiPerFect™ transfection reagent (Qiagen). For silencing of beclin-1, 40 nM per well of scrambled non-targeting siRNA (siControl) or beclin-1 siRNA (Cell Signaling, #6222S) were transfected.

Plasmid transfections were performed using X-tremeGENE 9 (Roche) according to manufacturer's protocol. The mRFP-LC3B expression construct was purchased from Addgene (plasmid 21075) and originally constructed by Tamotsu Yoshimori (Kimura et al., *Autophagy* 3, 452-460, 2007). For experiments with conditioned media and purified exosomes, cells were transfected, exposed to media 24 h later, and fixed 48 h post-transfection. For all other experiments, the cells were assayed 48 h post-transfection.

C19MC BAC Preparation and Transfection

The BAC RP11-1055017 containing 160,970 bp of genomic DNA from region q13-42 of chromosome 19 was obtained from the BACPAC Resource Center located at the Children's Hospital Oakland Research Institute (CHORI) in Oakland, Calif. The BAC clone harbors the entire C19MC miRNA cluster spanning around 100 kb and contains an additional 60 kb of flanking sequences. The nucleotide sequence of the genomic insert in BAC RP11-1055O17 is set forth herein as SEQ ID NO: 60. Recombineering of the BAC was performed as described (Warming et al., *Nucleic Acids Res* 33, e36, 2005). A GFP::zeocin cassette from the pSELECT-GFPzeo-mcs plasmid (InvivoGen, CA), was PCR amplified and cloned into the Hind III and Bam HI sites of pBluescript II SK(+) (pBS-SK). BAC specific homology arms of ~500 bp each were PCR amplified and cloned into pBS-SK using the restriction sites flanking the GFP::zeocin cassette (5'arm: Xho I and Hind III; 3'arm: Bam HI and Xba I). The whole targeting cassette was then PCR amplified, gel purified, and electroporated into the recombinogenic SW106 bacterial strain containing the recipient BAC. In addition to the construct that was simply tagged with the GFP::zeocin cassette at the 3'end of the C19MC cluster, a BAC with a deletion of the entire C19MC coding sequence was created and used as a control in transfection experiments. By choosing a 5' homology arm located upstream of the miRNA cluster and keeping the same 3' homology arm, the recombination led to the actual deletion (BAC "trimming") of the entire miRNA locus (~100 kb). The construct contain ~60 kb of genomic DNA flanking the GFP::zeocin cassette. Bacteria harboring the BAC with the desired alteration were selected on selective medium with chloramphenicol (12.5 μg/ml) and zeocin (25 μg/ml). The correct BAC constructs, confirmed by using restriction mapping and PCR, were transformed back into DH10B bacterial cells for propagation. BAC DNA for transfection was prepared using the PhasePrep BAC DNA kit following the recommendations from the manufacturer (Sigma).

RNA Isolation, Microarrays and miRNA RT-qPCR

For miRNA analysis, total cellular RNA was purified from cells using miRNeasy Mini Kit (Qiagen, Valencia, Calif.), according to the manufacturer's instructions. Prior to RNA isolation, non-exosomal RNA were degraded using 400 ng/μl RNase at 37° C. for 15 min (Valadi et al., *Nat Cell Biol* 9, 654-659, 2007). For miRNA analysis, reverse transcription and quantitative PCR (RT-qPCR) of duplicate samples was performed using the miScript PCR system (Qiagen, Valencia, Calif.), following the manufacturer's instructions. Detection of all miRNAs was performed using respective miScript primers (Qiagen, Valencia, Calif.). Dissociation curves were run on all reactions to ensure amplification of a single product. Control $H_2O$ samples were included in all RT and PCR reactions. Total RNA input was normalized using RNU6B RNA as an endogenous control. The fold increase relative to control samples was determined by the 2-ΔΔCt method (Livak and Schmittgen, *Methods* 25, 402-408, 2001). Microarray analysis of C19MC miRNA expression in PHT cells and in PHT exosomes was performed using Agilent's Human miRNA V3 8×15K arrays.

For analysis of C19MC miRNA targets, total cellular RNA was purified from U2OS or HTR8/Sv-Neo cells using miRNeasy Mini Kit (Qiagen), according to the manufacturer's instructions (Agilent Technologies, Santa Clara, Calif.). The quality of RNA was confirmed using 2100 Bioanalyzer (Agilent Technologies, Santa Clara, Calif.). A total of 100 ng of RNA was used for labeling, generating cyanine 3-labeled lineary amplified cRNA. Six hundred ng of cRNA was used for microarray hybridization as per Agilent protocol, performed using Agilent's SurePrint G3 Hmn GE 8×60K human arrays. Array data were extracted using a High-Resolution C scanner (Agilent) and a GE1 107 (September 9) feature extraction protocol (Agilent).

All data were from the three experimental paradigms were log 2 transformed and normalized separately using the cyclic loess normalization method (Wu et al., *BMC Bioinformatics* 6:309, 2005). Identical probes targeting the same mRNA transcripts were averaged by probe set intensity values. A moderated student's t test, which is based on an empirical Bayesian algorithm, as implemented in the R package "limma" (G. K. Smyth, "Linear models and empirical Bayes methods for assessing differential expression in microarray experiments," Statistical Applications in Genetics and Molecular Biology, 3:Article 3, 2004) was applied to test, for each gene, if it was differentially expressed between the cells transfected by the empty BAC or by the C19MC BAC. The Storey's q-value method (Storey and Tibshirani, *Proc Natl Acad Sci USA* 100, 9440-9445, 2003) was used to calculate the adjusted p values for the p values of the moderated t test to control the false discovery rate. Up- or down-regulated genes were subsequently identified that satisfied the following conditions: (1) down (or up) regulation in the C19MC-transfected HTR8 cells with adjusted p values ≤0.05 and log 2 fold change ≤−0.5 (or ≥+0.5), (2) down (or up) regulation in the C19MC-transfected U2OS cells with adjusted p values ≤0.05 and log 2 fold change ≤−0.5 (or ≥+0.5), and (3) down (or up) regulated in the U2OS cells exposed to conditioned medium, with log 2 fold change ≤−0.5 (or ≥+0.5, note that because each group in the U2OS conditioned medium experiment had only one sample, no statistical testing was performed). Finally, the TargetScan miRNA target database (version 6) was searched to identify, among the down regulated genes, those that are predicted targets of at least one of the 4 most abundant C19MC miRNAs: miR-517-3p, miR-517b, miR-516b, and miR-512-3p. All the analyses were performed using the statistical computing program R and its packages (R Development Core Team, 2011. R: A language and environment for statistical computing. R Foundation for Statistical Computing, Vienna, Austria. ISBN 3-900051-07-0).

For cellular mRNA analysis, total RNA was extracted using TRIreagent (MRC) or RNeasy (Qiagen) according to manufacturer's protocol. RNA samples were treated with RNAse-free DNAse (Qiagen). Total RNA was reverse transcribed using iScript cDNA synthesis kit (Bio-Rad) or $RT^2$ First Strand kit (SABiosciences). For each sample, 0.25-1 μg RNA was used for cDNA synthesis. Real-time PCR as performed using iQ SYBR Green Supermix (Bio-Rad) in a Applied Biosystems StepOnePlus real-time PCR machine according to the manufacturer's instructions. Dissociation curves were run on all reactions to ensure amplification of a single product. Gene expression was calculated using the ΔΔCt values with normalization to human actin

```
(ACTGGGACGACATGGAGAAAA, SEQ ID NO: 61;
GCCACACGCAGCTC, SEQ ID NO: 62).
```

Primers used were as follows: VSV (TGCAAGGAAAGCATTGAACAA, SEQ ID NO: 63; GAGGAGTCACCTGGACAATCACT, SEQ ID NO: 64), GFP (CACATGAAGCAGCACGACTTCT, SEQ ID NO: 65; AACTCCAGCAGGACCATGTGAT, SEQ ID NO: 66), hCMV Towne strain (GCGGTGGTTGCCCAACAGGA, SEQ ID NO: 67; ACGACCCGTGGTCATCTTTA, SEQ ID NO: 68), ATG4C (TAGAGGATCACGTAATTGCAGGA, SEQ ID NO: 69; GTTGTCAAAGCTGAGCCTTCTAT, SEQ ID NO: 70), UVRAG (ATGCCAGACCGTCTTGATACA, SEQ ID NO: 71; TGACCCAAGTATTTCAGCCCA, SEQ ID NO: 72), PIK3C3 (GAACAACGGTTTCGCTCTTTG, SEQ ID NO: 73; GCTTCTACATTAGGCCAGACTTT, SEQ ID NO: 74), Tk (ACCCGCTTAACAGCGTCAACA, SEQ ID NO: 75; CCAAAGAGGTGCGGGAGTTT, SEQ ID NO: 76), VV rpo35 early (GCCAATGAGGGTTCGAGTTC, SEQ ID NO: 77; AACAACATCCCGTCGTTCATC, SEQ ID NO: 78), CVB3 (ACGAATCCCAGTGTGTTTTGG, SEQ ID NO: 79; TGCTCAAAAACGGTATGGACAT, SEQ ID NO: 80), and ISG56 (CAACCAAGCAAATGTGAGGA, SEQ ID NO: 81; GGAGACTTGCCTGGTGAAAA, SEQ ID NO: 82).

Autophagy and toll-like receptor qPCR arrays (SABiosciences) were performed with 1 μg RNA per 96 well plate and subjected to RT-qPCR using SYBR/ROX $RT^2$ qPCR 2× master mix (SABiosciences) according to manufacturer's protocol. Gene expression was defined from the threshold cycle (Ct), and relative expression levels were calculated using SABiosciences $RT^2$ Profiler PCR array analysis automated software.

RNA library construction and miRNA sequencing was performed by Ocean Ridge Biosciences (Palm Beach Gardens, Fla.) using extracted RNA. The small RNA libraries were aligned to the NCBI-37 human reference genome using Bowtie, then intersected with the mature miRNA sequenced annotated by miRBase (v.18) using BEDtools. The miRNA counts in each library were normalized using established algorithms (Anders and Huber, *Genome Biol.* 11:R106, 2010). The C19MC miRNAs and the non-C19MC miRNAs in the six libraries were Laplace smoothed by adding 1 to the normalized counts, log 2 transformed, and clustered respectively by the agglomerative hierarchical clustering, using the complete linkage method. Heat maps were then generated separately for the clustered C19MC miRNAs and non-C19MC miRNAs.

To quantify the differences in miRNA expression between U2OS cells that were exposed to PHT conditioned medium vs. cells that were exposed to fresh medium, the differential expression test was applied, which assumes that the in all libraries were follow negative binomial distributions (Anders and Huber, *Genome Biol.* 11:R106, 2010), and a shrinkage estimator was used for the dispersion parameters of the miRNAs. The p-values of the tests were adjusted using the Benjamini and Hochberg's method (Hochberg and Benjamini, *J. Roy. Statist. Soc. B.* 57:289-300, 1995) to control for false discovery rate. Statistical analyses were performed using statistical computing software R and the DESeq package of R.

Pharmacological Agents

Cells were pre-treated with 3-methyladenine (3-MA; 5 mM, Sigma) for 30-60 min prior to infection, and cells were incubated with drug throughout the duration of infection. For mRFP-LC3B punctae assays, 3-MA was added for 30 min prior to conditioned or non-conditioned media exposure, and was present throughout. Rapamycin (5 μM, Calbiochem) treatment or serum-starvation with Hank's Balanced salt solution (HBSS) for 4 h was used as a positive control for autophagy.

Immunofluorescence and Confocal Microscopy

Cell monolayers were cultured in 8-well chamber slides (LabTek) at 37° C. Cells were then washed and fixed as indicated with either ice cold methanol, 3:1 methanol-acetone, or 4% paraformaldehyde in PBS and permeabilized with 0.25% Triton X-100 in PBS. Mouse anti-VSV-G and mouse anti-hCMV gB were obtained from Santa Cruz Biotechnology, and mouse anti-enterovirus VP1 (NCL-Entero) was purchased from Novacastra Laboratories. Mouse-anti clathrin heavy chain (CHC) and mouse anti-caveolin 1 (Cav1) antibodies were obtained from BD Transduction Laboratories. Rabbit anti-Dynamin II (DynII) was purchased from Abcam. Fixed monolayers were incubated with primary antibody, washed, incubated with Alexa Fluor-488 or -594-conjugated secondary antibodies (Invitrogen), washed, and then mounted with Vectashield (Vector Laboratories) containing 4',6-diamidino-2-phenylindole (DAPI). Cholera toxin B (CTB) conjugated to Alexa Fluor 488 (8 μg/mL; Invitrogen) and transferrin conjugated to Alexa Fluor 594 (Invitrogen) uptake was performed essentially as previously described (Patel et al., *J Virol* 83, 11064-11077, 2009).

Images were captured with an IX81 inverted microscope equipped with a motorized stage or with an Olympus Fluoview 1000 laser scanning confocal microscope. Images of infected cells were taken using an Olympus PlanApo 10×/0.40 NA dry or Apo 20×/0.75 NA dry objective, whereas all other images were taken with an Olympus PlanApo 60×/1.42 NA oil objective.

For virus infection assays, cells were fixed and stained for markers of virus infection (CVB and PV (VP1), VSV (VSV-G), hCMV (gB)) or assessed for GFP-expression (VV-GFP, HSV-1-GFP, VV-YFP). A minimum of three independent fields per condition were counted (at least 600 cells total). Infection levels are reported as the percentage of virus positive cells among the total number of cells, determined by DAPI staining. Quantification of percent virus positive cells was performed using ImageJ (National Institutes of Health) analysis. For LC3B autophagy assays, at least twenty individual cells from a minimum of four independent fields were captured per condition. The total number of mRFP-LC3B-positive punctae were quantified per cell using ImageJ analysis with identical settings per condition. Analysis of the extent of VSV and mRFP-LC3b punctate co-localization was performed using ImageJ.

Electron Microscopy

Cells were washed, fixed with 2.5% gluteraldehyde in PBS for 1 h, then processed for electron microscopy as previously described (Gao et al., *J Biol Chem* 285, 1371-1383, 2010). Sections were imaged using a JEOL JEM 1011 transmission electron microscope (Peabody) using an 80 V fitted with a bottom mount AMT 2k digital camera (Advanced Microscopy Techniques). At least five to ten individual cells were captured per condition. The number of autophagosomes (including amphisomes, autophagosomes, autophagic vacuoles, and autolysosomes) were quantified per cell manually.

Immunoblots

Cells were grown in 6-well plates and lysates were prepared with RIPA buffer (50 mM Tris-HCl [pH 7.4]; 1% NP-40; 0.25% sodium deoxycholate; 150 mM NaCl; 1 mM EDTA; 1 mM phenylmethanesulfonyl fluoride; 1 mg/ml aprotinin, leupeptin, and pepstatin; 1 mM sodium orthovanadate), and insoluble material was precipitated by brief centrifugation. Protein concentration of lysates was determined by BCA protein assay (Thermo Scientific). Lysates containing equal amounts of protein were loaded onto 4-20% Tris-HCl gels (Bio-Rad) and transferred to polyvinylidene difluoride membranes. Membranes were blocked in 5% nonfat dry milk, probed with the indicated antibodies, and developed with horseradish peroxidase-conjugated secondary antibodies (Santa Cruz Biotechnology), and SuperSignal West Pico or Dura, chemiluminescent substrates (Pierce Biotechnology).

For beclin-1 immunoblotting, cells were lysed on ice in a 50 mM Tris-HCl, pH 7.5 buffer that contained 150 mM NaCl and 0.5% NP-40. After centrifugation at 12,000×g at 4° C., the supernatant was subjected to 10% SDS-PAGE, transferred to PVDF membrane, and signal detected using monoclonal antibodies as indicated. Densitometry was performed using Image J.

Reporter Gene Assay

Activation of interferon β (IFNβ) or interferon-stimulated response element (ISRE) promoters was measured by reporter assay. Cells were transfected with 1 μg of DNA/well of a 24 well plate, a 30:1 ratio of IFNβ or ISRE firefly luciferase reporter plasmids to pRL-null (Renilla control) as per manufacturer's protocol. Cells were lysed in 100 μL of lysis buffer and the levels of firefly and Renilla luciferase levels quantified using the Dual-Luciferase Reporter Assay System (Promega) with a dual injector equipped Synergy 2 SL Luminescence Microplate Reader (BioTek). Levels of firefly luciferase were normalized to control Renilla luciferase levels. For poly(I:C) treatment, cells were transfected with 1 μg poly(I:C)/well using XtremeGene-9 for 16 h as per the manufacturer's protocol.

Statistical Analysis

All experiments were performed at least three times, as indicated in the figure legends. Data are presented as mean±standard deviation. Except where specified, Student's t test was used to determine statistical significance for virus infection and autophagy assays when 2 sets were compared, and one-way analysis of variance (ANOVA) with Bonferroni's correction for multiple comparisons were used to determine statistical significance for reporter gene assays. A $p<0.05$ was determined significant.

Virus Entry Assays

Virus entry assays in PHT cells were performed with CVB and PV as previously described (Coyne and Bergelson, *Cell* 124, 119-131, 2006; Coyne et al., *EMBO J* 26, 4016-4028, 2007). VV and HSV-1 internalization assays were performed by incubating PHT cells with virus (MOI 25) at 37° C. until fixation at various time points (30, 60, 90 min). VSV entry assays in U2OS cells exposed to either non-conditioned or conditioned PHT medium for 24 h was performed by incubating cells with virus (MOI=500) for 1 h at 37° C. until fixation in 4% PFA followed by permeabilization in 0.1% Triton X-100. VSV particles were visualized with anti-VSV-G antibody.

Modified TCID50 Virus Titering Assays

Vero or PHT cells were seeded to confluence in 96 well plates. Cells were incubated with serial dilutions of the indicated viruses for approximately 40-45 h, then stained with 0.05% crystal violet (in 10% ethanol). For experiments performed with conditioned medium, Vero cells were incubated in non-conditioned or conditioned medium 24 h prior to incubation with virus. Serial dilutions of virus were made in either non-conditioned or conditioned medium, and cells were incubated and developed with crystal violet as described above.

Neutralizing Virus Plaque Assays

VSV virus stock was diluted 1:20 in either non-conditioned or conditioned PHT medium, then incubated at 37° C. for 1 h. Plaques assays were performed on Vero cells. Plaques were visualized after 36 h by staining with crystal violet.

Example 2: Human Placental Trophoblasts Confer Viral Resistance to Recipient Cells by the Release of miRNAs and the Induction of Autophagy This example describes the finding that PHTs are highly resistant to infection by a number of different types of viruses. This resistance is mediated by exosomes containing miRNAs encoded by the primate-specific chromosome 19 miRNA cluster (C19MC).

PHT-Derived Exosomes Protect Recipient Cells from Viral Infection

Figure 1D:
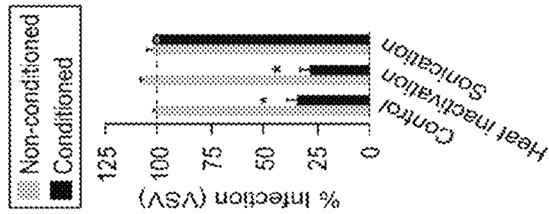
Figure 1C:
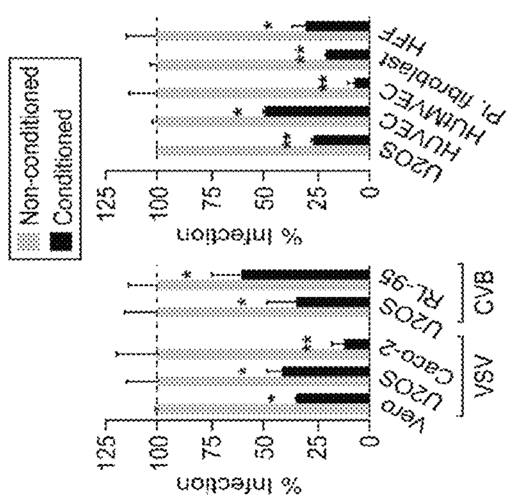
Figure 1B:
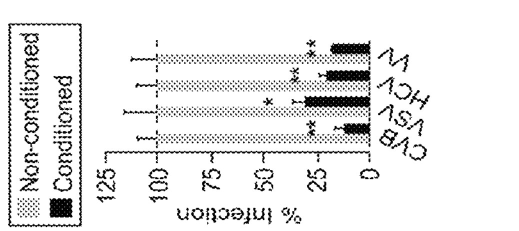
Figure 1A:
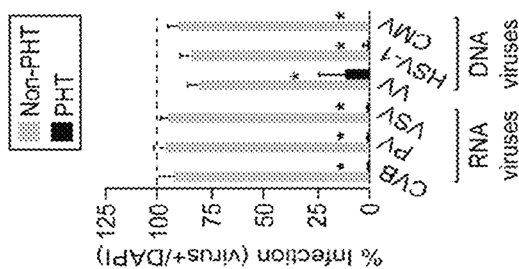
Figure 6A:
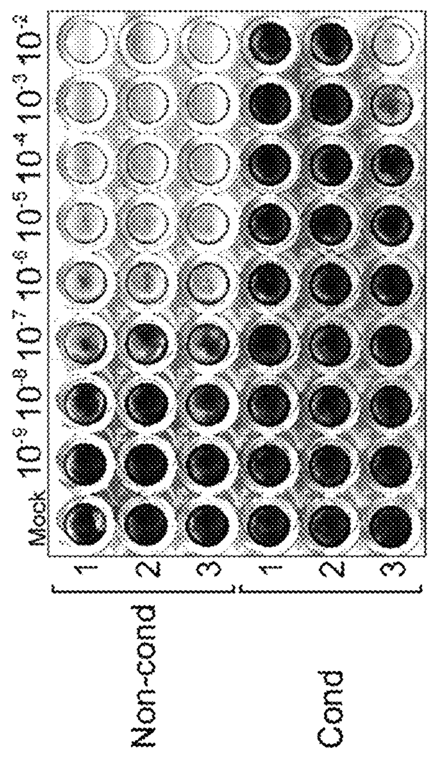
Figure 6B:
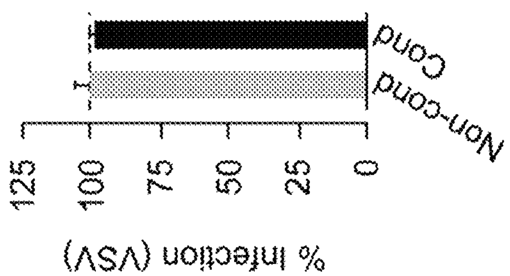
Figure 6C:
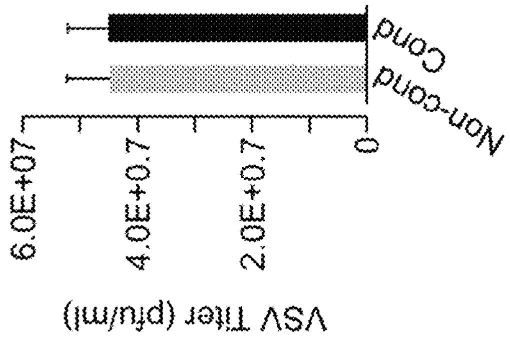
Figure 6E:
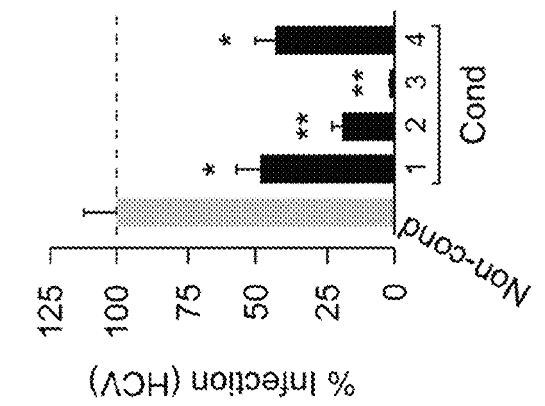
Figure 6D:
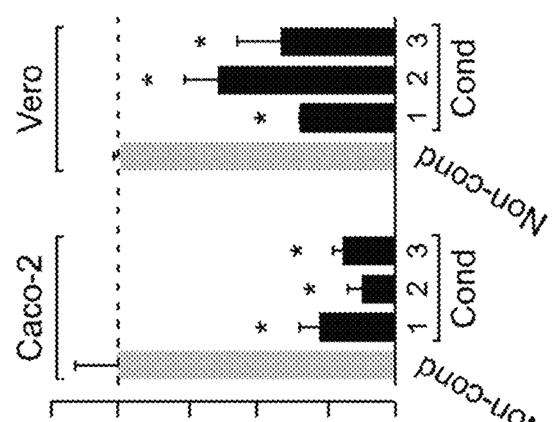
Figure 6D:
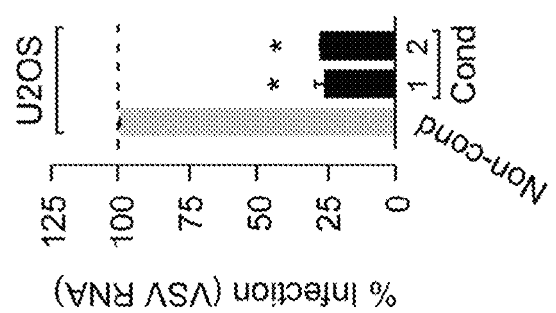

The studies described herein determined that PHT cells were resistant to infection by a panel of viruses, including coxsackievirus B3 (CVB), poliovirus (PV), vesicular stomatitis virus (VSV), vaccinia virus (VV), herpes simplex virus-1 (HSV-1), and human cytomegalovirus (CMV), when compared to non-PHT cells (FIG. 1A). This lack of viral replication was not due to inefficient viral binding and/or entry, or to defects in common endocytic pathways utilized by viruses for their entry, such as clathrin- or caveolar-mediated pathways. It was found that exposure of diverse non-PHT recipient cells for 24 h prior to infection to PHT conditioned medium (isolated from naïve PHT cells 48-72 h post-plating) decreased the replication of CVB, VSV, hepatitis C virus (HCV), and VV (FIG. 6A). The antiviral effect of conditioned PHT medium was also observed in several physiologically relevant fetal and/or maternal primary cells, including human umbilical vein endothelial cells (HUVEC), human uterine microvascular endothelial cells, human placental fibroblasts, and human foreskin fibroblasts (HFF; FIG. 1C, right panel). In contrast, conditioned medium from other cell types, such as immortalized trophoblast BeWo cells, had no effect (FIG. 6B). This effect was not the result of direct neutralization of the virus as conditioned medium had no direct effect on viral titers (FIG. 6C). Furthermore, antiviral effects were observed across multiple conditioned medium samples isolated from independent and unrelated PHT preparations (FIGS. 6D-6F). Together, these data indicate that PHT cells release specific components to the medium, which are capable of conferring viral resistance to non-placental recipient cells.

To better define the component in conditioned medium of PHT cells that is responsible for conferring viral resistance, the conditioned medium was exposed to heat inactivation or RNAse treatment; however, no effect was observed (FIG. 1D). In contrast, repeated freeze-thawing partly attenuated the effect, and sonication completely abolished the antiviral effect of PHT conditioned medium (FIG. 1D). Because exosomes, which function as "cargo nanovesicles" (Valadi et al., *Nat. Cell. Biol.* 9:654-659, 2007; Skog et al., *Nat. Cell. Biol.* 10:1470-1476, 2008), are characteristically released from trophoblasts and are sensitive to sonication (Donker et al., *Mol. Hum. Reprod.* 18(8):417-424, 2012; Taylor et al., *J. Immunol.* 176:1534-1542, 2006; Montecalvo et al., *J. Immunol.* 180:3081-3090, 2008; Luo et al., *Biol. Reprod.* 81:717-729, 2009; Pegtel et al., *Proc. Natl. Acad. Sci. U.S.A.* 107:6328-6333, 2010), their role in PHT-mediated transfer of viral resistance was examined. It was found that exosomes purified from PHT conditioned medium attenuated VSV infection in recipient cells (FIG. 1E). The antiviral effect was abrogated using exosome-depleted PHT conditioned medium (FIG. 1E). In addition, exosomes isolated from other cell types, such as an immortalized human placental choriocarcinoma cell line (JEG-3) or primary murine dendritic cells, had no effect on viral infection (FIG. 1E). Taken together, these data point to a direct role for PHT-derived exosomes in the transfer of viral resistance to non-placental recipient cells.

C19MC-Associated miRNAs Confer Viral Resistance

The transfer of RNA and/or miRNAs via exosomes may play an important role in exosome-based intercellular communication (Valadi et al., *Nat. Cell. Biol.* 9:654-659, 2007; Pegtel et al., *Proc. Natl. Acad. Sci. U.S.A.* 107:6328-6333, 2010; Zhang et al., *Mol. Cell.* 39:133-144, 2010). The human C19MC is the largest known miRNA cluster, comprising 46 miRNAs that are highly expressed almost exclusively in the human placenta. Moreover, as a group, C19MC miRNAs are also the most abundant miRNA species in trophoblastic exosomes, with a strong correlation between C19MC miRNA levels in PHT cells and in PHT-derived exosomes (Noguer-Dance et al., *Hum. Mol. Genet.* 19:3566-3582, 2010; Donker et al., *Mol. Hum. Reprod.* 18(8):417-424, 2012; Taylor et al., *J. Immunol.* 176:1534-1542, 2006;

Mouillet et al., *Placenta.* 31:781-784, 2010). To date, the function of these miRNAs has remained elusive. To test whether the expression of C19MC miRNAs could induce viral resistance in non-PHT cells, which do not naturally express these miRNAs, U2OS cells were stably transfected with a BAC that contained the entire human C19MC cluster. When compared to U2OS cells transfected with a control BAC (that is deficient for the C19MC expression sequence), cells stably expressing C19MC-BAC or cells exposed to PHT conditioned media expressed a higher level of C19MC miRNAs, as confirmed by RNAseq (Table 3), and exhibited resistance to VSV infection (FIG. 2A). Likewise, transient transfection of U2OS cells with miRNA mimics of 16 C19MC-associated miRNAs (representing highly expressed miRNAs, or the two subfamilies of the C19MC; Lin et al., *Comput. Biol. Chem.* 34:232-241, 2010) markedly reduced VSV infection (FIG. 2B and Table 2). It was also found that transfection of mimics of the six highest expressed C19MCs (Donker et al., *Mol. Hum. Reprod.* 18(8):417-424, 2012; Taylor et al., *J. Immunol.* 176:1534-1542, 2006; Mouillet et al., *Placenta.* 31:781-784, 2010) attenuated VSV infection, whereas transfection with mimics of the lowest expressed seven had no significant effect (FIG. 2B). To define the impact of individual miRNAs, individual mimics from among the highest expressed C19MC miRNAs were expressed, and a significant inhibition of VSV infection was detected with mimics of miR-517-3p, -516b-5p, and -512-3p, but not with mimics of several non-C19MC-associated miRNAs (miR-1, -424, -630, and -720; FIGS. 2C-2D) Likewise, a mimic of miR-517-3p also attenuated infection by the DNA viruses VV and HSV-1 (FIG. 2E).

TABLE 2

Groups of mimics to C19MC miRNAs used in the described experiments. The 16 miRNAs are listed in order of expression level (highest to lowest)

| 16 C19MC miRNAs | Subgroup 1 9 C19MC miRNAs | Subgroup 2 7 C19MC miRNAs | 6 highest expressed C19MC miRNAs | 7 lowest expressed C19MC miRNAs |
|---|---|---|---|---|
| miR-517-3p | miR-517-3p | | miR-517-3p | |
| miR-1323 | | miR-1323 | miR-1323 | |
| miR-516b-5p | | miR-516b-5p | miR-516b-5p | |
| miR-525-5p | | miR-525-5p | miR-525-5p | |
| miR-512-3p | | miR-512-3p | miR-512-3p | |
| miR-515-3p | miR-515-3p | | miR-515-3p | |
| miR-518e | miR-518e | | | |
| miR-515-5p | | miR-515-5p | | |
| miR-517c | miR-517c | | | |
| miR-519c-3p | miR-519c-3p | | | miR-519c-3p |
| miR-520h | miR-520h | | | miR-520h |
| miR-519d | miR-519d | | | miR-519d |
| miR-518b | miR-518b | | | miR-518b |
| miR-512-5p | | miR-512-5p | | miR-512-5p |
| miR-520c-3p | miR-520c-3p | | | miR-520c-3p |
| miR-518a-5p | | miR-518a-5p | | miR-518a-5p |

TABLE 3

Differences in miRNA expression between U2OS cells exposed to conditioned or non-conditioned medium, analyzed by RNAseq*

| C19MC miRNA | Conditioned medium | Non-conditioned medium | Fold change (CM/FM) | Log2 fold change | p value | p adjusted (BH) |
|---|---|---|---|---|---|---|
| miR-517-3p | 2374.403 | 765.215 | 3.103 | 1.634 | 2.66E−32 | 4.68E−30 |
| miR-519a-3p | 1738.835 | 1144.108 | 1.520 | 0.604 | 9.81E−07 | 4.60E−05 |
| miR-522-3p | 1662.638 | 1245.641 | 1.335 | 0.417 | 0.001083036 | 0.021856025 |
| miR-1323 | 1454.781 | 459.377 | 3.167 | 1.663 | 8.06E−35 | 3.31E−32 |
| miR-516a-5p | 1093.955 | 635.203 | 1.722 | 0.784 | 7.75E−09 | 4.34E−07 |
| miR-521 | 631.942 | 494.047 | 1.279 | 0.355 | 0.014010033 | 0.215579384 |
| miR-1283 | 565.757 | 341.747 | 1.655 | 0.727 | 4.06E−06 | 0.000166442 |
| miR-516b-5p | 424.862 | 188.208 | 2.257 | 1.175 | 1.08E−13 | 9.49E−12 |
| miR-512-3p | 337.442 | 44.576 | 7.570 | 2.920 | 3.44E−38 | 2.48E−35 |
| miR-524-5p | 269.386 | 37.146 | 7.252 | 2.858 | 2.06E−33 | 6.34E−31 |
| miR-515-3p | 249.009 | 17.335 | 14.365 | 3.844 | 4.03E−38 | 2.48E−35 |
| miR-517c-3p | 228.786 | 116.392 | 1.966 | 0.975 | 2.02E−07 | 1.03E−05 |
| miR-525-5p | 216.140 | 26.002 | 8.312 | 3.055 | 2.73E−30 | 4.20E−28 |
| miR-520d-3p | 200.409 | 21.050 | 9.521 | 3.251 | 4.39E−30 | 6.01E−28 |
| miR-520a-3p | 141.669 | 35.908 | 3.945 | 1.980 | 2.43E−14 | 2.50E−12 |
| miR-518e-3p | 122.653 | 16.097 | 7.620 | 2.930 | 4.67E−19 | 5.75E−17 |
| miR-519d | 113.300 | 38.385 | 2.952 | 1.562 | 4.05E−09 | 2.37E−07 |
| miR-518b | 105.055 | 58.196 | 1.805 | 0.852 | 0.000622055 | 0.013434194 |
| miR-518c-3p | 76.726 | 32.194 | 2.383 | 1.253 | 2.34E−05 | 0.000823018 |
| miR-518a-5p | 70.166 | 34.670 | 2.024 | 1.017 | 0.002164332 | 0.040989113 |
| miR-520g | 65.535 | 61.911 | 1.059 | 0.082 | 0.848007306 | 1 |
| miR-518e-5p | 65.366 | 26.002 | 2.514 | 1.330 | 5.44E−05 | 0.001594773 |
| miR-519a-5p | 65.366 | 26.002 | 2.514 | 1.330 | 5.44E−05 | 0.001594773 |
| miR-519b-5p | 65.366 | 26.002 | 2.514 | 1.330 | 5.44E−05 | 0.001594773 |
| miR-519c-5p | 65.366 | 26.002 | 2.514 | 1.330 | 5.44E−05 | 0.001594773 |
| miR-522-5p | 65.366 | 26.002 | 2.514 | 1.330 | 5.44E−05 | 0.001594773 |
| miR-523-5p | 65.366 | 26.002 | 2.514 | 1.330 | 5.44E−05 | 0.001594773 |
| miR-524-3p | 57.113 | 2.476 | 23.063 | 4.527 | 1.85E−13 | 1.42E−11 |
| miR-520h | 54.554 | 34.670 | 1.574 | 0.654 | 0.048469819 | 0.547397683 |
| miR-526b-5p | 48.663 | 28.479 | 1.709 | 0.773 | 0.020670659 | 0.277189278 |
| miR-515-5p | 43.639 | 34.670 | 1.259 | 0.332 | 0.311332029 | 1 |
| miR-498 | 38.128 | 17.335 | 2.199 | 1.137 | 0.003592299 | 0.06503118 |
| miR-527 | 34.719 | 17.335 | 2.003 | 1.002 | 0.032552612 | 0.396755106 |
| miR-526a | 33.466 | 8.667 | 3.861 | 1.949 | 0.000139813 | 0.00374151 |
| miR-519c-3p | 32.153 | 4.953 | 6.492 | 2.699 | 3.16E−06 | 0.000138861 |
| miR-520a-5p | 26.509 | 11.144 | 2.379 | 1.250 | 0.014724591 | 0.223777425 |
| miR-518f-5p | 25.322 | 4.953 | 5.113 | 2.354 | 0.000166051 | 0.004258507 |

TABLE 3-continued

Differences in miRNA expression between U2OS cells exposed to conditioned or non-conditioned medium, analyzed by RNAseq*

| C19MC miRNA | Conditioned medium | Non-conditioned medium | Fold change (CM/FM) | Log2 fold change | p value | p adjusted (BH) |
|---|---|---|---|---|---|---|
| miR-520d-5p | 24.485 | 3.715 | 6.591 | 2.721 | 4.17E−05 | 0.001426038 |
| miR-518a-3p | 24.118 | 17.335 | 1.391 | 0.476 | 0.300976907 | 1 |
| miR-525-3p | 20.871 | 14.859 | 1.405 | 0.490 | 0.270466957 | 1 |
| miR-519e-5p | 17.257 | 4.953 | 3.484 | 1.801 | 0.008673863 | 0.14013828 |
| miR-518d-5p | 16.733 | 3.715 | 4.505 | 2.171 | 0.005073798 | 0.086747848 |
| miR-520c-5p | 16.733 | 3.715 | 4.505 | 2.171 | 0.005073798 | 0.086747848 |
| miR-518c-5p | 14.673 | 7.429 | 1.975 | 0.982 | 0.150512908 | 1 |
| miR-523-3p | 14.119 | 3.715 | 3.801 | 1.926 | 0.016108611 | 0.241825612 |
| miR-518d-3p | 11.457 | 1.238 | 9.252 | 3.210 | 0.006515171 | 0.108380746 |
| miR-517-5p | 9.017 | 1.238 | 7.282 | 2.864 | 0.018394499 | 0.263298001 |
| miR-512-5p | 8.716 | 8.667 | 1.006 | 0.008 | 1 | 1 |
| miR-518f-3p | 7.288 | 2.476 | 2.943 | 1.557 | 0.215985658 | 1 |
| miR-519b-3p | 7.132 | 4.953 | 1.440 | 0.526 | 0.60445537 | 1 |
| miR-526b-3p | 6.258 | 1.238 | 5.054 | 2.338 | 0.13991013 | 1 |
| miR-520e | 2.789 | 3.715 | 0.751 | −0.414 | 0.91188741 | 1 |
| miR-519e-3p | 1.506 | 0.000 | Inf | Inf | 0.579448235 | 1 |
| miR-520b | 1.458 | 1.238 | 1.177 | 0.235 | 1 | 1 |
| miR-520c-3p | 1.157 | 0.000 | Inf | Inf | 0.94380054 | 1 |
| miR-520f | 0.428 | 0.000 | Inf | Inf | 1 | 1 |
| miR-516a-3p | 0.000 | 0.000 | NA | NA | NA | NA |
| miR-516b-3p | 0.000 | 0.000 | NA | NA | NA | NA |

*Counts were normalized by the median of ratio of the observed counts in each library to the geometric mean of the observed counts of all libraries, as described in Methods. Columns of conditioned and non-conditioned medium represent the mean of the normalized miRNAs counts in those samples.

PHT-Derived Exosomes and C19MC-Associated miRNAs Upregulate Autophagy

Figure 3B:
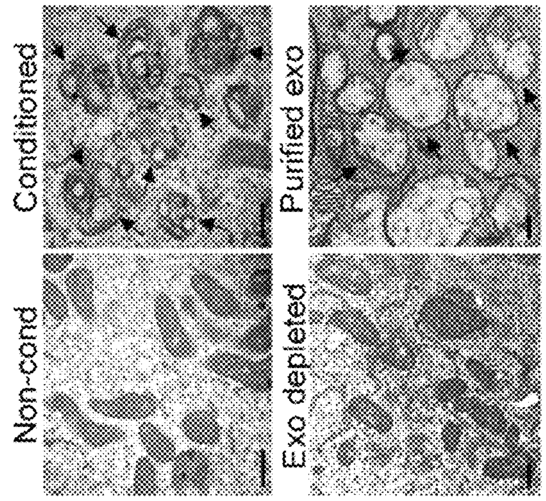
FIGS. 3A-3D: PHT-derived exosomes induce autophagy in recipient cells.
Figure 3B:
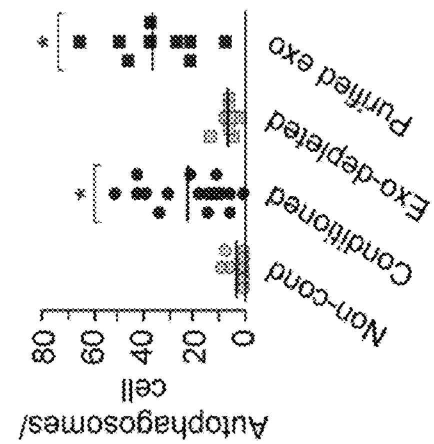
Figure 3A:
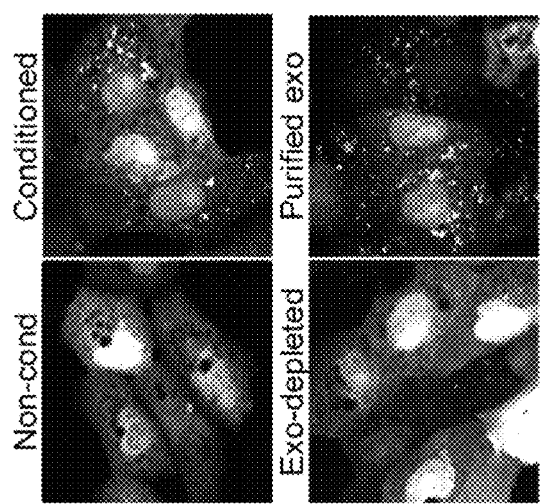
Figure 3A:
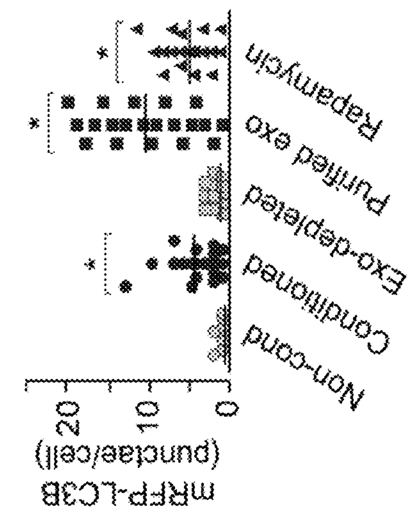
Figure 7B:
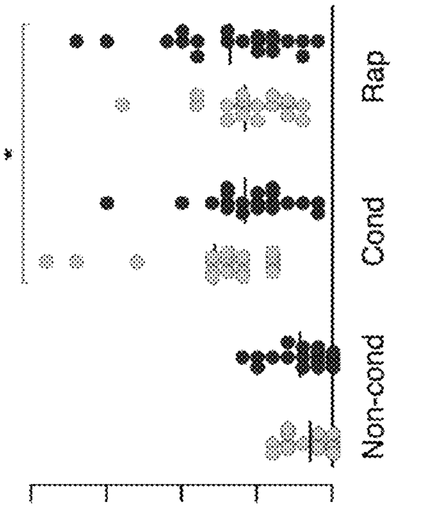
FIGS. 7A-7D: Medium from PHT cells induces autophagy in recipient cells.
Figure 7D:
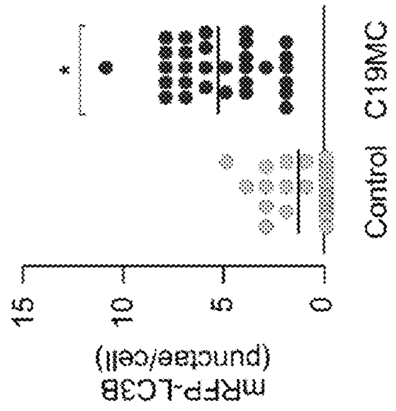
Figure 7A:
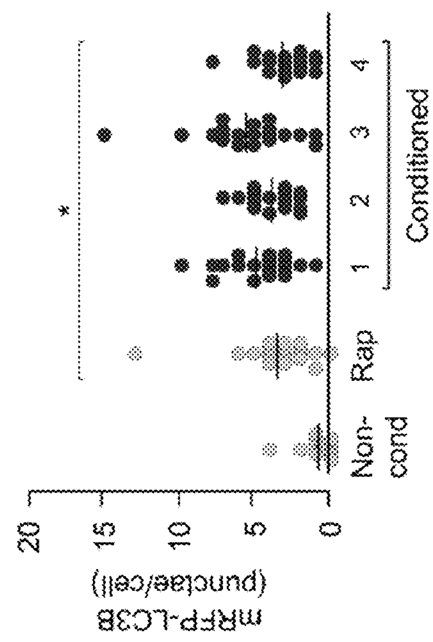

Mammalian cells utilize diverse defense mechanisms to combat microbial pathogens. One crucial mechanism is the induction of autophagy, an evolutionarily conserved lysosomal degradation pathway that has been associated with an array of cellular functions. Autophagy also degrades intracellular foreign microbial invaders (a process sometimes referred to as xenophagy) and thus serves as an important cellular response to suppress microbial infections. Exposure of U2OS cells to PHT conditioned medium or to purified PHT-derived exosomes markedly stimulated autophagy, as assessed by the formation of mRFP-LC3b-containing punctae and by electron microscopy, whereas conditioned-medium depleted of PHT-exosomes had no effect (FIGS. 3A-3B and FIG. 7A). In contrast, no effect of PHT conditioned medium or C19MC-miRNAs on type I interferon (IFN) signaling was observed in recipient cells, and antiviral activity of conditioned PHT medium was observed in cells that fail to respond to type I IFNs. In addition, PHT cells themselves also do not exhibit enhanced type I IFN signaling.

Figure 3C:
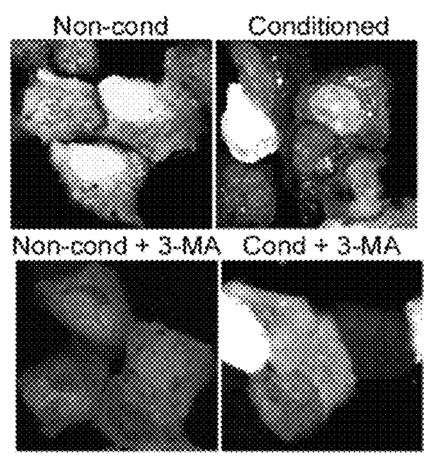
Figure 3C:
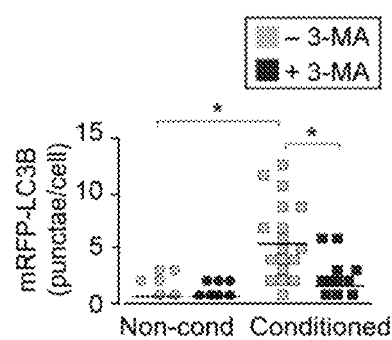
Figure 3D:
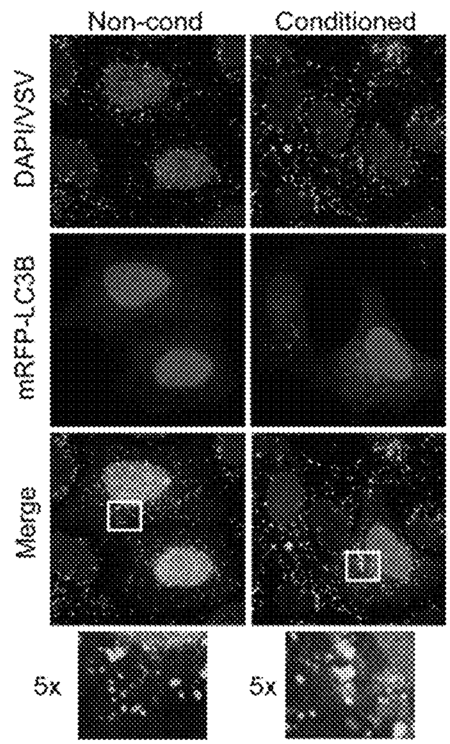
Figure 3D:
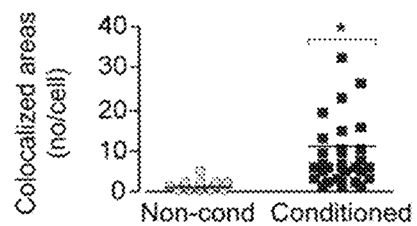
Figure 7C:
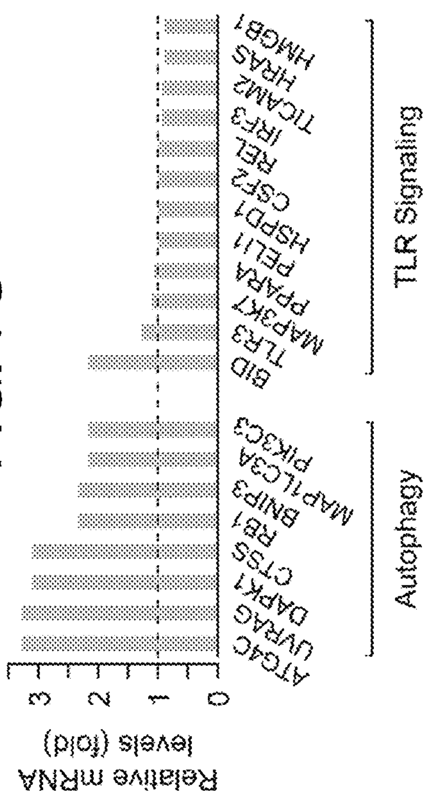

Autophagy induction was observed in diverse cell types (FIGS. 3A-3B and FIG. 7B), and was absent in cells exposed to exosome-depleted PHT conditioned medium (FIGS. 3A-3B). In addition, PHT conditioned medium induced the upregulation (>3-fold) of several key pro-autophagy transcripts (e.g., ATG4C, UVRAG, and LC3A) while having no effect on other innate immune pathway components (e.g. toll-like receptors, interferon regulatory factors, cytokine-mediated signaling) in U2OS cells exposed to conditioned PHT medium (FIG. 7C and Table 4), further supporting the induction of autophagy. 3-methyladenine (3-MA), an inhibitor of autophagosome biogenesis, inhibited autophagosome formation in recipient cells exposed to conditioned PHT medium (FIG. 3C). Lastly, incoming VSV particles were trafficked to LC3b-positive punctae formed following exposure of cells to conditioned PHT medium, suggesting that the mislocalization or targeting of incoming viral particles to autophagosomes and/or autolysosome might impact viral replication (FIG. 3D).

TABLE 4

Summary of expression changes in autophagy-related transcripts

| Gene | Fold-change | Gene | Fold-change |
|---|---|---|---|
| ATG4C | 3.2861 | MAP1LC3B | 1.2209 |
| UVRAG | 3.2696 | CHUK | 1.2054 |
| CCL2 | 3.1764 | HSPA1A | 1.1822 |
| DAPK1 | 3.119 | ATG12 | 1.1791 |
| CTSS | 3.1154 | RIPK2 | 1.1446 |
| EIF2AK2 | 2.5184 | ATG16L1 | 1.1417 |
| RB1 | 2.3295 | PTGS2 | 1.1354 |
| BNIP3 | 2.3171 | TOLLIP | 1.124 |
| MAP1LC3A | 2.1561 | EIF2AK3 | 1.1192 |
| PIK3C3 | 2.1554 | IL8 | 1.1002 |
| BID | 2.149 | UBE2N | 1.0968 |
| AMBRA1 | 1.9193 | MAP3K7 | 1.0954 |
| ARSA | 1.849 | TLR4 | 1.0872 |
| BCL2L1 | 1.7855 | APP | 1.0846 |
| PRKRA | 1.7526 | PPARA | 1.0624 |
| ATG4D | 1.7454 | PELI1 | 1.0265 |
| SQSTM1 | 1.7187 | PRKAA2 | 1.0185 |
| NFKBIA | 1.6335 | FAS | 1.0149 |
| ATG4A | 1.6288 | BECN1 | 1.0139 |
| LY96 | 1.4979 | HSP90AA1 | 1.0107 |
| NFKB1 | 1.45885 | HSPD1 | 0.9957 |
| TBK1 | 1.3469 | CSF2 | 0.9879 |
| TP53 | 1.3446 | HGS | 0.9745 |
| MAP3K1 | 1.3294 | REL | 0.9743 |
| DRAM1 | 1.3204 | CXCR4 | 0.9529 |
| ATG3 | 1.289 | MAPK14 | 0.9497 |
| AKT1 | 1.2812 | IRF3 | 0.9437 |
| TLR3 | 1.2655 | TICAM2 | 0.9347 |
| ATG16L2 | 1.2457 | ATG4B | 0.9261 |
| TGFB1 | 1.2354 | ATG5 | 0.9159 |
| ULK2 | 1.2352 | HRAS | 0.9159 |
| SNCA | 1.2286 | CTSB | 0.9132 |
| HMGB1 | 0.9027 | ATG10 | 0.724 |
| TNFRSF1A | 0.901 | FADD | 0.7218 |
| ELK1 | 0.8971 | BAX | 0.7145 |

TABLE 4-continued

Summary of expression changes in autophagy-related transcripts

| Gene | Fold-change | Gene | Fold-change |
|---|---|---|---|
| IL1B | 0.8966 | PIK3R4 | 0.7073 |
| UBE2V1 | 0.8948 | MAP2K3 | 0.6992 |
| GABARAP | 0.8913 | HSPA8 | 0.6945 |
| IKBKB | 0.8859 | MAPK8 | 0.68385 |
| PTEN | 0.8814 | ATG7 | 0.6794 |
| EIF4G1 | 0.8792 | MAPK81P3 | 0.6767 |
| GABARAPL2 | 0.8772 | NFRKB | 0.6665 |
| MAP4K4 | 0.8748 | TAB1 | 0.6663 |
| CD180 | 0.8699 | ULK1 | 0.6621 |
| CLN3 | 0.8339 | TICAM1 | 0.6597 |
| PRKAA1 | 0.8324 | CDKN1B | 0.6285 |
| FAM176A | 0.8304 | TGM2 | 0.6192 |
| TRAF6 | 0.8257 | DRAM2 | 0.6166 |
| MAP2K4 | 0.8234 | RPS6KB1 | 0.6072 |
| NR2C2 | 0.8234 | RGS19 | 0.6005 |
| BCL2 | 0.8218 | NFKB2 | 0.5946 |
| HTT | 0.8135 | TMEM74 | 0.576 |
| TLR6 | 0.809 | ATG9A | 0.5758 |
| ECSIT | 0.804 | CASP8 | 0.57545 |
| BAD | 0.8011 | JUN | 0.5644 |
| BAK1 | 0.7987 | SARM1 | 0.5564 |
| MYD88 | 0.7962 | NFKBIL1 | 0.5528 |
| GAA | 0.7936 | IRAK1 | 0.5404 |
| IRF1 | 0.7825 | FOS | 0.5091 |
| CASP3 | 0.7749 | TP73 | 0.5061 |
| GABARAPL1 | 0.7581 | TNFSF10 | 0.4193 |
| HDAC1 | 0.7541 | IRGM | 0.2952 |
| RAB24 | 0.7351 | TNF | 0.2475 |
| RELA | 0.7325 | ATG9B | 0.2436 |
| | | IFNA4 | 0.1286 |

Figure 4A:
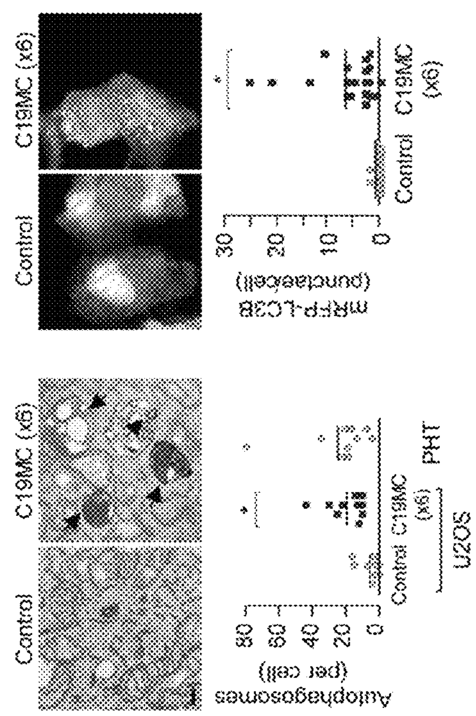
FIGS. 4A-4D: C19MC miRNAs induce autophagy.
Figure 4B:
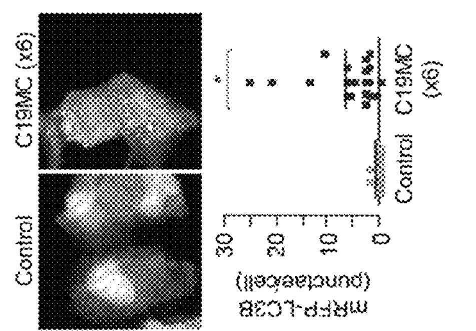
Figure 4C:
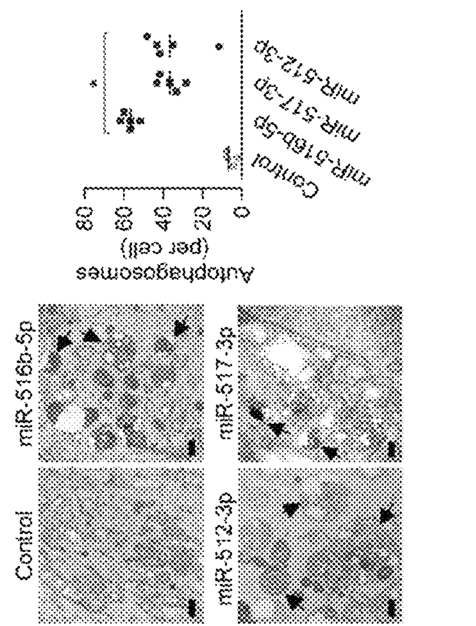
Figure 4D:
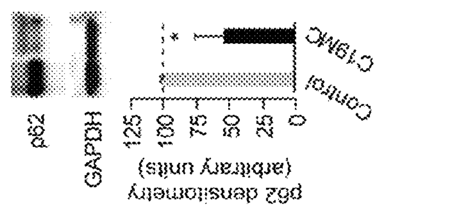

Because a role for C19MC-associated miRNAs was observed in the induction of viral resistance, it was assessed whether these miRNAs could induce autophagy. Transfection of cells with mimics of six of the highest expressed C19MC miRNAs (FIGS. 4A-4B), the entire C19MC (FIG. 7D) or mimics of individual C19MC miRNAs that attenuated viral infection (FIG. 4C), also stimulated autophagy, as observed by mRFP-LC3b punctate formation or by electron microscopy. Furthermore, C19MC-associated induction of autophagy occurred via the upregulation of autophagic flux, as supported by a decrease in p62 levels in cells expressing the entire C19MC (FIG. 4D).

The Antiviral Effects of C19MC-Associated miRNAs Require Autophagy

An inhibition of viral replication and a pronounced upregulation of autophagy was observed in cells exposed to PHT conditioned medium and in cells expressing C19MC-associated miRNAs. To determine if the antiviral effects of these conditions involved autophagy, autophagy was suppressed by treatment of cells with 3-MA or by RNA interference (RNAi)-mediated silencing of beclin-1, a key factor in autophagic induction (Liang et al., *Nature* 402:672-676, 1999). Inhibition of autophagy using 3-MA or by RNAi-mediated silencing of beclin-1 expression significantly restored the level of VSV infection in U2OS cells expressing the entire C19MC (FIGS. 5A-5B). Furthermore, addition of 3-MA to PHT cells enhanced VSV infection (FIG. 5C). These data show that the induction of autophagy is critical for the antiviral effect of C19MC miRNAs.

Discussion

The placenta shields the embryo from the spread of a number of diverse pathogens, including viruses. Disclosed herein is the striking finding that placental trophoblasts transfer viral resistance to non-placental cells. Viral resistance is transferrable via trophoblastic conditioned medium, trophoblastic exosomes, or miRNA members of the C19MC primate-specific cluster. It is shown that multiple members of the C19MC primate-specific miRNA cluster, which is localized to chromosome 19q13.41 and expressed by a specific RNA Pol-II primarily in the placenta (Noguer-Dance et al., *Hum Mol Genet* 19, 3566-3582, 2010; Bortolin-Cavaille et al., *Nucleic Acids Res* 37, 3464-3473, 2009; Bentwich et al., *Nat Genet* 37, 766-770, 2005), are packaged within exosomes, which are capable of carrying their nucleic acids and other types of cargo to neighboring or distal targets (Valadi et al., *Nat Cell Biol* 9, 654-659, 2007). Although the C19MC is the largest known human miRNA cluster, its function remains unknown. Specific members of the C19MC miRNA family are known to be up-regulated in cancers, such as aggressive primitive neuroectodermal brain tumors (miR-517c and miR-520g) (Li et al., *Cancer Cell* 16, 533-546, 2009), hepatocellular carcinoma (miR-519d) (Fornari et al., *J Pathol*, doi: 10.1002/path.3995, Jan. 19, 2012 [Epub]), breast cancer (miR-516-3p,miR-520c) (Foekens et al., *Proc Natl Acad Sci USA* 105, 13021-13026, 20081; Huang et al., *Nat Cell Biol* 10, 202-210, 2008), prostate cancer (miR-520c) (Yang et al., *Int J Clin Exp Pathol* 2, 361-369, 2009), and thyroid adenomas (Rippe et al., *PLoS One* 5, e9485, 2010). Thus, the data described herein are the first to suggest a unique role of C19MC miRNA members in an antiviral response that is transferable to either neighboring cells within the placenta such as villous fibroblasts, macrophages or fetal endothelial cells, and to maternal systemic cells, such as maternal endothelial or immune cells. Whereas the nature of recipient cells and the mechanisms of targeting remain unknown, exosome-mediated delivery of C19MC family members may constitute a powerful evolutionary adaptation by which a developing fetus is protected from viral invaders during pregnancy.

Primary human trophoblasts produce robust levels of miRNAs throughout pregnancy, as well as other small RNAs (piRNAs, snRNAs, and snoRNAs) (Mouillet et al., *Placenta.* 31:781-784, 2010; Luo et al., *Biol. Reprod.* 81:717-729, 2009; Mouillet et al., *Birth Defects Res. A. Clin. Mol. Teratol.* 91:737-743, 2011; Barad et al., *Genome. Res.* 14:2486-2494, 2004; Pineles et al. *Am. J. Obstet. Gynecol.* 196(3):e261-266, 2007). Many of these miRNAs, including members of the C19MC, are found in the maternal blood throughout pregnancy and rapidly decline in the first 24h postpartum (Ng et al., *Proc. Natl. Acad. Sci. U.S.A.* 100, 4748-4753, 2003; Gilad et al., *PLoS One.* 3:e3148, 2008), suggesting a miRNA-based mechanism for fetal-maternal communication (Mouillet et al., *Placenta.* 31:781-784, 2010; Chim et al., *Clin. Chem.* 54:482-490, 2008). The data disclosed herein thus provide evidence for a novel paracrine and/or systemic function of placental trophoblasts—utilizing exosome-mediated transport of a unique set of primate-specific effector miRNAs to directly communicate with maternal cells, and possibly neighboring placental cells, and regulate their immunity to viral infections. It is possible that PHT-derived, C19MC miRNA-containing exosomes specifically target their cargo to a discrete subpopulation of maternal cells, or may aid in the selectively eliciting antiviral responses and upregulating autophagy. Although placental-derived miRNAs are found in low levels in the fetal circulation, it is possible that these miRNAs are sufficient to regulate specific pathways in the developing fetus, such as the induction of autophagy, which is critical for neonatal survival (Kuma et al., *Nature.* 432:1032-1036, 2004).

The data disclosed herein show that conditioned media from PHT cells, purified PHT-derived exosomes, and miRNA mimics of several members of the C19MC family potently induce autophagy. Autophagy is an important component of host antimicrobial signaling and often functions to restrict viral replication. Although some of the viruses used in the disclosed study (such as CVB (Schlegel et al., *J Virol* 70, 6576-6588, 1996; Jackson et al., *PLoS Biol* 3, e156, 2005) and HCV (Dreux et al., *Proc Natl Acad Sci USA* 106, 14046-14051, 2009)) are thought to benefit from the formation of autophagic vesicles during their replication, these viruses were also sensitive to the antiviral effects of C19MC miRNAs. Unlike the induction of autophagy via an innate immune pathway in response to virus replication, recipient cells exposed to C19MC miRNAs exhibit robust levels of autophagy prior to their first exposure to viruses. Thus, preexisting C19MC-induced autophagosomes, which fuse with lysosomes to become autophagolysosomes, could profoundly impact the ability of incoming viral particles to properly traffic or release their genomes. It was found that PHT cells themselves also exhibit a high level of baseline autophagy which indicates that this mechanism plays a role in conferring viral resistance to these cells. Alternatively or in addition, autophagy may underlie other important functions of placental trophoblasts, such as those related to feto-placental nutrition or neonatal survival.

Recipient cells exposed to C19MC miRNAs exhibit robust levels of autophagy when first exposed to these viruses versus a typical setting in which autophagy would be an innate immune pathway that is upregulated in response to virus replication. Thus, C19MC miRNAs would greatly enhance the formation of autophagosomes, which fuse with lysosomes to become autophagolysosomes at a very early stage in the virus life cycle, which could have profound impacts on the ability of incoming viral particles to properly traffic and/or release their genomes. The high level of constitutive autophagy in primary human trophoblasts also implies that this mechanism confers viral resistance to these cells. Autophagy may underlie other important functions of placental trophoblasts, related to feto-placental nutrition primarily when resources are scarce. For example, autophagy is critically involved in neonatal survival during the period of starvation that occurs immediately post-birth, when the mother's milk supply has not yet been established (Kuma et al., *Nature* 432, 1032-1036, 2004).

Unlike the other viruses tested in the studies disclosed herein, conditioned PHT medium and expression of C19MC miRNAs significantly enhanced hCMV infection (FIGS. 6G-6H), indicating that while C19MC miRNAs attenuate the replication of many viruses, they may function in a proviral manner to enhance the infection of CMV, and possibly other viruses. The findings disclosed herein (FIG. 1A) and the work of others (Chan et al., *Am. J. Pathol.* 161:1371-1381, 2002) suggest that PHT cells are resistant to CMV infection, and studies of CMV-infected placentas suggest that CMV specifically targets invasive and endovascular cytotrophoblasts as a means of entry into the fetal compartment (Chan et al., *Am. J. Pathol.* 161:1371-1381, 2002; Maidji et al., *J. Virol.* 81:4701-4712, 2007; Maidji et al., *Virology* 304:53-69, 2002).

The studies disclosed herein are the first to define an unprecedented role for miRNA members of the C19MC in transferrable autophagy-mediated antiviral responses. The results show that placental-associated C19MC miRNAs are robust inducers of autophagy, a beneficial pathway in states of nutrient deprivation and a powerful suppresser of microbial infections. C19MC-derived placental miRNAs, released into the maternal circulation by exosomes, communicate an antiviral signal to maternal host cells, thus providing an unprecedented mechanism to protect the developing embryo.

Example 3: C19MC MicroRNAs Inhibits HIV Replication

This example demonstrates that PHT-conditioned media, as well as particular miRs encoded by the C19MC, also are capable of inhibiting infection by human immunodeficiency virus (HIV).

TZM-bl cells are HeLa cell derivatives that express high levels of CD4 and the HIV co-receptors CXCR4 and CCR5. These cells are stably transfected with LTR-driven firefly luciferase and LTR-driven β-galactosidase cassettes. Infection of TZM-bl cells with HIV-1 and HIV-2 isolates results in the induction of luciferase and β-galactosidase, allowing for the detection and quantification of infection.

Figure 9:
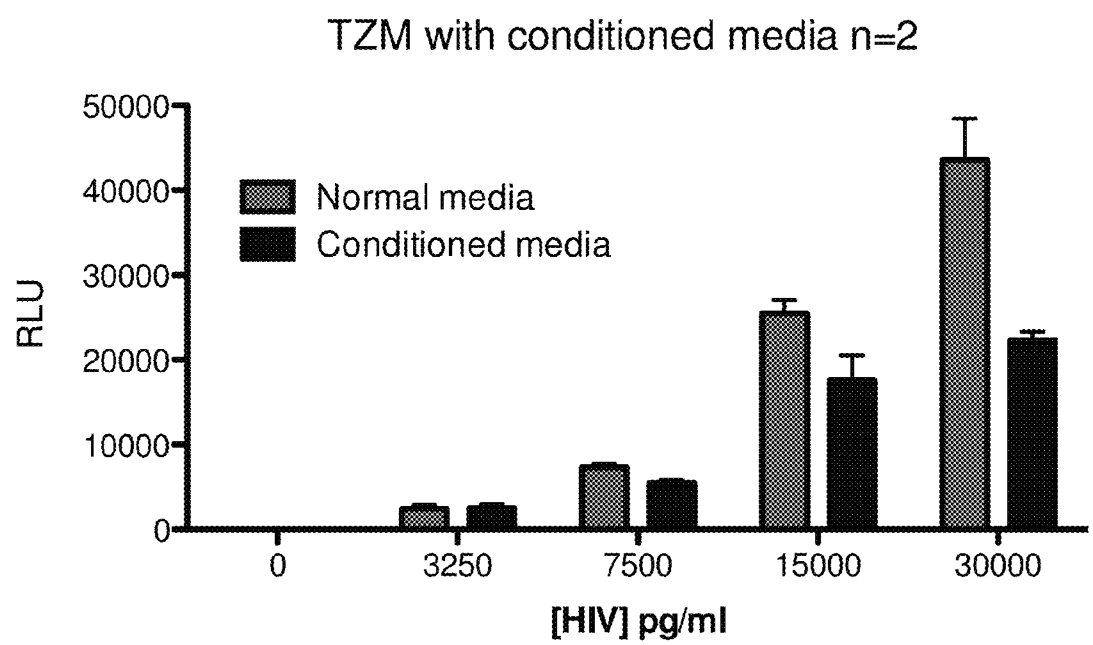
FIG. 9 is a graph showing inhibition of human immunodeficiency virus (HIV) replication by medium from PHT cells. TZM-bl cells were pre-incubated with PHT conditioned medium or control medium for 24 h prior to infection with HIV-1. Cells were then infected with serial dilutions of HIV for 48 h, and infection levels were assessed by Tat-induced luciferase reporter gene expression, in triplicate. The results represent two independent experiments.

TZM-bl cells were pre-incubated with PHT conditioned medium or control medium for 24 h prior to infection with HIV-1. Cells were then infected with serial dilutions of HIV (0, 3250, 7500, 15,000 and 30,000 pg/ml) for 48 h, and infection levels were assessed by Tat-induced luciferase reporter gene expression, in triplicate. As shown in FIG. 9, PHT-conditioned medium inhibited HIV-1 replication, particularly at the higher doses of virus.

Figure 10:
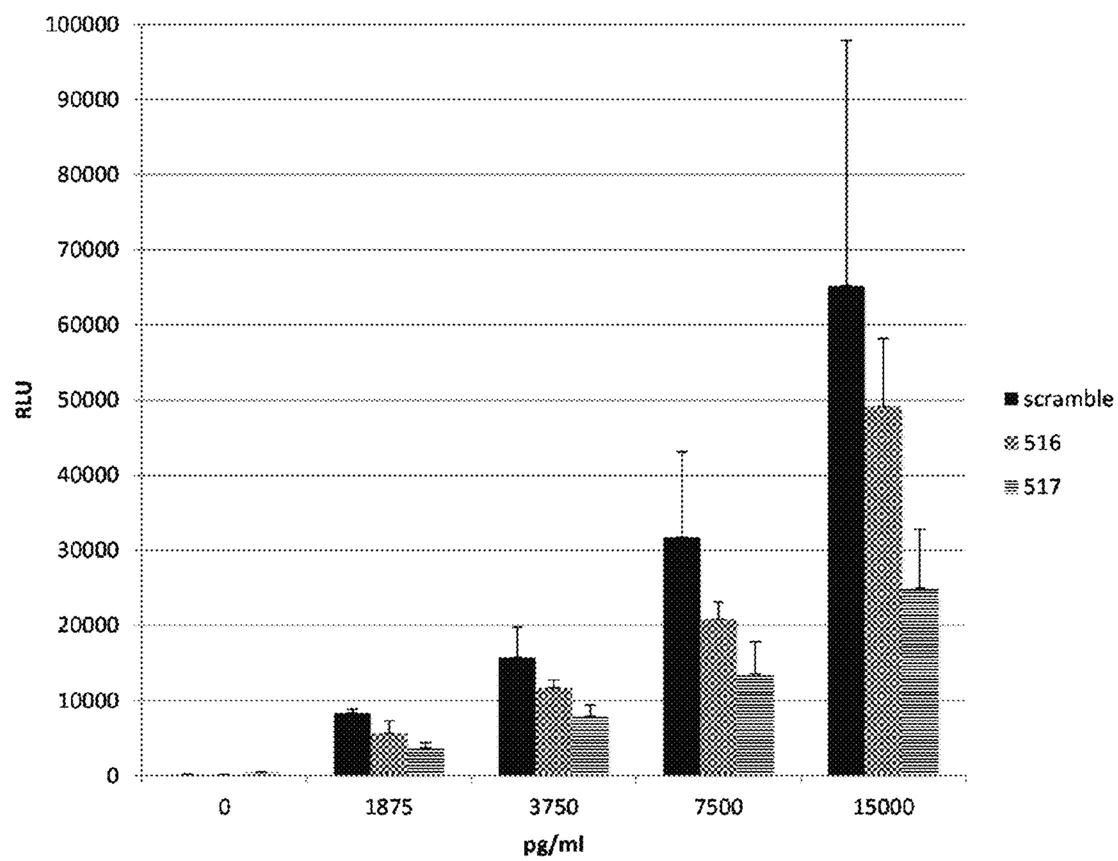
FIG. 10 is a graph showing inhibition of HIV replication in cells transfected with control (scrambled), miR-517-3p (517), or miR-516-5p (516) mimics. TZM-bl cells were transfected for 48 h prior to infection with HIV-1. Cells were then infected with serial dilutions of HIV for 48 h, and infection levels were assessed by Tat-induced luciferase reporter gene expression, in triplicate. The results represent one independent experiment, performed in triplicate.

In another experiment, TZM-bl cells were transfected with a scrambled control, miR-517-3p, or miR-516-5p mimics for 48 h prior to infection with HIV-1. Cells were then infected with serial dilutions of HIV (1875, 3750, 7500 and 15,000 pg/ml) for 48 h, and infection levels were assessed by Tat-induced luciferase reporter gene expression. As shown in FIG. 10, both miR-517-3p and miR-516-5p inhibited HIV replication at all dilutions of virus that were tested.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of inducing autophagy in a cell, comprising contacting the cell with an effective amount of one or more miRs encoded by the C19MC, wherein the one or more miRs comprise miR-517-3p, miR-516b-5p, miR-512-3p, or any combination thereof, thereby inducing autophagy in the cell.

2. The method of claim 1, wherein the one or more miRs comprises miR-517-3p, miR-516b-5p, and miR-512-3p.

3. The method of claim 1, wherein the one or more miRs comprises miR-517-3p, miR-1323, miR-516b-5p, miR-525-5p, miR-512-3p and miR-515-3p.

4. The method of claim 1, wherein the method is an in vitro method.

5. The method of claim 4, wherein contacting the cell with the one or more miRs encoded by the C19MC comprises transfecting a nucleic acid molecule encoding the C19MC or a biologically active portion thereof.

6. The method of claim 5, wherein the nucleic acid molecule comprises a vector.

7. The method of claim 1, wherein the method is an in vivo method and contacting the cell comprises administering to a subject an effective amount of the one or more inhibitory miRs encoded by the C19MC.

8. The method of claim 7, wherein administering the one or more inhibitory miRs to the subject comprises administering a nucleic acid molecule encoding the C19MC or a biologically active portion thereof.

9. The method of claim 8, wherein the nucleic acid molecule comprises a vector.

10. The method of claim 7, wherein the subject suffers from a disease associated with a deficiency in autophagy.

* * * * *

SEQUENCE LISTING

```
<160> NUMBER OF SEQ ID NOS: 82

<210> SEQ ID NO 1
<211> LENGTH: 23
<212> TYPE: RNA
<213> ORGANISM: Homo sapiens

<400> SEQUENCE: 1

cacucagccu ugagggcacu uuc                                            23
```

<210> SEQ ID NO 2
<211> LENGTH: 22
<212> TYPE: RNA
<213> ORGANISM: Homo sapiens

<400> SEQUENCE: 2
aagugcuguc auagcugagg uc 22

<210> SEQ ID NO 3
<211> LENGTH: 22
<212> TYPE: RNA
<213> ORGANISM: Homo sapiens

<400> SEQUENCE: 3
ucaaaacuga ggggcauuuu cu 22

<210> SEQ ID NO 4
<211> LENGTH: 23
<212> TYPE: RNA
<213> ORGANISM: Homo sapiens

<400> SEQUENCE: 4
uuucaagcca gggggcguuu uuc 23

<210> SEQ ID NO 5
<211> LENGTH: 21
<212> TYPE: RNA
<213> ORGANISM: Homo sapiens

<400> SEQUENCE: 5
aaagugcuuc cuuuuugagg g 21

<210> SEQ ID NO 6
<211> LENGTH: 24
<212> TYPE: RNA
<213> ORGANISM: Homo sapiens

<400> SEQUENCE: 6
uucuccaaaa gaaagcacuu ucug 24

<210> SEQ ID NO 7
<211> LENGTH: 22
<212> TYPE: RNA
<213> ORGANISM: Homo sapiens

<400> SEQUENCE: 7
gagugccuuc uuuuggagcg uu 22

<210> SEQ ID NO 8
<211> LENGTH: 22
<212> TYPE: RNA
<213> ORGANISM: Homo sapiens

<400> SEQUENCE: 8
uucuccaaaa gggagcacuu uc 22

<210> SEQ ID NO 9
<211> LENGTH: 22
<212> TYPE: RNA
<213> ORGANISM: Homo sapiens

<400> SEQUENCE: 9
aagugccucc uuuuagagug uu 22

<210> SEQ ID NO 10
<211> LENGTH: 22
<212> TYPE: RNA
<213> ORGANISM: Homo sapiens

<400> SEQUENCE: 10
aagugcuucc uuuuagaggg uu 22

<210> SEQ ID NO 11
<211> LENGTH: 22
<212> TYPE: RNA
<213> ORGANISM: Homo sapiens

<400> SEQUENCE: 11
cucuagaggg aagcgcuuuc ug 22

<210> SEQ ID NO 12
<211> LENGTH: 22
<212> TYPE: RNA
<213> ORGANISM: Homo sapiens

<400> SEQUENCE: 12
aaagugcauc uuuuuagagg au 22

<210> SEQ ID NO 13
<211> LENGTH: 22
<212> TYPE: RNA
<213> ORGANISM: Homo sapiens

<400> SEQUENCE: 13
ucuacaaagg aaagcgcuuu cu 22

<210> SEQ ID NO 14
<211> LENGTH: 21
<212> TYPE: RNA
<213> ORGANISM: Homo sapiens

<400> SEQUENCE: 14
cuccagaggg aaguacuuuc u 21

<210> SEQ ID NO 15
<211> LENGTH: 22
<212> TYPE: RNA
<213> ORGANISM: Homo sapiens

<400> SEQUENCE: 15
aaagugcuuc ccuuuggacu gu 22

<210> SEQ ID NO 16
<211> LENGTH: 23
<212> TYPE: RNA
<213> ORGANISM: Homo sapiens

<400> SEQUENCE: 16
cucuugaggg aagcacuuuc ugu 23

<210> SEQ ID NO 17
<211> LENGTH: 22
<212> TYPE: RNA
<213> ORGANISM: Homo sapiens

<400> SEQUENCE: 17
gaaagugcuu ccuuuuagag gc 22

<210> SEQ ID NO 18
<211> LENGTH: 22
<212> TYPE: RNA
<213> ORGANISM: Homo sapiens

<400> SEQUENCE: 18
cucuagaggg aagcgcuuuc ug 22

<210> SEQ ID NO 19
<211> LENGTH: 22
<212> TYPE: RNA
<213> ORGANISM: Homo sapiens

<400> SEQUENCE: 19
aaagugcauc cuuuuagagg uu 22

<210> SEQ ID NO 20
<211> LENGTH: 21
<212> TYPE: RNA
<213> ORGANISM: Homo sapiens

<400> SEQUENCE: 20
cuccagaggg augcacuuuc u 21

<210> SEQ ID NO 21
<211> LENGTH: 22
<212> TYPE: RNA
<213> ORGANISM: Homo sapiens

<400> SEQUENCE: 21
gaaggcgcuu cccuuuagag cg 22

<210> SEQ ID NO 22
<211> LENGTH: 22
<212> TYPE: RNA
<213> ORGANISM: Homo sapiens

<400> SEQUENCE: 22
cucuagaggg aagcgcuuuc ug 22

<210> SEQ ID NO 23
<211> LENGTH: 23
<212> TYPE: RNA
<213> ORGANISM: Homo sapiens

<400> SEQUENCE: 23
gaacgcgcuu cccuauagag ggu 23

<210> SEQ ID NO 24
<211> LENGTH: 22
<212> TYPE: RNA
<213> ORGANISM: Homo sapiens

<400> SEQUENCE: 24
cucuagaggg aagcacuuuc uc 22

<210> SEQ ID NO 25
<211> LENGTH: 21
<212> TYPE: RNA
<213> ORGANISM: Homo sapiens

<400> SEQUENCE: 25
gaaagcgcuu cucuuuagag g 21

<210> SEQ ID NO 26
<211> LENGTH: 21
<212> TYPE: RNA
<213> ORGANISM: Homo sapiens

<400> SEQUENCE: 26
aaagugcuuc cuuuuagagg g 21

<210> SEQ ID NO 27
<211> LENGTH: 22
<212> TYPE: RNA
<213> ORGANISM: Homo sapiens

<400> SEQUENCE: 27
caaagcgcuc cccuuuagag gu 22

<210> SEQ ID NO 28
<211> LENGTH: 22
<212> TYPE: RNA
<213> ORGANISM: Homo sapiens

<400> SEQUENCE: 28
cucuagaggg aagcacuuuc ug 22

<210> SEQ ID NO 29
<211> LENGTH: 22
<212> TYPE: RNA
<213> ORGANISM: Homo sapiens

<400> SEQUENCE: 29
cucuagaggg aagcacuuuc ug 22

<210> SEQ ID NO 30
<211> LENGTH: 22
<212> TYPE: RNA
<213> ORGANISM: Homo sapiens

<400> SEQUENCE: 30
aaagugcuuc cuuuuagagg gu 22

<210> SEQ ID NO 31
<211> LENGTH: 23
<212> TYPE: RNA
<213> ORGANISM: Homo sapiens

<400> SEQUENCE: 31
ucucuggagg gaagcacuuu cug 23

<210> SEQ ID NO 32
<211> LENGTH: 23
<212> TYPE: RNA
<213> ORGANISM: Homo sapiens

<400> SEQUENCE: 32
caaagcgcuu cucuuuagag ugu 23

<210> SEQ ID NO 33
<211> LENGTH: 22
<212> TYPE: RNA
<213> ORGANISM: Homo sapiens

<400> SEQUENCE: 33
cuacaaaggg aagcacuuuc uc 22

<210> SEQ ID NO 34
<211> LENGTH: 21
<212> TYPE: RNA
<213> ORGANISM: Homo sapiens

<400> SEQUENCE: 34
gaaggcgcuu cccuuuggag u 21

<210> SEQ ID NO 35
<211> LENGTH: 22
<212> TYPE: RNA
<213> ORGANISM: Homo sapiens

<400> SEQUENCE: 35
ccucuagaug gaagcacugu cu 22

<210> SEQ ID NO 36
<211> LENGTH: 22
<212> TYPE: RNA
<213> ORGANISM: Homo sapiens

<400> SEQUENCE: 36
aucgugcauc ccuuuagagu gu 22

<210> SEQ ID NO 37
<211> LENGTH: 22
<212> TYPE: RNA
<213> ORGANISM: Homo sapiens

<400> SEQUENCE: 37
caaagugccu cccuuuagag ug 22

<210> SEQ ID NO 38
<211> LENGTH: 22
<212> TYPE: RNA
<213> ORGANISM: Homo sapiens

<400> SEQUENCE: 38
aacgcacuuc ccuuuagagu gu 22

<210> SEQ ID NO 39
<211> LENGTH: 20
<212> TYPE: RNA
<213> ORGANISM: Homo sapiens

<400> SEQUENCE: 39
cuacaaaggg aagcccuuuc 20

<210> SEQ ID NO 40
<211> LENGTH: 22
<212> TYPE: RNA
<213> ORGANISM: Homo sapiens

<400> SEQUENCE: 40
aaagugcuuc ucuuuggugg gu 22

<210> SEQ ID NO 41
<211> LENGTH: 22
<212> TYPE: RNA
<213> ORGANISM: Homo sapiens

<400> SEQUENCE: 41
aucgugcauc ccuuuagagu gu 22

<210> SEQ ID NO 42
<211> LENGTH: 24
<212> TYPE: RNA
<213> ORGANISM: Homo sapiens

<400> SEQUENCE: 42
acaaagugcu ucccuuuaga gugu 24

<210> SEQ ID NO 43
<211> LENGTH: 22
<212> TYPE: RNA
<213> ORGANISM: Homo sapiens

<400> SEQUENCE: 43
aucuggaggu aagaagcacu uu 22

<210> SEQ ID NO 44
<211> LENGTH: 18
<212> TYPE: RNA
<213> ORGANISM: Homo sapiens

<400> SEQUENCE: 44
ugcuucccuu cagagggu 18

<210> SEQ ID NO 45
<211> LENGTH: 22
<212> TYPE: RNA
<213> ORGANISM: Homo sapiens

<400> SEQUENCE: 45
cucuagaggg aagcgcuuuc ug 22

<210> SEQ ID NO 46
<211> LENGTH: 21
<212> TYPE: RNA
<213> ORGANISM: Homo sapiens

<400> SEQUENCE: 46
aaagcgcuuc ccuucagagu g 21

<210> SEQ ID NO 47
<211> LENGTH: 20
<212> TYPE: RNA
<213> ORGANISM: Homo sapiens

<400> SEQUENCE: 47
cugcaaaggg aagcccuuuc 20

<210> SEQ ID NO 48
<211> LENGTH: 22
<212> TYPE: RNA
<213> ORGANISM: Homo sapiens

<400> SEQUENCE: 48
gaaagcgcuu cccuuugcug ga 22

<210> SEQ ID NO 49
<211> LENGTH: 22
<212> TYPE: RNA

<213> ORGANISM: Homo sapiens

<400> SEQUENCE: 49
cucuagaggg aagcacuuuc ug 22

<210> SEQ ID NO 50
<211> LENGTH: 21
<212> TYPE: RNA
<213> ORGANISM: Homo sapiens

<400> SEQUENCE: 50
caaagcgcuu cccuuuggag c 21

<210> SEQ ID NO 51
<211> LENGTH: 22
<212> TYPE: RNA
<213> ORGANISM: Homo sapiens

<400> SEQUENCE: 51
aucgugcauc cuuuuagagu gu 22

<210> SEQ ID NO 52
<211> LENGTH: 22
<212> TYPE: RNA
<213> ORGANISM: Homo sapiens

<400> SEQUENCE: 52
acaaagugcu ucccuuuaga gu 22

<210> SEQ ID NO 53
<211> LENGTH: 22
<212> TYPE: RNA
<213> ORGANISM: Homo sapiens

<400> SEQUENCE: 53
cucuagaggg aagcgcuuuc ug 22

<210> SEQ ID NO 54
<211> LENGTH: 22
<212> TYPE: RNA
<213> ORGANISM: Homo sapiens

<400> SEQUENCE: 54
aaaaugguuc ccuuuagagu gu 22

<210> SEQ ID NO 55
<211> LENGTH: 22
<212> TYPE: RNA
<213> ORGANISM: Homo sapiens

<400> SEQUENCE: 55
cucuagaggg aagcgcuuuc ug 22

<210> SEQ ID NO 56
<211> LENGTH: 22
<212> TYPE: RNA
<213> ORGANISM: Homo sapiens

<400> SEQUENCE: 56
aaagugcauc cuuuuagagu gu 22

<210> SEQ ID NO 57
<211> LENGTH: 20

<212> TYPE: RNA
<213> ORGANISM: Homo sapiens

<400> SEQUENCE: 57
cugcaaaggg aagcccuuuc 20

<210> SEQ ID NO 58
<211> LENGTH: 23
<212> TYPE: RNA
<213> ORGANISM: Homo sapiens

<400> SEQUENCE: 58
uucucgagga aagaagcacu uuc 23

<210> SEQ ID NO 59
<211> LENGTH: 18
<212> TYPE: RNA
<213> ORGANISM: Homo sapiens

<400> SEQUENCE: 59
ugcuuccuuu cagagggu 18

<210> SEQ ID NO 60
<211> LENGTH: 160970
<212> TYPE: DNA
<213> ORGANISM: Homo sapiens

<400> SEQUENCE: 60
cctttatggt cagtgtttac agggaagatg gagggaaaat tagagtcaga gattttaggt 60
tttatggcag gatttgggga aaagggattc tggtgtctat ggctcacttt gggaaagaca 120
gtttctagtt tctatggcta gccttggggg agaaggaggg tcaggaagaa acttccgctt 180
ctgaagctgc ttcggaagcc tttgttttga ggttatcggt ttctgagccc caatattagc 240
ctgccacagt ctaagctttc aaagcgcctg tcaaactctt gtggatctat gtatttcaaa 300
gaccaaaatc aacagctcac atatggggtc caagaggagg ggggaggtca ctgcacgttg 360
tcacgtgtga gatctttgtt gttgttgttg agatggaatc tcgctctgtc acccaggctg 420
gagtgcagtg gcaccatctc agctcgactg taaccttcac ctcccaggtt ctagcaatta 480
tcctgcctca gcctcccaag tatctggaat tacgggtgcg tgccatcatg ccccgctaat 540 ttttttttt tttttgtatt tttagtagag acgggggttt caccatgttg gccaggccag 600
tctcaaactc ctgaccccaa gggatctgcc cacctcggcc tcccaaagtg ctgggactac 660
aggcatgagc caccgcgcct ggcctcttgt gagatctgat aagaagtcac gcactagaag 720
gaagggaaga gtgtactcca caaccccaaa cgatgcgttt ggaatcattt caaacccaca 780
taacaagagt ttcatacgga attgggacag aacatggccc ctaatgagcc cccctaaata 840
attctcaagg accacttctc caatgacgaa ggagattgag gatttttttt tcctacgttt 900
attggccgtg tggatatttt gcctttgtaa aatatgtgtc caagcctttt gcccatttct 960
ccagtgggta gtatttcctt tgtttttttt ttttgagaca aagtctcact ctgttgccca 1020
ggctggagtg cagtggcctg atctcggctc actgcaaacc ctgcctcctg ggttcatgcc 1080
agtcttctgc ctcagcctcc caagtgctgg gactacaggt gcacaccacc acgccctgct 1140
aattttttgt atttttagta gagatggggt ttcaccatgt tagctaggat ggtctcaatt 1200
tcctgacctc gtaatctgcc cgcctcggcc tcccaaagtg ctgggattac aggcgtgagc 1260
cactgcacct ggcctaaaag aatctttaaa ttgtccatga gcgatggtgc gtgcctgtgg 1320

```
tcccagctac ttggaggctg agaaggaagg atcccttgag cctgggagtt tgaggcagca   1380
atgagctatg ctcttaccac tgcactccag cctgggtgaa agaggaagaa gacccttaat   1440
aggcggacca cggtggctca cgcctgtaat ctcaatactt tcagaggcct aggtggaaga   1500
attacttgag accaggagtt caagaccaac ctgggcaaca tagcgagacc ctcatctctc   1560
caaaagtttg aaaaagaaaa aaaaaatttt taatgaaaca gaagtcgtta attttatttt   1620
attttctaag acatcttgtt atagcaaaaa gtccttaatt ttaatatagt ctaatttata   1680
tattttcttc attgtaaaaa tttttgggtc ctatctagca aatgttagct tacctctatg   1740
taataaagac attcttctgt gttgtcttct aaaacaaaac attgttttat tttctgattt   1800
taggtctgca gttcatttgt agatttttgt gtctaggatt aggtagggtt aagatcattt   1860
gtggccaggc atggtggctc acaccagtaa tcctaacact ttgggaggct aaggcaggag   1920
gatctcttga gcccaggagt ttcagaccag cctggggaac atagaaagac cctgtctctc   1980
tatttttttt ttcagttaaa tatatacttt taaaaagatc atttgtggtg ctatagttgt   2040
gggtgtttaa tttgtaattt actttgttct gttgatctat ctaatttttt ttttagacgg   2100
attcttcctc tgtcacccag gctggagtgc ttcagcctct caatgccatc atgcccagct   2160
aatttttttgg acttgtagta gagacagagt ttcaccatat tgaccaggct ggtctcgaac   2220
tcctggcctt aggtgacccg cccacctcag cctcccaaaa tgctgggatt ataggcatga   2280
gctactgtgt ccagccagat ctgtctaatt tttttttttc tttgagacgc agtctcactc   2340
tgtcactcag gctggagtgc agtggcgtga tcttggctca atgtaacctc cacctcctgg   2400
gttcaagtga ttttcctacc tcagcctcct gagtagctgg gattacaggt gcgtgccacc   2460
acgcctggct aatttttgta tttttagcag agacggggtt ttgccatgtt ggccaggctg   2520
gtctcaaact cctgacttcc agtgatccgc ccaccttggc ctcccaaaat gctaggatta   2580
caggtgcgag ccactgtgcc tggcccagag ctgtctaatt ttaaagaatg tatgaagatt   2640
cagatttagg ttcctgctat tatgttatgg gaaatctttt cctagtttct tctgattaat   2700
ataaatcctt aattttattt ttatttattt ttttactaca gtcctctttt attacttttt   2760
atttttctta attttaatat aatgaaaagt tcgatttttc ctgttatggt tagcattttt   2820
ttcttctgtt taagaggtgt ttcctggctg ggtgtggtgg ctcacacctg caatcctagc   2880
actttgggag gccaaggtgg gaggatcact tgaacccagg agttcaagac cagcttgggc   2940
aacatagtga aacccttgtc tccaattttt ttaaattaaa aattaaaaaa ggcggggctg   3000
ggtgtggtgg ctcacccctg taatcccagc actttgggac gccgaggcgg gtggatcacc   3060
taaggtcagc agttcgagac cagcctgacc aacatggaga aaccctgtct ctactaaaag   3120
tacaaaatta gctgggcgtg gtggtgcatg tctgtaatcc cagctattcg ggaggctgag   3180
gcaggagaat cgcttgaatc caggaggcgg aggttgcagt gacccgagat tgcgccattg   3240
cactccagcc tgggcaacaa gagtgaaact ctgtctcaaa aaaaataaat aaataaaaaa   3300
taaaataaaa aagaagtgtt tccctagcgt gaagacatga agctcttctg taaacttcat   3360
tgttctgcct ttacaattca atctacaacc cactagaatt aatcttccgt atatatagca   3420
tggggtggag gtcaaacacc ttttttccat atggatgttc agctgtccca gtgtcattta   3480
tttaaaagac tgtactggac ctggcatggt ggctcacgcc tgtaatccca gcactttggg   3540
aggctgaggc gggtggatca cttgaggtca ggagttcgag accagcctaa ccaacatggc   3600
aaaaccccat ctctgctaaa aatacaaaat tagccaggtt tggtggtgca tgcctgtaat   3660
tccggctact tgggaaactg aggcgggaga atcccttgaa cctcataggc agaggttgca   3720
```

```
atgagccaag atcgcaccat tgcattccag cctgggcaac aagagcgaaa ctctgtctca   3780

aaaaataaga aaaaatagag gccgagaatg gcccttgctg ccaccaacat ggagactttg   3840

taccgtgtcc cgttcttagc gcttgaatgt cccaacctga agctgaagaa gccgccctgg   3900

ctgcacatgc cgttggccat gactatgtat gctctggtgg tggtgtctta cttcctcatc   3960

accagaggaa tcgtttatga tgttacggtt gaaccgccag gtgttggctc tatgactgat   4020

gaacaagggc atcagaggcc agtagctttc ttggcctaca gagtaagtgg acaatattat   4080

tatggaagga cttggatcca gcttcctgtt tacaatggga ggtttaggtt tcataatcct   4140

ggaccgatcg aatgcaccaa atatcccaaa actcaataga tttcttcttc tattcgttgg   4200

attcgtctgt gtcctattga gttttttca cggctagagt attcgtgaga atgaaactac   4260

cgggctctct gatgggttag agtgccttta agaagaaatc aggctgggtg cagtggctca   4320

cgcctgtaat cccagcactt tgggaggccg aggcgagcgg attatctgag gtcaggagtt   4380

cgagatcagc ctgggcaaca tggtaaaacc ccatccctac tacaaataca aaattagcca   4440

ggcgtggtga cacatgtctg taatcccagc tactcgggag gctgaggcag gagaattgct   4500

tgaacccggg aggcagagga tgcggtgagc cgagatcgca ccattgcact ccagcctgga   4560

caacaagagt aaatctccgt ctcaccaaaa aaaaaaaaaa gaaaaaaaaa aagaaatcag   4620

tgcatactgg atttgctcct gtcaatgaag ttttaaaggc tgtccaatcc tctaatatga   4680

gatgtagaaa agaaggaaga gcagcagtaa aagaaatatc tagtgaaaaa ccaggaagtg   4740

tattgaagct tggactagaa tttcttcttt attaaagaga caaatttatc acagtatttt   4800

cttttcctgc tgaccacatt gctataccaa tgatgatgag tggcattttc ttcttagttt   4860

tttatttctt taagaaaata caagccaggc gcggtggctc acttctgtag tcccagcact   4920

ttgggaggcc aaggtgggca gatcacgagg tcaggagttc cagaccagcc tggccaccat   4980

gttgaaaccc catctctact aaaaatacaa aaattagccg ggcgtggtgg tggcggggca   5040

cctgtaatcc cagctacttg gaaggctgag gcaggagaat cacgtgaacc tgggaggcgg   5100

aggctgcagt gagcctagat cgctgccact gcactccagc ctgggcgaca gagcgagact   5160

ctgtttcaaa aaaaaaaaaa gaaagaaaga aagaaaagaa aatatactgc atacctacaa   5220

ctataatagc aaatatagtg attatttttt acaacccccct taacactttt tggagatgac   5280

atttctgact ttcagaaatt aacataaaat caagaagcaa gattccatga gctgagaact   5340

ctggacagct ggtcagcttt acctacggag ctttggcttt aactagagtg tgtgatggta   5400

gattatttca gataggtatg taagactgct gcctgaacaa taacatgtat gaaaggaaca   5460

gaaataaata ctaattaaaa aacaaaataa gaaaaaataa aaaataaaca ctactatgga   5520

catggtagct catgcctgta atcctagcac tttgggatgc caaggtgggt ggatcgcttg   5580

aaccaaggag ttcaaggagt tgggagacca gtctgggcaa catagcaaga ccccatctct   5640

aaaaaaaaaa aaaaaaaaag agtactaaag actcagagat agaaaaatgg aaattattca   5700

tattgtctcc agattttttt tttttggac ggagacttgc tctgtcaccc aggctggagt   5760

gcagtggcac tatcttggct cactgcaacc tccacctccc aggttcaagc aattctcctg   5820

cctcagcctc ccaagtagct gggattacag gcatacgcca ccaaacccgg ctaattttgt   5880

acttttagca gagacagggt tttgccatgt ttgtcaggct ggtcttgaac ccctgacctc   5940

aggtgatcca cccgcctcgg cctcccaaag tgctgggatt acaggtgtga gccaccgcgc   6000

ccagccagta gtcttttatc cttgtaacag attaatcttt tctagggaaa tggagacctt   6060
```

```
tcattttcat gtccttttta catccctgtt gattgtatct ctgcctccat tctgttgatc   6120
ggaatgacac taacttaatt tgggttctct aaagcagaca ctgatacaaa ggcttcagtt   6180
ccagaggttt atttagaatg tgatcctaaa ccaagaggga ggtagcaggg agagtaagac   6240
aggaaaggat ggggagccaa caccttatct aaggacatgt tgaggccagg cgtggtggct   6300
catgcctgta atcccagcac tttgggaatc cgaggcgagc agatcacaag gtcgggagtt   6360
tgagaccagc ctggccaaca tagtgaaact ctgtctctac taaaaatgca gaaaacaggc   6420
cgggtgcggt ggctcacgcc tgtaatccta gcactttgtg aggccgagac gggcggatca   6480
cctgaggttg ggagttagag accagcctga gcaacatgga gaaaccctgt ctctactaaa   6540
aatacaaaaa ttagccttgc gtggtggtgc atgcttgtaa tcccagctac ttgggaggct   6600
gaggcaggag aatcacttga acctgggagg cggaggttgc gatgagccga gatcgtgcca   6660
ttgcactcca gcctgggcga caagagtgaa acttcatctc aaaaaaaaaa aaaacaaaaa   6720
acagaaaaaa ttagctgggc ctggtggcag acgcctgtgg tcctagctac tcaggaggca   6780
aaggcaggag aattgcttga acctgggagg tggagattgc agtgagccga gatcatgcca   6840
ctgcactcca gcctgggtga cagagtgaga ctctatctca aaaaaaaaaa aaaaaaagga   6900
taagttgctg aagtctgtga agtggacaat gagggcttga ttcctttgaa gcctgttgaa   6960
gactgtttac gcttcctctt atcatcccct gcctcatccc ctgtcacaga gatgaaagac   7020
tgggacattt ctgtgccaaa tttcatccca cattgggtga ggctttccct gagacatgtt   7080
gacttcctgc agttcaaagc tactttcttc tttagacagg gtctcgctct gtcccccagg   7140
ctagagtgct atagcgtgat ctcgcctcac tgcaagctcc gcctcccggg ttcaagccat   7200
tctcctgcct cagcctcccc agtagctggg actacaggca cctgccacct tgcccggctg   7260
ttttttgta tttttagtag agacagggtt tcaccatgtt agccaggatg gtctcgatct   7320
cctgacctca tgatccgccc accttggcct cccaaagtgc tgacattaca ggtgtgagcc   7380
accgtacccg gcctattttc ttctttagac agggtcttcc tctgtcccct aggctggagt   7440
gcagtggtgt gatcttggct cactgcaacc tctgcccccct gggttcaaga gattctcctg   7500
cctcagcctc ctgagcagct gggattacag acatgcgtca ctatgcccgg ctaatttttt   7560
gcatttttg gtagagatgg ggtttcacca tgttggtcag gctggtctcg aactcctggc   7620
ctcaagtgat ctgtctgcct tggcctccca aagtgctggg attacaggtg tgagccaccc   7680
cgcccggggc aaagctattt tccattttaa attttttgtt attgttgttt tgagaccaag   7740
tctcactctg ttgcccaggc tggagtgcag tggcatgatc tctaaatttt gtatttttag   7800
tagagacggg ttttcacctt gttgcccagg ctggtctcga attcctgacc tcaggtgatc   7860
cacttgcctc agccgcccaa agtgctggga ttacaggcgt gggccaccat gcccagcctg   7920
ccaaagctat tttctatggg ataaatgaca gcagaaagga ccccagagca aaatactaca   7980
aagatgtatg gcacgtgcat gaggtgagag tatggtagaa tcaagtgagt ctctgctttc   8040
atgagactga acagtgaggc tcaggttaaa attagaggtg tacaagagag tatgatatgg   8100
acatctgcta ctgaacaatc cttgtgcttc ttgaaaatgc tcatttccat attttttatt   8160
ttttattttt tttcagatac aaggtctcac tgtgtcaccc aggctagatt gcaggggcac   8220
aattaaggtt cactaaagtc ccaaccccccc gggttcaagc aatcctcctg cctcagcctc   8280
tggagtagct gggactgcag ttgcatgcca cagtgcccgg ctaatttttt tatttttttgt   8340
agaggcaagg gcttgctctg ttgcccagat tggtcttgaa ctcctggcct caaatgatcc   8400
tcccacccgt gcctcccaaa gtgctgggat tacaggcata agccactgca cccagcctca   8460
```

```
tttctatatg taagttcatt tagtcattaa gtcttgaagc aaagatccag ccacgatcta   8520
tataaaattt tcaatacagg ccaggcatgg tggctcacgt ctataatccc ggcactttgg   8580
gaggctgagg cagactgatc actttaggtc aggagttcca gaccagcctg gccaacatgg   8640
tgaaacgcta atacaaaaaa ttagctgggc atggtggtca gcacctgtaa tcccagctgc   8700
tagggaggtt gaggcaggag aatcggttga acctggaggt agaggttgca gtaagtcaag   8760
atcacgccac tgcactccac cctgggaaac agagcaagac tctgttccaa aaaaaaacaa   8820
aaggcaatct ttcctagaaa aaaatagttt ctgcacattc ttaggcacgc atttgtaggc   8880
tgctatagct atttaaaatt ttcaatacaa tatgtttacc agagcaaact acaatcctca   8940
ttgttatgtg ggccccaaac cattactgat actcatctgt ttccccccacg tcgtctacat   9000
ttcctcatgg tgggccagta cttcattttt tgtaactcat ttgcctgcta gggtgactca   9060
ggcctttgtt tctgagagat ctgagtctgg tgttgctagg aaggaaaagg ttaactagtc   9120
tataatccat tctttctccc aacctggtga tgtctgagga ggcatccctt ggtcaaactt   9180
ctttgtaaac atgctaatca gatctcatgg tatttattag aggaaaacaa ccagagattc   9240
ttatctgtga gatgctttca gcaggacata cttgttcttt cttgatgtct tgcagtaaac   9300
aaggaattta ggggtttatg ggcatgagcc actggaaaat gtcagcgtca catatttagt   9360
taagagagag agagagaggg gctgggcgtg gtggttcatg cctacaatcc cagcattttg   9420
ggagactgag gcaggaagat cacttgagcc cagaagcgta agatcagcct aggtaacata   9480
atgagacctc gtcttattaa gagtctgatt ctaccctccc ttggtgttat ctcagttact   9540
gtacttttac agggctgtgg ttgtgcaact tcctgctggg catggggaat tctctgagtt   9600
ccagacaaga accttcctgc ccaatatgca gcagcaaccc agtctcttca taatgctcgt   9660
ggttgattat ccatgcccgc caactacctc atttctctgc ccagtgcttt atcagcctga   9720
agagcccaca gtcaccaggc agaaaacctt actgtgcttc ttggtgaaag tgttccctct   9780
tcaaaaatga agacatcacg ccagataagg tttggggact agaagcacaa tttcttcaag   9840
tgggtcccta gacaggatat tgataaatgc caattctgtt tcactccctg gtagctacac   9900
ctgtatattc taactactag ggtcacagcc ccttatattg actgttggtt atatgcagat   9960
attgcatctt agaggacagc accccaaacc catgggatgt tatacctggg ctgacacttt  10020
agttgagccc tttaaaaagc cattcctggg ccaagcccgg tggctcacac ctgtaatccc  10080
agcactttgg gaggctgagg cgggcggatc acgaggtcag gagatcgaga ccatcctggc  10140
taacatggtg gaaccctgta tctaccaaaa atacaaaaaa aattagctgg gcctggtggc  10200
aggcgcctgt agtcccagct attcagaagg ctgaggcagg agaatggcgt gaacccagga  10260
ggtggaggtt gcagtgagct gagactgtgc cactgcactc cagcctgggc gacagagtga  10320
gactctgtct caaaaaaata aataaataaa taaataaata aataaataaa aggccattcc  10380
tggctgggca tggtggctca cgcctgtaat cccagcactt tgggaggccg aggagggcgg  10440
atcacctgag gttgggagtt tgagaccagc ctgaccaaca tggagaaacc ctatttctac  10500
taaaaataca aaattagcct ggcatggtgg cacatgccta taatcccagc tacttgggag  10560
gctgaggaag gagaatcgct tgaatccggg aggcagaggt tgcagtgagc agagattgca  10620
ccattgcact ccaacctggg caacgagagt gaaactccat ctcaaaaaaa acaaaaagcc  10680
attcctggcc tggcgcaatg gctcacgcct gtaatcccaa cactttggga ttacgcttgc  10740
caaagtaagt gaattacctg aggtcaggag tttgacacca gcctggccaa catggtgaaa  10800
```

-continued

```
ccccgtctct actaaaaata cacaattagc tggacatgat ggcaggcgcc tgtaatccca  10860
gttactcagg aggctgaggg aggagaacct cttgaaccca ggaggcaggg gttgcagtga  10920
gccaagattg cgccattgca ctccagccag ggcaacaaga gtgaaactcc gtctcaaaaa  10980
ataaataaat aaataaataa ataataacca ttatgttatc ccatgatggc agctctttct  11040
gtataaggta ataaatatgc gatgtaaaga gtgtatttca tattaatgca ctgattgttg  11100
taccttttt ttttttttt ttttttttt gagacagggt cttgctctgt cacccaggct  11160
ggagtgcagt ggcgcaatct cgactcactt caacctctgc ctcccaggtt caagcaatcc  11220
ttctgcctca gcctcctgag tagctgggat cacaggtgcc cgccaccacg cccagctaat  11280
ttttgtactt ttttagtaga gacggggttt tgcctgttgc ccaggctggt ctcaaactcc  11340
tgacctcagg tgatctgccc tccctggcct cccaaagggc tgggattaca ggcacaggga  11400
gccaccatgc ccagctgttt ttttgttttg tttttttgttt tttttgagac agagtctcac  11460
tctgtcgccc aggctagagt gcagtggctt gatcttggct cactgcaacc tcggttcact  11520
gaagcctccc agtttcaagc cgtactctta cctcagcctt ctgagtagtt gggattacag  11580
gcgtgagcca ctgtgcccag ccttttgttt tgtattttta gtagagatgg ggtttcacca  11640
tgttggccag gctggtcttg aactcctggc cacaagtgat ccacctgcct tggcctccca  11700
aagtgctggg attacaagga tgttagaaaa tggctgggcc tggtggctta cacctactcg  11760
ggaaactgag gcacgagaat cgcttgaacc cgggagacgg gcattgcagt gagctgagat  11820
caggccattg cactccagcc tgggcgacag tcacaaaaaa aaaaaaaaag aaagaaagaa  11880
agaaagaaaa cacatcaatt ccaggaaata caaatcagat gagatcgggc gtgttcccgg  11940
tggtatggtc acagaaacag gaagcacaaa tcaatcacct ccaccactgc cctctccggg  12000
ggaaaggatg aaatgtaatc aacttaccac taactagtca gtcattcccc ttaaaggaca  12060
atagcagatc aaggtgtcat catgggcttt ttttttttt tttttgagac agggtctcgc  12120
tctgtcgccc agcctagagt gcagtggcac caccatagct caaccttctg ggctcaagcg  12180
atcctcctgc cttagcctct ggagtactag gactataggt gcatgcctcc atgcctggct  12240
aattgaaaaa ttttttttgt agagacagga tttggctttt ttacccagac tcatctcaaa  12300
ctcctggcct caagcgatcc tcccgcctcg gcctctcact ggtactctta tcacaggcat  12360
gagccagcgt gtctggccct gatcacagcc agaaactccc aggctgtgat aatgagctca  12420
gctttcatga gagacagctc atgctattag gcacatcctt cgtctcttct cctgctaccc  12480
tgctaccgcg tctctgttca tgggtgcatt atacaagcag tggtctgagg atagagcctc  12540
agtgatgccc actgcacaag gcaccctctc ttcctggttg ctcaggatct tctctgtggt  12600
gagcactccc tggagaacat taacatgaga cacagagatc tcatgcctct gcctcttctc  12660
ataattcctt ttttttttt gagagggagt ctcaccgtgt tgcccaggct ggagggcaat  12720
ggtgtgatct cagctcactg caaccttcac cttccaggtt caagtgattc tcctgcctca  12780
gcctcccagg tagctggggc tacaagtgtg tgtcaccgca cccggctaat ttttgtgtct  12840
ttagtagaga cggggtttca ccatgttggc caggctggtc tggaactcct gacctcaggt  12900
gatctgcctg cctcagcctc ccatagtgct gggattacag gtgtgagcca ctgtgcccag  12960
tgcccccct tttttgtgtg tgtcagggtc tcactctgtc acccaggcta gagtgcaggg  13020
gcataatctc ggctcactgc aacatctgcc tccaaggctc aagtggtcct cccacctcag  13080
cctcctgagt aacagggact acaggcacgt gccaccaaac ccagctaatt ttttgtattt  13140
ttggtacaga cgagacttca ccatgttgcc caggctggtc acaaactcct gacctcaagc  13200
```

```
gatccaccag ccttggcttc ccaaaatgct gggaatacag acgtgagcca ccgtgactgg  13260
ccccagctaa tttttgtatt tttagtagag atgggttttc accatgttgg ctaggctggt  13320
ctcacactcc tcacctcagg tgatccacct gcctctgcct cccacagtgc tgggattaca  13380
ggcataagcc accacgcccc accgtgagac ccccatctct acaaaaaaag ttttaattag  13440
ctgtgcatgg tggcaggcac cctagtccca gctacctact gaggaggctg atcgcttgag  13500
cccaggaggt caaggctgca gtgagctggg atcacagcac tgcactccag cctgggagac  13560
agagggagac tctatctcca aaaagaaaaa aagactagag attgtgcccc aggcacagat  13620
catattaatc ccagtgatat tctgggagtg gtggccagac tccttcccag gactggtctt  13680
ccggtttggc aatgagtgtt agtcaaggcg tgaggttctc atgggccgtc tcaagcactc  13740
tgttcgacat ctttttactc tctcccaggc tggggtgcag tggcgtcatc ttggcttact  13800
gtagcctccg cctccagggt tcaagcaatt ctggtgcctc agcctcccga gtagctggga  13860
ttataggcgc ctgccatcac gcctggctaa tttttttgt atttctagta gagtcagggt  13920
ttcactatgt tgcccaggct ggtcttgaac tcctgacctc aggtgatctg cctgcctcga  13980
cctcccaaag tgctggggtt gactgctcgt ggcccctctg ttgcacatct tgacttctca  14040
gcctccaagg tgattcttta ggacaccaat ttaatccctc taaacatggc aacagagcca  14100
gcggtttcca gccctatttg cgcagtagaa ggattattta caaatcctcg tacttagact  14160
ccacccgcag agattcaagt ggactgagcc tggagtgaag ccgaaggcat tttcttataa  14220
tcctgagaat gataatatac agctgtcttt gaaaaccacc actaagactt gtaaactttg  14280
ttcattcaag tcttctttc tcccccttaaa agcaggctta tccttgaggt gtgctttttc  14340
agactccagt aagcatcact gagaacactt aattaatata ctgaggcctc tcacaagagg  14400
gaaggagtgg aagaactcct ggagaaggac ttggaaggga gagatgtttt tctttctttc  14460
tttctttttt tttttttgg agacagagtt cactcttatt gcccaggctg gagtgcaatg  14520
gcgtgatctt ggctcactgc aacctctgcc tcccaggttc aagcaattct cctgcctcag  14580
cctccccagt agctgggatc acaggcgcct accaccatgc ccagctaatt tttgtacttt  14640
tttagcagag acgggctgtc gccacgttgg cctggctggt ctcgaactcc tgacctcagg  14700
tgatccgccc acctcggcct cccaaagtgc tgggagtaca gacatgagcc accgtgccca  14760
gccaagatgt ttttcttaac acaaaaagtt tttgtctggg tgtggtggct cacgcctgta  14820
ctcccagcac tttgggaggc cgaggcgggg agatcacttg caatcaggag ttcgagacca  14880
gcctggccaa cgtggcaaat acaaaaatta cctgggcatg gtggcgcttg cctgtaatcc  14940
cagttattta ggaggctgag gcaggagaat tgcttgaatc cgggaggcgg aggttgcagt  15000
gagctgagat caagccactg aactccagcc tgggcgacag agtaagactc catctcaaaa  15060
ataaaaaaaa atttctaaag caagcgcttg ggctgttctg atgtcaacat acagtagctg  15120
gccctacctt taacccagga taaggggcaa aagtataccc aaagatacat gtaatcaaag  15180
ttgctgggtg cagtggccca cgcctataat cccagtgatt tgggaggctg aggtgggagg  15240
attacttgat cctggaggtt gagaccagcc tgggtaacac agtgagacct tgtctctgaa  15300
acctaaaata aaataaaata aaataccact gtgctctatc ctgagcaaca gagcaagacc  15360
ctgtctcaaa tataataaaa ataaaaataa tcagtccttg ggtttagcat ctttggacta  15420
atggtaccag catgagggaa agcaggtctt tgtagctctg ataagtgaac tttgacactt  15480
cttagtgttt ttctctaact gtggtgacat acgaataaca tataattaac catttaaaaa  15540
```

```
taagcggttc ggtggcattt agtacatcac agtgttgtgc aaccaccacc tctaggtagt  15600
tccaaaactt tttctttctg ttttttttt tgagacagag tttcgctctt cttgcccggg  15660
caggagggca atgacacgat ctccactcac cgccacctct gcctcccagg ttcaaatgat  15720
tgtcctgcct cagcttcccg agtagctggg attacaggca tgtgccaccg cacccggcta  15780
attttgtatt tttagtagag atgaggtttc tccatgttgg ccaggctggt ctcaaattcc  15840
tgacctcagg tgatccaccc gcctcggcct ctcaagtgct gggattacag atgtgagcca  15900
ccatgcctgg ccccaaaaca ctttcctaac tctaaaataa agtcccataa gcaggtattc  15960
cccactccct cctcctcccg gcctgtccat ccacaaatga atggattaaa caatatggtt  16020
tatccataca atggagtata attcagctgt aaaaggggct tggcgcagtg gctcacacca  16080
gtaatctcag cactttggga ggccgaggcg ggcagatcac ttgaggccag gagtttgaga  16140
ccagcctggc caacatggtg aaaccaggtc tctactaaaa atacgaaaat tagccaggcg  16200
tgttagtgca cacctgtaat cccacctact caggagactg aggcatgaga atcacttgaa  16260
tttaggaggc agagaagttg cagtgagctg agatcctgcc actgcactcc agcctgggca  16320
acagagcaag actctgtctc aaaaaaaaaa aaaaaaaaga ggaatgagat accgacacat  16380
tataccatga ggataaacct tgaaaacaac atgctcagta aaagaagcca gcacacaaaa  16440
ggttacatat tatataatgt aattttattt tagtttttga aaagctggtc tcctgggctc  16500
aagcgatcct cccttcttgg cctcccaaac tgctgggatt acaggtgtga gccactgtgt  16560
ccggcctatg attttttttt tttaatgaaa tacctggaaa agataaatcc agagaaacag  16620
acggcagatt acaggctctt tttaaattgg tttctgacac tatcacaaga taaaaatgtg  16680
gtttaaaatt gttgcttggt atgtcttatt cacctctaaa gatatactgt tcatcaggcc  16740
gggtgcagtg gctcacacct gtaatcccag cactttggga ggctgaggcg ggaggatggc  16800
ttgaacccag gagttctagg ctgtaatgtg ctctgccaat tgggcatcca cactaagttc  16860
ggcatcaata tggtgacctc ccaccaggtt gcctaagaag tggggaaatg gtctaggttg  16920
aaaatggagc aggtcaaaat tttcatgctg gctgggcaca gtggctcaca catgtaatcc  16980
cagcactttg ggaggccaag gcagatggat cacctgaggt caggagtttg agaccagtct  17040
ggccaacatg gtgaaaccct gtctctacta aaaatacaaa aaaaaaaatt agctgggcat  17100
ggtggcatgt gcctataatc ccagctattt gggaggctga ggcaggagag ttgcttgaac  17160
ccaggaggca gaggttgcag tgagccggga tcacgccact gcactctaac ctgggcgaca  17220
gagtgagact ccatctcaaa aaaaaaaaaa aaaactttca tgctgatcag tagtggaatc  17280
agcttgtgaa ttgccctcca gcctgagcaa cacagactgc ctcttactaa tcccagcact  17340
ttgggaggct gaggtgggag gatggcttgt gcctaagact ttgagactag cctagccaaa  17400
atcccttctc tacaaaaaat gcaaaaatta gctgggtatg gtagtgtgca cctgtagtcc  17460
cagttactca ggaggcttag gtgagaggct cacctaggcc caggaggtta aggctgcatt  17520
gagctatgat tttgccactg cactccaggc tgggcctagg cctttgtagt cacagctact  17580
tgggggcaaa tgtaggagga tcacttgagc ccagtaggtc gaggctgcag tcagctgtgt  17640
tttttgagac atagcaagac cctgtctcaa aaagaaaaaa aaaagtagct acaagctcat  17700
ttatgcaaag gctaaccact gtcacaagta gagatgtgca gaactgagat tcaaatggat  17760
ggaatggcaa gaaaaactgc cacttctgtg aacctgaagt caaactgccc ttgtcgtcaa  17820
gataaaaggt atacatggtg tgagcctggg catctgaaag gtgttgcagc tttttctttt  17880
attttttga gatggagtct cactcctgtc acccaggctg gagtgcagtg gtgcgatctc  17940
```

agctcactgc aacctctgcc tcctgggttc aagcaattct cctgcctcag cctcctgagt 18000
agctgggatt acaggtgccc accaccacac ccagctaatt ttcgtatttt tagtagagat 18060
ggggtttcgc catgttggcc aggctggtct cgaactcctg acctcaggtg atccgcctgc 18120
ctcagcctcc caaagtgctg ggattacagg tgtgagccac ctgtaattag ccaggcttgg 18180
tggtgggtgc ctgtaatccc agctactggg aaggctgagg caggagaatt gcttgaacct 18240
gagaggcgga ggttgctgtg agccgagatc gtgccactgc actccagcct gggtgacaga 18300
gtgagactcc atctctaaat aaataaataa ataaataaaa tgagatgatt tctgagtgag 18360
ttaactaaat caggatatgc agaacaatgc caagcatata ttagccacta aagaatatat 18420
aagttgcctg aaagcccctt tagggtttaa acctggactt cattattcac aatcacattc 18480
ccggtcccca ttacggagcc tggtcacctg ggtgcttgtt agatatggaa atcatcagat 18540
cccaccccag accgagtcag aaacgttgag ggcaggagtt caagaccagc ctggccaaca 18600
tggcggaaac tccgtctcta ctaaaaatac aaaaattagt caggagtggt ggcacaggcc 18660
tgtgatctca gctactcggg aggctgagac atgagaatcc cttgaacctg ggaggcagag 18720
gctgcagtga gccaagatgg tgtcattgcg ctccagcctg ggtgacagag tgggactctg 18780
tctcaaagaa aaagaaaaaa agaaaagaaa ttgcagcttc tgctcaggaa gtctggagtg 18840
ggccaggatt ctgcatttta acaactccca ggagtgttag tggggctggt ttgtggactc 18900
gcctttgagt cgttggtctc cgctcaatca atattagata aaatgacagt attgggagaa 18960
atccaggggg ctctggagga ccgagggatc atattggagg cagatagggc agagaaaggt 19020
ggaggaggtg ggagtcgggt gtggctgtgg aggaagctac ttaaatccgg atttgatctt 19080
tgctagttct tatccctgga cctgaaccca ggcgcacatc tggattagaa gatgccaggc 19140
tcagaggatc ttcgtaaagg taagccagaa aaaatgagaa ccgaagcaaa gacacgtgaa 19200
gaagtggaaa gcagctggcg gcgggaaaag gcagagggac caggcggccg aagctggtgc 19260
ttcgtccacg tgggtggcag ggacttccca cagaggctgt catcgttttt gttgttgttg 19320
ttttgttttg ttttgtttgt cttttgagac agtctcactc tgtcgctcag gctggagtgc 19380
agtggcacga tttcggctca ctgcaacctc cacctcccag gttcaagcaa ttctcctgcc 19440
tcagcctccc gagtagctgg gatgacaggc acacgccacc acacctggct aattttttt 19500
ttttttgtat ttttagtaga gccgggggtt tcaccatatt gaccaggctg gtctcgaact 19560
cctgaccttg tgatccgtct ggctcagcct cccaaagtgc tggggtgaca ggcgtgagcc 19620
actgcacccg gcccaagttt tgtatcttta tagagatggg gtttcaccat gttagctagg 19680
ttggtctcaa gcccctgacc tcatgtgatt ggctggcctc ggcctcccaa agtgctggga 19740
ttacaggcat gagcctcggt gcccggccgc ggctgtcatc tgacagcaca ggcaaatgca 19800
gggaagcctg tttctgcctt caaatccgaa atcttctccc tcgtagttgt gtcctaattc 19860
ttcccacccc gatgcttgtt cttgagcaca ggggaatctg attcctatga ggatgattag 19920
gtcctagata gaatataggc ttagccaagc tggaaatctc atgttcatga gcacttacta 19980
gactctggag ctgctgccaa accattttca ggcatgatgc gattcagatc ttttagagcg 20040
aggcatgcgg tggctcatgc ctgtaatccc agcactttgg gaggccgagg tgggcagatc 20100
gcttcagccc aggagttcaa gaccagcctg ggcaacaaaa caagacgttg tctctacaaa 20160
aaatacaaaa attagccggg catgtcagtg ttgtgtagtt ccagctactc gggaggctga 20220
ggtgagagga tcgcttgagc ctggggaggt tgaggctgaa gtgagctgtg atcatgccac 20280

```
tgggcaacac agcagtacac tgtctcaaga aaaagaaagt aaaaggtgac atccgtgaca  20340
gcagtgatgt tatttttctg cttatttcct tgctatattc ctaaaagaat atacttaatg  20400
aacattgaat aaatgataag aataaaacca tgtccatcca tttcaccttg gattgagttg  20460
cctatttcta cacaaagaaa atagaaccca agaggtaagg cacaagcgat cccttattta  20520
cgtatttatt tatttattta tttattattt tcttgagaca gggtctccct ctgtctcagg  20580
ctggagtgca gtggcataat ctcggctcac cacagcctct gcctctgagg ttcaagcgat  20640
tctcctgcct cagcctcccg agtagctggg actacaggcg tgcaccatca cgcccagcta  20700
atttttgtac ttttagtaga gacagggttt caccatgtta gccagaatgg tcttgatctc  20760
ttgacctcat gatccgcccg ccttggcctc ccaaagtgct gggattacag gcatgagcca  20820
ctgtgcccgg ccaaattttt gtgtttttaa tagagatggg gtttcaccat gctggccagg  20880
ctggtctcaa actcatgacc tgatatgatc tgcccgccct ggcctcccaa agtgctggga  20940
ttacaggcgt gagcaaggga tcccatattt aaatgataac agaaaaaaag gatggaggaa  21000
ccaaggggga aaggaacaac cttttcctat gaaaatgaca aatgaggctt ggaaaaacaa  21060
ggacaaaagg cagatcaagt tgtcctcccg cttcagcctc ccacagtact gggactgcag  21120
cctgaggcac gaccccggcc agcagtgtct ccatatctaa gaacctcagt cacggccggg  21180
cacagtggct cacgcatgta atcccaacac tttgggaggc cgaggcgggt ggatcacctg  21240
aggtcaggag ttcgagacca gcctagccaa catggtgaaa ccctgtctct gctagaaata  21300
caaaaattat ccgggcatgg tggcgtgcgc ctgtaatccc agctactcgg gaggctgagg  21360
caggagaatc gcttgaactc aggaggtgga ggttgcagtg agctgagatt gtgccactgc  21420
actccagcct cggtgacaga acctcagtca cttgatcatc acgttgtacc tcagtggaaa  21480
ggaaaggaaa gctcaggctt ttgagaatgg agttgttagc atttcccatt tgtgtctttt  21540
tcctcctctt tcaaggcaag gaccagatgc attcacacag gaaacgaacc atgttcacta  21600
agaagcaact ggaagatctg aacatcttgt tcaatgagaa cccataccca aaccccagcc  21660
ttcagaaaga aatggcctcg aaaatagaca tacacccaac agtactgcag gttggaaaat  21720
gatccctctt ctcactaaac tgccttcctg atctaatcta aattcagagt ccctctagga  21780
taattcctga ggtctcattc caatcgccaa tattccccaa acccacactc tcctactcac  21840
gtccccgtaa acctttcttc aacccccctag agcaagaatg ggaaaatttt tccagtaaag  21900
gaccaggtag taaataattg aagctttgtg ggccataccg tctctctagc aactatttta  21960
actatgccac cacagtgcga aggcagccac agacaacgta aacaagaggc ccatctgtgt  22020
tcccagaaac tcttttactc aggttggagc acggtggtgc aatcacagct cactgcagcc  22080
tcgacctccc gggctcaagc aatcctacca cctcagcacc ccaagtagct gggactacag  22140
gtctacaggt gcacactacg cctcccaaag tgttgggatt acaagcatga gcccggctgt  22200
attttatttt ttgtagagat ggggtttcgc tatattgccc aggaggctga tcttgaactc  22260
ctggtctcaa gtgattcacc tgccttggcc tcccaaagtg tcaggattat aggcataagc  22320
cactgcgcct ggcctgaagt ttatacaatt ttcacattac aaaatagtgt tgttttgttt  22380
tgttttaaga cagggtgttg ctcttgccca cattggagtg cagtggcacg atcatagctc  22440
actgcagctt tgaattcctg ggctgaagcc atcctcccac tcagattccc aagtaggtgg  22500
gactacaggt gtgtggtact acagcctccc gagcagctga tactactggt gtgtaccacc  22560
aggcccagcc aatttgtgtg ttttttgtag agatggggtt tcgtcatgtt gcccaggctg  22620
gactcaaact cctgaaatca agtgatccac ccacctcagc ctcccagagt cctgggatta  22680
```

```
taggcatgag ccactgtgcc tggccagtag tattctttta ttttctctct tttttctttc  22740
agtcccaaca cacatacaac acaaaatagt actcttattg tgtttgtttt ttctcaacca  22800
ttttaaaacg taaagcctat tcttagtgca tgggtgatac aaagacaggg ggtggtcaga  22860
tttggccacc agccttagct ggctggcctg agccccagag cagcccctgc gactgatccc  22920
cttgctctcc tatcccctgc tctgggtttt ctgacccctg tctcaatttc tgtccccaaa  22980
atctctcatt tctgctcctt cctgggagta gattgagtag ggttccacaa agaggatgta  23040
agtggccaag ctgtggcact agctgttctc acctagaagt actcatatta tcaactaaaa  23100
ggaaaacttg ggttgggtat ggtggctcat gcctgtaatc ccagcagttt gggaggccga  23160
ggtgggcgga tcatgaggtc aggagttcga gaccagcctg gccaatatgg tgaaaccctg  23220
tctgtactaa aaatacaaaa attagccagg catagtggtg tgagcctgta gtccccgcta  23280
ctcaggaggc tgaggcagaa gcatcgcttg aacctgggag gcggaggttg cagtgagccg  23340
agatggtgcc actgaactcc agcctgggcg acaaggtgag actccatctc aaaaataaaa  23400
taaaataaaa taaaaataaa taaataaata aatattagga gagtttaagg gccaaaaaaa  23460
ggaaaaaaaa agaaaagtta aaaacttaaa ggttaaaaaa aagaatataa ataaataaaa  23520
tacgtttaac aaaataaaaa ttaaaaagta aaaatttttt aaaaatagaa tgacaagtca  23580
tctgaattcc accccattct cttctctctc ttcccttcag gtctggttca agaatcacag  23640
agcaaaactc aagaaagcga aatgcaagca tattcatcaa aaacaagaaa ctccacaacc  23700
gccaatacca gagggtgggg tctccaccag tgtcggcctg agaaatgcag acacactacc  23760
cagattgccc aacgctgctc acccgatcgg cctggtgtac acgggtcatc gagtcccctc  23820
attccagctc atcctgtacc ccaacctcaa ggtccctgca aatgacttca ttggccacag  23880
aatagtccat tttggctgct gccgagatcc taatatatac tgcctctacc ccattttgga  23940
atcccaagtt tgcgctccaa gcttccattc tggctctcct gcctgttcat ctaaccaaag  24000
tcgagagaga tgataaatac aaaaagtcac atgttgtaat gatgtgtgtg tggtactgtg  24060
acatttgcgt ttggtcttcg tgcctgtttc ctggaaagca gctccagagt tccatggagt  24120
ctccaaagtg ccatcttttt gtattttgtg tgctaatgtt gaccgatagc ttcaggatgg  24180
ggactggtct ctggaaagac cccagtagga ttagagggca aacttctggg aggggaagga  24240
agctgagggt gaggctgatc accattggcc agtggtttca tcagtcatgt ctgggtaagg  24300
aagcatccat caaaacccag gaggacaggg tttgaagaga tccctgacag ctaagcatgc  24360
ggacgtacct ggagggtggc atatccgggg agggcatgga agctccgggc ccctcgtcat  24420
acgcctcatc ctagcagggt gcggtggctc atgcctctaa tcccagcacg ttgggaggcc  24480
aaggcaggcg gatcacctga ggtcaggagt ttgggaccag cctggccagc atggcgaagc  24540
ccatctctac taaaagtaca aaaattagcc gggcgtggtg gcttgtgcct gtaatcccag  24600
ctactcggga ggctgaggca ggaggatggc gtgaacccgg gaggcagagg ttgcagtgag  24660
ctgaggggat tgtgccactg cattccagcc tgggtgacag agcaagaatc tgtctcaaaa  24720
aaaagaaaca agaaagcaca gaggaccagc tggaatattt ggaagaccag aaaatgtcct  24780
taaaactcaa aatgcctggg catataggtc aggtccacct agccttttga atcaatgcga  24840
acccttcctc aaggcctgga ggttggcaac acaaaatcac cctgtggaga acctaaagca  24900
ttccctctct gagagttgag tcaattggga ttccaccccc aaaattccta aaaatctcaa  24960
gttcctagaa aattctcaga aaaagcaagc tctcctatac ctccctggct gtactctgat  25020
```

```
gcaacttggc aaccatcaga gaatctccat ccccttgaac cttggtcctc tgccaatgtt  25080
cctcacgcct gtaatcccag cactttggga ggctgaggcg ggcggatggc ttgagcccag  25140
gagttcgaga ccagcctggc cagcatggta aaacctcatc tctaccaaaa acatcaaaat  25200
tagccagtct catatactgg tctcaaaata aataaataga ttaaaattta aacataaaat  25260
aaacatgagt gtgttagaaa gaacctactg gcccggcgtg gtggctcaca cctgtaatcc  25320
cagcactttg ggaggcagag gcaggcggat catctgaggt tgggagttcg agaccagccc  25380
gaccaacatg gagaaacccc gtctttacta aaaatacaaa attagccagg catggtggcg  25440
catgcctgta atcccagcta ctggggaggc tgaggcagga gaattgcttg aacccgggaa  25500
ggggaggttg ccatgagccg agattgcgcc attgcactcc aagcctcctg ggcaagaaga  25560
gcaaaactcc atctcaaaaa aaaaaaaaaa aaaaaggaac ctactgtagg atttggagtt  25620
gagtaatttc agatagaatc aaaggaagag aaaggtctgg attgggtggt gccagcggca  25680
gcttctatga ctgagtatct caatacatct tatctatagg acggctgact agaaagagga  25740
caaacctata atagataaat gggcggcagc cattgcttag ccataggcga atatttgatg  25800
ggttggggct caggacaaat gttaaaaaca atcttaataa cagcatgccg gcccggcggc  25860
ccacacctgt aatcccaggg gatttcagag gtggaggggg aggcggaagg attgcttgag  25920
cccaggaggt tgaggctgca gtgagctgtg attgcaccgc tgcactccag cctgggtggc  25980
agagcgagcc cctatatcaa aacaaacatt atcaagaaaa attattaaat gaataacaaa  26040
aacaggctgg gcacggtggc tcacgcctgt aatccaagta ctttgggagg ctgaggcagg  26100
tggattgctt caactcagga gtttgagacc agcctaggca acacggtgaa accctgtccc  26160
tacaaaaaca caaagaagga gtctcgcttt gtcgcccagg ctggagtaca gtggtgtgat  26220
ctcggctcac tgcaacctcc tccatctcct gggttcaagt gattctcctg cctcagcctc  26280
ccaagtagct gggactacag gcatgcacca gcacacctgg ctaatttttg tatttttagt  26340
agagatgggg tttcatcatg ttggccaggc tggtctcaaa ctcctgacct caggtgatcc  26400
acctgcttca gcctcccaaa gtgctggaat tacaggcttg agccaccatg cccagcctct  26460
acaattaatt aaaaaagaac cataacccca aaacttgtac aaccaccagt ccaagaaacc  26520
aagtcacaat ttctgcagca atcagcccca aatgcccagg gcttgatcca tcactcgtag  26580
cttccctagt ttttgtgccc atcccccaac cttgatttca atttaggacc aaccagagaa  26640
acccaatgtt tggctaaaca atcccacagg atcctacttc tggttagctc cctggcggcc  26700
tcccaacgtc agcagccttt ggtcaggaca tatctgaaga cttcgttttt tttctgctat  26760
aaagctttct ttcctttttt tttttctcc tgaggtgaag tctaactctg tctcccaggc  26820
tggaatgtag tggcatgatc tcggctcact gcaacctccg cctccctggt tcaagcgagt  26880
ctcacacctc agcctcctga gtagctgaga ttacaggcat gcaccaccac acctggctaa  26940
tttttatggt gttttttttt gtttgttttt ttgtttcttt ttgtagagac ggggtttcac  27000
catgttgccc aggctggtct cgaactccta acctcaaatg ttctgcccaa ctcggcctcc  27060
caaagtgctg ggataacagg cgtgagccac tgcgcctggc catggaacct cactctttaa  27120
agtgtgcagg gaccccagtc attccccact gtgtcgcggt tcccataaca gtgcctgtca  27180
ccaagtatgt tttcaaaata catttttgga agagagagag aaacagaagg ggagggggta  27240
ggaagagaaa gtaggggaag aggaaagtga gagagggaga caggaaggga gagggaaggg  27300
agacacagag atgaagacaa agggaaagag acagaggccg ggtacagtgg ctcatgcctg  27360
taatcccagc actttgggag gccgaggtgg cggatcacct gaggtcagca gttccagacc  27420
```

```
agcctggcca acatggtgaa acccccgtct ctaccaaaaa tacaaaaatt atctgggagt  27480
gatggtgtgt gcctgtaatc ccagctactc gggaggctga ggcaagagaa tcacttgaac  27540
ctgggaggtg gaggttgtgg tgagccgaga tcgcaccctt gaactccatc ctgggcaaca  27600
gaacgaggct ctatctcaaa aaaaaaaaaa aaaacagaaa gaaaagaaaa gaaaaggaac  27660
agcttccaag catctttgga gaagggcttc actaacatca aatcctgtct tcctctcatc  27720
accttctagc ccagtatttc cccaacgtga gaataataag aatcatctgg ggagctgtta  27780
aaacccagac tctgagacca gacaggggca tgcttcccag gtgtgggcat gatttttccc  27840
tggggttgta tttaacaaag ttcaaaaccc aggaggtaca atcaaaacct gagccgtctg  27900
gagactcaag acttcttagg gaagacgaaa aagagaaatt ccggccaggt gcagtggctc  27960
tcgcccgtaa tcccagcact ttgggagtcc aaggcaggag gatcgcgtga tcccaggagt  28020
tggagaccag cctggccaac atggtgagac cctcatctct acaaaaaaaa aaaaaaaaaa  28080
agagagagag agagaaagaa gttcccagag aaagttccca gaggaaacag gagggaaaag  28140
ggcgaggact gcacccagcc agctagggta tgagtgtgaa ccatagtcta gggggctggg  28200
tgtgaattcc cagtccaggg gctgtgaata cgtggagaca ccgatgctgg ccctgcaccc  28260
agcctcctcc ctgggcgaac tattgactga agccacccct cgtgtcccca ctgttcctgg  28320
tctcaacttc ctcacctgat gaatgggcgg ggagggtaat tcccctacgg tggggctttt  28380
ctcactctgt tatgtgttct tacaaaatgt gctctctgat atcatctata tctccctaga  28440
aggaatcatt agtttatctt tttttttttt tgtgggacag ggtttcactc tggtcgccca  28500
ggccggagtg cagtggtgcg atctcggctc actgtaacct ccacctcctg ggttcaagcg  28560
attctcccac ctcagtctcc caaggcctgg tgcggtggct tacgcctgta atcccagcac  28620
tttgggaggc caaggtgggc ggatcacttg gggtcaggag tttgagacca gcctggccaa  28680
tatggtgaaa ctccctcttt actaataata caaaaattgg ccaggcgtgg tggcgggcag  28740
gtgtaatccc agctactcgg aaggctgagg caggagaatt gcttgaaccc agaaggcgga  28800
ggttgcagtg agccgagatc gtgccactgc actccagcct ggggacagag tgaaactgtg  28860
tctcaaataa taataataat aataataata ataatttagg ccaggtgcag tggctcacgc  28920
ctgtaaaccc agcactttgg gaggccgagg cgggtggatc acgaggtcag gagttcaaga  28980
ccagcctggc taacatggtg aaaccccatc tcaactaaat atacaaaaaa attagccggg  29040
cgtggtggca catgcctgta atcccagcta cttgggaggc tgaagcagga gaatcgcttg  29100
aacccaggag gggaggttg cagtgagcca agaccgtgct actgcactcc agcctggcaa  29160
cagagcaaga ctccgtctca aataataata ataataataa tttaaaaaaa aaataaaaaa  29220
taagaaataa aagaatgaac cacaatgtcc ctttgttcta caggccactc ttgtgctatc  29280
cacagttgcc aaaaaccccc acctgccttg tctatggacg cccatcgggt gataccacaa  29340
acacctttga tcctacagat accagggtaa attcagcatc caagtccttg aattcttccc  29400
gtgagtataa gctgccctgg ctcagccctc ttctttgcca ggaacccaat ccttcaaact  29460
tccctcaaag actgggtact tttagcatga ctgctctaga gattctgggt ggggctcaaa  29520
gtttaacctt cagggtcagc aacattttat ggaaagagcc acagagtaaa tatttgaaac  29580
attctcgtac actgacactc agctggactg gcaaagcaga atatctgtgt gtcagtgtgc  29640
gttttattca gccgttgttt gggtcagggt ctgtgggcgg cccctggcag ctaatgccct  29700
cctgtgagga acaatacctc accatcaagc acagtccgtc acatattctt gccctggtcg  29760
```

```
ctcgctcttt ctttcttttc tttctcttct ttctttcctt tctttctcat tttcgtttct  29820
ttctttcttt ccttcttttc tttttctttc tgtctctctt tatctatttc tgtttctttc  29880
tctctctctc acctttcttt ctttccttcc ttccttcttt ctcttccttt ctttctctat  29940
ctctctttct ttctttcctt ccttctttcc ttgtttcctt ctttcttttc ttttctttct  30000
ttttctttct ttcttttctt tctttctctc tctctctttc ctttctttc tctctctctc  30060
tctctctttc tctctttctt tctttctgac agggtcttgc tgtgtcaccc aggctggaat  30120
gccaagatgc actcataggt cactgcagcc caaataaatt tccccaggct caggtgatcc  30180
tcccacctca cccttccaag tagctaggac caacaggtac atgccaccat gcacgtctaa  30240
tttttatttt tattttttga gactggtctt gctctgtcac ccaggctgga atgcagtggc  30300
acgatcacag ctcactgcag cctcgacaac ccggcccctc caagcaatct ccccctcac  30360
cctcccaagt agctgggacc tcaggcatgt accaccatgc cctgctaatt ttttattgtt  30420
tgtagaggcg gggtctccct atgttgcgca gggtggtctt gaacacctgg cctcaagcaa  30480
tcctcctgcc ttggccaccc aaaatgctgg gatcatgggc gtgagccact gtgcctggtc  30540
tggtcttcct cctttcatcc tcttagtcct tgacctgtcc ctcttctaga gtcctccctc  30600
ttcatgaccc tctccccctt gttggggctc agaaactgat acctctaaat acagcatgtt  30660
aaaggtgcct caagggccgg gtgcagtggc tcatgcctgt aatcccagca ctttgggagg  30720
ccgaggcagg cagatcactt gaggtcagga gttcaaggcc agaccgacca acatgcaaaa  30780
ccctgtctct actaaaaata tggaaaaaga aaattagttg ggtgctgtga cacacgcctg  30840
taatcccagc tacttgggag gctgaggcag gagaatctgg gaggcggagg ttgcagtgag  30900
ccgaggtcac accactgcac tccagcctgg gcaacagagc gagactctgt ctcaaaaaat  30960
aataagaaat aaataaatga gcctcaaggt ctctgacctc ccccgatcat ctcttccaaa  31020
gcacaggcct ttatctgtgt aagatccaga cctgccaaga ggaataattg tttttttcttc  31080
tcctccctgt gagacaaaga atgtaaccac acctgaacag atcccatcac tgtcaatagg  31140
aatgatttcc aggacccatt catgctctct agtaatcctt tattgccctc aatggaattc  31200
ctctagcccc ctcccataat cagtttgcca ggagaacata taagcttctg aaccccccttg  31260
ggggatgggc gatcactggc tctccccatg ctcaggttaa agacatttgt aagccttttc  31320
tcctgctaat ctgcttccta tcagttcttt tcagccaacc ttcagagagc caaaggcagc  31380
cttcaccttg gcctcaacac cttccatgcc ttttgcttct cctcctcccc tgcaaagcat  31440
tccccactcc ttgggttccc cactttcaag catcccaccc tccctgttat atgtcatcct  31500
cctcattctc tgcttttata accctttaa aattatgggc ccagccaggt gcagtgatgc  31560
atgcctgtaa tcccagctct ttgggaggct gaggcaggca gttcacttga gctcaggagt  31620
cctacacagc tggggcaaca tggtgagacc cccatctcta ccaaattgca aatattagcc  31680
gggtgtggtg gtgtgagcct gtattcccag ctactcagga ggctgaggta ggagaatggt  31740
ttgaccccag gagatggaag atgtagtgag ccaagatcac gacactgcac tccagcctgg  31800
gcaacagagc aagatcgagc ctaaaaaaaa aaaaattagg tggggtgcgg tggctcacac  31860
ctgtaatccc agcactttgg gaggtcgagg caggtggaac acctgaggtc aggagtttga  31920
gaccagcctg gccaacatgg caaaaacccca tctctactaa aaatacaaaa aaattagctg  31980
agtgtggtgg cgggtgcctg taatcctggc tacttgggag gctgaggcag gagaatcact  32040
tcaacctggg agccagaagt tgcagtgatc tgagataatg ccattgcact ccagcctggg  32100
tgatagagtg agactctatg tcaaaaaaaa aatacataaa aaaattaaaa attaaaaatc  32160
```

```
aatttaaaaa atgccagcta gtatactttt cctctctccc ttccttttc tatctctctc  32220
tcttttttttt ttttttttt ttttttttt tttttttgag acagtttcac tcttgtcgcc  32280
caggctggag tgcaatggcg tggggatctt ggctcactgc aacctccacc tcctacactc  32340
aaatgatcct tctgccttag cctcctaagt agctgggatt acagatacaa gcaacaaatc  32400
ctaattcttg tatttttcgt agaggcaggg ttttgccatg ttctccaggc tggtctcaaa  32460
gcgaatgctg gccaggctca tttttttaat ttgaattgtg ggaaaactga ggctggatcg  32520
aatggtcctg gacatgccct ggaacaaaca acatttagct gtgcaaggca cagtgtcagt  32580
gtctggtatt ggggtgcccc agtctcaagt cccaagaaaa agacaaggca gaccatgaat  32640
tttgtgtggc tccaactcag ttttcttcat ctgttgcttc acttgcagtg ccagaccaga  32700
atcactttga cctaaaacta gctacgataa ttaacattca gtatgactca ttacctaaca  32760
aattcaaaat gtaaggaact gtctttagaa cttgttctat ataaacatgt tattaaggtc  32820
tgctgcggct gttctatgca gctctttttt ttttttttct ggcgatagga tctcactcta  32880
tcgcccaagc tggagagcag tggcatgatc acagctcact gcagcctcaa cctcctgggc  32940
tcaagcaatc ctcccacctc agcctcccaa agtgctggga ctacaggcgt gcacccctgc  33000
acccaactag ttttgtattt tttgtagaga tggagtgtca ctatgttgcc caggctggtc  33060
tccaactcct ggcctcaagc aatccaccaa ctcggcctcc caagtgctgg gattacaggc  33120
ggacgccact gctcccagcc ccagattttt ttctcattta tatttccgca aacctcaaaa  33180
aaacccccaa aggtccctag gtcagtcact tcccactagt aaataagtca gcatctttgc  33240
aaagatcaaa ggaaaagcaa ttttccttac cacagagcct cttacaggaa agagagctct  33300
gattttccat atgttcccca accatgctag gatgttcctg tgccctgatg gcattcttac  33360
taacccattg ttccattcct ttccagccct ccttcctgta acgtaagtgc aggtgggagt  33420
tggggattgg tccgctaact gggtatagag aaaacagatg ggtatgctat tctcagtaag  33480
ggagcttctg tcctgggaaa aatgtggcct ctcctaagga accctatccc attgaatcac  33540
cctgattcac ttttttttt ttttttttt tttttttttg agatggagtc ttgctctgtt  33600
gcctaggctg gagtgcaatg gtgtgatctc ggctcactgc aacctctgtc tcccggttct  33660
agtgattctc ctgcctcagc ctcccaagta gctgggacta taggcataca ccaccaagcc  33720
tggctaattt ttttttttt ttttttttt tttgagacgg agtcttactc tgtgccaggc  33780
tggagtatag tggcgtgatc ccggcccgct ggctcactgt aacctccgcc tcctggattc  33840
aagtgatttt cttgcctcag cctcttgaat agctgggact ataggcgccc accaccacac  33900
ccagctaatt tttgtatttt tagtagaaac aggttttcac catgttggcc aggatggtct  33960
cgatctcttg acctcgtgat ccacacgcct tggcctccca aagttctggg attacaggcg  34020
tgagccactg cgcccggccc taatttttgt gtttttagta gagatggggt tttgccatgt  34080
tggccaggct ggtctggaac tcctggcctt aggtgatctg cccacattgg tcttccaaag  34140
tggcgagatt acaggcaaga gccactgtgc cctgcctctc acattttctc tcttcccaga  34200
tttggttcaa gaacttaaga gctaggccat gtgcggtggc tcacgcctgt aatcctagca  34260
ctttgagagg ccaaggcagg cagatcgctt gaactcaaga gttccagacc accctgggca  34320
acatggtgag atccctgact acaaaaaattc gccaggtgtg gtggcatgtg tctgtagtcc  34380
ctgctattca ggaagctgag gcaggcggat cgcttcagcc tgggaggtca agactgcagt  34440
gagctgagat ggagacacag cactccagcc tgagcgacag agccagaccc tgcctcaaga  34500
```

aaacaaaaca aaacgataac actggagagc cagagcagga accagtctcc tctccaatct 34560
ccaaacctga gagagacatg agtcacactg acggctttgc ctgcctgcga tctctctatg 34620
tgtgttgatt cttgcggaac aaggcgcttc gagcatctcc tctgccccta cgcccgtgac 34680
cctgtccctc ttcttgtctc cattgccccc caagcgggta catttgccca ccttctcacc 34740
tgggacaccc tgggcgtgga tctcctcacc tgcagcgcta ggtgtgctcc cagggtctcc 34800
acatccctaa cccccgcaag gctggcctct ttacctgcaa agccccccgc cgcggcctcc 34860
tccctctacc ataccccaat gccaggctca cttcctgccg cctgcctgga acggggctgc 34920
tcatgcatcc cccacgccct ctgaagcccc cccggcgcac tccacgccct ctcgcctgac 34980
ccctgtttcc gctgccggcg tctccacacc ccctgacgcc gccacgccct ggaccgaggt 35040
ctctagagct gcgcgccggc tgcacgtccc ttaggagttt ccgtgcgcca cgaggcgctg 35100
gcgcgcgtct cccggcccat ccaccccggg cccggcgaca cctttctttg ccacctggaa 35160
ccaacatctt ggttcccttt tgagggatca gaacttgttt aattggaata cggcaaaatt 35220
ctgaattttt ctgccgtctc tattccaact tcagagttct gccgtccagc cctgcgacaa 35280
tcttccggtg ccaacgcggc aggtcagtat gtatccccca cgatgccccc cgggccacgg 35340
gcccctagtt aacaggtttc cctttcgccc gctgcctgga agtatcgcca cctcgccccg 35400
cccaaccccc caccagacag ctctgcagcc acagcccctc atccaaccag gaagtccagg 35460
gcccatctgg cccgctagac ctcgggaaac cacggcgtca gagcacccat taagaggggt 35520
ccaggccggg cgcggtggtt cgcatcaggg cgcccattaa gaggggtcca ggctgggcac 35580
ggtggttccc atcagggcgc ccattaagag gggtccaggc cgggcgcggt ggttcgcatc 35640
agggcgccca ttaagagggg tccaggctgg gcacggtggt tcccatcagg gcgcccatta 35700
agaggggtcc aggctgggca cggtggttcc catcagggca cccattaaga ggggtccagg 35760
ccgggcgcgg tcgttcgcat tagagcaccc attaagaggg gtccaggctg ggcacggtgg 35820
ttcccatcag ggcgcccatt aagaggggtc caggccgggc gcggtggttc gcatcagggc 35880
gcccattaag aggggtccag gctgggcacg gtggttccca tcagggcgcc cattaagagg 35940
ggtccaggct gggcacggtg gttcccatca gggcacccat taagaggggt ccaggccggg 36000
cgcggtcgtt cgcattagag cacccattaa gaggggtcca ggctgggcac ggtggttccc 36060
atcagggcgc ccattaagag gggtccaggc tgggcacggt ggttcgcatc agagcacccg 36120
ttaagagggg tccaggctgg gcacggtagt tcgcatcgga gcaccagtta agagggatgc 36180
aggccgggca cggtggctct aatccgagca ctttgggagg atcacccgag gtgaggagtt 36240
cgagaacagc ctggccaacg tggtgaaacc ccgtctttac ggaaaaatac aaaatttatc 36300
agggcgtggt ggcgggcgcc tgtaatccca gctattcggg aggctgaggt gggagaatcg 36360
gttgaacgcg ggaggcggag gttgcagtga gccagtgagc cgagattgtg ccgctgcact 36420
tccagcctgg gcggcagagt gggactccgt cttggggaaa aaaagggtag tccaggccgg 36480
gcgtggtggc tcaggcctgc aattccagca ctggaggagg ccgcggcagg aggatcgctt 36540
gagaccagga gttaagagac ctgcctgggc aatatagtga gacccctgtg tttgtttgtt 36600
tgttgagacc cttgtgttaa agcaaactaa atatggcctg agaaggactc cgtaattcta 36660
tatttgagtc cttgtggatg aactgcaacc taacttaata ggtacaaaag attgaaaacc 36720
taagttaggc cctgcgtggt ggctcacgcc tgtaatccca gcactttggg aggccgaggc 36780
gcgcgaatca cctgaggtcg ggactttgag actagcctga ccaacatgga gaaaccccgt 36840
ctcttctaaa aatacgaaat tagccagacg tggtgactca tgcctgtaat cccagctact 36900

```
cgggaggccg aggcgggagg atagcttgaa cccggaaggc ggaggttgca atgagccgag  36960
attgcgccat tgcacactct agcctggtca acaagagcgg gaaactccat atcaaaaaaa  37020
aaaaaaagga agcctaactt acgttttatg cgcctgtaac cgccactgag tgttggccaa  37080
tcccagcagc ccagcagctg tacttcatcc actcacaggc tgctgagcat tcaaactgtg  37140
ttcaaataag gcaaacgctg agcggtaacc aatccagctc tttctgtacc tcacttccga  37200
tttctgtatg tcactttcct tttcttgtcc ataaatttgt tctgaccacg aggcacccct  37260
ggagtccgtc tgaatctgcc gtgactttcg gagctgcccg atttgcaaga ggttcattgt  37320
tcagttgaac tcctttacat ttatttattt tatgtatttt attttattta ttttatgtat  37380
tttattttat tttatgtatt ttgttatttt attttatttt atttatttta tttttatttt  37440
gtttcatttt tatttttatt ttattttatt tttattttca tttttttgag acggagtctc  37500
gctctgtggc ccaggcggga gtgcaatggc accatctctg cgcactgcaa cctccgcctc  37560
ctaattcaag tgattctccc gcctcagcct tacgagtagc tggtattaca ggtgcccacc  37620
accacacctg gttaattttt tctgttttta gtagagatgg ggattcacca cgttggcccg  37680
gctggtcttg aactcctgac ctcaagtgat ctgcccacct cagcctccca aagtgctggg  37740
attacaggtg tgagccactg tacctggccc cctttaaatt taattcggct gaagtttttc  37800
ttttaacaga tggtgtcaga agcggagtcc agagtagagc ttctaggaac cttcgggagt  37860
gctgagtgaa cacgcaaggt gcctgcggaa cccacttgtg tccattgacc tctccgagtg  37920
gccggggatc gtgggtaagt tccctctcgg atttcagagc tccacagatt tgtgttttga  37980
gctctccgag tttcattgag caaatatctg atccaaactg ggtttggaag ctgtgacaga  38040
aactggactg gttctgggaa tggatctgat gtggtaatta gctggcttgg acccagttag  38100
aggcctctta catgtgactg ggtcagaaag aaactggtag caaatggtaa tattgcagga  38160
ggtgtaaaat ttggctttta aaaattaaca gggatgtttg tgttctaccc ctttgtttca  38220
tttttcttgt gcacttaggt attaaaaaaa aaattactgg gtaagttaat caagggaacc  38280
tgagagtaat gaatgccaat attttaggta aaaatgggat cttttttttt tttttttga  38340
gatgaagtct cgtttggtcg cccaggctag agtgcagtgg cgcgatctcg gctcactgca  38400
agctccacct cccaggttca cgccattcta ctgcctcagc ctccccagta gctgggacta  38460
caggcgcccg ccaccacgcc cggctaattt tttttttttg tattttcagt agagacgggg  38520
tttcactgtg atggccagga tggtcttgat ctcctgacct cgtgatctgc ccgcctcggc  38580
ctcccaaagt gctgggatta caggcatgag ccaccacgcc ctgccaaaaa tgggatcctt  38640
aaattctgaa aaactgagtt ccttctggct tatacattag gcacgggaag gagcaaagac  38700
ttacagaaat ggcaaaatct gcctgagcgt ggtggctcac gcctgtaatc ccagcacttt  38760
gggaggctaa ggtgggtgga tcacctgagc tcaggagttc gaaaccagcc tggccaacat  38820
ggtgaaaccc atctctacta aaaagacaaa aattagtggg gcgtggtagc ttgtgcctgt  38880
agtcccagct acttatgagg ctgaggcacg agaattgctt gaacccagga ggcggagttt  38940
gcagtgagtg gagattgcac cactgtactc caacctgggt gacagagcga gactctgtct  39000
caaaaaataa aaatggctgg gcgcagtggc tcacgcctat aatcccagca ctttagaagg  39060
ccaaggcagg tggatcacct gaggtcggga gtttgagacc agcctggcca acatggtgaa  39120
actctgtctc tactaaaaat acaaaaaatt agccaggtgt ggtggcatgc acctgtaatc  39180
ccagctactt gggaggctga ggcgggagaa tcttgaaccc aggaggctga ggttgcagtg  39240
```

```
agccaaggtt gctccattgc actccagcct gggcaacagg agcgaaacac tgtctcgaaa  39300
ataaataaat aaataaataa aaattaaaaa attaaaatga gggctcccga aagttaaatc  39360
tgctaatctt tcagcttcgt tactatcctg atccaaagga agcagactgc agcaccagtt  39420
ggctgacttt ggataagtaa tggggtccat tttacctgag taaagtatgg gatggggtca  39480
gaggccctcc cctcagtaaa gtccccccttg gttaaaaatg ggttaaagat gacagggccc  39540
agctggggtc aagtttgagc cttgcgagtt cagtattggg tgctaagcac agtggccagt  39600
gtctgtgttt tgtcacgtat tttgctttgg cgccatgatg aaaaaatgtt aattggctta  39660
ccccacgcaa ccccttcggc cacacttgca aaactaagag gcttttgctt aaggttccat  39720
aaaacagaaa aagaatttcc tttgtgatgc cgcaggcttg gccctcagga ctatagtgtg  39780
gcaagcagag tcactaggac cacctgggca aagggaacct agaagcctgg catgctggca  39840
aaaggtaaag tatttcttac caattagact gtggcccctc tgtgcaaact ggttagatga  39900
acggtaaaaa tcactgttta tctcctctgt aatgctttga ttaatacaaa aaagaattct  39960
gaggttggtc ttaggaagct gtaataaatc tggtatgctt tgtgtctttc tgtattctgt  40020
cacgaagagg ggtaccttcg gatgaaatgc gtgcccaggg ccgcataagc ccgctgttca  40080
agacggccca gcaaactggt caatcatgtc cttggaagct taacctccta ataccatgtg  40140
gccctgcttt ctcttttcac aacggcaggc caggttcagg gttccattcc cggcttactc  40200
agcgagtact ttctggtgtc acctttacca tgtgttgatt ctcttccctc tgtttcttat  40260
agaacacaga aatattagct gtttggccta gccaaggttg ggtaataaaa gatttaaaag  40320
gactttttaa aacaagcgct atagttaaaa ctcaggtaca ttaaaagtgg atatttggcc  40380
aggcatcgtg gctcatgctt gtaatcccag tacttgggga ggctgaggca ggtggatcac  40440
ttgaggtcag gaattcaaga caagcctggg caacatggca taactctatc tctactaaaa  40500
aaaaaaaatt agctgggcat gttggtgcac gcctgtaatc ccagctattc aggaaggcgg  40560
gaaaattgct tgaacccggc aggcggagct tgcagtgagc caagatttca ccactgcgct  40620
ccggcctggg tgacagagcg agactccgtc tcaaaaaata aaaataaaat aaaaataaaa  40680
taaaataaaa taaataaaat aaaagtgtag tgctcgcttc agcagcacat atactaaaat  40740
tggaatgcta cagagaagat tagcatggcc cctgcacaag gatgacatgc aaattcatga  40800
agcgttccat attttgtgca tcctggcaag atcatttctg tatctgctaa ctagcactaa  40860
agaaatagtg tgaatctaag caaaaatgag tggcacccaa aaacaaaatt gtggttttca  40920
ttaaaaaata taaatattta tataataaaa tatatatgat atataaaaaa taaaatatgt  40980
ataataaaat atacataata tatataaaat aaaaaagtat ataaaaaata tatatgtgtg  41040
tgtatattca aattcttttt tttttttttg agacggagtt tcactcttgt cacccaggct  41100
ggagtccaat ggcacgatct cggcttaccg caacctccac ctcctgggtt caagtgactc  41160
tcctgcctca gcctcccgag tagttgggat tacaggcacc tgccaccacg cccagctaat  41220
tttgtatcc ttagtagaga cagggtctcg ccatgtaggc caggctggtc tgaactcctg  41280
accttgggtg atccacccgc ctcggcctcc caaagtgctg ggattacagg tatgagccac  41340
cgtgcccggc aatgtatata ttcaaattct aacagcctgg gactccttgg gaaaaacagg  41400
aggcaccaga gacgccattt tggaaaaaaa cctgttttcc tcatggaacc acaggaattg  41460
gaaatggata gattcccctt cagaaatcta aggctctgtt ctttttggga ttcaggatct  41520
ggtataaaaa tgggaccctt aatttttgga gacctgtgtt gctttctgct gtgcccactt  41580
attatattgg gccctagaaa ctgcatgctt tcctggtcct tttgtccaa ggactccacc  41640
```

```
ctaaagccag taatctcaaa taaataaata aacacctaaa tcaaatattt tgaaagaaca  41700
ataaaaacta atgcctttta gttcacataa ctttagtaat ctttgggaaa taaaaagttt  41760
taaagattat tgggaaaaat gaagacattt agtctaaatt aggcaggtca gatattaggt  41820
ttgttcgatg ctttaaggtc atcaactgct tcttaggctt ttgaaaattg ttcagtttac  41880
ctacttggga gcattagatt ctagataagg cctgggaaca tgtggaatta gccatgcact  41940
ctatctatgc aaaggttata aagaaaagag attttttttt taattaacaa aaaccacagg  42000
tggttgtgct ccgcctaccc agcacagcag gtgagatggt gcaccctcag tggactgaag  42060
aggccatggg atcccacctc agccggatag cacgctggcc ttcaccttca ttgtgccatg  42120
gcagctttcg tgtgagccac tgactcgtgt acatgttaga ctccttggtc tataagaaag  42180
catcttgtat ggtaaattgt tgttctaaag taaaataact ggtttgttca aaaaggggat  42240
gctaaggaga agtcagaaag tcaaagcatg ttgtagatgg tctgggaaag tcgtgaaagg  42300
gttcgtgaaa ggaaatttaa gccaccaaaa gtaaaagttg ctagttacca ttataacata  42360
tgattgaaac tactgaaaaa atagttttac atggaaagtg tgtgagaaga gtgaaacatg  42420
tttttggtaa aatattttta aaaggcagga gaatgtcaaa tttcacctag ttgagagggt  42480
tatgtgattt ttaaattaga taagaataag ctcacggttt gaacaagttg tggaaggttt  42540
gtaaaaacta atcttgcaaa aaaaattctg tgtgcaaaca cgttgactaa atttaaaggg  42600
gtattttcca gttttccata aattaaacat tgaaatgaaa ggacaaacag ggtttctttt  42660
tttgtttttt tgttgcccag gctatgggca actatgtagc taggcatgtt ggtgcatgcc  42720
tgtaatccca gctactcagg aagctgaggc aggaaaattg cttgaaccca agaggcagag  42780
gttgcagtga gccaagatcg caccactgca ttccagcctg ggtgacagag caagacccta  42840
tctcgaaaaa aaagaaaaaa gaaaagcaat agctccctgg gtgtcaggta tcagtgagaa  42900
tgggaagtca ggtcttctct gactcctagg acattcctct ctctgtcttt gggggttgaa  42960
ttccttgtta gaactccatc ttgttaaagg ggcctcgcac ctgcccttgc cttctgcagc  43020
agccctcctt aatcctctcc aaacttccat ctccagacca ccggattctc ctcatgagtg  43080
ccctgggtgg acattggtga aaggtcactg ccttcaggac acaccatagg tacagtcacc  43140
gaggtaaccc agttcaaaga agagcaggat gttcagtatt tacaaaggga tctagcaatt  43200
ggtccaaacc agtcagtgct ggcatgcacc gttcatcgtg ccatcagtgg caagatggag  43260
atctggcaat gcatggctca cagtaagata cacgccctgt gccattccac cctatcatta  43320
gaaaaggagt cttcttttc tttctttctt tcttttttt tttttttgg agacagggtc  43380
tcactctgtt gcccaggttg tagtgtaatg gtgcaatctt ggctcactgc agcctctgcc  43440
tcctggggtc aagtgatcct ctcacctcag cctcctgagt ggctgagatc acagatgcca  43500
gccaccacgc ctggctaata tttttgtttg tttgtgttat gtttttgag actgagtctt  43560
gctctgttgc acaggctgga gtgcaatggc gcaatctcgg ctcactgcaa cctccacctc  43620
cctggtacaa gcaattctcc tgtctcagcc tctcaagtag ctgggattac aggcgcctgc  43680
cactacgccc gcctaatttt tgtattttta gtagagacga ggttttgcca tgttggccag  43740
gaatggccag acctcaaatg atctgcccgc ctaggcttcc caaagcgctg ggattacagg  43800
tgtgagccac tgcacccagc caatttttgt attttttttt tttttttttt ttgtagagac  43860
agggttttgc cgtgttgccc aggctgatct cgaactcctg acctcaggtg atcaccttcc  43920
ttggcctccc aaagtgttgg gattacaggt gggagccacc atgtccagcc gctttttctt  43980
```

```
tttaaaaaaa atttttttg acataacaga caacaccact ctcttttatt tttttataga  44040
gacggggtct cattatgttg accagtctgg tctttttaaa ttttattttt ttgagatgga  44100
gtctcactct gttgcccagg ctggagtgta gtggcgggat cttggctcac tgcaacgtct  44160
gtaccccaga ttcaagtgag tctcctgcct caggcttcca agtagctggg attacaggct  44220
catgccacat cgctggctaa tttttttttt ttgtatgttt ttaaatttta tcttttaagt  44280
agagacaggg tttccccatg ttggccaggc tggtcctgaa ctcctgactt caggtgatcc  44340
accctcctca acctcccaaa gtgctgggat tacaggcatg agccaccata cccagccttc  44400
ctgctatttt tgaactacct gtaccaggct ggtttctctg ggtgagggga gtggtcaggc  44460
agaggcaggc cccgtcatgg taagcagcta ggagactgct agagattgac agggcactca  44520
tgagtgccct gggtggacac tggtgaaagg tcactgcctt caggacacac cataggtaca  44580
gtcaccaagg taacccagtt caaagtagag caggatgttg ggtatttaca aaggagatct  44640
agcaattggt ccaaaccagt cagtgctggc atgtaccgtt catcgtgcca tcagtggcaa  44700
gatggagatc tggcaatgca tgggctcaca gtaagataca cgccctgtgc cattccgtag  44760
acgtagatca agcgattatt actgcagaaa tctccgtgga cgtagagcaa gcaattatta  44820
ctgcagaaat tgcaggagca ggttctgcag catgtcacat ccaaagaagc ttcccttgca  44880
agttggtaac cttgagggct tcaataccac acagagttgg tctaggtgat ggctgaccat  44940
ccaggcataa taatttgggg aacaattcca ggatggaggt tatgttgcta gacttgtttg  45000
tccgggaaag tggtagacag gaagttcctg tctgcacacg tctcctggct ccagcccttt  45060
cccctgtcca tctgtcctac agactccgcc tcaggcatgt tgtcttggag gacgtgcaga  45120
aaggcagcca tgcactttct aggtttcgat gccgtcttag agtcactggt caccaggtct  45180
gggtcaaacg ggagtctctg gctgtcaaga ctggactggg aggaatcaca tcgcttcttc  45240
accatcagct ttatctgctt tgccttttcc gacttcagct ttctctgcag ggggtatcag  45300
tggggttgac aaagattgac atctttttgt tatcctcatc cctaatcttg ccactgacat  45360
tcttcagtgc ctaggcgatg ctggcattct ccacaaagat gtgggcctgc attttctcat  45420
agcgaaactg aatcaggagg aaggggcatt gcattgactc tgaatcaaat tcagcagcca  45480
cttctcattt tatgcagatc ttgaactagc agctccctaa ggtccgatct ggcctgtttc  45540
cctctgttct tttctctgga ggtttttggc gctttctctg tgttaacatg ggtttggtct  45600
tgtttatggc aagtgcctct ccatggctgg gtgcggtggc tcacgcctgt aatcgcagca  45660
ctttgggagg ccaaggctgg cgaatcacca gaggtcagtt cgagaccagc ctagccaaca  45720
tggcgaaacc ccgtctctac taaaaatata aaaaaattag ccaggtatgg tggcgggcgc  45780
ctgtggtccc agctactcag gaggctgagg caggagaatc gcttgaaccc gggaggcgga  45840
ggttgcagtg agctgaaatt gtgccattgc actccagctt gggtgacaga gtgagactct  45900
gtttaaaaaa aaaaaaagta agtaaataaa taaatgttga tattatgtag ccatgttatg  45960
tagttttgca tagcctttct ctgtcttata gctatgaaag acaatttcca aaacatagcc  46020
tagaatggag aattgaagat aaagtgagaa ctgttgggca tagtaaccta aaaagggatc  46080
ccctctggtg tggaaagatt gttccaacgc aaaagggact gagatccaga gatggcagtt  46140
gtttgagatc tggaatcttc agaagaggta gatcagactt gctcaggaaa taatgggtcc  46200
taccatcaca gcgggtacgg atggggctac aagatgagag aggctggata ggagagtatt  46260
taaggaaaaa aaaaagacag aaaaggacca aaggacagtc tgtgagaccc cagagaatgc  46320
attaaacctg aagaatttct gaacaatgac gtctgatatt caggcttccg ttgtttcttt  46380
```

```
ttgtgctgta atcttccgtg ttttctctgc acatagctca gtaaagctct attcaccagt  46440
taacctagag tctgtcttga gataagcagg gagggctgtg acggctgcac aagggcggag  46500
tggtttgtag acctgaaaag gaacttgtaa gagctggcag atcttaacca ggagagggag  46560
cccctttcca cagcctagaa gcttctgaag tcatttaaat ggaactgaat tatatgaagt  46620
caaatgtcag ttggggaaaa agtcaaactt tattatttat ttatttattt gtaattgtgc  46680
gtatacatat atatatatat atatatatat atatatatat atatatatat aatttttttt  46740
aaattatgat ctccgtgata gtaccaaatc aaactttttt tggagacaga gtcttgctct  46800
gtcacccagg ctggagtgca gtggcgtgat ctcggctcac tgcaacctcc gcctcccagg  46860
ttcaagcaat tctcctgcct cagcctcctg aagagctggg attacaggcg cgtgccacca  46920
tgcccggcta atttttgtat ttttagtaga gatagggttt caccatgttg gccaggctgg  46980
tcttgaactc ctgacctcag gtgatccacc cgccttggcc tcctaaagtg ttggaattac  47040
tggcatgagc gaccacgctg gcccaaaccc tgctttttac tggagagacg aggtagccct  47100
aagttaaaaa aaaaaaaaaa aagaccctgt ttcacttctt ttggatatac ccggggtgac  47160
attgctagat cattctgcaa ttcctccttt tttttttttt tttttttgct gggggtggga  47220
tagagtctca ctcccaggct ggagtgcaat ggtgtgatct tggctcactg caacctccgc  47280
ctcctgggct caaacgactc tcctgcagtg aggagctggg attacaggtg cctgccacca  47340
caacctgcta attttttttt tattttttgt atttttagta cagacggggt ttcactatgt  47400
tggccaggct ggtcttgaac tcctgacccc gtgatccgcc cgccacagcc tctcaaagtg  47460
ctgggatgac aggcatgagc ctccgcgccc agtagatcat tctgtaattc tgtgtttaac  47520
tttttccccc ctaaacttaa ctgaagtgat atttaacttt ctgaggaatc accaaatcaa  47580
aggtgacttt tgagacaaat acaggaagtg gaggtggttt tcctcatgta gatgaagaca  47640
ttctaaaccc agaactgaaa acacacatgg aatcctttta agtatcagga tgccttggtg  47700
gacaaaatgg atacatccaa cttctcaagg agcttaatat tcagtattaa agctgaggtg  47760
agctcaggtg attcacgcct gtaatcccaa cattttggga ggccaaggca ggcggatcac  47820
ttgagcccag gagtttaaga ccagcctggg caacatagtg agacccctcc cccctgcccc  47880
cgtctctaca aaaaataaaa aaattacaga cgcatggtgt agtcccagct acttggcagt  47940
caaaggtaga aggactgttt gaacccagga gtgggttgaa gctgcagtga gccttgattg  48000
taccagtaaa ctttagcttg ggaggcagtt gagaccctgt ctcaaaaaaa aaaagaaagg  48060
aagaatttct ctctcccaac ttcccttggt ttctcctcgc cccccggcta aaaagtgatt  48120
ggggaccttt taaaaaactt cctgctctcc acagaatggg attacagccc cgagatgatc  48180
cataaaagat tttcaggaag aatgaagagt ttagggagtg aaggttctaa aacagtaaat  48240
agagtgtcac aaagaaatcc attcatctct ttgaaggctg ggtatttgga aaaagagaga  48300
aagaaagctt cattcagaga gcgctcgcct gtatttaggg gtgtttggag ggggcggggt  48360
gactatagaa ttagggtaaa gttcagtgtc ttgcaaatca gccctgaaat agccctgatc  48420
cctgcaggcc tgtctggttt cccaaaccct ccactagctt tcaaatttgc attaaaaagc  48480
ttttggcttg ttcattctgt tctttctttc ttttctttct tttatttatt tatttttttt  48540
gagacggagt ctggcactgt cacccagact ggagtgcaat ggcgcgatct ccgctcactg  48600
cagcctctac ctcccgggtt caagcaattc tcctgcctca gcctcccgag tagctgggat  48660
tacaggcgcc caccgccaca cctggcttat ttttttaatt tttaatagag atggggtttc  48720
```

tccatgttgg ccaagctgtt ctcaaacttc tgacctggtg atccacctgc ctcagcctcc 48780
caaagtgctg ggattacagg cgtgagccac tgcgccaggc cctcattctg ttacttcttt 48840
ctttcttttt tcattaattt aagttctggg atacacatgc gggatgtgca ggtttgctac 48900
ataggtaaat gcgtgccgtg gtggtttgct gaacctattg acctaggtat taagcctcac 48960
agccattagc tatttgtcct gatgcccttc tgcctcctgc ccattctttg ttatttcttc 49020
atattccaat taatgttcat tttgaggacc tggctctggc caggcaaggt tccagtctgg 49080
agtcaaactg aggaaagtat tacctttcac aaacacttag accacgttgg gaggggagaa 49140
tgattgtcct ccacatgcgt atgggtgtgt tataaacccc aggaaggtaa atactaagca 49200
aaggcgtgca cagataatta ttgcaactga tgattccacg tcaattgtac tgtactgtga 49260
gtaggtttat aggctgccgt gacaggggcc atcacctggg tacgagggtg ctggcttcct 49320
cttgaagacg tgactttaaa attgtgagtt gaatagatgc aaggatattg gcccagtgga 49380
ggaactttga ggggaggggg cagggtatcc tggttgggag gaaattacat acagaaattg 49440
gggagtggtg acaacattga ctcttccagt aattgtctgg gtgtggtaac tcaggactgt 49500
aatcccagca ctttgggagg ctgagatggg aggattgctt gagcttggga gttccagatc 49560
agcctaggta acacgaggag atctaaaatt gaaaaaaaac gtagctgggt gtggtggctc 49620
attcctataa tcccaacaac tttgactcag gaggctgaag tgggaggatc ccttaaggtc 49680
aggaggttga ggctgaagtg agctagcact ttgggaggcc gaggtatgtg gattacttga 49740
ggccaggagt tcgagaccag gctggctaac atggtgaaac cccatctcta ctaaaaataa 49800
aaaaattagc caggcatggt ggtgcgcgcc tgtaatccca gtgactcggg aggctgaggc 49860
aggtgaatca cttgacccct ggaggcagag gctgcagtga gccaagatca taccactgca 49920
ctctagcctg gacaaccaga gtgaaactct gtctcaaaaa aacaataata attttaaaaa 49980 aatttttaa ataaaaaaat taacaaatga cccgcacatc tggggtgaag taagacgagg 50040
ctggcagcat agctctgtca cctgtggtta ggattaatta agctcagctt taaaggctgg 50100
atcttggcct cctgggtttt aattttgact tctccacttc tcagccatgt tttgttttgt 50160
tttgtttgct tgaggaggga caaatcaggc cagcattgag cctctttccc ccgtgtgtca 50220
actgagattg ataattacaa gattaaatga tgcttgtctg tgattttagc atctgttcag 50280
cccatcattc atttcaagag tattgactgg gcttcagggt aggttccatg ttagtactgg 50340
ggacgccgtg ggtgggaggg agactgggtc tccaccctcc tagagttata gtctaggcct 50400
gcggttaagc agatttttgt gcaggaatca aacccactac actacctgtc agaaatcaag 50460
ccctgttcca ggcactggga aactcagaat ttaaagggga tgtaccaggt ctctgtcctt 50520
gcggagcatt atcgatcagt agaagagaga aaataaacaa gcaaacacct gagacaattg 50580
taatagcaat aatgtgatat caataaaatg aaacagagca acagaaatag ggtagatggg 50640
ccgggcgcgg tggctcaccc ctgtaatccc agcactttgg gaggccgagg tgggcggatc 50700
acgaggtcag gagatcgaga ccatcctggc taacacggtg aaaccccgtc tctactaaaa 50760
atacaaaaca ttagccgggc gtggtggcgg gcgcccgtag tcccagctac tcgggaggct 50820
gaggcaggag aatggcgtga agccgggagg cggagcttgc agtgagccga gatggcgcca 50880
ctgcactcaa gcctgggcaa cagagtgaga ctgtctcaac aaaaaaagaa aagaaaagaa 50940
acagagtaga tggtcttaga aatgacaagg aatcccaatg agaggttcta cctgggacaa 51000
aatagaaaaa tgggaaatca taataagctc tggaattggg gcagtggtat tgtttatttc 51060
ctagttgtgg caaatctaat gtaaaatatg gacattaaag aaaactgggt ggagaacata 51120

```
gagaactttc tgtacttttt gcaacttttc tgtaagtcta aatttattcg aaggccgggc  51180
gcagaggctc ctgcctgtaa tcccaaaacg ttaggaggct gaagcaggta gatcacttga  51240
gcttggtagt ttgagaccag cctgggcaaa aaagtgagac ttcatctcca ttaaaaattt  51300
aaaaaattag ctggctttgc tggtgagcac ctgcaccaga ctggttagcc tgggcagcat  51360
agtgagaccc cgtttctata aataagataa aaatcagctg ggtgccaggc gtgatggctc  51420
atgcctgtaa tcccagtgct tcgggaggcc gaggggggcg gatcacctga ggtcgagagt  51480
ttgagaccag cctgaccaac atggagaaac cccgtctcta ctaaaagtac aaaaattagc  51540
tgggcgtggt ggcacgcgcc tgtaattcca ggtactaggg aggctgaggc aggagaatca  51600
cttgaacctg ggaggcggag gttgcagtga gctgagatca ctccactgcc ccccagcatg  51660
gctacagagc aagactccgt agcgggatat tgcatgcatg taatcccagc tactctggag  51720
actgaggcag gagaatcatt tgaacctggg gggcggaggt cacagtgagc caagatcatg  51780
ctattccagc ctgggtgaca gagtgagact acctctcaaa aaaaaaaaaa agaaaaagaa  51840
aaagaaaaag aaatgcattt acagaagcta ggaaaatcaa attcagggag gaggctggag  51900
ggcaaagagt gggtgtggcc agactttaat ccattctcca tctgtggggt ggtccctagg  51960
gtataaaaga gctccagggc ccctgccctg cctttcatcc tcaggatggg aagtcctcac  52020
agagttcagt aagtattggc ttcccatggt gtttctgcac ttcccccggg gtcatatgag  52080
cctcacattt aggttgtaag actcccccta aaatctccaa cactgagtcc tctctatttg  52140
tagtcatgac tccgacacct tgattctctg cccctaatac tctttttttt tttttgagac  52200
ggagtttcac tcttgttgcc caggctgcag tgcagtggtg tgatcttggc tcactgcaac  52260
ctctgcctcc cggattcaag caattctcct gcctcagcct cccgagtagc tgggattaca  52320
ggcatgcacc accatgccca gttgattgtt tttgtatttt tagtagaggt ggggtttcac  52380
catgttggcc aggtctcaga ctccaagcct cgagtcatcc gccctcttca gcctcccaaa  52440
gtgctgggtt tacaggtgtg agccaccatt cctggaccgc attattgatt ttttaaaatt  52500
tttggatttt gttcaattag tgattgagtc tcactgtgtt gcccagatgg gcttgtctcc  52560
caggctggag tgcagtggtg agatcgtgac tcacagtagc ctcaacctcc ctcaccccag  52620
cgtcccgtgt agttgggatg gcaggcatac aggaccatgc ttagctaatt tttttttttt  52680
tttgtagggt tggggtctcc caccattgtc taggctggtc atcaacacct gggcacaaac  52740
atcctctcac cccggcctct gagccactgc acccagtagg ttttaggttc attttatttt  52800
ttatttaggt gtccacaaag gcagcttttt ccttttcttt attttttaaa gagacagggt  52860
ctcactctgt tgcccagggt ggagtgcagt ggccagatct tggctctctg caacctctgc  52920
cttccagact caagtgatcc accttcgtct ccagagtagc tgggactata ggtgtgcaca  52980
aacacaccca gctgagtttt aaatcttttg tagagaaggg ggcctcagta tgtttcccag  53040
gctggttttg aagtcctgtg ctcaagcaat ccttctgcct tggcttccca aactgctagg  53100
attacaggtg agccaccaca ccgggcctgt ccacgtaatt taaaaggtgc tggacgtgtg  53160
cggtggctca cgtctgtaat cccagcactt tgggaggctg aggtgggcgg atcacgaggt  53220
caggagttcg agaccagcct ggccaatatg gtgaaaccct gtctctacta aaaatacaaa  53280
aattagccag gtgtggtggc aggcgcctgt aatcccagct tctcaggagg ctgaggcagg  53340
agaattgctt gaacccagga ggcggaggct gcagtgagct gatgatcgct ccatggcact  53400
ccagcctggg caacagagca agactaagaa aaaaaaagaa agaaaaagaa aaagaaaaca  53460
```

```
aagtaatgta aaaggtgtta ttcaggctgg ggacccccaa agtgctggga ttacaggcat  53520
gagccccagg gcaggcctag gatttgcatt acaaggctct gcattgttcc tgagaactgg  53580
agagagtgct caatctacct ttcgctattg agcaacattc agaagtcagt tttaaatctc  53640
ttatcttctg catagaggat gtgcctgcag tttccaggta ctggacaata cagggagggt  53700
acttctcagt ctgtggcact cagccttgag ggcactttct ggtgccagaa tgaaagtgct  53760
gtcatagctg aggtccaatg actgaggcga gcaccgaaga aacaccatgg gggggagggg  53820
gggcgggggg ctccaggagc cactgcaggt aaaagctaaa ccgtggtgct tgttctgcgc  53880
cataaactgg acttcagccc agctttaagg aaatgaccac ggtctctggg ttgtgaggct  53940
gggttccgta gcagctataa tgcttggatt cagggatagc ctgggtcaca ccattgccag  54000
agaagaggca accaatccag accccaaaag cgggttcttg gatctcttgc tggaaagaat  54060
ttcgaggcaa gtcacaacac agcgaaagaa gcaagctgag gcctgggctc aatcctcctg  54120
cttcgtcctc ccaaagtgct gggattacac gcatgatccc ctgtgccctg ccaatatttg  54180
gtaattataa ctggtggtca gcttacaatg tggctatttc cagaccataa gtaccaactc  54240
tataggtgcc ttgtgagtga gtgccttgct acttcaagca gttactttcg tgtgttatta  54300
aaccagaggc ctgctaagcc tctgtgccta gtaaagatta caatttggaa tgtcagcccc  54360
cagctgtcct gtgtgattgg caggttaggt ccttgttgaa ccagaagcaa ctggccagtc  54420
gtacagatgc aactttcgga ccagtagaaa atttctatgt caacctggag acatagggat  54480
tgtacctttc tgatacccta ttagtaaata aatagtattt atttataaat tatgtataat  54540
agtatttatc tgaatatatc ccaagcagcc caagtgtgtt ccagacataa catttttatt  54600
tacatttaaa tatcactaag attagagata cacatctaac tcaggttttc aactagtctt  54660
accattgaaa gaactattgt ggcaggacgc agtggcgcac gcctattatc ctagcacttt  54720
gggaggccga ggagggcgga tcacaaggcc aggagttcga gaccagcctg gccagcatgg  54780
tgaaacccca tctctactaa aaatacaaaa aaattagctg ggcatgatgg cacaggcttg  54840
cagtcccagc tactcggtag gctgaggcag gagaactgct tgaacccggc agacggaggt  54900
tgcagtgagc cgagatcgcg ccaccgaact ccagtctggg caacagagca agacgcttgt  54960
cttaaaaaag agagagaaag aactacttgt tctctgtaag ccatgctggt ttagccaaaa  55020
tgctgcagtt gtgtatggcc agggacgttg aggctgcagt gagccgacgg ctgtgttgcc  55080
gctctgcagt ctgggggaca gagcaagaac ctgtctcaaa aaaacaagaa gttagtgaga  55140
cagacatgcc gttctgttac ttttcccctt gctggttcaa agctaggtag ttgccaatta  55200
aatgtaatct tgtagagcaa aaatgttttt catttttga gacaggatct cactctattg  55260
cccagcctgg agtgcagttg tgggaactca cagcaacctc cacctcctgg gtttaggcag  55320
ttcttctgca tcagtctccc gagtagctga gactacaccg gtgcccagag ggcagtggcc  55380
agatcttggc tctctgcaac ctctgccttc cagattcaag tgagccacct ccgcctcctg  55440
agtagctggg actataagta cgtaccacca tacccagtta atttttgcat tttttgtaga  55500
taagggggct aagtatgttt cccaggctgg tttcgaagtc ctgtgctcaa gcaatccttc  55560
tgccttggct tcccaaactg ctaggattac aggtgagcca ccacaccggg cctgtccacg  55620
taatttaaaa ggtgctggac gtgtgcggtg gctcacgtct gtaatcccag cactttggga  55680
ggctgaggtg ggcggatcat gaggtcggga gttcgagacc agcctggcca atatggtgaa  55740
accctgtctc tactaaaaat acaaaaatta gccaggtgtg gtggcaggcg cctgtaatcc  55800
cagtttctca ggaggctgag gcaggagaat tgcttgaacc caggaggcgg aggctgcagt  55860
```

```
gagctgatga tcgcgccatg gcactccagc ctgggcaaca gagcaagact aagaaaaaaa  55920
aaagagaaaa agaaaaagaa aacaaagtaa tttaaaaggt gttattcagg ctggggatcc  55980
ccaaagtgct gggattacag gcatgagccc cagggcaggc ctaggatttg cattacaagg  56040
ctctgcattg ttcctgagaa ctggagagaa tgctcaatct acctttcact attgagcaac  56100
attcagaagt cagttttaaa tctcttatct tctgcataga ggatgtgcct gcagtttcca  56160
ggtactggac aatacaggga gggtacttct cagtctgtgg cactcagcct tgagggcact  56220
ttctggtgcc agaatgaaag tgctgtcata gctgaggtcc aatgactgag gcgagcaccg  56280
aaaaaacacc atgggggga ggggggcgg ggggctccag gagccactgc aggtaaaagc  56340
taaaccgtgg tgcttgttct gcgccataaa ctggacttca gcccagcttt aaggaaatga  56400
ccagggtctc tgggttgtga ggctgggttc cgtagcagct ataatgcttg gattcaggga  56460
tagcctgggt cacaccattg ccagagaaga ggcaaccaat ccagacccca aaagcgggtt  56520
cttggatctc ttgctggaaa gaatttcgag gcaagtcaca acacaatgaa agaagcaagc  56580
tgaggccggg cgcggtggct cacgcctgta atcccagcac tttgggaggc tgaggtggat  56640
ggatcacctg agatcactat ttttcttttt attttctgag atggagtttc actcttgttg  56700
cccaggctag agtgcaatgg cacgatctcg gctcacagca acctctgcct cccgggttca  56760
agccattctc ctgcctcagc ctccggagta gctgggatta ctggcatgcg ccaccacgcc  56820
cagctaattt tgtattttta gtagagacgg ggtttctcca tgttggtcag actggtctcc  56880
aactcccaac ctcaggtgat ccgcccgtct cggcctcaca aagtgctagg attacaggcg  56940
tgagccaccg cacccagcct gttttctgca tttttagtag agacagagtt tcactatgtt  57000
ggccaggctg gtctcaaact cccgaccttg tgatctgccc gcctcggatt cccaaagtgc  57060
tgggattaca ggcgtgagcc accgcgcccg gccttatttt tcttttttt tttttgagac  57120
aggatcccac tctattgccc agcctggagt gcagtgcagt gatctcagct cactgcaacc  57180
tctgcctccc gggttcaagc aattctcctg catcagccgc ccaagtagct gagattacag  57240
ccgtgcctgg cttatgtttt gtgtttttag tggagatggg gtgccaccat gctggccagg  57300
ctggtcttaa actcctgacc tcagttgatc ctcccacctc agtctcccaa agtgctggga  57360
ttacaggtgt gagccaccgc gcccagcaag cataagattt tttgacacat ggaggatcac  57420
ttgctggatg tgcactgaga agtaatgtgc ccatttccca gccacactct cccaaaggct  57480
tttacaggcg ctgtccccgt gaggtggtag aacagaatgt cagaattcaa cacattccaa  57540
cactgtcttc tgttgagctg taggaggact gcctgtggag ggacatgggt tctatgctac  57600
cttgcaggtt ttccctgggg cttgtgatca ctgtctcctt ggtgacatgc aatctgggag  57660
tgctttctgg agtctgataa gaacatactg gcacattgcc tgtgacgtgt gggacccagg  57720
cattttcagt gctgaggtga gtccttgatt gtaactgatg gggactggta tcttaactcc  57780
aggttactga agactaggaa tttcttgcct tacagtaaaa ttgcaaagaa gagtagcata  57840
agaggtagat cagaagactg cagaatagat taacaaatga atgcccaaat gaggatgcta  57900
aacttggatt tgcatcaaga agacagatat tggtcgggcg tggtggctca cgcctgtaat  57960
cccagcactt tgggaggctg aggcgggtgg atcatcctgg ctaacacggt gaaaccccgt  58020
ctctactaaa aaatacaaa aaaattagcc gggcgtggtg gcaggcgcct gtagtcccag  58080
ctgctgggga ggctgaggca ggagaatggc atgaacccag gaggcggagc ttgtagtgag  58140
ccgagatcgt gccactgcac ttcaccctgg gcgacagagc gagactctgt ctcaaaaaaa  58200
```

```
aaaaggacag gtattaggat agttttgaag cccacttgct cctatcatgg cattgaagca  58260
tcagtttgct gccaatcact ccttcttctg tgttcataga caggactgtg gaaatgtaca  58320
cttggattct ttcacaggta atgctgagaa atttaaaacc aaaaacggcc gggtgccgtg  58380
gctcctgcct gtaattctag cactttggga ggctgaggcg ggcggatcac aaggtcagga  58440
gttcgagagc agcctggcca atatggtgaa accccatctc cactaaaaat acaaaaatta  58500
gcctggcata gtggcgggcc cctgaagtcc cagctactca ggagactgag tagacgagga  58560
gaatggcttg aacatggggt gcagaggttg cagtgagctg agatcgcacc gctgcactcc  58620
agcctgggca acaagagtga aactctgtct caaaaaaaaa aaaaaatttg aaattaaagt  58680
gtatgattag agtgcatgat tggttctgac tggatgtgta acatgtgcat agccttctca  58740
taaatcaaag gtttttatgt gaaacctacc actagtgatg taactgaatt tgtgtaaatg  58800
ctggtgtgtc tgccttttcc tagcaactcc ctgggcagcc tgaggattct ttgaggttat  58860
tttttttcaa gatctggctg ggagcttctg catgagtgct gtgtgaacgt cctccatctg  58920
cagtgtgagg acagcgaacc ctagtgtgag ttaaccacgt aggaagagtt tgaagtcaga  58980
catgacattc agactgaggt cctcaaaact gaggggcatt ttctgtggtt tgaaaggaaa  59040
gtgcacccag ttttggggat gtcaattgtg aatcctcatc ataacccatc cccagtcccc  59100
catcgcattg caccacatgg atgcacccag tggactggcc tttgcttttc tattgtttct  59160
ttttctctcc actgcaatca gctttctcac gttgaatgca ttccattttc taagcgctct  59220
cctaggcaaa aatccctcta atgcaaagca aaaatgtctg ttatgcaaca ttgttctgag  59280
accccaggaa ttgcagttaa cttggctcct tagtatgtgc ttcctaaggc gggtggggtg  59340
gctcgcgcct gtagtcccag cactttggga ggcaggcgag gcacttgaaa ccctgtctct  59400
actaaaaata caaaaattag ctggacatgg tggcatgtgc ctgtaatccc agctacttgg  59460
gaggtgcaga caggagcatc gcttgaaccc aggaggcaga ggttgcagtg agccaagata  59520
atggcactgt actgcaacct gggtgacaga gcgagactca aaaaaaaaaa aaagtgcttc  59580
ctgtgaaggt ttcctttccc ttctgccccc cataccagtc catctattta gtagatgtcc  59640
tggtttctac ccaggatatc atggaccagg ggttctgtct tccagccttg agtacaatgg  59700
tgcgactata gctcactgca gtctcaacct cctgggctca agtgatcatc ctgcctcagc  59760
ctccaagtag ctggtattac agatgcacgt gcccccattc ccagaggttc ttaaatttat  59820
gacaaaaacc cagaagcttg gctgaagcag cttgttgggg cccacccaca gattttgttt  59880
ggtgccatag acctgggttg ggatctgggg agccattttt cttagtctca atgtaaatgt  59940
ctaagcattt tctttttttc tttcttttt tttttttgag acagggtttc gctcttgttg  60000
cctaaactgg agtgcagtgg cacaatctcg gctcactgca acctctgcct cctgggttca  60060
agtgattctc ctgcctcagc ctcccaagta gctgggatta caggtgtgca ccaccatgcc  60120
cggctaattt ttttttattt ttttattttt tttatttttt gagatggagt cttgctctgt  60180
tgcccaggct ggagtgcagt ggtgtgatct cggatcactg caagctccgc ctccttgatt  60240
catgccattc tcctgcctca gcctcccgac tagctgggac tacaggtgcc cgccaccacg  60300
cccagctaat ttttttgtat ttttagtaga gacggggttt cactgtgtta gccagggtgg  60360
tctcggtctc ctgatctcgt gatctgcctg cctcggcctc ccaaagtgct gggattacag  60420
gcttgagtca ctgcccctgg ccaatttttt gtatttttag tagaaatgga gtttcaccat  60480
gtttcctgcc tatctctcta tgtatttaga cagggtctca ctatgttgcc caggttggtc  60540
tcaaactcct ggactcaagc aatcctcctg cctccacctt ccaaagtgct gggactacag  60600
```

```
gcttgagcca tcctgcctga ccatttgaga gttttttttt tttgagatgg agtctctctc  60660
tgtcacccat gctgtagtgc agtagtgtga tcttgcctca ctgcgacctc tgcctcccgg  60720
gttcaagcaa ttctcctgcc tcagcatccc cagtagctgg gattacaggc gcccgccact  60780
acacccagct aatttttgta tttttagtag agacagggtt tcaccatgtt ggccaggctg  60840
gtctcgaact cctgacctca ggtggtctgc ccacctccgc ctcgcaaagt gctgggataa  60900
gaggcgtgag ccaccgtgcc tgtcttcaac aatgatttct aattgcattt tatggtggtg  60960
attgaacata atgtactttg gtccttctcc attgtatgcc tcgtgtatta tgtgtctcat  61020
aacgtctgtc ccgtcctatg ctatgtgtgc atttgaatgt tggggagggt tcagtagatg  61080
tccattgagt tggtttgcaa acttatttga aacttctact tacttctgcc taattctgct  61140
tattattgag agtggactgc tctgggatgc cttttgtttg cactctgatt tcagatggac  61200
cctgagaatg ctcaagcccc aaaccctcct tgggaagtga agctcaggct gtgatttcaa  61260
gccagggggc gtttttctat aactggatga aaagcacctc cagagcttga agctcacagt  61320
ttgagagcaa tcgtctaagg aagttgatgg caatgttaat agtttttttaa acaagcatga  61380
aatcagattc ctgtgtttac ttctggatgc tgttgatcca ggaaatgtac ttagaaaatt  61440
cattttaacg gaaatagtca taagcgtctt ggtaatttca tgaagctaca gtgagtaaat  61500
tgcctgagaa tttccctgcc tgaaaggtct tcaggagtgt aatttttttt taatatagct  61560
tatttaatac aaatagagat gcggtctcac tcttgcctag actggtgtgc agtgtcatgt  61620
tcacagctca ctgcagcctc tcaacctccg gggctcaagc atcctcctgc ctcagcctcc  61680
caaagtgctg gaattacagg tgtcagccac cactccctac tcatacttgt atatttctct  61740
ttaaattctg ttgaggtttt atggcctagc ctgtggtcta tcctggagaa tatttgtgtg  61800
catgacaatg tgtatatata tatatatata tatatttttt tttttttttc ttttttttga  61860
gatggagttt cactcttgtt gccctagctg gagtacagtg gcatgaatct cagctcactg  61920
caacctccgc ctcccgggtt caagcgattt tcctgcctca gcctcccgag tagccgggat  61980
taccctccac cacacccggc taatttttgt atttttagta gaggtggggt ttcgccatat  62040
tgaccaaggt ggtcttgaac tcctgacctc aggagtcccg cctcggcctc tcaaagtgct  62100
gagattacag gcgtgagcta ccctgcccag gctgaccatg tatattccta atttttgtac  62160
tttttttttt ttgagacgga gattcactct tgtggcccaa gctggagtgc aatggcatga  62220
tctcggctca ctgcaacctc tgcctcctgg gttcaagcaa ttctcctgcc tcggcctccc  62280
gagtagctgg gattacaggt gtgcaccacc acgcctgact gacaatatat attcttaaac  62340
agctcagatt ccattttgga tcctcccatc aggactggaa cttaggtgta ctggaactta  62400
ggtgaacact tggctcaaaa ttcattgctg ttctctataa atctagccag ttctcttggt  62460
taaatttaag gtatgtatag tagtcgctgc tttttctttc gggggacaaa actcaggagg  62520
attgcttctt gattcataag ggcaacctgt tgagattttc acgcaaggaa cccgagatgt  62580
tcatttaatg ggcttataat ttgggattcc agaacacatg caaacagggc aaatgaatgt  62640
ttggctgtat ctttattttt gtgttcattt cagcctggtc aaggttttag aatccaagga  62700
aaccaataaa cacccagagt gctggagcaa gactgtctcc tgctgtgacc ctcaagatgg  62760
aagcagtttc tgttgtctga aaggaaagaa agtgcttcct ttttgagggt tactgtttga  62820
gaaaagcaac cttgaggttg atgctgatgt ttgtaacaca cctgcagagt atacttataa  62880
tcagacttgg gtgatgtgag gttttgtttt tactccaaga tgagggtctc cacccaggct  62940
```

```
ggaatgcagt tgcccttcca acctagaact cctgggatga actggtcctc tatgcctcag  63000
cctgccgagt agctgggact ataatatagg ggtgtgccgc catatttggt agatttttca  63060
attttttgta gagatggggc ctcaccctgg ccaggatggt ctcaactcct gagctcaagc  63120
aatcctacag gtgtgagcca ccgtgcccat tttaaagata gttgacatga tcaagcatag  63180
tgggacacac agccccagct actgcagagg ctggggtggg agagtctctt gatttcaatg  63240
ctataccgtg cactaatgac acctttgaat agccactgca ctccagcctg ggccaacata  63300
gcaagatccc atctcttaaa aaaaaataca ttacatggca cctggttcca gagacaccat  63360
ttgtgttggt caaacaatgg cctcctataa atttagttta atgaatccaa accatgtttc  63420
cttcattaag agagtaaata agcctccaag tctatccagt ctttttgaga cagagcttgg  63480
ctcttgtcac tcaggctaga gtgcaatggt gcaatctcag ctcactgcaa cctctgcctc  63540
ctgagttcaa ggagttctct cacctcagcc tcccaagtag ctagaatgac aggcgcctgc  63600
caccatgacc agctaatttt tgtgttttta ctagagatgg ggtttcacca tgtcggtcag  63660
gctggtctcg aactcctgac ctccgtgatc cacccacctc agcctcccaa agtgccggga  63720
ttacagacga gagccaccac gcccggcctg tccagtcttg ttctgcagtc cccaatgggg  63780
attttttttt tcctgttcat ttgtcttttt attttaatct acttgtccct gacactgaaa  63840
atttttcctt cctaacagct taccatcatt tctcagaata gacctgcttc ctctgtgaga  63900
agcttatagt tgattcaacc ctcaaccact aatgccaaca accctagtga gttcttttga  63960
ctacagctgg accatttatc ctgtttcctg tgggtagcgg ttccaatgta ccattccaac  64020
aggcaaaacc tcgcctctga atacaggttg cttggcaaga tctaaaatgt ttgctgtgcc  64080
taatataaac tattgtaaag aaaatccatc tcaatcacag tgacaaatgt cacatgagac  64140
aaaaccacag atattttcgc aaaaataggg tcctttagaa ccctagaagg gtctctctag  64200
taacaggtgg gatgttcagc agctcttgtt gttgccacag tgagcgatgc ctgttcgtcc  64260
agcccttaac acctcttact ccatggaagt tctgcctgca ctgctttata gaacacctct  64320
tgggttgagg tagagttgga ggggacctca gtgtcccttg ctgatgggat gtgcactgct  64380
tagcaagcgc acggaggtgg agtgcatggg ctctgagttt ttattgggta aatgcagccg  64440
aaatgtagtg tgcatgaaca ggtcaaaaaa ttgcacattt gatttaattt ttaaatttta  64500
gagatggggg tctcactgtg tcacccagac taaactgggc tgtgctccta tgcgtaccct  64560
agtagctggg acttcaggtg aatattaacc catgcatagg caaggagaga ggaaggctct  64620
gacagtctgt gatctcccct cactgcaacc tccaccctct ggactgggaa cgtcagggca  64680
ctgcaccgat gcaggcagga tgagccgagg ggaaaggaga gccaggcatc actggctggg  64740
gacattttgg gtttgatctg gatggagcag gtgtctcctg gagagagagc ccctgggatt  64800
ttcactctgc tccctggctg tcttagtcat ggaatctgac aacagagact cctgcccagg  64860
gccacttcat ttggtttctg gaccccagtg gtccttcctg cctggactta ggatcttttg  64920
gggaagtttg ggatctggca gggcatctgc ataatccata gaaatccctg agagtcactt  64980
cccttggctg acatctccat gttcctaccc attaccttcc aaaggagacc cttaactgaa  65040
ttaccaaagg gggcttccca gagcagggaa acccggttaa ctttctattt caggtcaaca  65100
gtatacttga gatgtacttg aactagaaat gattggttgt ttaggtgtgg gcatttgttt  65160
ttcctaactt agtctccaag aaaaaaaatt attgaggttt tacagcctag cctgtggtct  65220
atcctgaaga atgttcgtgt gtgtgacaat gtacattctt tttttccccc cagctctgtc  65280
aaatcttact gaggagcttt tacggcctag cctgtggtct gtcctggagg gtatttgtgt  65340
```

```
gtacaacaat gtatattctt aaacattatc ttagattcca ttttggatgt tcccatcagg  65400
actgtgtgtt tctgtgctgg aactcaagtg aacactggct caacatcctt agaaatccag  65460
cccaattctc ttggttaaag ataaggtatg tgtggtaggc attgcttttt ctctttgggg  65520
acaaaactca ggaggattgc cccttgatga acaaggctaa cctgctaagc ctttgaagca  65580
aggaactgga gatggtcctt tcaggggttt atgttctgga ttccataaaa catgcaaaca  65640
ggggcaatga atgcaccttt tttattttta tttttatttt tttttgagat ggagtcttac  65700
tcttgccagt ctggagtgca gtggcacgat ctcggctcac tgcaacttct gcctcctggt  65760
tcaagtaatt cccctgcctc agcctcccga gtagctggga ctacaggtac atgccaccac  65820
aggcggcaaa tggttgtatt tttagtagag acggagtttc accatgttgg ccaggatggt  65880
cgtggtctct tgaccagcct cccaaagtgt tgggattcca ggcgtgagcc accgcgcctg  65940
gccaatgaat gcatctttat ttttgtgttc attttaatct ggtaaggtaa attccaacaa  66000
aaaacccaga gttttggagt gagaagatct catgcagtca ttctccaaaa gaaagcactt  66060
tctgttgtct gaaagcagag tgccttcttt tggagcgtta ctgtttgaga aaaaccacgt  66120
tgaagttgat gctgatcttg gtaacacatt tgcagagcgt gcttatcatc agacttgcat  66180
gatgttgggg ttctgttttt gtttagtttt tttgcaacac agggtctctt gcccaggctg  66240
gagtgcggtg acacttccaa cctagacctc ttgggctcag ttggtccctg cccccacccc  66300
ctcccccttt tttttctctt gagacagtct ctctctgtgg cccaggctgg agtgcagtgg  66360
tatgttctct gctcactgca acctctgcct cccgagtagc tggtattaca ggcacatgcc  66420
accacgcctg gctaattttt gtatttttag cagagacgga gtttcatcat gatggccaga  66480
ttagtcttga actcctgacc ttaggtgatc cacctgcctc ggcctcgcaa agtgctggga  66540
ttacaggcat gagccactgt gcctggccca caacgtatat tcttaaatat catcttagat  66600
tccattttgg ttgctcccat cgggactgtg tgtccctgtg ctggaactca agtgaacaca  66660
tggctcaaaa tccattgctg ttctctagaa atccagccca attctcttgg ttaaatataa  66720
ggtatgtgtg gtaggctttg ctttttctct ttggagacaa tactcaggag ggttgcccct  66780
tcgtgaacaa ggctaacctg ctgagccttt gaagcaagga actggagatg gtccttttag  66840
gggtttatgt tctggattcc agaaaacatg caaacaggga caatgaatgc atctttattt  66900
ttgtgtccat tttaacctgg taaggaaaat tccaacaaaa acccagagtt ttggagcgag  66960
aagatctcat gcagtcattc tccaaaaggg agcactttct gtttgaaaga aaacaaagtg  67020
cctcctttta gagtgttact gtttgagaaa aaccacgttg aagttgatgc tgatcttggt  67080
aacgcatttg cagagcgtgc ttatcatcag acttgcatga tgttggggtt ctgtttttgt  67140
ttagtttttt tgcaacacag ggtttctgtt gcccgggcag gagtgcggtg gcgcttccaa  67200
cctagacctc ttaggctagt tggtcccccc tacttttttt gttgtttttg ttcttgagac  67260
agagtctcac tatgtgggcc aggcgggcag gcagtgacac attctctgct cactgcaacc  67320
tcggcctccc aagtagctgg tattataggc acgtgccacc acgcctggct aatttttgta  67380
tttttagcag agatggagtt tcaccacatt ggccaggtta gtcttgaact cctgacctca  67440
ggtgatctgc ccgcctctgc tttccaaagt ggtgggatta caggcatgag ccaccctgct  67500
cggactgcag ggtgtttttt tttttttttt taattattat ttgtattttt ttgtgctgcc  67560
aaagcaagca cttgtgtgta ggaattttgt ttgtttgttt gtttgtttgt ttgagatgga  67620
gtctcattct tgtcgcccag gctggagtgc agtggcatga tctcggctca ctgcaaccta  67680
```

cgccttccgg gttcaagcga ttctcctgcc tcagcctcct gagtagctgg gatttcaggt 67740
gcatgccgcc accccggcta atttttgtcc ttttggtaga atcggggttt tgccatgttg 67800
gtccggctgg tctcaaactc ctgacctcaa ctaatccacc tgcctcggcc tcccaaactg 67860
ctgggattac aggcatgagc caccgcaccc ggtgaggagt tatttttaat gtgagcaaac 67920
agtatattct tttttttttt tttcatagac agggtctcaa caatatatga tgtatattta 67980
atcatatagt cttatcatgt atataatgta gtcatatgta caccaaaccc tgttctacac 68040
acggagaata ctcttgtatc actttgggta tttatttact tgtttctttc tgtgtttttc 68100
ttgtttgttt gtttgttttg ttttgagaca aggtctagct ttatcaccca ggctggagtg 68160
cagtggtgcc atgtcgactt actgcaacct ccacctgcca cctcagcctc ctgagtactt 68220
gtctacaggt gcgcaccacc acacccagct aacttttcta ttttttgtgc ataaggtttc 68280
accatattac ccatgctggt tgagctcgaa ctcctgagct caagtgatcc tcctgccttg 68340
ccctctttaa gtgctgggtt tattggtgtg agccaccacg ccccacccat acttgtgtat 68400
ttctgtattt attgaggagc ttatacagca taccctgtgg tctatcctgc aggatgtttg 68460
tgtgtgagac agtgtatatt cttgaacata gtagattcca ttttggatgc tcccatcggg 68520
actgtgtgtc cctgtgctgg aactcgagtg aacacttggc tcaaaatcca ttgctgttct 68580
ctagaaatcc agctcaattc tcatggttaa atataaggta tatgtggtag gcattgcttt 68640
ttctctttgg ggacagaact caggaggatt gccccttgat gaacaaggct aacctgctga 68700
ttctttgaag caaaggactg gagatggtcc ttttaggggt ttatgttctg gattccagaa 68760
aacatgcaaa cagggccaat aaatgcatct ttttgttttg ttttgttttg tttttgagat 68820
ggagtctcgt tctgtcaccc aggctggagt gcagtggcac aatcttggct cactgcaagc 68880
tcagcctcct gggttcacgc cattctcctg cctcagcttt ccaagtagct ggggctacag 68940
gtgcccacca ccacgctagg ctaatttttt gtatttttag tagaggcggg gtttcaccct 69000
gttagccagg atggtcttga tctcctgacc tcgtgatctg cccgcctcgg cctcccaaag 69060
tgctgggatt acaggcatga gccactgcgc ccggccccaa taaatgcatc tttatttttg 69120
tgtccattta aacctggtca aggaagattc ccacaaaaaa tccacggtgc tggagcaaga 69180
ggatctcagg ctgtgaccct ctaaagggaa gcgctttctg tggtcagaaa gaaaagcaag 69240
tgcttccttt tagagggtta ccgtttggga aaagcaatgt tgaagttgat gctgatcttg 69300
gtaaaatatt tgcagagcgt gcttatcatc agacttggat gatggtgggg ttttgctttt 69360
gttttgttgt attccaagac aaggtccctg ttgcccaggc tggagtgcgg tgacacttca 69420
acctacattt cttgggctcc ggtcgttttt gtttgtttgt ttgtttgttt gacagggagt 69480
ctcactgtgt gtctcagcaa tgcagtggca ctatcttggc tcactgaaac ctcagcctcc 69540
tgagtagctg ggatcacagg tgcgtgcaac cacgcccatc taatttttgt atttttttgca 69600
ttttcagtag agacggggtt tcaccgtgtt agccaggatg gtctcgatct tctaacctcg 69660
tgatccgccc gcctcggcct cccaaagtgc tgggattata ggcgtgagcc accgcgcccg 69720
gccgagaaac taatcttttg agatgaactc tgagatgtgg attttagctt gtttgcagcc 69780
accaccactc tagttttgga agattttcat caccccgaag aggcttatac tcatttgcag 69840
tcagtaccca cccacctctt ccacccagac cgtggcaacg actccccatc tctctagctc 69900
tggatctgcc tcttgtaggc cggtcacgta gaccaatctt gtatgggtgt ccagttgagg 69960
ataatgggtt ggtcctggtt gtctgcaatg tgaatcttac cactgaaggg tggtccctgg 70020
agggaagcag gaggctggga gaactgggcg gaacatcctt tgggaatgga gtggggcggg 70080

```
cagaccctga tgtctgggaa gctcacaagg gtggaagacc ccatcttcct ccctgagaac  70140

tgcaaggtga ccctcctggg gcactggaag gagtgaaggc ctctgggctg ggaacgtcag  70200

ggcactgcac cgatgcaggc aggatgagcc gaggggaaag gagaagcagg catcattctc  70260

tggggacatt ttgggtttga tctggatgga gcaggtgtct tctgggagag agagcccctg  70320

ggattttcac tctgctccct ggctgtctta gtcatggaat ctgacaacag agactcctgc  70380

ccagggccac ttcatttggt ttctggagcc cagtggtcct tcctgcctgg acttgggatc  70440

ttttggggaa gtttgggatc tggctgggcg tctgcataat ccatagaaat ccctgagagt  70500

cacttccctt ggctgacatc tccatgttcc ttacccatta ccttccaaag gagaccctta  70560

tctgaattac caaaggggc ttcccagagc agggaaacct ggttaaattt gtatttcaga  70620

ttaacagtat acttgagatg tacttgaagt agaaatgatt ggctgtgggt gtcggcattt  70680

gtttttcta attttaaata tgggaccatc atgaatttgg gtgtcacttt gtgcagggga  70740

cgtgggaatc gctgtcattt tttttttt ttaacatatg ctgccagaga aggcacttag  70800

gtggagaaat tactcttcgt gtgagcattc agtatataga acttcctttt ctgggggcag  70860

tgtcttatat atgatacaca ttttatcata tcatcttcta tagataatat aatgattaac  70920

acaaaacact cttctacaca cacagaatac tcttgtatca ctttgggttt tttttccttc  70980

gtgtgtgtgt gtgtgtgtgt gtgtgtgtgt gtgtgtgtgt gttatgagac aaggtctggc  71040

tctgtcaccc aggctgcagt gcagtgttgc agtcttggcc catgccccac cgcagcctct  71100

ggaatagctg tctgcaggcc aggcacggta gctcaggcat gtcgtctcag cactcttgga  71160

gaccaaagca ggctaatcac ctggagtcag gagtttgaga ccagcctggc caagatggtg  71220

aaacctcatt tctactaaaa gtacaaaaat tagccgggcg cggtggctca cgcctgtaat  71280

cccagctctt agggaggcag aggcaggagg atagcttgag cccaggagtt tgagacctgc  71340

ctgggcaata cagtgagacc ctgttctcca caaaaagaaa agaaaaaaaa gaaaaaaaaa  71400

ttttaaaaat gcaaaattag gtgggcatcg tggcacgtgc ctgtaatccc aggtacccca  71460

gaggctgaga caggagaatt gctggaaacc tggaggcaga gcttgcagtg agctgagatc  71520

acggccctgc actacagcct gggcaacaaa gtgagacttg tttcaaaaaa aaaaaaaaaa  71580

tttattgagg agcttttatg gcctagcctg tgttctatcc tggagaatgt gtgtacaaca  71640

gtgtatattc ttaaacatca tcttagattc cattttggat gcttgcatgg ggactgtgtg  71700

tccctgtact gggacttatg tgaacacttg gcttcaaatc cattgctgtt ctctagaaat  71760

ccagcccaat tctcatggtt aaatataagg tatgtgtggt aggcattgct tttctctttt  71820

ggggacagaa ctcaggagga ttgtctcttg atgaacaagg ctaacctgct gagcctttga  71880

agcaaggaac tggagatggt ccttttaggg gtttatattc tggattccag aaaacatgca  71940

gagagagtca ataaatgtat ctttattttt gtgtccattt taaccaggtg aggaaaattc  72000

cgtcaaaaaa cccagacttt tggagcgaga agatctcatg cagtcattct ccaaaagaaa  72060

gcactttctg ttgtctgaaa gcagagtgcc ttcttttgga gcgttactgt ttgagaaaaa  72120

ccacgttgaa gttgatgctg atcttggtaa cacatttgca gagcgtgctt atcatcagac  72180

ttgcatgatg ttggggttct gtttttgttt agttgttttg catcatgggg tctctgttgc  72240

ccaggctgga gtgcggtggc gcttccaacc tagatctctt gggctcaagt ggtcccgtgc  72300

ttgcttttt tttttttctt gaaacagagt ctctgtctct ggcccaggct tgagcgcagt  72360

ggcatgttat ctgctcactg caacctctcc tcccaagtag atgggattac aggtgcacgt  72420
```

gccacgacgc ctggctaata tttgcatttt tagcagagat gcagtttcat catgatggcc 72480
aggttagtct ccaactcctg acctcaggtg atccgcctgc ctcagcctcc caaaatgctg 72540
agattatagg tgtaagccac ccagcctagc ctccaatttt ttttaatgtg tgctgccaat 72600
gcaagcacat atgtgtagga attatttttc atgtgagcac atagtatatg gaacttaatt 72660
tttattgatg tacggtctca aaaatatata ttttatcata ttcttattat acatgtaaca 72720
tagtcatata cacacaaaac actcttctat acacagagaa tactctcgta tcactttggg 72780
taattttttg tttgtgtgtg tatgtttttg tttttttttt agataaggtc tgggtctgtc 72840
acccaggcta gagtgcagtg gtgccatctc agcttattgc aacctccacc tgccacttca 72900
gcctcttgag tagctgtcta caggcgcaca ccaccacgcc cggctaactt ttctgttttc 72960
tctacacatg aggtatcacc atgttgccca ggctggtctc aaactcttga actcaagtga 73020
tactcctgcc tcagcctcct aaagggctgg gtttagaggt gtgagccacc acacctcacc 73080
tgtacctgtg tgtttctgct cattttattg aggagctttt acagcctggc ctgtggtctc 73140
tcctggaggg tgtttgtgtg tgtgacaatg catattcttc aacatcgtag attccatttt 73200
ggatgccccc gtcgggactg tgtgtcactg tactggaact cgagtgaaca cttagctcaa 73260
aatctattgc tgttctctag aatccagccc aattctcatg gttaaatata aggtatgtat 73320
agtcggcatt gctttttgaa acaaggaact ggagatggcc ctgatagggg tttatgttct 73380
ggattccaga aatcatgcaa acagggccaa taaatgcatc tttatttttg tgtccatttt 73440
aacctggtca aggaaaattc caacaaaaaa tcaatggtgc tggagcaaga agatctcagc 73500
ctgtgaccct ctagagggaa gcgctttctg ttgtctgaaa gaaaagaaag tgcatctttt 73560
tagaggatta cagtttgaga aaagcaacgt taacgttcat gctgatctcg gcaatacatt 73620
tgcagagcgt gcttatcatc agacttggat gagggtgggc ttttgttcct ggtttgtttg 73680
ttttctaaga cggggtctct tttgcccagg ctggagagca gtggcacttc caacctagct 73740
ctcttgggct caggtggtcc tctttgcagg gtcacgatct ctgctcacta caatctcccc 73800
ttcccgggtt gaagtggttc tcccatctca gtctcctgtg ttgctgggag tacaggccca 73860
tgccaccacg cccggctaat tttgtattt ttagcagaga tggggtttca ccgtgttgac 73920
caggatggtc tccatctcct gacctcgtaa tccacctgcc tcggcctccc aaagtgctgg 73980
gtttacagtc atgaaccact gcacccggcc tttgatctta attttcaata tgagacccat 74040
catgaatttg ggcatcacct ctgcacaggg gccatggtga tctctgtcac tccattcatt 74100
tcttatgtgt ggagcaaaca tttatgtgta ggagtaattc tttatgtgag catacagtat 74160
atggaacttt cttttttttt gagatagggt ctggaaaata aatgatgtac agccaggcgc 74220
atgagtatat gagcagtttt tgtgtgtata cgacatgagc ggtggctcat gcctgcaata 74280
tcaacacttt ggcaggttga ggcgagtgga tcacttgagg tcaggagttt gagaccagcc 74340
tgaccaacat ggtgaaaccc tgtctctact aaaaatacaa aaaattagcc agctatggtg 74400
gcgcacgcct gtattcccat ctgctgggga agttgaggga ggagaatcac ttgaacggac 74460
agatggaggt tgcagtgagc caagatcacg ccaccacact ccagcctggg cgagagaata 74520
agactgtctc aaaaaaaaaa tatatatata catatatatt tatatagaga gagagactct 74580
gtctcaaaaa aaaaaatata tatatgggtg tgtttgtgtg tatatatata ttatatatga 74640
tgtatatttc atcatatagc catatatata attatataca caaaaaatac tcttctacac 74700
acagagatga ctgatatcac tttggggtgg tttttgcttg tgtgttcttt taaatttttt 74760
tttgcaacaa gatctggctc agtcgcccag gttggagtgc agtgtttcag tcttggctca 74820

```
ctgcaacctt cgcctcccac cccagcctcc tgaattagtg tctacaggca tgtaccacca  74880
cacctggcct acatttgtat ttttttacag acagggtttc accgtgttgt acacgctggt  74940
cttgagctcc tgagctcaag tgaatctcct gccttggcct cctgatgtgc tgggattaga  75000
ggtatgagcc accacaccca actggtactt gtgtattcct gttcaaattt tattgaggag  75060
cttttaccac ctagcctgtg gtctatcctg gaggatgttt gtgtgtgcga caatgtatat  75120
agttcaacat cttagatcac attttggatg tttccaatgg gactgtgtgt ctccgcactg  75180
gaactcaaat gaacacttgg ctcagaatcc atttgctgtt ctctggaaat ccagtccaat  75240
tctcttggtt aagtataagg tatgtctagt aggcattgct ttttctgttt gagaacaaaa  75300
ctcgggagga ttgtcccttg atgaacaagg ctaacctgct gagcctttga agcaaggaac  75360
tggagatggt ccttttcagg cgttttattc tggattccag aaaacatgca aacagggcca  75420
ctaaatgcat ctttattttt ctgtccattt aaacctggtc aaagaaaatt ccaacacgaa  75480
acccagagtg ctggagcaag aagatctcaa gctatgagtc tacaaaggaa agcgctttct  75540
gttgtcagaa agaagagaaa gcgcttccct tttgagggtt acggtttgag aaaagcagtg  75600
ttgaagttga tgctgatctt ggtaatacat ttgcagagca tgcttatcat cagacttgga  75660
tgatagcggg gttatgtttt ggttttgtgt ttttctaaga cagggtctcc gttgcccagg  75720
ctggagtgcg gtggcacttc caacctagct ctcttgggct caagtgatcc tctttttatt  75780
tatttatgta ttcatttttg agatggagcc tggctctgtc acccaggctg gagtagagtg  75840
ggatgatctc cactcattgc atcctctgcc tcccaggttc cagaaattct cccacctccg  75900
tgtcactagt agctgggatt acaaatgctc accactatga cctgccagtt tttgtacttt  75960
tggcacagac ggggtttcac catgtttgcg gggctggtct caactcctga cctcaagtga  76020
tctgcctcct tggcctccca cagtgctggg gattatagat ataagccacc gtgcccggcc  76080
cattcctgtc tttttaattt aatctgctcg tccctgacat cgaaaatttt tcttgcttaa  76140
cagcttccac ttatttctcg gaatagacct ttttctgcag gaagggtgta gttgattcaa  76200
ccctcaccca ctcatgccaa ccgtagtgag tgctgtgact gcagctgcac tgtttatcct  76260
gttttctgca ggtaattttt ccagtgtacc attccaacct gcaaaacctc acatttaaat  76320
gcaaatttct tggtaagctg tgaaatgttg gctgtggcta atatgagaaa caagctatta  76380
tagacaagat gaatctcagt tgcagtgata aatgtcacat gggacaaaac cacagatact  76440
ttcacaaaaa ccttgaggac cctagaaggg cctccctagt aacaggtggg atgcgcatcc  76500
gctcttgttg ccatagtgag tgatgcctgt tcgtccagcc ctcaacacct ttcactccgt  76560
ggaagttatg cctgcactgg tttacagaac ctcccttgac ttgacttgag gtagagttga  76620
agggaacctc agtgtccctt gcagatggga tgtgcattgc ttcgcaagag cacagaggtg  76680
gagtgcatgg gctttgagtt tttattgggt aaatgaagct gaaatacagg gtgtatgacc  76740
acgttatcaa cgcacacttg atttaggttt tgtattttag agacgggggt gtgagctgcc  76800
aaagcaagga cttatgtgta ggaattattc tttctgtgag catacagtat atggaacttt  76860
ctttcttttg agacagggtc tcaaaaatat atgatgtatg gccaggtgcg gtggatcacg  76920
cctgtaatcc cagcagtttg ggaggccgag gcgggtggat aacctgagat caggagggcg  76980
agaccagact ggccaacatg gtgaaaccat gtctctgcta aaaatacaaa aaattagcca  77040
gggctggtgg cgcacgcctg tagtctcagc tactccggag ggtgaggcag gagactatca  77100
ctttgagtgt gtgtctttgt gtgtgtgtgt gtgtgtgtgt gtgtgtgtgt atgtgtttct  77160
```

```
agtttttaca agacacagcc tgactatatc accgaggctg gagtgcagtg gtgcaatgtt  77220
ggctcactgc aacctccacc tgccaccgca gcctcctgaa ttagtgtcta caggtatgca  77280
ccaccacacc tggctcactt ttgtattttt tgtacagatg aagcttcacc atgttgccca  77340
ggcttgtctg gaactcttga gctcaagtga tcctctcact tcggcgtcct gaagtgctgg  77400
ggttagagat gtgagccacc gcacccaaca ggtacttgtg tattttttta ttgaggagct  77460
tttacagcgt agcctgtggt ctctcctgga ggatgtttgt gtgtgcgaca atgtacattc  77520
ttcaacatct tagattccat tttggatgcc cccatgggta ctacatgtgc ctatactgga  77580
actcaagtga acacttggct caaaatccat tgctgttctc tagaaattca gttcgattct  77640
cttggttaaa gataaggtat gagtagtagg cattgctttt tctctttggg ggcaaaactc  77700
aggaggattg cccccttgatg aacaaggcta acctgctgag cctttgaaag aaggaactgg  77760
agatggtcct tttagggggt ttatattctg gattccagaa aacatgcaaa cagggccagg  77820
aaaaatgcat ctttattttt gtgtccattt aaacctggtc aaggaaaatt ccaacaataa  77880
acccagagtg ctggagcaag aagatctcag gctgtgaccc tccagaggga agtactttct  77940
gttgtctgag agaaaagaaa gtgcttccct ttggactgtt tcggtttgag taaagcagcg  78000
ttgaagttga tgctgatctt ggtaatacat ttgcagagca cgctcatcat cagactcgga  78060
tgatgttggg gttctgattt tgtttttctc caagacaggg tctctgttgc ccaggctgga  78120
gtgcagtggc agttccaacc tagctctcct gggcccaaga gaccctctat ttatttattt  78180
atttatttat ttatttattt atttatttat tcattcattc atttagagat ggaatctggc  78240
tctgtgaccc aggctggagt gcagtaggac aatctccact cactgcaacc tccatctccc  78300
aggttccagc agttctgcca cctcagcctc ccatgtagct gggattacag gcgcccacca  78360
ccatgtcatg ctaatttttg tatttttagc agagatgggg ttacaccatg tttgctgggc  78420
tgttctcaac tcctgacttc aagtgatttg cctccctggc ttcccaaagt gctggtatta  78480
caggcgtgag ccactgtgtc cggcctcaag tggtcttcct gagtcagcct cccaagtagt  78540
tgggattaca tggggcgtga cacaacactt ggttcagctt ttaatttttg gtagagatgg  78600
ggtctctgtt gctcaggacg gtctcaactc ctgagctcaa gcgatcctac aggtgtgagc  78660
caccttgtcc tgatgaccca tttcaaagat agttgacttg gccaggcatc atggggcaca  78720
cagtcccagt tactgcaggg gccggggcgg gagggtgctt tgattttaag gctataccgt  78780
gcacagatcc cacctttgaa tagccactgc actccagcct gggccaacat agcaagatcc  78840
catttcttta aaaacagatt acatagcacc tggtcccaca gatttcattt gggttggtca  78900
tgtcatacaa tggcctccca tcaatttagt ataatcaatc caaaccatgg ttccttcatt  78960
aagagagtgg gtaatcctcc aagtccatcc agtctattct gtaatcccca gtgggtgtcc  79020
gtattgatac aatttctttt tgttcctgtt cactcgtgtc tttttagtgt aatctgcttg  79080
tccgtaacac tgaaatttgt ttttccccaa catcttgcca tcatttctcg gaatagacct  79140
gctttctctg caggaagggt gtagttgatt caaccctcac ccactaatgc caaccccagt  79200
gagttctttg actgtagctg ccatgtttat cctattttct ttgggtaacg attccaaggt  79260
accattccaa tgggcttaaa ccttgcatct aaatgccagt tacttgctaa gatgtcaaat  79320
gtgtcttata ttagctgtgg ctaatataag aaactgttgt agacaagatg aatctcagtc  79380
acagtgataa atgtagcatg caacaaaacc agttgttttc acaaaaatct tgaggaccct  79440
agaaggggct ccctcgtaac aggtggaatg cacagcagct cttcttgttg ccatagtgag  79500
cgatgcatgt tcttccagtc ctcaacacct tttatttatt tatttattta tttatttatt  79560
```

```
ttattattat tatttttttt tgagacagag tctcgctctg tcacccaggc tggagtgcaa  79620
tggtgtgatc tcagctcact gcaaccactg cctcccgggt tcaagcgatt ctcttgcctc  79680
agcctcacgt gtcgctagga ctacaaccgt gcaccaccac gcccggctaa tttttgtatt  79740
tttaatagag acagggtttt gccatgttgg ccaggttggt ctggaactcc tgacctcagt  79800
tggtccacct gcctcagcct cacaaagtgc tgtgaataca ggtgtgagcc aacacgcccg  79860
gctatcaaca acttttccta cgtagaaatt attcgggcac tggtttatag aacctcacgt  79920
gggttcacgt agaattgaag gggacctcag cgtcccttgc agatgggatg tgcaatgtat  79980
ttgagatgta ctcgaacatt gctgttgagg tgtgggcatc ttttgctttt tcctaatttt  80040
aaatatggga ctagtctggg tatggtgact tccaccagta attctagcac tttgggaggc  80100
tgagacagga ggatcacctg aggtcagttg ttcgagacca gtctggccag catggtgaaa  80160
ccccgtctct actaaaaata caaaaattag ccgggtgtgg tggcactcac ctgtaatccc  80220
agctactcgg gaggctgagg caggagaatc acatgaatct gggaggcgga ggttacagcg  80280
agcagagatc acaccgttac actcctgcct gggcaacagt gtgagactct gtctctaaat  80340
aaataaataa ataaaaataa aaataattag gtgaatatgg gaccagcatg gacttgggtg  80400
tcgcctttgt gcagtggcca ggatattcta tgtcatttaa atttttttat gtgtacttcc  80460
aaagcaagca gttatgtata ggaattattc ttcctataag catgcaatat ttggaacttt  80520
ctttgagaca gggtctcaaa aatacatgat gtatatttca ttttatattc ttatatatta  80580
tgtacacaca aaatactctt ctaaacacag agaatactcc gatatcacct agggtgtgtg  80640
tgcgtgtgcg tgtgtgtgcg tgtgtgtgtg gttcttttct gagacaatat ctgcctctgt  80700
cacccaagat ggagtgtggt ggtgcaatct cggcttactg caacctccac ctcccaccta  80760
agcctgctga attagtctct acaggcatgc accaccacac ctggctaact tctgtaattt  80820
ttgtacacat ggggtctcgc catgttgccg gggctggtct cgagctcctg aggcaggtga  80880
tcctcctgcc tgggcctcct aaagttcgag gagttagagg tctgagccac tgggccccac  80940
ttgtacttgt gtatttctgc tcaaatttta ttgagtagtt tttacatcct agcctgtgat  81000
ctactctgga gagtgtttgt gcatatgaca gtgtatattc ttcaacatcg tagactccat  81060
tttggatgct cccttcgtga ctgtgggtcc tgtactggaa ctcgagtgaa cacttggctt  81120
aaaatccatt gctgttctcc agaaatcctg cccaatttc tcggttaaag gtacgtgtag  81180
taggcattgc tttttctctt tggggacaaa actcaggagg attgcccctt gatgaacaag  81240
gctaacctgc tgattctttg aagcaaggaa ctggagatgg tccttataga gttttatatt  81300
ctggattcca taaaacatgc atacagggtc aataaatgca tctttatttt tgtgtctatt  81360
ttaacttggt caaagaaaat tccaggaaaa aatccacggc atcagagcaa gaagatgtca  81420
ggctgtgacc ctcttgaggg aagcactttc tgttgtctga aagaagagaa agtgcttcct  81480
tttagaggct tactgtctga gaaaagcaac gttgtagttg atgctgatct ttgtaatatc  81540
tttgcagagc acgcttataa tcagacttgg atgatgttgg ggttttgttt ttcttttgtt  81600
tttttatcta agactgggtc tctgttgccc aggctgaagt gcagtggcac aatcttggct  81660
caccacaacc tccgcctccc gggttcaagt gattcttctg cctcagcctc ccaagtagct  81720
gggattatag gactgcgcca ccatgcctgg ctaattttgt atttttagta gagacagggt  81780
ttctttagga gcttttaagg cctcccttgt agtctatcct ggaggatgtt tgtgtgtgca  81840
acaatgtata ttcttcaaca tggtagattc cattttgact gctctaatca ggactgtgtg  81900
```

```
tccctgtgct ggaaatcaag tgaacacttg gctgaaaatc cactgctgtt ctctagaaat  81960
ccagcccaat tctcttggtt aaatataagg tatgcatagt aggcattgct tttctttct   82020
ggacacaaaa ctcaggagga tttcccttg atgaacaagg ctaacctgct gagcctttgt   82080
aggaaggaac gggagatggt ctttttaggg gtctatgttc tggattccag aaaacatgca  82140
aacagagcca ataaataggt ctttattttt gtctctattt taacctggtc aaggaaaatt  82200
tctacaaaaa acccagggtg ctggagcaag aagatcccat gctgtgaccc tctagaggga  82260
agcgctttct gttgtctgaa agaaaagaaa gtgcatcctt ttagaggttt actgtttgag  82320
gaaagcaaca gtgaagttga tgctgatctt ggtaatacat ttgcagagca tgcttatcat  82380
cagacttgga tgatggtggg attctgtttt tattttgttt ttttttctaa gacagagtct  82440
ctcttgccca ggctggagta gggtagcact tccaacgtag atcttttagg ctcaaacggt  82500
cctctttttt tttttttttt ttttgaggcg gagtcttgct ctgtgaccca gacgagagtg  82560
caatggcgcg atcttgtgtg caagctcacc tcctgagttc aagcaattct tctgccccag  82620
cctcccaagt agctgggact acaggtgcct gccaccactt ccagctaatt tttgtatttt  82680
tagtagagac agggtttcac cacgttggcc aggctggtct caaactactg acctcaagat  82740
ccacccacct cagcctccca aagtgctggg attacaggcg tgggccattg tgcccagcgg  82800
tcctcttttt tgagatggag tcttgctctg tgacccaggc tggagtgcag tggcaggaac  82860
ttcgctccct gtaccctcca cctcccagat tcaagccatt ctctcctgag tcagcctccc  82920
tagtagctga gatcgcagac atgagccacc atacccagct aatttttgta tttttattat  82980
ttatttattt actcatcgat ttttgaaaca gagtcttact ccgtccatca ggctggaggt  83040
cagtggcaca atcccacgtt caagcaattc tcctgcctca tcctcccgag tagctgggat  83100
cacaggcgca caccaccacg cccggctaat ttttgtgttt tttttgtttg ttcgtttttt  83160
tttttttgt agagacaggg tttcaacatg ttggccagcc cagtctccaa ctcctgacct   83220
taagtgagcc catacacaat caagaagaga gcgagacctg ttcttttttt ctgtctttga  83280
ctatttgaga cagtcttgct ctgtcacccg agatggagta cattagtgtg atcttggctc  83340
actgcaacct ctgcctcctg gactcaagca attctctttt tttttttttt ggagaaagag  83400
cctctctgtg tctcccaggc tggactgcag tggtgtgatc tcagctcact gcaacctcag  83460
ccttccaagt agctgggatt gcagacatgt acccccatac cagctatata tatatatgta  83520
ttttagacac agtttcacca tgttagccag gccattcttg aatcctgacc tcaggtgatt  83580
tgccgacgta ggcctcccga agtgctggga ttacaggtat gagccactgc actcagcctt  83640
ttttcctaat tttgaatatg ggacccatta tgaatttggg tgtcacctat gtgcgggggc  83700
tatggaaatc tctgtcaccc cattcatttg tgtgtgctgt caaagcacca atatgtggga  83760
attatgcttt atgtgagcat atagtatatg gaactttggt ttttttttat acagggtctc  83820
aaaaaaaaat gagtatattt catcacaatg ttctgtgtat aattccatac acacaaaata  83880
gtcttctata cacagagaac actcttatat cactttggag ttgtttttgt ttgtgtattt  83940
tgttttaatt tttatgagac agggcctggc tatgtcgctg aggctggagg gcagtggtga  84000
gatcttggct cactgcaacc tccacctgcc acctcagcct cctggattag tgtctacagg  84060
caggcaccac cacccctggg taagttctgt atttttggta ctgatgaggt ttcagcacgt  84120
tccacaggct ggactcttaa ctcctgcgat caagtgatcc tcccgctgtt caaattttac  84180
tgaggagctt ttaaggcctc gcctgtggtc tgtcctgtag tgtccctgtc ctggaactca  84240
agtgaatact tggtttaaaa ttgattgctg ttctctagaa atccagccca attctcttgg  84300
```

```
ttaaatataa ggtatgtgta gtaggcactg ctttttcttt ctggaggcga aactcaggag  84360
gattgcccct tgatgaacaa ggctaacctg ctgagccttt gaagcaagga actggagatg  84420
gtcgttttag gggtttatgt tctggattcc agaaaacatg gaaacagggc caataaatgc  84480
atctttattt ttgtgtccat tttaacccag tgaaggaaga tttcaaccaa aaacccacgg  84540
tgctggagca agaagatctc aagctgtgac tctccagagg gatgcacttt ctcttatgtg  84600
aaaaaaaaga aggcgcttcc ctttagagcg ttacggtttg ggtaaagcaa cgttgaagtt  84660
gatgctgatc ttggtaatat atttgcagag catgcttata attaagactt ggatgatggt  84720
gggtttctgt tttgtttttt gttttaaatc agagtctcac tctgtcaccc aggctggagt  84780
gcaatggcgc aatctcggct cactgcaact tccccctcct gggttcaagt gattctcctg  84840
cctcagcctc ctgagtagtt aggattacag acatgcgcca cctcacccgg ctcagttttt  84900
gtatttggtg gagatggggt ttcaccatgt tagtcaggct ggtcttgaac tcctgatctc  84960
aggtgatcca cctgcctcag cctcccaaag cattgggatt acaggcgtga gccaccacgc  85020
caggcctgtt caacatctta gatttcattt tggatgttcc tgtgaggact gcgtgtccct  85080
gtgctggaac tcaagtgaac gcttggctca aaatccattg ctgttctcta gaaatccagc  85140
caaattctat tggtgaaata taaggtatgt ctagtagtca ttgctttttc tctttggaga  85200
caaaactcag gaggattgcc ccttgatgaa caaggctaac ctgctgagcc tttgaaacaa  85260
ggaactggag atggtccttt caggggttta tattctggat tccagaaaac atgcaaacag  85320
ggccagtaaa tgcatcttta tttttgtgtt cattttaacc tggtcaagga aaattgctac  85380
aaaaaaccca gggtgctgga gcaagaagat ctcatgctgt gaccctctag agggaagcgc  85440
tttctgttgt ctgaaagaaa agaacgcgct tccctataga gggttaccct ttgagaaaag  85500
cagcattgaa gttgatgctg atcttgctaa tacatttgca gagcatgctt atcatcagac  85560
ttggatgaag gtggggttct gttttttttt tttttctaag acaggatctc tgttgcccag  85620
gctggaatgt ggtggcactt ccaacctagc tctcttgggc tcaaatggtc ctctcttttg  85680
ggatagagtc ttactctgtg acccaggctg gagtgcagtg gcgtgatctc agcttactgc  85740
cacctccacc tcccagtttc aagccgttct cctgcctcag attcctgagt atctgggatt  85800
ataggtacct gacaccacgc ctggctaata cttgcatttt tctttctttt ttcttttctt  85860
tttttttttt ttttttttga gatggagtct tactctgtca ccaggctgga gtgcagtggt  85920
gcgatcttcg cttatttcaa cctccgcctc ccagtttcaa gtgattctcc tgcctcagcc  85980
acccgactaa ctaggatttc aggcatgcac cacacgcctg gctaattttt tgtattttta  86040
gtagagacag ggtttcacca tgttggtcag gctggtctcg aactcccgac ctctggtgat  86100
cttcccgcct tggcctccga aagtgctggg attgcaggca ttagccaccc cgcccggcca  86160
ttatatattc ttatatatat aataccatat acgtgcaaaa tactcttcta catgaagaga  86220
atactcttat atcactttgg ggtttttttt gtttgtttgt gtgtgtgtga gtgtatgttt  86280
tatttgtttt tggataaggt ctggctctgt cacccagtct agagtgcagt tgtgccatct  86340
ctctcagctc actgcgactt ctacctccca cctaagcctg ctgaattagt gtctacaggc  86400
atgcaccacc acacctggct ccgttttgta ttttttatac acatgggctt acaccatgtt  86460
gccgagactg gtctcgaaca cctgagctca ggtgatactt cagtttcagc ctcctaatgt  86520
gctgggatta gaggtgtgag ccaccgtgcc ccacttgtag ttgtgtgttt ctgttcaaat  86580
tttattgagg agtttttagg gcctagcctg tgatctaccc tggaggatgt ttgtgtgtac  86640
```

```
aacaatgtat attctttaac atcgtagatt ccattttgga tgctcccatc gggactgtgt  86700
gtccctgtgc tggaactctg gtgaacacct ggctcaatat ccatttctct tctctagaaa  86760
tccagcccag ttctcttggt taaatataag gtacatatgt ctatgaggca ttgcttttgc  86820
tctttgagaa caaaactcag gaggattgct ctttgatgaa caaagctaac ctgctgatcc  86880
tttgaagcaa ggaactggag atggtccttt taggggttta tattctggat tccagaaaac  86940
atgcaaacag ggccaataaa tgcatctttg tttttgtgtc cattttaacc gggtgaagga  87000
aaattccaac aaaaaaccca gagtgttgga gcaagaagat ctcatgctgt gaccctctag  87060
agggaagcac tttctcttgt ctaaaagaaa agaaagcgct tctctttaga ggattactct  87120
ttgagaaaag caacgttgaa gttgatgctt atcttggtaa taaatttgca gagaatgctt  87180
ataatcagac gtggatgatg ttggtgtttc atgtttgttt tgttttgttt ttaatacagg  87240
gtgtctgttg cccaggctgg agtgtggtgg tccctctcca acctagatct cttgggttca  87300
agtggccctc ttttttgggt cagagtcttg ctctgtggcc ctggctggag tgcagtgtca  87360
ggatctctgc tcactacaac ctctgcctcc tgggtaaaag cgattctcct gcctcagcct  87420
cccaagcaac tgggattaca ggcatgtgct accatgcccg gctaattttt gtaatttcct  87480
ttatttattt ttgagacaga gtcttactct ttcgcccagg ctggagtgca gtggtgcaat  87540
ctcggctcac tgcaacctcc aactcccacc tcagcctcct gaatagctgt ctacaggcat  87600
gcaccaccac acctggctaa cttttgtatt ttttgtacag acatggtttc tccatgttgc  87660
ctgggctggt cttgaactcc tgaactcaag tgatcctccc acctcggcct cctaaagtgc  87720
tgtgattaga ggtatgagcc accgtgcccc acctgtactt gtgtgtttct gctcaaattt  87780
tattggggag cttttatggt atagcctgtg gtctctctgg agaatgtttg tgtctatgac  87840
aatgtatatt cttcagtatg ttatgttcca ttttggatgc ttgcatgggg actgtgtgtc  87900
cctgtactga aactcaggtg aacacttggc tctccgtcca ttgctgttct ctagaaatcc  87960
agcccagttc ccttggttaa agataaggta tgtctagcag gtattgctct ttctcttgca  88020
gacaaaactc aggaggattg cccccttgata aacaaggcta acctgctgat tctttgaagg  88080
aaggaactgg agattgtcct tttaggggtt tatattctgg attccagaaa acacacaaat  88140
agaaaacagg gcaaataaat gcatctttct tttcgagtcc attttaacct ggttaaggaa  88200
gattccaaca aaaaatccac ggtgccacag caagaagatg tcaggctgtg tccctctaca  88260
gggaagcgct ttctgttgtc tgaaagaaaa gaaagtgctt ccttttagag ggttaccgtt  88320
taagaaaagc aacgtttagg tggatgctga tcttggcaat aatacatttg cagagcatgc  88380
ttatcatcag agttggatga tggtggggtt ctgttttttt gttttttttt ttctgagaca  88440
gagtgtctat tgcccaggct ggagtgcagt ggcactttta acctagatct cttgggctca  88500
agtggtcctg ttttttggga taatctcaca ctgtgaccca gtccggagta cagtggcatg  88560
aacaccactc attgcatgct ttgcctccca ggttcaagtc attcttatga cccagcttcc  88620
agagcagctg ggattacagg catgagccac cacactggct aatttttgta tttttaatag  88680
agatggggtt caccatgttg gccaggctgg tctccaacta ctgacctcat gatccaccca  88740
cgtcggcctt ccaaagtgct gggattacag acgtgagcca ctgtgcccgg ccaacacaga  88800
gaatactctt atatcacttt ggggttgttt ctgtttgtgt attttttaaa tattttttga  88860
gacacagtct ggcgctatta cctaggttgg agtgcagtgt tgtgacctcg gctcacagca  88920
acctctacct cccagctgag cctcctgagt tagcatctgc aggcatgaac cacaacacct  88980
ggtaaccttt gtatttttgg acacatgagg tttcaccatg ttgcccaggc tagtcttgaa  89040
```

```
ctcctgagct caagtaatcc tcctgcctcc gactcctaaa gtgctgggat tacaggtgtg  89100
agccactgca ccccacctgt acttgtgtat ttctgttcaa attttattga ggagctttta  89160
cggcctagac agtagtctat cctggagaat gtttgtgtgt atgacaatgt atattctttt  89220
tttttatttt tattttttgg agacggagtc tcactctgtc acccaggctg gagtgcaatg  89280
gcatgatctc ggttcactga aacctccgcc tcctgggttc cagcgatcct cctgtctcag  89340
cctgctgagt agctaggatt acaggtgggc gcctggctaa tttagattcc attttggatg  89400
ctcccatcgg gactgtgtgt ccctatgttg gaactcaggt gaacgcttgg ctcaaaaatc  89460
cattgctgtt ctctagaaat cctgcctaat tctcttggtt aaagataagg tatatgtagc  89520
aggcattgct ttttctcttt ggggacaaaa ctcaggagga ttgcgccttg atgaacaagg  89580
ctaacctgct gagcctttga agcaaggaac tggagatggt ccttttaggg gtttatgttc  89640
tggattccag aaaacatgca aacagggcaa ataaatgcat ctttattttg tgtccatttt  89700
aacctggtca aggaaaattc caacagcaac atcaaaaaac cagtgttgga gcaagaatat  89760
gtcatgctgt ggccctccag agggaagcgc tttctgttgt ctgaaagaaa acaaagcgct  89820
ccccttaga ggtttacggt ttgagtaaag cagcgttgaa gttgatgctg atcttggtaa  89880
tacatttgca gagcgtgctt atcatcagac gtggacgatg gtggggttct gttttggttt  89940
tgttttttc taagacaggg tctccgttgc ccagactgga gtgcggtggc acttctacct  90000
agatctcttg ggctcagatg gtcttctttt tatttcattt ttttaattgt ttgagatgga  90060
gtctcactct gtcacccagg ctggagtaca gtggcaggat ctccacaact acagcctccc  90120
aggttccaga cattctccca cctcagcctc ccgagtagct ggaattataa gcacccaccg  90180
ccatgccctg ctttttgtat ttttagacaa gaaagggttt caccatattg gccaggctca  90240
tctcaactct tgcccttaag taatcctcct ccctggcctc ccaaagtgct gagattacag  90300
gcgtgagcca ccgcgcccag cctcaagtgg tcctcttgag tcagcctctc aagtagttgg  90360
gactacgtgg ggcgtgccac catacttggc taagttttta atttttggta caattggggt  90420
ctctttttcc caggatagtc tcatctccac agcttatgtg gtcctacacg tgtgagccac  90480
ctcgtcttga tgacccattt caaagagagt tgacatggcc aggcattgtg gggcacacag  90540
tcccagccac tgcagaggcc agggtcggag ggacctttga tttccagact gtaccatgca  90600
ctgatcacac cttcgaatag ccactgcgct ccagcctggg ccaacatagc aagatcccat  90660
ctctttaaaa acagattaca tggcacctgg ttacagaggc tccatttggg ttggttattt  90720
gaaatgggtc tcccatcaat ttagtgtaat caatcgaaat catttccttc attaagagag  90780
taagtagccg gggcatggtg cctcatgcct gtaatcccag cactgtggga ggcaaaggca  90840
ggcggatcgc ctgaggtcag gagttcaaga ccagcctggc caatatggtg aaaccctatc  90900
actactaaaa atacaaaaat tagccgggtg tggtggcgtg aacctaggag gctgaggttg  90960
cagtgagctg agattgcacc attgcactcc aacctgggcg actgagctgg acttaaaaaa  91020
aaggtaagta agccttcaag tctatccaat cttaatttgt aatctcaaat ggatgtccat  91080
attaacaaaa ttttcttgtt tttcctgttt gtgtcttttt agtttaatct tcttgtcctt  91140
gacactgaaa tttttttctc tccaacaact tgccgtcgtt tctcggaata gagctgcttt  91200
ctctgcagga agggtgtagt tgattcaacc gccacccact cacgccagcc ccggtgagtt  91260
ctttgactgc agcttccctg attatgctat tttcttcggg taatgaaccc aaggtacctc  91320
gcatttaaag gctagttgct tggtaagctg tgaaatgttg gctgtggcta atatgagaaa  91380
```

```
caaactatgg tagacaagat gagtctcagt ggcagtgata attgtcacat gggacaaaac  91440
cacagatact tttcacaaaa accttgagga ccctagaagg gcctctctag taacaggtgg  91500
gatgcgccgc agctctcgtt gttgccgtag tgagcgatgc ctgttcgtcc agccctcaac  91560
accttttact ccgtggaagt tatgcctgca ctggtttaca gaacctccct tgacttgggt  91620
tgaggtagag ctgaagggaa cctcagtgtc ccttgcaggt gggatgttca ctacgtagca  91680
agagcacaaa ggtggagtgc gtgggctttg agtttctatt gggtaaatga agctgaaatg  91740
tagggcacat gagcacgtca tcaatgtaca attgatttaa tttttgtatt ttagaaacgg  91800
aggtctcgct atgccgccca gggtagaatg tgctctctcc ctctcctctt cctagtatct  91860
gggactacag gtgaatattt taatctatgc acaggcaaga agagggcaag gagggttctt  91920
ttgttctgtc tttgactttg tgaggcagtg tcactctgtc actcaagctg gagtgcaata  91980
atgtgatctc ggctcactgc aacctctgcc tcctgggttc aagcaatttt tttttttttt  92040
tttttttgag tcagtatctc actctgtccc tcagggtgga gtgcagcggc ccagtctctg  92100
ctcctgcaac ttctgactcc caagtaggta caattgcaga cacgtgtcac cacgcttggc  92160
aaaatttttt ttgtattttt agagctggga ttttaccttg ttggcgaggc tggtctggaa  92220
ctcctgacct caggtgactc gcccaccttg gcctcccaac aagttatgct gatcttggta  92280
ataacttcgc agagcgtgct tccatcagac atggaggatg gtggggtcct gttttgttgt  92340
tgttgttttt ctaagatagg gtctcttgcc caggctggag tgtgttggca cttccaacct  92400
aggtgtcttg ggctcaaatg gtcctctttt ttcggacagt cttgctctgt gacccatgct  92460
ggagtgtagt gacgtgatct cagctcactg caacctccac ctcccagttt taggcagttc  92520
tcctgcctca cattcctgag tagctgggat tataggtgcc tgacaccatg cctggctaat  92580
atttgcatgt tatttattca tgtatttatt tgttttgaga tggagtctca ctgtcactca  92640
ggccagaggg cagtggcagg acctcggctc actcaaacct ttgcctctca ggttcaagca  92700
agtcttctgc ctcaacctcc tgagtagctg gaatcacagg cacccgtcac cacgcccggt  92760
tacttttgta tttttttttt caccatgttg gccaggctgg tctgaaaccc ctgacttcat  92820
gtgagccgcc cgcctcagcc acccaaagtg gtgggattac aggcataagc cactgcgccc  92880
ggccaacaat gtatattttt caacatggga gattcagttt tgaatgctcc catcgggact  92940
gtgtgtccct gtgctggaac tcaagtgaac gcttggctca aaatccattg ctgttctcta  93000
gaaatccagc ccaattctct tggttaaatg taaggtatgt gtagtaggca atgctttttc  93060
tggagacaga actcaggagg attgtccctc gatgatctag gctaacctgc tgagactttg  93120
aagcaaggaa ctggagatgg tccttttagg gttttatgtt ctggattcca gaaaacatgc  93180
aaacagggcc aataaatgca tcctcatttt tgtgtccatt ttaacctggt gaaggaaaat  93240
tccaacaaaa aacccacagt gctggagcaa gaagagctca ggctgtgacc ctctagaggg  93300
aagcactttc tgttgcttga aagaagagaa agcgcttcct tttagaggat tactctttga  93360
gaaaaacaac attgaagtta atgctgatct tggagatcat gcttataatc agacttggat  93420
gatgttgggg ttttgtgggg tttttttggt tttttttcct aagacagggt gtctgttgcc  93480
caggctggag tatggtggcc cctccaacct agatctcttg ggttcaagtg gccctctttt  93540
ttgggacaga gtcttgctct gtgaccctgg ctggagctca gtatcaggaa ctttgctcac  93600
tgcaacctct gcctcccagg ttcaaatgat tctcctgcct cagcctcccg agcagctggg  93660
attacaggca tatgccacca cgcccagcta atttttgtat tattgttatg tatttatttt  93720
ttaacttatt cattttagag acagagtctc actctgtcgc ccaggctgga gtgcagtggt  93780
```

```
gcgatctcgg ctcactgcaa cctccaactc ccagctcagc ctcctgaata gctgtctgca  93840
ggcatacacc accacacctg gctaactttt ggtttttttg tacagatgtg gtttccccat  93900
gttgcccagg ttggtctcga actccttagc tcaggtgatc ttccaccttg gcctcctaaa  93960
gtgctaggat tagtggtgtg agctgttgtg ccccacctat actcgtctgt ttctgctcag  94020
attttattga ggagcgttta cagggtagcc tgttgtctac cctgcaggat gtttgtgcct  94080
acaacagtgt atattcttca acatcttaga ttccatttcg gatgccccca tgaggactgt  94140
gcgctcctgt actggaactc aagcgaccac ttggctcaaa atccattgct attctctaga  94200
aatccagccc aattctcttg gttaaagata aggtatgtgt agtaggcatt gccttttctc  94260
tttgggaaca aaactcagga ggattgcccg ttgatgaaca aggctaacct gctgattctt  94320
tgaagcaaag aactgcagat ggtcctttta gggatttatg ctctggattc cagaaaacat  94380
gcaaacaggg caaataaatg catctttatt tttgcgtcca ttttaacctg gtcaaggaag  94440
attcccacaa aaaatccaca gtgccagagc aagaagatct caggctgtcg tcctctagag  94500
ggaagcactt tctgttgtct gaaagaaaag aaagtgcttc cttttagagg gttaccgttt  94560
gagaaaagca acattgaagt tgatgctgat cttggtaata cattttcaga gcatgcttat  94620
catcagagat ggatgatggt gggcttctgt ttttgttttg attttttctt ttttttttt  94680
ttgagatgga gtttcgttct tgctgcccaa gcactagtat gtaggaatta ttctttatgt  94740
gagcatatag tacatggaac tttgtttttt tgagacaggg tctccaaaat atatacatgt  94800
tatcatataa tcttctatgt ataattatat tcacacaaaa tagtcttctg cacacagaga  94860
atactcttat atcactttgg ggttgttttt gtttgtgtat ttttttttt tttaattttt  94920
tttgagacac catctggctc tattgcccag gctggagtgc agtgttgtga cctcaactca  94980
ctgcagcctc tacctcccac ctcagcctcc tgaattagtg tctacaggca tgaaccacta  95040
cacctggcta tcttttgtat ttttacagat gaggttttac tatgttgggc aggctagttt  95100
tgaactcgag ctcatgtaat tttcccgcct tcgactccta aagtgctggg attagaggtg  95160
taagccactg cactccaccc gtacttctgt acaaatgtta ttgaggagct tttacggcct  95220
aggcagtgct ctatcctgga gaatgtttgt gtgtaagaca atgcatattc tttttttctt  95280
tcctgtcacc caggctggag tgcattggca cgatctcgtc tcactgcaac ctccgcctcc  95340
cgggttcaag caattctcct gcctcagcct cctgagtagc tgggattaca ggtgggcacc  95400
accacgcctg gcaaatttag attccatttt ggatgctccc atcatgactg tgtgtccctg  95460
tgctggaact caagtgacca tgtgactcaa tccattgctg ttctctagaa atccacctca  95520
attctcttgg ttaaaggtaa ggtatgtgta gtgggcattg ctttttctcc ttggagacaa  95580
aacttaggag gattcccctt gatgaacaag gctaatctgc tgagcctgga gattgtcctt  95640
ttagaggttt atgttctgga ttccagaaaa cggtcaaaca gcgaataaat gcatctttat  95700
atttgtgtcc atcttaacct ggtcaaggaa aatttcaaca aaaatcccag atggctggag  95760
cgagaagatc tcatgctgtg actctctgga gggaagcact ttctgttgtc tgaaagaaaa  95820
caaagcgctt ctctttagag tgttacggtt tgagaaaagc aacgttgaag ttgatgctga  95880
tcttggtaat acattcgcag agcatgctta tcaggcttgg atgacggcag ggttctgttt  95940
tggttttatt tttttccaag accagtctct gttgcccagg ctggagaggg aggggttgca  96000
ctccaaacta gatctcttgg ggtcatgtct tgctctatta ttattattaa ttcttatttt  96060
tgtgtgtgtg tgagacggag tctcgctctg tcaccaggtt ggagtccagt ggcggaatct  96120
```

```
cagctcactg caacctccga ctccgtggtt caagcgattc tcctgcctca gcctcctgag  96180
tagctgggat tacaggcacg caccgccatg ccgagctaat ttttgtattt ttagtagaga  96240
ccgggtttca ccacgttggc caggatggtc tcaaactcct gacctcatga tccacccgcc  96300
tcggcctccc aaagtgctgg gattacaggt gtgagcctcc gtgcccagcc tgttatttta  96360
ttttgtttta ttttatttat tttattttat tttgagatgg agactggctc tgtcgcccag  96420
gctggaatgc agtggcagga tctccactca ctgtaactcc cacctctgtc gcccaggctg  96480
gagtgcagtg gcaggatctc cactcaccgt ggagttccag tgattctttc accttagcct  96540
cgcaaatagc tggtattaca agcacccacc aacacaccct gccaattttt gtatttttag  96600
acaagaaagg gtttcgccat gttggccagg ctggtctcga ctcctgacct taagtgatcc  96660
acctccctgg cctcccaaag tgctgggatt acaggcgtga gccaccacgt ccagcctcaa  96720
gtggtcttct tgtcagcctc gcaagtagtt gggctcaggt tttaattttt ggtagagatg  96780
gggtctcttt tgcctgggat ggtctcagct gagcttaagt gatcctaaat gtgtgagcca  96840
ccttgtccca tttcaaagat aggtgacacg gccaggcatc ctgggacaca cagggtccca  96900
gttactgcaa aggctagggt gggagggtcc tttgatttta aggctatacc atgcactgat  96960
cacacctttg aatagccact gcactccggc ctgggccaca tagcaagatc ccatctcttt  97020
aaaaacgcag attacatgcc atctggttcc tgaggctcca tttgggttgg tcacttcaaa  97080
tacaggcctt tcatcagttt agtttaatca atccaaacca tgtttccttc attaggagag  97140
taagggccag gtgtgtaatc caagcacttt gggagactga agcaggcgga tcaggaggtc  97200
aggagttcga gaccagcctg accaatatgg tgaaaccccg tctctactaa aaatacaaag  97260
attaagtggg cgtggtggtg cgtgcttgta atcccagcta ctcaggaggc tgaggcagca  97320
gaatctcttc aacccaggag gcggaggttg cagtgagcca agatcgcgca ggtgcactcc  97380
agcctgggcg acagagcgag gctccatctc aaaacaaaac aaaacaaaaa atataggcct  97440
ccacatctat ccagtctatt ctgtaatccc aatggatgtc aatattaata caatgttctt  97500
attttttcta tttatttgta tctttttagt tgaatctcct tgtccctgac actaaatttt  97560
ttttattttt atttatttat ttttttttgaa acagtcttgc tctgtcgccc aggctgcagt  97620
acagtggcgc aatctcggct tactgtagcc tctgtctccc gggttccagt gattctcctt  97680
ccccaactcc cgggtaactg ggattttcag gcacacacca ccaccccagc taattttttt  97740
gtacgtttag tagagacagg gtttcaccat attgggcagg ctggccttga actcctgaac  97800
taaggtgatc cgcccacctc ggcctcccaa agtgctggga ttagggataa ggctaacctg  97860
cttattcttt gtagcaagga actggagatg gtcattttag gggtttatgt tctggattcc  97920
agaaaacatg caaacaggcc caataaatgc atcctcattt ttgtgtccat tttaacctgg  97980
gcaaggaaaa ttccaacaaa aaacccagag ttctggagca agaagatctc atgctgtgac  98040
cctacaaagg gaagcacttt ctcttgtcca aaggaaaaga aggcgcttcc ctttggagtg  98100
ttacggtttg agaaaagcag cgttgaagtt gatgcttatc tcggtaatac atttgtagag  98160
catgcttatc atgaggcttg gacgatggcg gggttctgtt ttggttttgc tttttttattc  98220
taagacagga tctctgttgc ccaggctgga gtgcggtggc acatccaacc taggtctttt  98280
ggattcaaat ggtttttttta gcggacagag tctctctatc acccaggctg aagtgcagtg  98340
gtgtgatctc ggctcactgc aacctccacc tcccaggttc aagcgagtct cctgcctcag  98400
cttcccaagt aggtgagatt acaggtgccc atcaccacac ctggataata ttttcatttt  98460
ttaaaattca tttatttatg tttttgagat ggagtctcac tgttacccag gctggagggc  98520
```

```
cgaggcgtga tctctgctca gtgcaacctc tgcctcccgg attcaagcaa ttcttctacc  98580
tcagcctcct gagtagctag aattacggga gcccaccacc acacctggct actttttgtt  98640
ttttgttttt tgtttttttt ttagtagaga tgggatttca ccatgtttgc caggctggtc  98700
tcaaacccct gacctcaagt tagccaccgg cctctgcctc ccaaagtgct gggattacag  98760
gcatgagcca ccacgcctgg cctaattttt atattttcag cagaggcggg gtttcaccat  98820
gttggccagg ctggttgcga actcctgacc tcaggtgatc tgcccacctc agcctcccaa  98880
agtgctaaga ttacaggcgt gagccaccac acatggccat taacaccttt tagtccatgg  98940
aaattattct ggcactgatt tataaagcct catgtggggt caggtagagt caaaggggga  99000
cctcagtgtc ccttgcagat gggatgtgct cagcaagagc acggaggtgg agtgcatggg  99060
gtttgagttt tcactgggga aatgaaacca acatcttggg tgcatgacca ggtcatatat  99120
gcagtcatat atgcaatatg catggtggtg ggtgcctcta atcccagcta ctcaggaggc  99180
tgacgcagaa gaatcgcttg aacccaggag gcagaagttg ccatgagccg agatcccacc  99240
accgcatcca gcctgggcgg cagagtgaga ctccgtgtca aaaaaaagaa gatctcaggc  99300
agtgaccctc tagatggaag cactgtctgt tgtataaaag aaaagatcgt gcatcccttt  99360
agagtgttac tgtttgagac aagcaacgtt gaagatgctg ctgatcttgg taatacattt  99420
gcagagcgtg cttatcatca gacttgcatg atgtcggggt tctgtttgtg atttgaaatt  99480
tttccaagac aggctttcta ttgcccaggc gtgggtggat agcaccttcc accaagattt  99540
cttgggctta agtggtcctc tttttatttt ttgatttttt gagacacact cttgtttcgt  99600
tgggagtgca gtagcaggat ctctgctcac cggaaactcc acctctcggg ttccagtgat  99660
tctcccacct cagcctgccg aattgttggg aattcaggca tcaggcaccc accatcgtgt  99720
cctgcactct tgctgcccat cctggagagc actggcatga tctaggctca ctgcaacctc  99780
cgcctcctgg gttcgagtga tgcttctgcc tcagcctccc aggtagttgg gattacaggc  99840
acctactgcc ccacccagct aatttttatg tttttagtag agacgggttt caccatgttg  99900
gccaggctag tcttgaactc ccgctttcag gtgatccact agcctgtggt ctatcctgga  99960
ggatgtttgt gtgtgtgaca atgtatattc ttcaacatct tagactccat tttggatgct 100020
cccatcggaa ctatgtatcc ctgtgctgga actcaagtga acactcagct caaagtccat 100080
tgctgttctc tagaaatcca gcccagttct cttggttaaa tataaggtat gtgtagtagg 100140
cattgctttt tctctttaga ggcaaaactc aggagggttg ccccttgatg aacaaggcta 100200
acctgcagag cctttgaaga aaggaactgg agatggtcct tttaggggtt tatgttctgg 100260
attctagaaa acaggcaaac agggccaata aatgcatctt tattgttgtg gccattttaa 100320
cctggtcaag gaagatttca acaaaaaacc cagagtgctg gagcaagaag atcccatgct 100380
gtgaccctcc aaagggaagc gctttctgtt tgttttctct taaacaaagt gcctcccttt 100440
agagtgttac cgtttgggaa aagccacgtt gaagatgatg ctgatcttgg taatacattt 100500
gcagaccatg cttgtaatca gacttggatg atgttgggag tctgtttttt tgtttgtttg 100560
tttggttggt ttttttgttt gttaggtttt tgttttttgt tttggtgtgt gtgttttgtt 100620
ttgtgttttt tttttttctt aagacaaggt ctctgttgcc caggagagac tagagaagca 100680
ctttttaaga taggcctgtt gggctcagat ggtcctttta tgggatacag tcttgctctg 100740
tgacccagac tggagtgcag tggcgcgatc ttggctcaat gcaacctcca cctcccgggt 100800
tcgagtgatt ctcctgcctc agcttcctgg gtagctggga ttacagatgc ctgacatcac 100860
```

actcggctaa tatttgtatt tttctttttt attcattcat tcatttttga gatggagtgt 100920
tgctgtcacc cagcctggag ggcagtggca tgatcccggc tgactccaac ctctgcctct 100980
caggttcaag ccattctcct gcctcagtct cctgagtagg tggaattaca ggcacccacc 101040
actacaacca gctacttttt gattttgatt tttttttttt tttttttttt ttagtaaagg 101100
tggggtttca ccatgttggc caggctagtc tcaaacccct gacctcaagt gagccgctgg 101160
cctcggcctc ccaaagtgct gagaatacag gcgtgagcca ccgggcacag ccatcagcac 101220
cttttacttt atggaaattt ttctggcact ggtatagaac ctcacgtggg gtcaggtgga 101280
gttgagggga cctcagtgtc cctgcagatg ggatgagcaa gagcacggag gtggagtgca 101340
tggggcttca gtgtttattg gggaaatgaa gctgaaatct gggtgcatga ccaggagata 101400
aatgcatgag acggcggtct cactatgctg ccctggctga agtgggctta gatcctcctg 101460
cctctgcccc tccccagtcc ttggtagatg ggaccacatg tgaatattaa ccccccatgc 101520
acagacaaga agaaagtaag gactgttctt tggttcatac ctgaccccag ttaaacttgt 101580
attttagata aacaatgtat ttgagatgta cttgaacaac aaacgatttg ctgttcaggt 101640
gtgggcatct ttgttttgtt tttttttttc ctaattttaa atatgggact agtgtgcata 101700
tggtggctct tgtctgtaat tcctgcactt tgtgaggctg agacaggagg atcacctgag 101760
atcagttgtt cgagaccagc ctggccaaca tgaagccagg aggctgagct ttcagtgagc 101820
tgaaatcttc tgctgcactc caccctgggc aacagagtga gactcagtct caagaaagta 101880
aaaaataggc cgggcgcggt ggcgcatgcc tgtaatccca gcactttggg aggccgagac 101940
gggaggatca cctgaggtca ggagttcaag accaacaggg ccaacatggc aaagcctcgt 102000
ctctactaaa aatacaaaaa ttagctgggt gcaatggtgc acatctgtaa ttccagctac 102060
tccggaggct gaggcaggag aatcccttga acccaggagg aggagatttc agtgagctga 102120
aatcaagcca tggcattcca gcctgggcca gagagcaaca ttccgtctca aaaataaatg 102180
aataaataaa ataaataaaa ataaatagat aaatatggga catcataaat ttgggtgtca 102240
cctttgtgta gcagccagcg taatctctgt cattccaatt tttttttatg tgaactgcca 102300
aagcaagcac ttgtgtagga atttttcttc ctgtgagcat acaatatatg gaactttctt 102360
tgacacaggg tctcagaaat atatggtata tatttcgtta tatatatact tatatataat 102420
ataatcatat acacacaaaa tactgttcta aatacagaga atactctgat ataaccttgg 102480
gtattttttt ctttctttgt gtgtgtatgt tttttatttg tttggctggt tttttttttgt 102540 ttttgttttt tgtttttttgt tttttgtttt tgtttttgtt ttgagacaga gtctcactct 102600
gtcgccgagg ctggagtgca gtgacaggat ctcgggtcac tgcaagctcc gcctaccggg 102660
ttcacgccat tctcctgcct cagcctcctg agtagctggg accacaggca cccaccacca 102720
cacctggcta attttttttt gtatttttag tagagacagg gtttcgccat gttagccagg 102780
atgatctcga tctcctgacc tcgtgatcca cccgcctcgg cctcccaaag tgctgggatt 102840
acaggcgtca gccaccgcgc ccggccagtt ggttattttt gagacaaggt ctggctctat 102900
cacccaggct ggagtgtagt ggtgcgatct tggctcactg caacctccac ctcccaccta 102960
aacctgctga attagtgtct acaggcatgc accaccacac ctggctcact tttgtgtttt 103020
tcatacacat gggtttacac catgttgctg gggctggtct caggaactcc tgagctcagg 103080
tgatcctccc gtcttggccc cctaatgtgc taggattaga ggtgtgagcc aacccacccc 103140
acccatactt acgtatttct gttcagattt tattgagttt ttatgaccaa gcctatggtc 103200
tatcctggag aatatttgtg tatgtgacaa tgtatattct tcaacatcgt agactcgatt 103260
ttgggtgctc ccatcgggac tgtgtgtacc tgtcctggaa ctcaagtgca cccttggctc 103320
ataatccatt gctcttctcc agaaatctta ccaattctcc tgcttaaata taagctacgt 103380
gtagtaggca ttgtttttc ttagcagata cgaaactcag gaagattgtc ctatgataaa 103440
caaggctaac ctgctgattg tttgaagcaa ggaactggag atggtccttt taggggttta 103500
tgttttggat tccagaaaac gtgtaaacag ggccaatacg tgcatcttta ttttgtgtcc 103560
agtttagcct ggtcaacaaa aatgtcaaca aaaaacccag agtgctggag taagaaggtc 103620
tcgggctgtg actctccaaa gggaagaatt ttctcttgtc taaaagaaaa gaacgcactt 103680
ccctttagag tgttaccgtg tgagaaaagc aatgctgaag ttgatgctga tcttgcaaat 103740
aactttgcag agcctgctta taatcagact ttgacaatgg tgggcgtctg ttttttttt 103800
tctaagacag gatctctgtt gcccaggctg gagtatggtg gcacttccaa cctaggtctc 103860
ttgggctcaa atggtcctct tttttgggac agagtcttgc tctgtgaccc aagctagacc 103920
acagtggcac gatcttggct cacggcaatc tctgcctccc agtttcaagt gattcccctg 103980
cctcaacttc ctgagtagct gggattatag gtgtctgaca ccatgactgg ctataatttt 104040
catttttctt atttatttat ttttgagtct cgctgtctct caggctggag tgcagtggca 104100
gcctttgcct cttgggttca agcaattttc ctgcctcagc ctcccaagta gttggaatta 104160
tatgtgtcac catcatgccc tttttgtttt tttttagtag aaaatgggtt tcaccacgtt 104220
ggccaggcta gtctcaagcc cctgacctca agtgatcctc ccgcctcaga ctcccaaagt 104280
gctgaaaatg caggcgtgag ccactgcacc gagccatcaa caccttctac tccatggaaa 104340
tgatactggc gctggtttat agaacctcac ttggggtcgg gcagatttaa aagggacctc 104400
aggctgggtg tggtggctga cgcctgtaat cccagcactt tgggaggccg aggcgggtgg 104460
atcacgaggt caggagatcg agaccatcct ggctaacatg gtgaaaccct gtctctacta 104520
aaaatacaaa aaattagcca ggcgtggtgg cgggtgcctg tagtcccagc tactcgggag 104580
gctgaggcag gagaatggtg tgaacccggg aggcggagct tgcagtgagc cgagatggca 104640
ccactgcact ccagcctggg cgacagagca agactctgtc tcaaaaaaat aaataaataa 104700
ataagggggt gggggacctc attgtccctt gcagatggga tgtgccctgc ttagcaagag 104760
cacggaggtg gagtgcatgg ctttgagttt tcactggggc acggaggtgg agtgcatggc 104820
tttgagtttt cactgggtaa atgcagctga actcttggct gcacgaccag gtcatatgtg 104880
caacgagaca ggggtctcac tatgctgccc aggctaaaat gggcttaggt ccttttgcct 104940
ccacctctcc ccagtcctta gtagctggga ctacatgtga atattaacca tgcacaggca 105000
agaggaaaga aaggaccgtt ctttggttca cacctagccg ccagtcaaat tagtatttta 105060
gatgaagact gcatttgaga catacttgaa caacaaatga tttgctgttt aggtgtgggc 105120
atctttcttt tttcctagtt ttaataatgg caccaggcag agtacagtgg cccacgcctg 105180
taattccagc actttgggag gctgagacag gaggatcacc tgaggtcggg aatttgattc 105240
cagcctggcc aacatggtgc agccccatct ctactaaaaa tacaaaatta gcccagcatg 105300
gtggtggtat atgcttgtaa tcccagctac tctggaggct gaggcaggag agtcgcttga 105360
agctggaagg ctgatctttc aatgagctga gatcacgcca ctgcactcaa gcctcggcaa 105420
aaagagtgag actccatctc aaaaacataa aaaataggcc agacacggtg gtccactcct 105480
gtaatcccag cactttgaga ggccaggaca ggcggatctc ctcaggtcag gagtccaaga 105540
ctagctgggc aaacaaggca aaacctcgtc tatactaaaa ttaggaaaaa tggctgggaa 105600

```
cagtggtgga cacctgtaat ctcagctact tgggaggcca cggcaagaga atctcttgaa 105660
cctgggaaaa ggagattgca gtgagacgaa atcacaccat tgtactccat cctgggtgac 105720
agagtgagat tctgtttcaa aaattaaata aataggccga gcacagtgac tcatgcctgt 105780
aatcccagaa ctttgggagg ccgaggtggc ggatcacctg aggtcgggag ttcaagacca 105840
gcctaaccaa cacgtagaaa ccccatctct actaaaaata caaaattagc cgggcatggt 105900
ggcgcatgcc tgtaatccca gctgctcggg aggttgaggc aagagaatca cttgaacccc 105960
agggggcgga ggttgtggtg agccgagatt gtgccattgt attccagcct gggcaacgag 106020
tgaaactctg tctctaaata aataaataaa actattaaat aaacattaaa cgttaaaaaa 106080
taaaaataga taaatatgag atcatcatga atttgagtgt cacctttgcg cagggcccat 106140
ggtaatcttt gtcattccaa ttttttcatg cgtgctgcca aagctagcac ttgtgtgtag 106200
gaagtattct tcctgtgagc atacaatata tggaagtttc ttttattatt attatttttt 106260
atgtttttgc gactgagttt tgctcttgtc gcataggctg aagtgcaatg gtgtgatctg 106320
ggctccctgc gatgtccacc tcttgggtta aagcgactct cctacctcag cctcctgagt 106380
agctgggatt acaggcatac acttccaggg ctagctaatt tgttgtattt tagtagacgg 106440
gatttctcca tgttggtcag gctggtctca aactcccgac ttcaggtgat ctgcccacct 106500
tggctttcca aagtactggg attgcagaca gccaccgcgg ctggccttca tatattctta 106560
tatatataat atcatgtaca cacaaaagac tcttttacac cctgagaata ctcttatatc 106620
actttgggca tttttttgtt ggtgtgtgca tttttttgttt gttcgttcgt ttgtttttga 106680
gacaagatct ggccctgtca cctatgctgg agtgcagtgg tgtgatctcg gctcccggca 106740
acctcaacct cccacctcag cctcctgaat tagtgtctac aggcatgcac ctctatacct 106800
ggctaacttt tgtattttta cagatgaggt tttaccatgt ttcccaggct ggtgtctaac 106860
tcctgagaat ataaggtata tgtagtaggc gttgcttttt ctctttgaag acaaaaccca 106920
ggacagttgt ccctcgatga acaaggctaa cctgctgaac gtttgaagca aggaactgga 106980
gatggtcttt gtatcggttt atgttctaga ttccagaaaa tatgcaaaca ggaccaataa 107040
atgcatcttt atttttgtgt ccattttgac caggtcaagg aaaatttcaa caagaaaccc 107100
agagtgccgg agcaagaaga tctcaagctg tgagtctaca aagggaagcc ctttctgttg 107160
tctaaaagaa aagaaagtgc ttctctttgg tgggttacgg tttgagaaaa gcaacgttga 107220
agttgatgct gatttcggta atacatttgc agagcatgct tatcacactt ggacgatggt 107280
ggggttctgt tttggttttg ctttttttatt ctaaggctct gtgttgctca tgctggagtg 107340
cagtgacatg tccaatatat ctcttggctt caaatggtca gcctgggcaa cacagggaaa 107400
ttctgtctca aaaaataaac aaatgaataa aaatacaaaa taaagccggg catggtggct 107460
catgcctgta atcccagcac tttgggaggc cgatgcaggt agatcatctc aggtcaggag 107520
tttgagacca gtctgaccaa cgtggtgaaa atccgtctct actaaaaata caataacaac 107580
aaaaattagc ccagtgtggt ggtgggcacc tgtaatccca gctacttagg aggctgaggc 107640
aggagaattg cttgaacccg ggaggcagag gctgcagtga gccgagattg tgccacagca 107700
tccagccagg atgacagagt gagattccgt ctgaaaaaaa aaaaaaaaaa aaaaagctgg 107760
gcgctgtggc tcacgcctgt aatcccacca ctttgaaagg ccgaggcggg tggatcacga 107820
ggtcaggaga tcgagaccat cctggctaac acggtgaaac cccatctcta tttaaaaata 107880
caaaaaatta gcgaggcgtg gtggtgggtg cctgtagtcc cagctacccg ggaggctaag 107940
gcttgagaat ggcttgaacc caggaggcgg agcttgcagt gagccgagat cgtgccattg 108000
```

```
cactctagcc tcggcaacag agcaagactc cgtcaaaaag aaacaaaaac aaaaacaaaa 108060
aaaagaaccc tacagtactg gagcaagaag acctcatgct gtgaccctct agatggaagc 108120
actgtctgtt gtctaagaaa agatcgtgca tccctttaga gtgttactgt ttgagaaaag 108180
caacgttgaa gatgctgctg atcttggtaa tacatttgca gagcgtgctt atcatcagac 108240
ttgcatgatg ttggggttct ctttggtttg ttttttttcca agacaggttc cctgttgccc 108300
aggcgggagt gggtggcacc tccaaccgag atctcttggg ctcaagtggt gatcttttta 108360
tttttgattt tttgagatgc gctctcattc cgtttcccag gctggagtgc agcggcagga 108420
tccctgttga ccggaaactc cgcctcccag cttccggcga ttctcccacc tcagcctgcc 108480
gaatagttgg gaatagagat gcccgccatc gtgtcctgct agttattatt tttattgttg 108540
ttgttgttgt tgagatggag tttcactctt gatgtccagg ctggagtgca gtgttgcaat 108600
ttaggctcac tgcaacctcc acctcctggg ttcaagcgat tctcctgccg cagcctcctg 108660
ggtagctggg attacaggtg cctactgccc cacccagcta atttttgtgt tttgaataga 108720
gactgggttt caccatgttg ggcaggctgg tctcaaactc ccgacctcag gtgatccacc 108780
agccttggcc tcctaaagtg ctgggattac aggcgtgagc caccgcccct aatctcacgt 108840
ggtcctctag agtcagccta gactctggtc tatcctggag gatgtttgtg tgtgagacaa 108900
tgtatattct tcaacatcag cccaattctc ttagctaaat gtaaggtatg agtagtaggt 108960
attccttttt ctctttgggg acaaaactca ggacgatcgc cccttgatga acaaggctaa 109020
cctgctgagc ctttgaagca aggaattgga gatggtcctt tcaggggttt atgttctgga 109080
ttccataaaa catgtaaaca gggccaataa atgcattttt atttttgtat ccgttttaac 109140
ctggtcaagg aaaattccaa caagaaaccc agagtgctgg agcaagaaga tcccatgctg 109200
tgaccctcta gaggaagcac tttctgtttg ttgtctgaga aaaaacaaag tgcttccctt 109260
tagagtgtta ccgtttggga aaagcagtgt tgaagttgat gctgatgttg gtaatatatt 109320
tgcatgctta ttatcagact tggatgatgt tggggttctg ttttgttttt gttttctaag 109380
acagggtctc tgtggcccag gctggagtac agaggcactt ccaacctagg tctcttgggc 109440
tcatatggtc ctttttggga cagtcttcct ctgtgaccca ggctggagtg cagtggcacg 109500
atcttggctc actgcaatct ccacctcgcg ggttcaagct attctcctgc ctcagcttcc 109560
tgaatagctg ggattgcagg ggcccgacat cacacttggc taatatttgt atttttcttt 109620
tttattcatt tatttatttt tgagatggag tctcgtttcc ccagctggag agcggtggca 109680
tgatcccgac tgactccaac ctctgcctct caggttcaag caattctcct gcctcagcct 109740
ctgaagtagc tgaaactaca ggtggccgcc accacgcctg gctacgtttt gaattttttt 109800
tttttttttt ttcagtagag atggggctta ccatgttggc caggctggtc tcaaacccct 109860
gacctcaagt gagccactca ccttggcctc cgaaaatgct gagaatacag gcatgagcca 109920
ccaccgcgcg cctcccaaag gcgtgagcca tggtgcgtgg ccatcaacac ctcttacttt 109980
atggaaattt ttctggcact ggtatagaac ctcacatggg gtcaggtgga gttgagggga 110040
cctcagtgtc cctgcagatg ggatgagcaa gagcacggag gtggagtgca tggggcttca 110100
gtgtgtattg gggaaatgaa gctgaaatct tgggtgcatg accaggagat aaatgcatga 110160
gacgggggtc tcactatgct gccctggcta aagtggtctt agatcctcct gcctctgccc 110220
ctcccaggcc ttgttagatg ggactacatg taaatattaa cccatgcaca ggcaggaaga 110280
aagtaaggac catttttggg ttcgtcccgg ccctcagtta aacttgtgtt ttagataaac 110340
```

aatgtatttg agatgtgctt aaacaataaa tgatacgcta tttaggtgtg ggcatctttg 110400
tttcccccta attttaatga tgggactagt ccaggtatgg tggctcctgc ctataattcc 110460
agcactttgg gaggccgaga caggaggatc acctgaggtc agttgttcga gaccggcctg 110520
gccaacatgg tgaaaccccg tccatactaa aaatacaaaa atcagccagg cctggttgca 110580
cacacctgta atcccagcta ctcgggaggc tgaggcagga gactcgcttg aagccaggag 110640
gctgagcttt cagtgagctg agattgcgcc actgcattcc agcctgggca actgagtgag 110700
tctcagtgtc aacaaagtaa ataatagtct aggcacagcg gcacacgcct gtaatcccag 110760
cactttagga ggctaagacg ggaggatcac ctgaggtcag gagttcaaga ccaacggggc 110820
caacgtggca aagccttgtc tctactaaaa ctacaaaaat tagctgggtg cggtggtgca 110880
catctgtgat tccagctact cgggaggcca agacaggaga accacttgaa cccaggagga 110940
ggcgatttca gtgagctgta atgaagccat ggcattccag cctgggccac agagcaagat 111000
tccgtctcaa aaataaataa aacaaataaa aatacgtaga taaatacggg accgtcgtga 111060
atttgagtgt cacctttgtg gagcagccac ggtaatctct gtcattccaa ttttttttat 111120
gtgcactacc aaagcaagaa cttgtgtagg aattattctt cctgtgagta tgcgatgtat 111180
ggaactttcc ttgagacagg gtctcaaaaa tatatcatgt atattttata tattcttatc 111240
atatataata taatcatgta cacacaaaat actcttctaa atacagagaa tactctgata 111300
tcaccttgcg tatttttttgt ttgcatgtgt ctgtgtttgg ttgttttttt tttgtcatat 111360
ttttgtatcc ctacttatat atttattttt aattttatta ttatacttta agttctaggg 111420
tacatgtgca caacgtgcag gttagttaca tatgtataca tgtgccatgc tggtgtgctg 111480
cacccattaa ctcatcattt agcattaggt atatctccta atgctatccc tccccgctac 111540
ccccacccaa caacagtccc cggtgtgtga tgttcccctt cctgtgtcca tgtgttctca 111600
ttgttcagtt cccacctatg agtgagaaca tgcggtgttt ggttttttgt ccttgcgata 111660
gtttgctgag aatgatggtt tccagtttca tccatgtccc tacaaagggg ttggttattt 111720
ttgagacaag gtctgactct atcgcccagg ctggagtgta gtggtgccat ctcggctcac 111780
tgcaacctcc acctcccacc taatcctgct gaattagtgt ctgcaggcat gcacaaccac 111840
atctggctca cttttgtatt ttttatacac atgggtttac accatgttgc aggcgctggt 111900
ctcaaactcc ctcccaagct caggtgatcc tctgtctcag cctcctaaag tgctgggatt 111960
agaggtgtga gccaccacac cccactggta tttgtgtgtt cctgttcaaa ttttattgag 112020
gagtttttat aaccaagcct gtggtccatc ctggaggatg tttgtgtgca tgacaatgta 112080
tattcttcaa catcgtagac tcgatgttgg atgctcccat cgggactgtg tgtccctgta 112140
ctggaactcg agtgaacact tggctctaag ttcattgctg ttttctagaa atccagccca 112200
attctcttgg ttaaatataa ggtgcacgta gtaggcattg ctttttcttt ctggagacaa 112260
aactcaggag gattgcccct tgatgaacaa agctaacctg ctgagacttt gaagcaagga 112320
actggagatg gtccttttaa gggtttatat tctggattcc agaaaatgtg caaacagggc 112380
caataaatgc atctttattt ttgtgtccat tttaacctag tcaaagaaaa ttacaacaaa 112440
aaatccacag tgctggagca agaagatctc atgatgtgac catctggagg taagaagcac 112500
tttgtgtttt gtgaaagaaa gtgcttcctt tcagagggtt actctttgag aaaagcagca 112560
ttgaagttga tgctgatctt ggtaatacat ttgaagagca tgcttatcat cagacttgga 112620
tgatcttggg gttttgtttt tttctaagac agggtgtctg tagcccaggc tcgagtgcgg 112680
tggcacttcc aacctagatc tcttgggctc aacaagtagc cctctttttc ggacagagtc 112740

```
tcgcgctgtg accctagctg gagtgcagtg gcaggaactt ggctcactgc cacctctgcc 112800
tcctgggttc aagcaattct cctgcctcag cctcccgagc agggttatag gcatgtgcca 112860
ccacacctgg ctaatttttg cattttatta tcgattgatt gattgattgt tgagacagag 112920
tctcactctg ttgcccaggc tgtagtgcag tggtgtgatc tcggctcact gcaacctcca 112980
cctcccacct cagccttctg aatacctgtc tacaggcatg caccaccaca cctcgccaac 113040
ttttgtgttt tttgtacaga tgaggtttca ccatgttgcc caggctggtc ttgaacccct 113100
gagctcaagt gatcctccca cctcggcctc ctaaagtgtg agtcactatg tcccgcccta 113160
cttgtgtgtt tctgcttaca ttttattgag gcgatttttt tttttttttt gagacggagt 113220
cttggtctgt tacctaggct ggagcgcagt ggcgcgatct tggctcactg caagctccgc 113280
ctcccaggtt catgccattc tcctgcctca gcctcctgag tagctgggac tacaggcgcc 113340
caccaccacg cccggctaat ttttttgtat ttttagtaga gatggagttt caccttgtta 113400
gccaggatgg tctagatctc ctgaccttgt gatcctcccg cctcggcctc ccaaagtgct 113460
gggattacag gcatgagcga ccgtattgag gcgcttttac aacatagcct gtggtctatc 113520
ctggggaatg tttgtgtgtg tgacaatgta tattcttaga catcttagat tccattttgg 113580
atgctcccat cggtactatg tgttcctata taggaactca agtgaacact tggcttaaaa 113640
tccattgctc ttgtctagaa atttagccca gttatcttgg ttaaagataa ggtgtgtctg 113700
gtaggcattg atttttcttt ccggagaaaa aacttaggag gatttcctct tgatgaacaa 113760
ggctagcctg ctgagccttt gaggcatggg acctggagat gatcctgtga ggggtttatg 113820
tttttggatt caggaaacac accagcagga caaataattg catctttatt tttgtgtcta 113880
ttttcaccag gctaaggaag attccaacaa catatccatg gtgctgaagt aagaagatct 113940
cgtgctgtga ccctctagag ggaagcactt tctgttgaaa gaaaagaaca tgcatccttt 114000
cagagggtta ctctttgaga agagcaacgt ttagtttgat gttgatcttg gtagtacatt 114060
tgcagagcat gcttttatca tcagacttgg ctgatggtgg tgttctgttt tttgttgttg 114120
ttttctacaa caggatgtct gttgcccagg ctagggtgtg gtggcactta caacctagat 114180
ctctagggct caaatggtcc tcttatttgg ggcagagtct tgctctgtga tccaggctgg 114240
agtgcagtgg caggaactct gctcactgca acctccgcct cccgggttca agtgattttc 114300
ctgccttggt tttctgagta ggtgggatta caggcgcaca ccaccacacc cagctagtat 114360
ttgtagtttt ctttattatt ctttttttta ttttaatttt tgagacgaag tctcgctgtt 114420
gcctacggtg gagtgcagtg gcgtgatctc ggctctctac aacgtctgcc tcccaggttc 114480
aagcaattct gctgcctcag cctcccgagt agctggaatc aacaggaaca caccaccatg 114540
cctggctact ttttggattt ttttttagta gagacggagt ttcaccatgt tggccaggct 114600
ggtctcaaac tcctgacctc atgtgagcca cccacctcgg ccttccaaag tgctggaatt 114660
acaggcatga accacgacgt ctggcctaat ttttgtattt ttagaagaga cagggtttca 114720
ccatgttggc caggctggtc tcagctcctg acctcaagtg atcctccccc tcggcctccc 114780
aaagtgctgg gattacaggc gtgagccacc tcgcccagcc tcaagtggtc ctcttgactc 114840
agcctcccat gtagttggga ctacatgggg cgtgccacca cacttggcta agtttttaat 114900
ttttcataca gatatgatct ctgttgctca ggaaggtctc aacacctgag ctcaaggatt 114960
ccacaggcgt gagccacatt ctcctgctga cccttttcaa agatagttga catggccagg 115020
catcatgggg cacacagtcc cagccaccgc agatcccggg gtgggagggt cctttgattt 115080
```

ccagactatt ccatgcactg atcacacctt gtttttttgt ttgtttgttt gtttgtttgt 115140
ttgtttgaca gagtctcagt ttgttgcctg gcgggagtgc aatgatgtga tctcgggtga 115200
ctgcaacctc tgcctccaag gttcaagtga ttctcctgcc tcaccctcca aagtagctgc 115260
ggttacaggc atgcaccacc acacccagct cagtttttgc atttggtaga gacaggtttt 115320
caccatgttg gtcaggctgg tctcgaactc ctgatttcag gtgatccacc tgcctcagcc 115380
tcccaaagag ctgggattat aggcgttagc ctatgcgccc ggtctgtatt tcctaatttt 115440
aaatatggga cccatggtga atttgggtgt cactgtgtac aggggacatg ggaatctctg 115500
tcattccaat ttttttaatg catgctgttc tgtgtaggaa ttattcttcc tgtgagcaaa 115560
caacatagag agctttcttt ttttgacacc gggtctcaaa aatatatcat atacatttta 115620
ttataatgtc tgatattgat aatataatca tacacacaca aaatactctt ctgtacacag 115680
agaatactga tatcactttg gggttttttt gtttgcgtgc gtttttttggg attttggggt 115740
gttttttttt ttttttttga gacaacatct ggctctgttg cccatgctgg agtgcagtgg 115800
tgcaattggc tccctgcaac ctccacctcc cacctcccac ttcagcctcc taaagagctg 115860
aatacaggca tgcaccacca cacctgacta acttttgtat tttttgtaca cacagggttt 115920
accatgtttc ccaggctgga ctggaactcc agagctcaag tgatcctccc gacttggcct 115980
ccttaagtac tgcagttaga ggtatgagcc gccgagaccc accgtacttg tgtttttcta 116040
ttcaaatatt attgaggagc ttttatggcc taacctgtgg tctatcctgg aggttgtttg 116100
tgcgtacaat acatagtctt caatatcttt tttttttttt tcattttttg agagggagtt 116160
tcgctcctgt cacctaggct ggagtgcaat gacatgatct cagttcactg caacctccgc 116220
ctcctgggtt caagtgattc tcctgcctca gcctcctgag tagctgggat tacaggcacc 116280
cgccaccatg cctagctaag tttgtatttt cagtagagac gggcttctcc atgttggtca 116340
ggctgggctc agactcctga cctcaggtga tccgcccgcc tcggcctccc aaagtgccgg 116400
gattacaggc gtgagccacc gcgcccagtc atcatatatt cttatcatat atatagtagg 116460
atgtttgtgt atataacaat gtacatttc aacattgtag attccatttt ggatgctccc 116520
attgggactg tgtgtccctg tgctggaact caagtgaaca cttggctcaa aatccattgc 116580
tgttctctag aaatccagcc caattctctt ggttaaatat aaggtatgtg tagtaggcat 116640
tgctctttct ctttagagac aaagctcagg attgcccctt gatgaacaag gctaacctgc 116700
tgattctttg aagcaaggaa ctggagatgg tccttttagt ggtttatgtt ctggattcca 116760
gaaaacatgc aaacagggcc aatacatgca tctttacttt tgtgtccatt ttaacccggt 116820
gaaggaaaat tccaacaaaa aacccacaat gctggagcaa gatctcaggc tgtgaccctc 116880
tagagggaag cgctttctgt tggctaaaag aaaagaaagc gcttcccttc agagtgttaa 116940
cgctttgaga aaagcaacgt tgatcttggt aatacacttg cagagaatgc ttataatcaa 117000
ccatggaagg tggtggggtt ttgtgtttgt ttgttttgtt ttgttttcta agacagggtg 117060
tctgttgccc aggctggagt gtggcggccc ctccaaccta gatctcttgg gttcaagtgg 117120
ccctcttttt tgggacagag tcttgctctg tgaccctgcc ctggctggag tgtcctgtca 117180
ggatctccac tcactgcaac ctctgcctcc tggggtcaag ggattctcct gcctcagcct 117240
cccgagcagc tgggattaca ggtatgtgcc accacacctg gcttatttat ttatttattt 117300
atgagacaga gtcttgctgt gtcatccatg ctggagagca gtggtgcaat ctcggctctc 117360
tgcaacctcc acctcccacc tcagtctcct gaattagtat ctacaggcat gtaccaccat 117420
acctggctaa cttttgtatt tttacagatg aggttttacc atgtttcccg ggctggtgtc 117480

```
taactcctga gctcaagtga tcctcctgcc ttggcctacg taagtgctgc ggttagaggt 117540
gtgagccacc gcgccccacc tgcccttgtg tatctctgtt caaatgttac tgagaagcat 117600
ttacgggata atgcccggag gatgtttgtg tgtgtgacag tgtacattct tcaacatctt 117660
agattccatt ttggatgctc ccctcgggac tgtgtgtctc tgtcctggaa ttcaagtgaa 117720
cacctggctc tccatccatt gctgttctct agaaatccag cccaattctc ttggttaaat 117780
ataaggtagg tgtagtaggc attgcttttt ctctttgggg acaaaactca ggaggattgc 117840
cccttgatga acaaggctaa cctgctgatt ctttgaagca aagaactgga gatggtcctt 117900
ttaggggttt ttattcagga ttccagaaaa catgcaaaca gggccaaaaa ttgcatcttt 117960
atttttgtgt ccattttgac ctggtcaagg aaaatttcaa caagaaaccc agagtgccgg 118020
agcaagaaga tctcaagctg tgactgcaaa gggaagccct ttctgttgtc tgaaagaaga 118080
gaaagcgctt ccctttgctg gattacggtt tgagaaaaac aacactgaag ctgatgccga 118140
tcgtggtaat acatttgcag agcatgctta tcatcaggct tggacaatgc cggggttctg 118200
ttttcggttt tgcttttta ttctaagaca ggatctctgt tgcccaggct ggagtgcagt 118260
gacatgtcca acccaggtct cttgaattca aatggtcctt tttagggggc agagtctttc 118320
tctgtcaccc aggctgatat gcagtgaggc gatctcggct cactgcaacc tctgcctccc 118380
aggttcaagc aattctcctg cctcggcttc ccaagcagct gagattacag gcgttcatca 118440
ccatacctgg atgatatttg tattttttaa aatttattta tttatttatt tttgagacgg 118500
agtctcgctg tcacccagtc tggagggcag tggcacaatc tcggctcact gcaacctctg 118560
cctccccggt tcaagcaatt cttctgcctc agcctcctga gtagctggaa ttacagaagc 118620
acaccaccgc acctagttac tttttgtata ttttttttaa gtagagactg gatttcaccg 118680
tgttggctag gctggtctca aattcctgac ctcaagtgat ccacccacct ctgactccca 118740
aatttctggg atcacaggta tgcgccccca tgcctggcct aatttttgta tttttagcag 118800
agacgtggtt tcaccatgtt ggccaggctg aactcagctc ctgaccttag gtgatctgcc 118860
cgcctgggcc tcccaaagtg ctgagaatac aggcgtgagc caccgtgcct ggccattaac 118920
accttttggt ccacggaaat tattctggca ctggtttata gaacctcgct tggggtcagg 118980
tagagttgaa ggggacccca atgtccttgc aggtgggatg tgcactgctt agcaagaaca 119040
cggaggtgga atgcatgggg tttgagtttt tattggagaa ataaagccaa aatcttgggt 119100
gcatgaccag gtcgtatatg caacaatacg ggcgtctcac tatgccgccc aggctaatgt 119160
gggcttagat cctcctgcct ctgcccctcc ccagtcctta gtagctggga ctacatgtga 119220
atattaactc acgtacagga agaggaaagt aaggactgtt ctttgattca cgtcccaccc 119280
ccagttaaat ttgtatttta gataaacaat gtatttgaga tgtacttgaa caacaaatga 119340
tttgctgttt agatgtgagc atcttttttt gctcctgatt ttaaacatag gacaaggtca 119400
ggtatggtgg ctcacgcctg taattccatc attttggtag gcagagacag gaggatcacc 119460
tgaggtcagc tgcttgagac cagcctggcc aacatggtga aaccccatct gtactaaaaa 119520
tacaaaaatt agccatgcgt ggttgtgctg cacgcctgta atcccagcta ctcaggagga 119580
tgaggcagga gaatcgcttg aagccgggag gcagaggttg cagtgagctg agatcgcgcc 119640
agtgaactac agcctgggca aaagaataag attcaatctc aaaaaaataa aaaataggcc 119700
aggcacggtg gcacacacct gtaatgctag cacttttgga ggtcgagacg ggggcatcac 119760
ctcaggtcag gagttgaaga ccagctgcgg catcacggca aagcctcatc tctacgaaaa 119820
```

atacaaaaat tagccaggtg cagtggcagg tgcctgtaat accagctact cgggagacca 119880
aggcaggaga atcgttccaa ctgggcggca gaggttgcag tgagccaaga tcgtgccact 119940
gcactgcagc ctgtcgacag agtaagactt ggtctaaaaa aaaaaaataa ataaataaat 120000
aaaagataaa tatggaacca tcatgaattt gggtgtcacc tctgtgtggg ggccagggta 120060
atctctgtca atccaatttt tttttatgtg caccagcaaa gcaagcactt atgtttaggt 120120
attattcttc ctgtgagcat acaatatgta gatctttatt ttctttgaga catggtctca 120180
aaaatgtatg atgtggctgg gcacagtggc tcaagcctgt aatcccagca ctttgggagg 120240
ctgaggcgtg tggatcaccc gaggtcagga gttcaagacc agcctggcca acatggtgaa 120300
aatccgtctc tacgataaat acatatatat atatatgtat atatgccggg catggtggca 120360
ggtacgggta atcccagcta cttgggagcc tgaggcagga gaatcgcttg aacctgggag 120420
gtagaggtta ctcatatcac tatgagattg ttttttgttc ttgtgtgtgt ggtttttgtt 120480
tgtttttgag acaaggtctg gctctgtcac ccaggcaaaa gtgtagtagt gcgatctcgg 120540
cttactgtaa cctccatctc ccacctatgc gtcctgaatt agtgtgtcta caggcatgca 120600
ccaccacagt gggctacctt ttttttttga gagggaattt tgctcttgtt gcacaggctg 120660
gagtacaatg gcaagatttc agatcactgc aacctccgcc ttccgggttc atgtgattct 120720
cctgcctcag cctcccaagt agctgcgatt acaggcatgc accatcacac ttggctaatt 120780
ttgtattttg agtagataca ggtttcccca tgcttgtcag gctggtctcc aactcctgac 120840
ctctagtgat ccacctgcct cggactccca aattgctggg attacaggca tgagctacca 120900
cacccagcca cctggctaac ttttgtagtt tttctacaga ctacaaaatg gtttcaccat 120960
tttacctgag actacaaaat ggtttcacca ttttacctga gactacaaaa tggtttcacc 121020
attttacctg agctggtctc caacacctga gctaaagtga tcctcctgcc tcggcctcat 121080
aaaatgttgg gattagaggt gtgagccacc gtgcctcacc cgtacttgtg tatttcttta 121140
tttttattga tttatttatt ttgagacaga gtttcactct tgttgcccaa gctggagtgc 121200
aatggcacaa tctcggctca atgcaacctc cttctcttag gttcaagcga ttctcctgcc 121260
tcagcttccc gggtagctgg gattaaaggc gtccaccacc acacccagct aatttttgtg 121320
tttttagtag agacagggtt tcagcatgtt ggccagactg gtctcaaact cctaacctca 121380
ggtaatccac ctgcctcagc cttccaaact gctgggatta caggcatgag ccactgcgcc 121440
tagcctcaag tggtcctctt aagtcagcct aaactgtggt ctatcctgga ggatgcttgt 121500
gtgtgtgaca atttatattc ttcaacgtct tagattctat tttggaggct cccaagggga 121560
ttgtgtgtcc ctgtgctgga actcaagtga acacttggct gtacatccat tgctgttctc 121620
tagaaattca gcccaattct cttggttaaa gataaggtat gtgtagtagg cattgctttt 121680
tctttccaga gacaaaactc aggaggattg ccccttgatg agcaaggcta acctgctgat 121740
tctttgaagc aaagaaccag agatggtcct tttaggggtt tatgttctgg attccagaaa 121800
acaggcaaac aggaccaata aatatatttt tatttttcta tccactttaa cctggtcaag 121860
gaaaattcca acaagaaacc cagagtgctg gagtgagaag atcccatgct gtgaccctct 121920
agagggaagc actttctgtt gtctgaaaga aaccaaagcg cttccctttg gagcgttacg 121980
gtttgagaaa ctcaatgttg aagttgatgc tgacttcagt aatacatttg tagaggatgc 122040
ttatcatcag acttggatga tatcggggtt ctgtgctttt tttttttttt ttctcctaag 122100
acaaaatctg tattttccag gctggagtcc ataagcactt ccaacctagg tctcttgcgc 122160
tcagatagtc ctcttttttg ggacagagtc ttgctctgtg acccaggctg gagtgcagtg 122220

```
gcgtgatctc ggctcactgc aacctctgtc tcctgggctc aagcaattct ccttcctgag 122280
cttcctgagg agctgggatt acaggcgcct gacatcatcc ttggctaaca tttgtatttt 122340
tctttttat tcatgtattt atttactttt cagatggagt ctcgctgtcg accaggctag 122400
agggcagtgg cacgatcccg gctgactaca acctgtacct ctcaggttca agcaattctc 122460
ctgcctcagc ctctggagta gctggaatta caggaacaca ccaccaggcc cggctacttt 122520
ttgtattatt attattatta ttattttttt ttttttcac taaagagggg gtttcaccat 122580
gttgtccaga gaatacaagc atgagccact gcgcagccat caacaccttt tactgcatgg 122640
aaattattct ggcactggta tagaacctca catggggtca ggtggagttg aggggacctc 122700
agtgtccctg cagatgggat gagcaagagc acggaggtgg agtgcatggg gcttcagtgt 122760
ttattgggga aatgaagctg aaatcttggg tgcatgacca ggaaataaat gcatgagaca 122820
ggggtctcac tgtgccgccc tggctaaagt ggtcttagat cctcctgcct ctgcccctcc 122880
ccagtcctag gtagatggga ctacatgtga atattaaccc atgcacagac aagaagaaag 122940
taaggactgt tattttgttc gtacccagcc cccagttaaa tttatcatat atataatata 123000
tcatatatat aacataatca tatacacaca aaatgctgat ttgaatacag agaatactct 123060
gatatcactt tgggtatttt ttggtttgtt tctgtgtgtg tgtgttttat ttgtttggtt 123120
ggttattttt gagacaaggt ctggctctat cacccaggct ggagtgtagt ggtgcgttct 123180
cagctcactg caacctccgc cttccaccta agcctgctgc attagtgtct acaggcatgc 123240
accaccacac ccggctcact tttgtatttt ttgtacacat ggggttacac catgttgccg 123300
gggctggtct cgaactcctg acctcaggtg attctcccgt cttggcctcc taaagtgcta 123360
gaattagagg tgtgagccac cgtgccccac ctgtacttgt gtatttatgt taaaattgtg 123420
ttaaggagtt tttatgacca agcctgtgat ctattctgga gaatatttgt gcgtatgaca 123480
atgtatattc ttcaacatcg tagattccat tttggatgct cccactggga ctgtgtgcct 123540
atactggaac tcaagtgaac acttggctca aaatccattg ctgttctcta gaaatccagc 123600
ccaattctct tggttaaata taaggtatgt gtagtaggca ttgctttttc tttctagaga 123660
caaaactcag gaggattgcc ccttgatgaa caaggtaacc tgctgattct ttgaaacaag 123720
aaactggaga tggttccttt aggggtttat gttctggatt ccaggaaaca tgcaaacagg 123780
gcccacaaat gcatctttat gtttgtgtcc attttaacct ggtcgaagaa cattccaaca 123840
aaaaatccac catgcaccga gcaagaatat ctcaggctgt gaccatctgg aggtaagaag 123900
cactttctgt tttgtgaaag aaaagaaagt gcttcctttc agagggttac tctttgagaa 123960
aagcaacgtt gaagttgatg ctgatcttgg taatacattt ggagagcatg cttatcatca 124020
gacgtggatg acggttgggt tttgtttttg ttttattttt tatcttaggc agggtctctg 124080
ttgcccaggc tggagtgtgt tggcacttcc aacctagatc tcttggtctt aaatggtcct 124140
ctttttgggg ggcggagtct cactctgacc caggctggag tgcaatggca ggaactcccc 124200
tcactgcaac ctccacctcc cgggttcaag cgattctcct gcctcagttt tccgagtcgc 124260
taggattaca ggctcactcc tccacacctg gctaatattt gtagttttct ttattattca 124320
tttatttatg tgtttttgag aaggagtctc gctgtcgccc aggctggagt gcagctgcac 124380
aatctcagct cactgcaact tctgccactg gagtaactgg gatttcaggt gcgtgccacc 124440
acacttggcc aattttttat gtgtgtattt ttagacccgg ggttttccca tgttggccag 124500
gctggtctgg aactcctgac ctcaggtgac ccatgcacct cggcctccca gagtgctggg 124560
```

attacaggca tcagccaccg cacccggccc tgtctctgac ttttgcgaac tgaggaagta 124620
accttttgaa atttactctg aagtgtgaat gattttagca tattttcaac caccaacatt 124680
ctagttcagg agattttcat caccccaaag aggcttattc ccatttgcag tcagttccca 124740
ccccactctt ccacccagac cgtgacaaac actttgcatc tctctagctc tggatctgcc 124800
tcttgtgggc atgtcacata gatcagtttt gaataggtgg cctgttgtga ccactgtaat 124860
tgaggataat gggttggtcc tggttgtctg cagtgtgaat cttaccactg aagggtggtc 124920
cctggatgga agcaggaggc tgggagaact gggcggaaca tcctttggga atggagtcgg 124980
gcgggcagac cctgatgcct gggaagctca caagggtgga agaccacatc ttcctccctg 125040
agaactgcaa ggtgaccctc ctggggtact ggaaggagtg aaggcctctg gactgggaac 125100
accagggcat tgcaccggtg caggcaggat gagccaaggg gaacggagag ccaggcatcg 125160
ctaactggcg acaatttggg tttgatctgg acggagtctg tgtcttctgg tagagagaac 125220
ccctgggatt ttcgctctgc tcctggctgt ctttcagtca tggaatctga tgacaaagac 125280
tcccgcccag agccaagaca tttggtttct ggaccccagt ggtcctttct gcctggactt 125340
gggatctttt ggggaagttt gggatctggc agggcatctg cataatccat agaaatccct 125400
gagagtccct tccctttgct gacatctcca tgttcctacc tattagcttc caaaggagac 125460
tcctatctga attgccgaag gcagcttccc aggccaggga tacccagtta aatttgtatt 125520
tcagatcaat agtatatttc agatgtactt gaacaagaaa tgatttgctg tttaggtgtg 125580
ggcatttgta tttcccctt ttttttttt ttttttttt tttgacagag ttttgctctt 125640
cttacccagg ctggaatgca atggcacaat cttgactcac tgcaacctcc acctcccagg 125700
ttcaagcgat tctcctgcct cagcagcccg agtagctggg attacaggca tgcgccacca 125760
cacccggctc agtttttgca tttagtggag atgggggttc accatgttag ccaggctggt 125820
ctcaaactcc tgacctcaag tgatttccct gcatcggcct cccaaagtgc tgggattata 125880
ggcatgagcc tccacgccta gcctcaagtg gtcctcttga gtcaacctag actacagtct 125940
atgctagaga atgtttgtgt gtgtgacaat gtatgttctt gaacatcata gattccactt 126000
tggatgctcc tgtcgggact gtgtgtccct gtgctggaac tcaagtgaga gttggctgaa 126060
aatccattgc tgttctctag aaatccagcc caagtctctt ggttagagat aaggtatgtc 126120
tagtgggcat tgctttttct ttttggggac aaaactcaga aggattgccc cttgatgaac 126180
aaggctaacc tgctgattct ttgaaggaag gaactggaga tggtctttta ggggtttata 126240
ttctggattc cagaaaactt gcaaacaggg ccaatacatg catctttata tttgtgtccg 126300
ttttgaactg gttaaggaaa atttcaacaa gaaacccaga gtgccggagc aagaagatct 126360
caagctgtgg gtctgcaaag ggaagccctt tctgttgtct aaaagaagag aaagcgcttc 126420
cctttgctgg attacggttt gagaaagcga cgttgaagtt gatgcatttg cagagcatgc 126480
ttatcatcag gcttggacaa tggcggggtt ctgttttggt tttgcttttt cattctaaga 126540
caggatctct gttgcccagg ctggagtgcg gtggcagtgg catgtccaac ctagccctct 126600
tggattcaaa tggtcctttt ttgcaagcaa agtctctctc tctcacccag gctggagtgc 126660
agtgatgtga tctcggctcg ccgcaacccc cgcctcctgg gttcaagcga ttctcctgct 126720
tcagcttccc aagtagctga gattacaggc acccatcacc acacctggat aatatttgta 126780
tttttaaaaa ttcatttatt tatttatgag acggagtctc gctgtcaccc atgctggagg 126840
gcagtgacac gatctcggct cactgcaatc tctgcctcct gggttcaagc aattcttcct 126900
cagcctcctg actagctgga attacaggag cacaccaccg cacctggcta ctttttgtat 126960

```
ttttttttta gtagaaatgg gatttcacca tgttggttag actggtctca aactcctgac 127020
ctcaagtcat ccgcccacct ctgactcttt ctgggattgc aggtatgcgc ccccacgcct 127080
ggcctaattt ttgaatgttt agcagagatg gggtttcacc atgttggcca ggctgaactc 127140
agctcctgac cttaggtgat ctgcctgcct cggcctccca aagtgctgag aatacaggcg 127200
tgagccaccg cgcctggcca tcaacacctt ttaccccaca gaaattattc tggcactggt 127260
ttatggaact tcacttgggg tcaggtagag gtgaagggga ccccaatgtc ccttgcagat 127320
gggatgtgta ctgctcagca agagcatgga ggtggagtgc atggggtttg agttttcatt 127380
ggggaaatga agctgaaatc ttgggtgcat gaccaggtcg tatatgcaac gagacgggcg 127440
tctcactatg ccgcccaagc taaagtgggc ttagatcctc ctgcctctgg ccctccccag 127500
tccttagtag ctgggactac atgtgaatat taactcatgt acaggaagag gaaagtaagg 127560
actgttcttt gattcatgcc ccaccccccac ttaaatttct atttcagata aacaatgtat 127620
ttgagatgta cttgaacaac aaatgatttg ctgtttaggt gtgggcatct ttttttgttc 127680
ctaattttaa gtataggaca aggctgggta ccacggctca cacctgtgat tccatcattt 127740
tgggaggcca agacaggagg atcacctgag gtcagttgtt tgagaccagc ctggccaaca 127800
tggtgaatcc ccatctctac taaaaataca aaacttagcc cagtgtggtg gtggtacacg 127860
cctgtaatcc cagctactca ggaggctgag gcaggagaat cacaggaagc cgggaagctg 127920
agctctcagt gagctgagat cgcaccactg aactccagcc taggcaacag tgagactcaa 127980
tctcaaaaaa ataaaaaata ggccgggtgc ggtggcacac gcttgtaatc ccagcacttt 128040
gggaggtcga gacgggtgga tcacctcagg tcagagttca agagcagccc cgccatcaag 128100
acaaaacctc ctctctacta aaaatgcaaa atatagctag gcgtggtggt acacacctgt 128160
agtctcagct acgtgggagg cggcagcagg agaatctctt gaacccgtga gaaggagatt 128220
gcagtgagct aaaatcacac cattgcactg cagcctgggc gactccatct caaaaaataa 128280
atacataaat aaataaatac ataaatacat aaaaaataac ccagagtact ggagcaagaa 128340
gatctcaggc agtgaccctc tagatggaag cactgtctgt tgtctaagaa aagatcgtgc 128400
atccttttag agtgttactg tttgagaaaa tcaacgttga agatgctgct gatcttggta 128460
acacatttgc agagcgtgct tatcatcaga cgtgcatgat gttggggttc tgtttgtttt 128520
gttttttttt tccaagacag tgtctctgtt gcccagacta gagtgggtgg cacctccaac 128580
cgagatctct tgggctcaag tggtcctctt tttatttttt gattttttga gacccactct 128640
ggtttcactg ggagtgcagt agcagaatct ctgttgaccg gaaactccac ctctcaggtt 128700
ccagtgtttc taccacctca gcctgccgaa tcattgggaa ttcagttgcc tgccatcagg 128760
tcttgctaat tattattgtt tttttgtttt ttttttttga ggcggagttt cgctcttgtt 128820
gcccaggctg gagggcaata gcgcgatctc ggctcaccgc aacctcggcc tcccgggttc 128880
aagtgattct cctgcctcag cctcccagat agctggaatt acaggtgcct accaccccac 128940
ccagctaatt tttgtgtttt cagtagagat ggggtttcac catgttgggc aggctggtct 129000
caaactcctg acctcaggtg atccaccagc cttggcctcc caaagtactg ggattacagc 129060
tgtgagccat cacccctaat ctcaaatggt cctgtagagt cagcctagac tgtggtctat 129120
cttggaggat gtttgtgtgt gagacaatgt atattcttca acattgtaga ttccattttg 129180
gatgcttcca tcgggactgt gtgcccctgt cctggaactc agctgaacac ttggctcaaa 129240
atccattgct gttctctgga aattctgccc taatctcttg gttaaatata aggtatgtgt 129300
```

```
agtaggcttt gctttttctc tttggggaca aaactcagga gggttgcccc ttggtgaaca 129360
aggctaacct gctgagcctt tgaagcaagg aactggagat ggtcctttta ggggtttatg 129420
ttctggattc cagaaaatat gcaaacaggg ccaataaatg catctttatt ttgtgtgtat 129480
tttaacctgg tcaaggaaaa ttccaacaag aaacccagag tgctggagca agaagatccc 129540
atgctgtgac cctctagagg aagcactttc tgtttgttgt ctgagaaaaa acaaagtgct 129600
tccctttaga gttactgttt gggaaaagca gtgttgaagt tgatgctgat gttggtaata 129660
tatttgcatg cttatcatca gacttggatg atgttggggt tctgggtttt ttttgttttc 129720
taagacaggg tctctgtggc ccaggctgga gtacagaggc acttccaacc taggtctctt 129780
gggctcaaat ggtccttttt gggacagagt cttgctctgt gactcaggct ggagtgcagt 129840
ggtgcaatct cagctcactg caccctccac ctcctgggtt caagtgattc tcctgcctca 129900
gcttcctggg attacaggca cctgacatca tgcccagcta atatttgtat ttttcttttt 129960
tattcattca tttatttatt ttttaggtgg agtcttgctg ttgccaagtc tggagggcca 130020
tggcacgatc ccggctgact ccaacctctg tctctcaggt tcaagcaatt ctcctgcctc 130080
agcctcctga gtagctggaa ttacaggcgc ttaccaccac gcctgactgc ttttcgaatg 130140
tgtgcgtatg tgtgtgtatg tgtgttagag agaaagagag agagagagat ggagtttcac 130200
tcttgttgcc caggctggag ggcaatgaca tgatctcggc ccatacaacc tcagcctcct 130260
gggttcaagt gattctcctg cctcagcctc ctgagtagct aggattacag gcatgtgcca 130320
ccacacctgg ctaattttgt atttttagta gatatggggc ttccccatgt tggtcaggct 130380
ggtctcgaac tcctgacctc aaatgattca cctgcctcag tctcccaaag tgctgggatt 130440
acaggtgtga gccaacatgc ccggcctgaa tttttttttt tttttttttt ttttcaagta 130500
aagacggggt ttcaccatgt tgaccaggct ggtctcaaac ctctgaactc acgtgagctg 130560
ctcgcctcgg cctcccaaag gcatgagcca tggtgcgtgg ccatcaacac ctcttacttt 130620
atcgaaattt ttctggcact ggtatagaac ctcacgtggg gtcaggtgga gttgaaggga 130680
cctcagtgtc cctgcagatg ggatgagcaa gagcacggag gtggagtgca tggggcttca 130740
gtgtttattg gggaaatgaa gctgaaatct tgggtgcgtg accaggaaat aaatgcatga 130800
gacgggggtc tcactatgcc accctggcta aagtgggctt agatcctcct gcctctgccc 130860
cccgcagtcc ttgctagatg ggactacatg tgaatattaa cccatgcaca gacaagaaga 130920
atgtaagaac cattatttgg ttcacaccgg gccctcagtt aaacttgtat tttagacaaa 130980
caatgtatct gagatgtcct tgaacaacaa atgatttgct gttcaggtgt gggcatcttt 131040
gtttttttccc taattttaat gatgggacta gtctgggtac ggtggctccc gcctgtaatt 131100
ccagcacttt gggaggctga gataggagga tcacctgagg tcagttgttt gagaccagcc 131160
tcgccaacat gatgaaacct cgtctgaact aaaaatatag atattagcca gacggggtgg 131220
tggtgcaccc ctgcaatccc agctactcag gaggctgagg caggagaatc acttgaagcc 131280
aggaggctga gctttcagtg agctgagatt gagccactgc actccagcct gggcaacaga 131340
gtgagactca gtctcaaaaa agtaaaaaat aggctgggtg tgggccgggc gcggtggctc 131400
acgcctgtaa tcccagcact ttgggaggcc gaggtgggtg gatcacaagg tcaggagact 131460
gagaccatcc tggctaacac ggtgaaaccc tgtctctagt aaaaatacaa aaaaaaaaaa 131520
aaaattagcc agacgtgatg gtgtgcgcct gtactcctag ctactcagaa ggctgaggca 131580
ggagaatggc ctgagcccgg gaggcggagc ttgcagttag ctgagatcgc accactgcac 131640
tccagcctgg gtgacagagc aagactccgt ctcaaaaaaa aaaaaaaaaa aaaaaaggcg 131700
```

```
gggtgtggta gtgcacatct gtaatcccag catttcggga ggccaagaca ggaattacct 131760
gaggtcagga gttcaagacc aacagggcca acatggcaaa acctcgtctc tactaaaaat 131820
acaaaaatta tctgggtgca gtggtacaca tctgtaattc cggctaccca gaggctgagg 131880
caggagaata gcttgaaccc aggaggagga gatttcagtg agctgaaatc acaccattgc 131940
acttcagcct gggccacaga gcaagattgt gtctcaaaaa taaataaata ataaaaatga 132000
cataaaatca ataaataaaa ataaatacat aaatacagga acatcattaa tttggatgtc 132060
acctttgtgc aggggccagg gtaatctctg tcattccaat ttttttatg tgcactgcca 132120
aagcaagcac tcatgtagga attatccttc ctgtgagcat ataatatatg gaacattctt 132180
tgagacaggg tctcaaaaat atgatgtgta tttcatcata tatataatat aatcgtatac 132240
acacaaaata ctgtttaaat acagagaata ccctgatatc accttgggta tttttctttg 132300
tttctgtgtg tgtgtgtgtg tgtgtgtgtg tgtgtgtgtg tgtgtttgtt tggttatttc 132360
tgagacaagg tctggctcta tcgcccaggc tggagtgtag tggtgtgatc tcaactcact 132420
gcaacctccg ccccccacct aaacctgctg aattagtgtc tacaggcatg caccagcaca 132480
cctggctaac ttttgtattt tttgtacata tggggttaca ccatgttgcc ggggctggcc 132540
tctaactcct gagctcaggt gatcctcccg cctcagcccc taaagtgctg ggattagagg 132600
tgtgagccac cgcaccccag ccatacttgt gtatttctat tcaaatttta ttgaggagtt 132660
tttaccgccc agcctgtggt ctatcctgga gaatgtttgt gtgtgcgaca atgtatattc 132720
ttcaccatcg tagattccgt tttggatgct cccatcggga ctgtgtgtcc ctgtgctgga 132780
actcgagtga acacttggct caaaatccac tgctgttctc tagagatctg tagggtccag 132840
ccctactggg cctgtgggtt tttctcttcg tgagcagata ggagagattg tagaaataaa 132900
gacacaagac aaagagagag aagaaaaggc agctgggcct gggggaccac taccaccaag 132960
acgtggagac cggtagtggc cccgaatgcg tggccgcgcc gttatttatt gtatacgagg 133020
caaaagggca gggtaagaag tgtgagtctt ctctaatgat aggtaagatg acgcgagtca 133080
cgtgtccacc ggacaggggg cccccttccct atttggtagc ttaggcggag agagattggg 133140
gacagcttac gtcattattt cttctatgta tttctcggag agatcaaaga ctttaatact 133200
ttcacttatt ctgctaccgt tatctagaag gcggagccag gtgtgcagag cggaacgtga 133260
aagtggacca ggagcgtgac cgctgaagca cagcatcaca gggagacgtt taggccacca 133320
gacggctgcg ggcgggcttg actgatgtca ggctttccac aagaggtggt ggagcagagt 133380
cttctctaac tcccctggag aaagggagac tccctctccg ggtttgggaa ggtaaggggg 133440
tccttcccag gcactggcgc taccgctgtg ctaagtgacg ggtgccttcc ccctggtgtt 133500
accgctggac cagggagccc tctagtggcc gtgtccgggc atgacagagg gctcacgctc 133560
ttgtcttctg gtcgcttctc accgtgtccc ttcagctcct atctctgtat ggcctggttt 133620
tccctaggtt atgattgtag aacaaagatt attataatat tggaataaag agtaatgcta 133680
caaactaatg attaataata ttcatatata atcatatcta taatctattt ctagtataac 133740
tagtcttatt ctatatattt tctttgttat actggaacgg cttgtggtga gtttctttat 133800
tataccggaa cagcttgtgc cttcggtctc ttgcctcggc acctgggtgg cttgccaccc 133860
acagaaatcc tgcccgtttc tcttggttaa atataatgta tttctagtag gcattgcttc 133920
ttctttccag agacaaaact caggaggatt gtgctatgat aaacaaggct aacctgctga 133980
ttctctgaag caaggaactg gagatggtcc ttctaagggt ttatattctg gattccagga 134040
```

```
aacatgcaaa caggacccat aaatgcatct ttattttggt gcccattttg acctggtcag 134100
gagaattcca acaaaaaatc cacggtgttg gagcaagatc tcaggctctc aggctgtggc 134160
catctagagg taagaagcac tttctgttgt cttaaagaaa agaaagtcct tttttttttt 134220
tttttttttt tttgagacaa tgtctcgctc tgtcgcccag gctggaatgc agtggcgtga 134280
tcttggctca ctgcaagctc cgcctcccgg gttcatgcca ttctcctgcc tcagcctcct 134340
gtgtagctgg gactacaggc gcccgccacc aagcccggct aatttttgt attttagta 134400
gagacggggt ttcatcttgt taggcaggat ggtctcgatc tcctgacctc atgatccacc 134460
cgcctcggcc tcccaaagtg ctgggattac aggcgtgagc caccacgccc gcccagaaag 134520
tgctttcttt cagagggtta cggtttgaga aaagcagcat tgaagttgac gctgatcttg 134580
gtaatacatt tgcagagcat gcttatggtc agacgtggat gatggtgggg ttttgttttt 134640
gttttgtttt ttatctgaga cagggtgtct ctgttgccca ggctggagtg cagtggcaca 134700
tccaacctag atctcttggg ctcaagtggt cctcttttg aaacagagtc tcactctgtt 134760
accctggctg gagttcagtg gcaggaactt ggctcactgc aatctctgtc tcctgggttc 134820
aagcaattct ctggcctcag cctcccgagc agggttacag gcatgtgcca ccacgcccgg 134880
ctaattttg catttttta attgatttat ttgtttgttg ttgagacagt ctcactctgt 134940
tgcccaggct gtagtgcagt ggtgtgatct cagctcaccg caacctccac ctcccatgtc 135000
agcctcctga atacctgtct ccaggcatgc acccccacac ctggctaact tttgcatttt 135060
ttgtacagat gaggtttcac catgttgccc aggctggtct tgaaccctg agctcaagtg 135120
gtcctcccac ctcggcctcc taaactgctg tgattaatgg tgtgagccac cgtgccacac 135180
ccgtacttgt ttgtttctgc tcaaattgta ttgaggagct tttacatcct agtctgtggt 135240
ctatcctgga ggatgtttgt gtatataaca atgtacattt tcaacatttt agattccatt 135300
ttggatgctc ccatcgggac tgtgtgtccc tgtgctggaa ctcgagtgaa cacttggctc 135360
aaaatccatt gctgttctct agaaatcctg ccctattctc ttggtgaaat ataaggtatg 135420
tctagtcggc attgattttt ctttctggag acaaaactca ggagggttgc ccctgcatga 135480
acaaggctaa cctgctgagc ctttgaagca aggaactgga gatggttttt ttaggggttt 135540
atattctgga ttccagaaaa catgcaaaca gggacaatga atgcatcttt atttttctgt 135600
ccattttaac ctggtaaacg aaaatttcac caaaaaaccc agagtcctgg agcaagaaga 135660
tctcaggctg tgaccctcca aagggaagaa ctttctgttg tctaaaagaa aagaacgcac 135720
ttccctttag agtgttaccg tgtgagaaaa gcaacgttga agctgatgct gatcttggta 135780
ataagtttgc agagcctgct tatcatcaga cttggacgac ggtgtagttc tgttttggtt 135840
ttgagttttt tgtttgtttg ttttgttttg cttttgagat ggaggcttgc tctgtcgccc 135900
aggctggagt gcagtggcgt gttctcagct cactgcaacc tccgcctccc aggttcacgc 135960
cattcttctg cctcttgagt agctgggact acaggcgccc gccaccacgc ctggctaatt 136020
ttttgtattt ttagtagaca cagagtttca ctgtgttagc caggatggtc ttgatctcct 136080
gaccttgtga tccacccgcc ttggcctcca aaagtgctgg gattacaggc gtgaaccact 136140
gcgcccggcc ttaatttttg tatttttagt agagacagga ggctgagctt tcagtgagct 136200
gagttcgttc cactgcactc cagcctgggc aacagagtga gactccatct caaaaaaata 136260
aaaaataggc cgagcgtggt ggcacatgcc tgtaatccca gccctttggg aggccgagac 136320
aggtggatca cctgaggtca ggagttaaag gctggctggg ccaacaaggc aaaacctcga 136380
ctctactaaa aatacaaaat tacacctgta atcttagctg cttggggggc tgtggcagaa 136440
```

```
gaacctcttg aacccaggaa gaggagattg cagtgagacg aaatcatacc attgcactct 136500
agcctgggcg acagagcgag attctgtctc aaaaaataaa taagtagggc agacagggtg 136560
gctcacgtct gtaatcccag cactttggga ggcaaggcgg gtaaatcaca aggtcaggag 136620
ttcgagacca gcctggccaa catggcgaaa ccccatctct actaaaaata caaaaaagta 136680
gctgggcatg gtggctggca cctgtagtcc cagctacttg ggaggctgag gcaggagaat 136740
cgtgtgaacc caggaagcgg aggttgcagt gagccgagat cgggccattg cactccagcc 136800
tgggcgacag tgcgagactc tgtatcaaaa ataagtaaat aaataaacaa aataaaagta 136860
aaaagaatta aatagataaa tatggtacca ttatgaattt gagtgtcacc tttgtgcagg 136920
ggtcatggta atctttgtta tttcaatttt tttatgcgta ttgccaaagc aagcacatat 136980
gcgtaggaat tatacttcct gtgagaatac aatatatgga gctttctttt ttgtttttttc 137040
tgtttgtttg ttttttgaga cacagtttca ctcttgttgc ccaggctgga gtgcaatgtc 137100
acgatctcag ctcacggcaa cctctgcctc ctgggttcaa gcgattctcc tgcctcagcc 137160
tcccaagtag ctgggattgc ttgcatgtgc caccaagcct agctaatttt ttgtatttag 137220
agtagagatg gggtttctcc atgttggtca ggctggtctc gaactcctga cctcagatga 137280
tccatccacc tcagcctccc aaagtgctgg gattacagat gtgagccacc atgcccggcc 137340
atgatatatt tttatatatg taatatcaca tacacacaaa atactcttct atgcacagag 137400
aatagtctta tatcactttg ggtatttgtg tgtgtgtgtg tgtgtgtgtg tgtgtgtgtg 137460
tgtgtgtgtg tgttttgttt ggttggttat ttttgagaca aggtctggct ctgtcatcca 137520
ggctggagtg tagtggtgtg atctcagctc actgcaacct ccacccccga cctaagccta 137580
ctgaattagt gtctacaggc acgcactacc acacctggct cacttttgta ttttttgtac 137640
acatggggtt tcacaatgtt gccggggctg gtctcaaact cctgtgctca ggtgatcctc 137700
ccatcacggc ctcctaaagt gctggaatta gaggtgtgag ccgccacgcc ccacctgtac 137760
ttgtgtatct ctgttcaaat gttactgagg agcttttaca gcgtaacctg tggtctatcc 137820
tggaaaatgt ttgtgtgtga gacaatgtac attcttcaac atcttagatt gcagtttgga 137880
tgctcccgtc aggactgtgt gtccctgtgc tgggactcaa gtgaacactg ggctctccat 137940
ccattgctgt tgtctagaaa tccagcccaa ttctcttggg taaatatgag gtatgtgtag 138000
taggcattgc tttttctttc tggagacaaa gctcaggagg attgcccctt gataaacaaa 138060
gctaacctgc tgattctttg aagcaaggaa ctggagatgg tccttttagg ggtttatatt 138120
ctggattcca gaaaacatgc aaacaggacc aataaatgcg tgcttatttt tgtgtctgtt 138180
ttaacctggt caaggaaaat tccaacaaaa aatccacgat gctggagcaa gaagatctca 138240
ggctgtgtcc ctctagaggg aagcgctttc tgttgtctga aagaaaagaa aatggttccc 138300
tttagagtgt tacgctttga gaaaagcatc gctgatcttg gtaacacatt tgcagagaat 138360
gcttataatc agacgtggat gatgttgaag ttttgcgttt gttttgtttt gtttttttttc 138420
ctagacaggg tgtctgctgc ccaaactgga gtgcggtggc acttccaacc tagacctctt 138480
gggtttaagt ggccctctat tttgggatag agtcttgctc tgtggccctg gctggagtgc 138540
agtgtcagga actctgctca ctgcgacctc tgcctcctag gttcaagcga ttctcttgcc 138600
tcagcctcct gagcagctgg gattacgggc atgtgccacc atgcctggct aatttttgta 138660
tttttatta tttatttatt tatttatttt tgagacagag tctcgctctg tcacccaggc 138720
tgaagtgcag tggtgcgatc ttggctcacc gcaacctcta cctcccacct cagcctcctg 138780
```

aacagctgtc tccaggcgtg caccaccaca cctggctaac ttctgtattt gttttacagt 138840
catggtttca ccatgttgcc cgggctcatc ttgaactcct gagctcaagt gatcctcccg 138900
cctcagcctc ctaaagtgct gtgagccacc gtgtcccaac agtacttgtg tgtttccgtt 138960
caaattgtat tgaggagctt ttacagcata gcctgtggtc tctccgggag aatgtttttg 139020
tttacgacaa tgtatattct tcaacatcgt agattccatt ttggatgccc tcattgggac 139080
tgtgtgtccc tgtactggaa ctcaagtgaa cacttggctc aaaatccatt gctgttctct 139140
agaaatccag cctaattctc ttggttaaag gtaaggtatg agtagtaagc attgcttttt 139200
ctctttggga acaaaactca ggaggattgc cccttgatga acaaagctaa cctgttgatt 139260
ctttgaggga aggaactgga gatggtcctt ttaggggttt atgttctgga ttctagaaaa 139320
cacacaaacc ggacaaataa atgcatcttt atttttgtgt ctattttaac ctcgtcaagg 139380
aagattccaa caaaaaatcc acagtgccgg agcaagaaga cctcaggctg tgacactcta 139440
gagggaagcg ctttctgttg tctgaaagaa aggaaagtgc atccttttag agtgttactg 139500
tttgagaaaa gcaacattga agctgatgct gatcttggta ataaatttgc agcgaatgct 139560
tataatcaga cttggatgat gttgggcttc tgagtttttt tttgttttgt tttgtttagt 139620
tttggggttt ttctgttttt tgttttttgt tttttttttt tttgaggccg agtcttgctc 139680
tttcgcccag gctggagtgc agtggcgcta tctcggctca ctgcaagttc tgcctcccgg 139740
gttcacgcca ttctcctgcc tcagcctcct gtgtagctgg gactacaggt gcccgccagc 139800
acacccggct aattctttgt atttttagta gagacggggt ttcaccgtgt tagccaggat 139860
ggtctcgatc tcctgacctc gtgatccacc cgcctcagcc tcccaaagtg ctgggattac 139920
aggcgtgagc caccgcgtcc agccttgtta ttgtttttga gactgagtct tgctctgtgg 139980
cccaggctgg agcgcagtgg cgtgatctcg gctcactgca acctccatct cccaggctca 140040
agcaattctc ctgcctcagc ctcctgagta gctgggatta caggcctgtg ccaccatgcc 140100
cggctaatta tttgtatttt tagtagagac agggtttgca ccatgttggc caggctggtc 140160
tcgaactcct gacctcaggt aatccaccca cgtcgatctc ccaaagtgct gggattacaa 140220
ctgtgagcca ctgcgcccgg cctgtttttc tctaccacag ggtgtctgtt gcccaggctg 140280
gagtgcggtg gcatttttaa catagatctc ttgggctcga gtggtccttt tttttggttc 140340
agtcttgctt tgtgacccag gctggagggc agtggcagaa actctcctca ctgcaacctc 140400
cgcctcctag gttcaagcca ttctcctgac tcagcctcct gagcagctgg gattaccggt 140460
gtgagccacc acacccagct aatttttgta tttttattta tttgtttatt tatttattta 140520
ttgttgagac ggagtcttgc tgtgtctccc aggctggagt gcagtggcgc gatcgtggct 140580
tactgcaacc tcctcctcct tggttcaacc aattctcctg cctcagcctc ctgagaagct 140640
aggattacag gcatgcacca ccatgcctgg ctaatttaga ttccattttg gatgctccca 140700
tcaggactgt gtccctgtac tggaactcag gtgaacactt ggttcaaaat ccgtcgcttt 140760
tctctagaca tccagctcag ttctcggtaa agataaggta tgtgtagtag gcattgcttt 140820
ttccctttag agacaaaact caggaggatt gccccttggt gaacaaggct aacttgcaga 140880
ttctttgaag caaggaactg gagatggtcc ttttaggggt ttatgttctg gattccagaa 140940
aacatgcaaa cagggccaat acatgcatct ttatttttgt gtccgttttg acctggtcaa 141000
ggaaaatttc aacaagaaac ccagagtgcc ggagcaagaa gatctcaagc tgtgactgca 141060
aagggaagcc ctttctgttg tctaaaagaa aagaaagtgc ttccctttgg tgaattacgg 141120
tttgagaaaa gcaacgttga agttgatgct gatctcggta atacatttgc agagcatgct 141180

```
tatcacactt ggacggtggt ggggttctgt tttggttttg ctttttttatt ctaagacagg 141240
gtctgtgttg cccatgctgg agtgcggtgg cacatcccac ctaggtctct tggattcaaa 141300
tggtcctttt tgggggcaga gtctctctat caccgaggct ggagtgcagt gatcccatct 141360
tggctcacta caacctccgc ctcccaggtt caagcaattc tcctgcttcg gcctcccaag 141420
tagctgagat ttacaggtgc ccatccccac acctggataa tatttggttt tattcatgta 141480
tttatttatt tttaagatgg agtctcactg tcacccagac tggagggcag tggcacgatc 141540
tcggctcgct gccacctgcg cttccctggt tcaagtaatg cttctgcctt agcctcctga 141600
gtagctggaa ttacagaagt acaccaccac acctggctac tttttatatt tcatttttaa 141660
tacagactgg atttcaccat gttggctagt atgatatata ttttgtcata tattcttata 141720
tatataatca tatacacaca aaatactctt ctgcacacga agagtattct tatatcgctt 141780
tgggtttttt tgtttgtgtg tttgttttgt gtttgtttct ttgtttttga gacaacgtct 141840
ggctctgttg ctcaggctaa agtgtagtat tgcaagctca gctcactgca acctccacct 141900
cccacctaaa gtcccctgaa ttagtgtcta caggcatgca ccaccacacc tggctcactt 141960
ttttttctga gaaggaattt tgcttttgtc gctcaggctg gagtgcaatg gggtgatttc 142020
agctcactgc aacctctgac tcccggcttc aagcaattct cctgcctcag cctcccaagt 142080
agctgggatt acaggcatgc accaccacac ctggctaatt ttgtattttt agtagagatg 142140
ggtttcacct tctttctcag gctggtcttg aactcctgac ctcaagtgat ccacctgcct 142200
cgacctccca aagtgctagg attacaggtg agagacattg cacctggcca cctaactttt 142260
gtagtttttt tacagacagg gcttcaccat attgcccaag ctggtctcca gctactgagc 142320
tcaagtgatg ctcctgtctc ggccactgtc cctcacccaa acttgtgtat ttcttttctt 142380
ttcttttttt tttttttttt ttgagatgga gtctggctct gtcacccagg ctggagtgca 142440
gtggcacgat cttggctcac tgcaagctcc gcctccccag ttcatgatat ttttctgcct 142500
cagcctccca agtagctggc actacaggca cccgccacca cgcctggcta attttttgta 142560
tttttagtga agacggggtt tcactggatt agccaggatg gtcttgatct cctgagctcg 142620
tgatctgcct gccttggcct cccaaagtgc tgggattaca ggcttgagcc accgcaccca 142680
gctttttttgt ttttttgttt tgtttttttg agatggggtc tcgctctgtc acccagcctg 142740
gagtgcaatg gcacgatctc ggttcactgc atcctacccc tcccgggttc aagcgattct 142800
cctgcctcat cctcccaagt aactgggatt acaggtgccc accaccgcgc ctggctaatt 142860
ttttgtattt ttagtagaga cggggtttca ccgtattagc caggatggtc ttgatctcct 142920
gacctcgtga tctccctgcc tcagcctccc aaagtgctgg gattacaggt gtgagccact 142980
gcacccggcc tttttttttt tttttttttt tttgagatgg gatctcgctc tgtcacccag 143040
gctggagtgc aacggcatga tctcagctca cggcaacctc cccctcccgg gttcaggtga 143100
ttctactgcc tcagcctccc aagtagctgg gattacaggt gcccacgacc acgcctggct 143160
aattttttgt atttttagta gagatggggt ttcatcaagg tggccaggct ggtctcaaac 143220
tcctgacctc atgatctact ggcctcggcc taccgaagtg ctgggattac aggcatgagc 143280
caccgcgccc agcttctgta tttcttttca aattttattg aggatttttt atgtcctagc 143340
ctgtggtcta tcctggagga tgtttgtgtg tgagacaatg tatattcatc aacatcttag 143400
attccatttt gattgcttcc gtagaaactg tgtgtccttg tgctggaact ccggtgaaca 143460
cctggctcaa tatccattgc tcttctctag aaatccagcc cagttctctt ggttaaatat 143520
```

aagatatgtg tagcaggcat tgctttttct ttccagagac aaaactcagg aggattgccc 143580
cttgatgaac aaagctaacc tgctgattct ttgaagcaag taactggaga tcctcctttt 143640
aggggtttat attctggatt ccagaaaaca tgcaaacagg gccaataaat gcatctttat 143700
gtttctgtcc attttaactt gatctaggaa aattccaaca aaaaacccac ggtgctggag 143760
caagatctca ggctgtgacc ttctcgagga aagaagcact ttctgttgtc tgaaagaaaa 143820
gaaagtgctt cctttcagag ggttacggtt tgagaaaagc aacgttgaag ttgacgctga 143880
tcttggtaat acatttgcag agcgtgctga tcatcagacg tggataatgg tggggttttg 143940
ttttttatct aagacagggt gtctgttccc caggctggag tgcggtggca cttccaactt 144000
agatctcttg ggttcaagtg gccctctttt tgggacagag tctcactctg tggccctggc 144060
tggagtgcag tggcaggaac ttggctcact gcaatctctg cctcctgggt tcaagcaatt 144120
ctcctgcctc agcctccgga gcagctgggg ttacaggctg tgccaccatg cccagctaac 144180
ttttgcattt ttattattga tttattgatt tatttttgag acagggtctg gctctgtcac 144240
ccaggctata gggcagtggt gcgatctcgg ctcactgcaa cctccacctc ccacctcagc 144300
ctcctgaata cctgtctcca ggcatgcact accacacctg cctaactttt gtatttttttg 144360 tatagatgag gtttcaccat gttgcccagg ctggtctcgg accettgagc tcaattgctc 144420 ctcccgcctg ggcctccaaa actgctgtga ttaatggtgt gagcaagcgt gccctactct 144480
tgtgtgtttc tgctcaaatt ttatggagga gcttttacat cccagcctgt ggtctatcct 144540
ggagaatgtt tgtgtgtgtg acaatgtata ttcttcaaca ttttagattc catttggatg 144600
ctcccatccg gactgtgtgc ccctgtactg gaactcaagt gaacacttgg ctcaacatcc 144660
attgctgttc tcatgaattc caggccaatt gtcttggtta aagacaaggt atgtgggctg 144720
ggcgtggtgg ctcatgcctg taatcccagc actttgggag accgaggtgg gaggatcacg 144780
aggtcaggag ttcgagacaa gcctgaccaa cacggtgaaa cccatctcta ctaaaaatac 144840
aaaaattagc tgggcgtggt ggctccacca gtaatctcag ctacttggga ggctgaggca 144900
ggagaattgc ttgaacccag gaagcggagg ttgcagtgag ctgagatcgc gccactgcac 144960
tccagcctgg gtgacagagc gagacttcat ctcaaaaaat aaaaaataaa aaggtatgtg 145020
tagtaggcat tgctttttct ctttgtagat aatactcagg aggactgcct cttgaacaag 145080
gctaacctgc tgagcctttg aagcaaggaa ctggagatgg tccttttagg gggttatgtt 145140
ctggattcca gaaaacatgc aaatagggac aatgaatgca tctttatttt tctgtccatt 145200
ttaacctggt caaggaaaat ttcaacaaga aacccagagt gctggagcaa gaagatctca 145260
agctgtgagt ctacaaagga aagcgctttc tgttgtctga aagaaaagaa atcgcttccc 145320
tttggagtgt tacggtttga gaaaagcagc gttgaagttg atgctgatct cggtaataca 145380
tttgcagagc atgcttatca cacttggacg gtggcggggt tctgttttgg ttttgctttg 145440
ttattctaaa acagggtctg tgttgcccat gctggagtgc ggtggcacat cccacctagg 145500
tctcttggat ttaaatggtc ctttttgggg gccagagtct ctctctgtca ccgaggctga 145560
agtgcagtca tcccatcttg gctcactaca acctccgcct cccaggttca agcaattctc 145620
ctgcttcagc ttcccaagta gctgagattt acaggcgccc atccccacac ctggataata 145680
tttgggtttt ttttttattt atttttaaga tggggtctca ccgtcaccca ggctgtagtt 145740
cagtggcttg atctcggctt actgcaatgt atgccaccca ggatcaagtg attctcctgc 145800
cccagactcc tgagtagctg gaattacacg cacctgccac tacacccggc tactttttga 145860
attttttttt ttttttttaa agtaaagatg ggctttcacc atgttggcca ggctggtctc 145920

```
aaacccctga cctcaagtca gctgcttgcc tcagcctccc aaagtgctga gaatacaaac 145980
atgagccact gcgtggccat caacacctct tactttatgg aaatttttct ggcactggta 146040
tagaacctca cgtggggtca ggtggagttg aggggacctc agtttccctt gcagatggga 146100
tgtgcactgc tcagcaagag cacagaggtg gagtgcatgg ggcttcagtg tttattgggg 146160
aaatgaagct aaaatcttcg gtgtgtgacc aggagataaa tgcatgagat ggggatctca 146220
ctatgctgcc caggctgaag tgggcttaga tcctcctgcc tctgcccctc cccagtcctt 146280
ggtacatggg actacatgtg aatattaacc ccccatgcac agacaagaag aaagtaagga 146340
ctgttctttg gttcatacct gaccccagtt aaacatgtat tttagataaa caatgtattt 146400
gaaatgtact tgaacaacaa atgatttgct gtttaggtgt gggcatcttt ttttttcttc 146460
ctaactttaa atatgggact agtccaggta cggtggctca tgcctgtaat tccagcactt 146520
tgggaggcgg agacaggagg atcacctgag gtcagttgtt cgagaccaga ctggccaaca 146580
tggtgaaacc tcgtctgtac taaaaataaa aaaattagtg agacgtggtc ttggtgcatg 146640
cctgtaatcc cagctactcg ggtggatgag gcaggagaat tgcttgaggc tgggaggctg 146700
agctttcagt gagctgagat caagcctctg cactccagcc tgggcaacag agtgagactg 146760
agtctcaaaa aagtaaaaaa tcagctgggt gcgctggcaa acacttgtaa tcccagcact 146820
ttgggaggcc gagacgggag gatcacctga ggtcatgttc aagactaaca gggctgaaat 146880
agcaaaacct catctctatt aaaaatacaa aaattagctg ggtgcagtgg tgtatatctg 146940
tatttccagc tacttggagg ctaaggcagg agaatcgctt gaacccagga ggaagagatt 147000
tcagtgagct gaagccatgc cattgcactc cagcctgggc cacagagcaa gattccatct 147060
caaaaataaa ataaataata aaaatgaaat taaatagata aaaataaata gataaatatg 147120
agaccatcat gaatttggat gtcacttttg tgcaggggcc agggtaatct ctgtcattcc 147180
aatttttttt atgtgcactg ccaaagcaag cactcatgtg taggaattat tcttcctgtg 147240
agcatataat atatggaact ttgagacaga gtctcaaaca tatataatgt atattttatc 147300
atatattctt tatatataaa atatcatata gacacaaaat actgttctaa atacagagaa 147360
tactctgata tcaacttggg tattttttgt ttctgtgtgt gtgtattttg tttggttggt 147420
tatttttgag acaaggtcta gctctatcac acaggctgga gtgtagtggt gcgttctcgg 147480
ctcactgcaa cctccgcctc ccacctaagc ctgctgcatt agtgtctaca ggcatgcacc 147540
accacacccg gctcactttt gtatttttttg tacacatggg gttacaccat gttgccgggg 147600
ctggtctcga actcctgagc tcaggtgatt ctcctgtctt ggcctcctaa agtgctggga 147660
ttagaggtgt gagccaccat gccccatcgg tacttgtgat ttaggttcaa attttgatga 147720
gtttttatga ccaagcctgt ggtctatcct agagaatgtt tgtgtgtttg acaattcaac 147780
atcgtagagt tgattttggg tgctcccatt gggactgtgt gtccctgtac tggaacttga 147840
gtgaacactt ggctcataat ccattgctct tctctagaaa tccagcccaa ttctcttggt 147900
taaatataag gtatgtgtag caggcattgc tttttccttc cagagacaaa actcaggagg 147960
attgcccctt gatgaacaag gctaacctgc tgattctttg aagcaaagaa ctggagatgg 148020
tcctttaga ggtttatatt ctggattcca gaaaacatgc aaacagggcc aataaatgca 148080
tctttatgtt ttcgtccatt ttaacttgat ctaggaaaat tccaaaaaaa aaaacccacg 148140
gtgctggagc aagaagatct caggttgtga ccttctcgag gaaagaagca ctttctgttg 148200
tctgaaagaa aagaaagtgc ttcctttcag agggttacgg tttgagaaaa gcaacgtcga 148260
```

agttgacgct gatcttggta atacatttgc agagcgtgct gatcatcaga catggataat 148320
ggtggggttt tgtttttgtt ttattttttt atctaagaca aggtatctgt tgcccaggct 148380
ggagtgcggt ggcacttcta acctagatct cttgggttca agtggccctc ttttcgggat 148440
agagtcttct ttgctctgtg gccctggctg gagtgcagtg gcaggaactc ggctcaccgc 148500
aacctctgcc tcctgggttc aagcaattct cctgcctcag cctgtcgagc agctggggtt 148560
acagacatgt gccaccacgc ctggctaatt tttgcatttt tattgtcgat cgattgattg 148620
atttttgaga cagagtctgg ctctgtcacc caggctgtcg ggcagtggtg cgatcttggc 148680
tcactgcaac ctccacctcc cacctcagcc tcctgaatac ctgtctacag gcatgcacaa 148740
ccacaccttg ctaacttttg tatttttttgt acagatgagg tttcaccatg ttgcccaggc 148800
tggtctcgga cccctgagct caagtactcc tcaaacctgg gcctcctaaa ctgctgtgat 148860
taatggtgtg agccaccgtg ccctactctt acttgtgtgt ttctgctcaa attttattaa 148920
ggagctttta tggcctcgcc tgtggtctgt cctggaggat gtttgtgtgt gtgacaatgt 148980
atattcttca acatcttcga ttccattttg ggtgcctcca tggggactgt gtgtccctgt 149040
actggaacgc aagtgaagac ttggctcaga gtccatttgc tgttctctag aaatccagcc 149100
taatcctctt gtgcaaatat aatatatatc tagtaggcat tgctttttct ttctggagac 149160
aaaacacagg aggattgccc cttgatgaac aggactaacc tgctgattct ttgaagcaag 149220
gaactggaaa tggtcctttt agggatttat gctctggatt ccagaaaaca cgcaaacagg 149280
gccaataaat gcatctttat ttttgtgtcc attttgacct ggtcaaggaa gattccaaca 149340
aaaaatccac agtgccggag caagaagatc tcaggctgtg tccctctaca gggaagcgct 149400
ttctgttgtc tgaaagaaag gaaagtgcat ccttttagag tgttactgtt tgagaaaagc 149460
aacgttgaag ttgatgctga ttttggtaat acatttgcag agcatgctta tcatcagact 149520
tggatgatgt tgggttctgt ttttgctttg tttttttttc caagacagtg tgtttgttgc 149580
ccaggctgga gtgcggtggt acttcccacc tagatctctt gggctcaaga ggtctttttt 149640
tatttttctt tctcaagaga gagtctggtg gtgacaccca ggctggagtg cagtggtgca 149700
ttatcagctc actgcagcct tcccctcccc ggttcaagtg attctttcac ctcagcctcc 149760
cgagtagctg ggattacagg tgtgggctac cacacccggc taatttttgt atttttagca 149820
gagacagggt tttaccatgt tggggaggct ggtctcaact cctgtcctca agcgatccac 149880
ctcccttgcc tcccaagtac tgagattaca ggcgtgagca actgcgcccg gcctcaagtg 149940
gtcctcttaa gtcagcctac caagttttgg gactacatgg ggcatgccac cacacttggc 150000
taagttttta attttttttt tttttttttt tttttttttt gagacggagt ctcactctgt 150060
cgcccaggct ggagtgcagt ggcaagatct cggctcactg caagctcggc ctccggggtt 150120
cacgccattc tcctgcctca gcctcccgag tagctgggac tacaggtgcc cgccaccacg 150180
cctggctagt tttttgtatt tttagtagag acggggtttc accctgttag ctaggatggt 150240
ctcaatctcc tgacctcgtg atccacccgc ctcggcctcc caaagtgctg ggattacagg 150300
cgtgagccac cgcgcccggc cgatagtttt taatttttga tagaaaggga atctctcttg 150360
cctaagatgg tctcaactcc tgagctcaag ggatcctaaa ggtgtgagcc gccttgtcct 150420
gatgacccat ttcaaacgta gctgacatgg ccaggcatca tggggcacac agtcccagct 150480
actgcagaag ccggggtggg agggtccttt gatttccagg ctataccatg tgctgatcac 150540
acttttgatc ccgagtagct gggattacag gcagccaccg ccaggccggc taatttttat 150600
ttatttactt attttttcag acggtgtttc cctcttgttg cccaggctgg agtgcaatgg 150660
catgatctcg gatcactgca acctccacct ccctggttca agcgattctc ctgcctcagc 150720
ctcccgagca gctgggatta caggcatgca tcaccacgcc cggctaattc tttgtatttt 150780
tagtagagat gggatttctc catgttggtc aggctgatct tgaactccca accttaggtg 150840
atccacccac ctcggcctcc caaagtgctg ggattacagg catgagccat tgtgcccggc 150900
ccatttcatt tatttttatg tgtgctgctg aagcaagcac ttatgtgtag gaattgttct 150960
tcctgtgagc atatgttggc cagcctggac cacataccaa gatcccatct ctttaaaaac 151020
acagattacg tggcacctgg cacctggtcc cagagacttc atttgggttg gtcatttgaa 151080
acactagcct cccatcaatt tagtgtaatc aatccaaatc atgtgtcctt cattaagaga 151140
ctaagaacgc ctccacgtct atccagtcta ttttgtaatc cccaacggtt gtcaatatta 151200
ataaaatttc ttttcttttt cctattcatt tgtgtcttta gtttttcttc cccaaaaact 151260
tgccatcatt tctcggaata gacctgcttt ctctgcagga agggtgtggt tgattcaacc 151320
cttacccact aatgccaacc ccagtgagtt cttttatcct attttctatg ggtaacgatt 151380
ccaaggtacc attccaccgg gcaaaagctc acatctaagt gtcagttgct cggtaagatg 151440
tgaaatgttt gctgtggcta atataagaaa caaactattg tagacaagat gaatctcagt 151500
ggcagtgata aatgtcgcac aagacaaaac cacagatcct tttttttttt tttttttttt 151560
ttagacaaag tttcactctt gttgcccagg ctggagtgca atggtgcgat ctcggctcac 151620
tgcaacctcc gcctcctgga ggcgattcaa gcgattctcc tgcctcagcc tcccaagtag 151680
ctgggattac aggcatgcac caccacgccc aggtaatttt gtatttttag tagagacggg 151740
gtttcgccat gctggtcagg ctggaactcc tgacctcaga tgatcctccc acctcagcct 151800
cccaaagtgc tgggattaca ggcgtgagcc actgtgcccg gccaaccaca gatactttca 151860
cgaaagcctt tagggcccta gaaggggctc cctagtaaca ggtgggatgc gaggcagctc 151920
tcgttgttgc cgtagtgagc gatgcctgtt cgtccagccc tcaacacctt ttactccgtg 151980
gaagttatgc ctgcactggt ttacagaacc tcccttgact tgggttgagg tagagctgaa 152040
gggaacctca gtgtcccttg caggtgggat gtgcactgct tagcaagagc acggaggtgg 152100
agtgcatggg ctttgagttt ttattgggaa aatgaagctg aaatgtaggg cgcatgacca 152160
catcataaat gcacatttga tttaattttt ctattttatt tttatttatt tattttgaga 152220
tggagcctcg ctctgttgcc caggctggag tgcactggcc tgatctcggc tcactgcaac 152280
ctccacctcc cgggttcaag caattattgt gcctcagcct cccaggtagc tgggattaca 152340
cgcatgcttc cacgcccggc cgatttttgt atttttagta gagacggggt ttcaccatgt 152400
tggccaggct ggtttcaaaa tcctgacctc aagtgatccg cccgcctcgg cctctcaaag 152460
tcctgagatt acaggcgtga gccaccatga ccagcctaat tttctattt tagagacagt 152520 ggtctagcta tgccacccgg gctaaactag gctttagaga tcttcctgcc tctgcccctc 152580
cacggtctct ggtagtttgg actacaaatg aacattagca tatttgcaac caccaccact 152640
ctagtttgga agatttttat caccccaaag aagcttatac ccatttgcct tcagtaccca 152700 ccccccctctt ccactcagac cctggcaact actctacatc tctctagctc tggatttgcc 152760
tcttgtgggc atttcacaaa aaccagtctt gaatgggtgg cctgttgtga ccacttttaa 152820
tataatgggt tggttctggt tgtctgaagt gtgaatcttg ccaatgaagg atggtccctg 152880
gatggaagca ggaggctggg agaactgggc ggaacatcct ttcggaatgg agtggggtgg 152940
gcacaccctg atgtctggga agctcacaag ggtggaagaa cccatcttcc tctctgataa 153000
ctgcaaggtg accctcctgg ggcactggat ggagtgaagg catctggact gggaacacca 153060
gggcattgca ctggtgcagg caggatgagc cgaggggaaa ggagtgccag gcatcattct 153120
ctggtgacag tttgggtttg atctggatgg agcaggtgtc ttctggtaga gagagtccct 153180
gggatttttg ctctgctcct ggctgtcttt cagtcatgga atctgatgac aaaggctccc 153240
actctgggcc acttcatttg gtttctggag cccagtggtc ctttctgccc ggactcagga 153300
tcttttgggg aaatttggga cctcgcagga catctgcaca atccatagaa atccctgaga 153360
gccccttccc tttgctgaca tctccgtatt cctacctatt gccttccaaa aaaagaccct 153420
tatctgaatt gccaaagggg gcttcccaga gcagggaaac ccggttaaat ttgtatttca 153480
gattaacagc atatctagaa tctactcgaa caagaagtga tttgttgttt aagtgtgaga 153540
aatttttttc ccctaatttt aaatacggaa cccatcatga atttggctgt cacctttgcg 153600
caggggccgt gggaacctat catttcattg tttaatgtgt gctgccaaag caagcactta 153660
agtgtgggaa ttattcttca cgtgaggata caatagatgg aacgttatta ctttttttctt 153720 tcataattga gattttattg gttgaagatc ggtacagaca tttcaatttg tacacaattc 153780
ttaacatacg taccgaaaat ctaaaaagcc atgtattgta aatcgttttg ttttgttttg 153840
tttttttgag acagagtttc gctcttgtca cccaggctgg agcgcaatga cgcaatctcg 153900
gctcaccgca acctccgcct cccgggttca agcaattctc ctgcctcagc ctcccaagta 153960
gctgggatta caggcaaatg ccaccatgcc cggctaattt ttgtattttt tttttttttaa 154020 gtagagacag ggcttctgcc tgtcggtcag gctggtctcg aattcccgac ctcaggtgat 154080
ctgcccgcct cggcctctta aagtgctgag attacaggcg tgagccaccg cacccggcca 154140
tgtattgtaa ttcttctaca aagttattcc ggcgactttc cagcttaaaa tttggaagca 154200
cattttcctt aagaggctat caagtaccag tatcttcaca tgttgatcag ctgttacgga 154260
cgtccctcca attcacaact aaaaatagca tgtaccctac atattcaaat ttttcatctt 154320
tcacaacgca gaaacaaact tattaggaga acagaactac cacaatcaaa gatgttacag 154380
agtccacaca attctaacag ggagagccat ggtcagggag tggttttctt taggaaacaa 154440
ttccaaaata cgacaggaga atagaagtaa tttaaaatgt tcaagacact aaatgcagag 154500
ctgattccat gctgccattt aatatgcttt gtattatagg atataaacac gaaccctggc 154560
cgggtgcagt ggctcacgcc tgtaatccca gcactctggg aggccgaagt gggcagatca 154620
cctgaggtca ggagttcaag accagcctgg cccacatggt gaaaccccat ccctactaaa 154680
aatatgaaaa ttagccaggc atggtggtgc gcgcctgtaa tcccagctac tccggatgct 154740
gaggcatgag aatcgcttga acccgggagg tggagattgc agtgaactga aatcacgcca 154800
ctgccctcca gcctgggcga caagaacaag actctgtttc aaaaaaaaaa aaaaaaaaaa 154860
agtttctgga actactaaaa aacttgcatt tacaaaatag ttgataaaaa gattcctctg 154920
ggttttacaa gaagcgagac agggagcact gatgagacgt ggtatacggt gaatcagact 154980
gggcatcaga ggctgggcct cctcagtttt cctttcccca ttttctgcag ataaatcttt 155040
agtttcttgg ttagccactt ctgcccgttt tccctttgct cccctttgcc cttctgttca 155100 cactttttttg tctgaagatg tatccttcgt tgctgccttt ttcggcttca tttccactgg 155160
tttttttgtt ttgttttgtt ttgttttgtt tgagacgtag tttcaccctg ttgctcaggc 155220
tggagtgcaa tggcgtgatc tcggctcaca gcaacttctg ccttccggtt caagcgattc 155280
tcttgcctca gcctcccgag tagctgggct tataggcgcg caccgccatg cccggcttat 155340
ttttgtattt ttagtagaga cgggggtttc accatgttgg ccaggctggt ctcgaactcc 155400
tgacctcagg tgatccgccc gcctcagcct cccaaagtgt tgtgattaca agcgtgagcc 155460
accgcacccg gccttgcttc cacttttgca ggagcaggtt tagctgacaa ccgtgcgatc 155520
tcctcgtggg ctcttccttg gcggccccta tggcggagct aacctgcctc ttgggcatcc 155580
tggtggcgga gagggcgcgt gccggctgtc tgcgggccgc ggctgccgag agccttggcg 155640
aagctgggct gcctggcggc tgcggctcct cccgccgccc gagctgctga gacccacagc 155700
ggggtcggtg ggagaaccga atggaacccg aaactttctt attttgagac aggatctggc 155760
tctgtcaccc aggctggagt gcttggctca ctgcaacgtc tgcctcaagt gatccttcca 155820
cctcaacctc ccaagtagct gagattacag gcgcgcgtgc cactatgcct ggctaatttt 155880
tgtactcttt gtagagatgg gggtctcgct atgttgccca cgctggtctt gaactcctgg 155940
gctcaaatga tcctcctggc ctggcttccc aaagtgctgg ttgtaacgcc agcagtttgg 156000
gaggccacag tcggcgggat ggattagcta gcaacaaaca ttccaggcag agaatggtgc 156060
tctctcaact ctcagtcagc aaggggctag tatatattga aggggctcag ggcatgtcac 156120
cccaaagtca tcgcgtcagc atatggatta tttcgacctg gaagcctgtg ggaaaaagca 156180
gatgcatctg acctcccccct tcctacgtaa aagtagattg taaaatttat caagaggaaa 156240
acgcccttcc tgcgccagga agagaagaat gttcctatca gcaggggcca ggagtccata 156300
tgctaaacaa ctcagctact aacccttatc ttccttaagt tccccactgt ttcctggtca 156360
cttcccctag cccaagcctc tttgtcttgt cacatcccca caacttatca ttcctttttt 156420 tttttgagg tggagtttag ctcttgttgc ccaggctaga gtgcgatggc gcaatcttgg 156480
ctcactgcaa cctctgcctc ccgggttcaa gtgattctcc tgcctcagcc tcccaagtag 156540
ctgggattac aggcgcccac caccacgctc ggctgatttt ttgtattttt agtagagatg 156600
gggttttgcc atgctggcca ggctggtctt gaactcctga tctccggtga tccgcccgcc 156660
tcagcctccc aaagtgctgg gattgattac aggcgtgagc caccgcgccc ggccatcatt 156720
ctcttttttg ttttgttgtg gttgttgttg tttgagacag cgtctggctt tgtcacccaa 156780
gctggagtgc agtggcgcca tctcagctca ctgcgacctc tgcctcccgg gttcaagcaa 156840
ttctcatacc tcagcctccc gagtagctgg aaccacaggc atgagccacc atgcccggct 156900
agttacaggg ttttcctatg ctctccaggc tggagtgcag tggcgcaatc atagttcact 156960
gcagtcttca actcctgggc tcaagcaatc ctcccacctc agcctcttaa actgctggga 157020
ttacaggtgg tagccatcat gccctgcccc agagaagtct ttaggcttca gccaggcacg 157080
gtggctcagg ccggtaaacc cagcactttg ggaggctgag gtgggaggat cgcttgtgcc 157140
caggagttga aggctgcaat cagctatgac tgcaccacag cactccagtc tgggcaacaa 157200
agtgagaccc tgtctcaaaa aacaacaccg taggcccagc acggtggctc ctgcctgtaa 157260
tcccagcact ttgggaggcc aaggcaggtg gatcacttga ggtccagagt tcaggaccag 157320
catgaccaac atggtgaaac cccgtctcta ctaaaaatat acaaattagc caggtgtggt 157380
ggcagacacc tgtaatccca gctacttggg agactgaggg aggataattg cttgaacccg 157440
ggaggcggag gttgcggtga gccaagatcg cgccattgca ctccagcctg gttgacagag 157500
caagaccctg tctcaaaaag aaaggaaaag aaaaagaata caccagaagg tacccagaga 157560
ggccagtgtg gatgtacagc cagcacataa gatgctggtt agggacaggc gcagtggctc 157620
acgcctgtaa tcccagcact ctgggaggcc caggcagggg gatcacctga ggtcaggagt 157680
tcaagaccag cctggccaac atggcgaaac cccgtctgta ctagcaaata caaaaattac 157740

```
ttgggcgcgg tggcacgtgc tataatccca gctactccgg aggctgaggg tggaaaattg 157800
cttgaacccg ggaggctgag gttgcagtga gccgagatcg caccactgta ctccagcctg 157860
ggcaacaaga gcgaaactcc gtctcaaaaa attaaataaa taggccgggc gcggtggctc 157920
acgcctgtaa tcccagcact ctgggaggcc gaggagggcg gatcacgggg tcaggagatc 157980
aagaccatcc tggccaacat ggtgaaaccc cgcctctact aaaaatacaa aaacttcgcc 158040
ctgtatggcg gcacacggct gtattcccag ctactcggga ggctgaggca ggagaacggc 158100
ttgaacccgg gaggcagagg ctacagtgag ccgggatcac accgctgcac tccggcctgg 158160
gcagcaagag caaaactctg tctcaaaaaa caaaaaacag aaaaacaaaa agaatcaagt 158220
aagtcgaagc cacactgata acagccaatt tttgtgaacc aagggagtgt caattcaaga 158280
atttacatag atgtctactt ttgctatctc ctatgtgcca agcaagatac aggctctggg 158340
caatcagaaa caaaagagac tcactcgttc ctctcacagt actcagtcct tactgagata 158400
aggacaaaag aaaatgtcct gtctggaatg cagggaaacc agaacttcag gtcaggggac 158460
atttccattg aattgtgtgg agttgaagct gaaaatactt tttttttttt tttttttttt 158520
acatcacggc atggtttatt acgtgatttt tttactatac aaacaaaaaa tacagaaatg 158580
caatatgtga atacagctaa atgcagaatg gtgacttttt tctcttcaag aggccatgat 158640
tcccatttct agtaaaataa agagaccgca tacaggttgg ttgtgagatt cacaattttg 158700
cctagaaatg atctataaat gcatttttcc cccctgctac ctaccgtaaa tcgtaaaaag 158760
ggagttaaag caaagtttcc ttgttggttc ctaccatatg gaagatgcta tattctattt 158820
tagcagggtc aatatttgga aaatatctaa attaaatatt attacaaaaa tgaagctgta 158880
atgagattct ggctaaagag ggcactaaat gagaataata tatatttaaa gaatccaaaa 158940
caaacaaaca aaaagaggtt attataaaaa gctctaggtg cactgtaagc atatagggtt 159000
tttttttcat gtgttttttt ttaaacaatg gaagtgtcaa aaatagggtc aactgtgtta 159060
gactaaatta cattattgta tatgctgcat tgaatggaac ctttgtatta taattatcat 159120
agagaagcac agtttgcatc atattatggc aattcatcgt caatgaaaac cttccagagt 159180
ccttttattt tggaatctcc tgtaaactat caaaccacca gaacatgact gtacaacagt 159240
aaaatgttct cttgcattaa actgaagaga cctgtttaat aaaaaaagaa aaagaaaatg 159300
taggaaaggt acttagagct gttactttct aagtacacaa caccctagac aattcgaggc 159360
atcttaatct ccatcaagaa caacaacaac aaaaataatt tttgtcatgt tgttaaatcc 159420
atcattatgg atcaaactgg tgcaacttgg tcaaatgaat ccaacaaaca ctgatgtcca 159480
agctggcata ttggcaacta atacacaact ggtggtcaat agagagttta aaagatcttc 159540
cctttcttgt tgttcttttc caaggttctc aaagagttct gttgctctaa aatacgttgt 159600
tgagcttccc agtttgcttt ctcatcctca aactgacgac gtttctcctc taattctttg 159660
tgccgtgctc ccaaattctt tttcagttgc acatggcact gctggagcta aatcacagca 159720
caatatatac cccaaggata ctgccttcct ctgacccttt ttccattaac ttcagtgata 159780
atatcactac ccaccacagc aagaggtaaa cggtccttta tctttttaac acgtttcttt 159840
tcttcttcat catctgtttc tggaaattca tatattttaa ttttatgttc ttggatttct 159900
ttcattatct gttttgtaaa ctgttgacat tcctctggtg tgagtgtgtc tgctttggca 159960
gtaagtggga tgatattcac tttttcatgc aaatgtttca taaactcaac atccagtggt 160020
ttaagtctca acaaaaggca atgtcaagta gttacaaaca tgcactaccc aatcctgcct 160080
gaaggtggga gtcttcagtt atgtaatggt cctgttatca ggcatctgac gtctgctcac 160140
```

tcgcgattct gcatttaggt agtcctcaaa tttactatca atgtaatcga taacaggctg 160200
ccagcaatta ctactatcca ctgcatctcc aaatcctgag gtatcaacta tcctgagcag 160260
caactaaaca ccaccttctt tgattaaaac tttggattgt tccatccagg cttctatttt 160320
cccatagagg tccaaaaaac gcccttgttt gttaagttga tatatgtaaa ccttttctcc 160380
aggctgttcc ttgaggttta cataattggg aactccttca agcatctgta aataaacctt 160440
ttcagctgta gatctctcta ttttcagtta atttgcagac caccaactat aggagccaag 160500
ttgaaagaga aaaaagtttc tcttcccagc actttcttta ggatgctttt cattgcttcc 160560
caactggagg cctcgcccct ccacccacct gccctagtcc tcagctgcct ccagttctgt 160620
ccacttaaat acagactccc ggtagtagag aactttttta aaattttatt attattatta 160680
ttattattat tgacacagtc ttactctgtc gtccaggctg gagagcagtg gcacaatctc 160740
agctcactgc agcctctgcc tcctgggttc cagcgattct cctgcctcag cctcctgagt 160800
agctgggatt acagacaccc gccaccatgc ccggctaatt tttgtatttt tggtagagac 160860
gggggtttca ccatgttggc caggctggtc ttgaactcct aacctcaggt gatcctccta 160920
cctcggcctc ccaaagtgct gggattacag gcgacagcca atgtgtgcac 160970

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
actgggacga catggagaaa a 21

<210> SEQ ID NO 62
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 62
gccacacgca gctc 14

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 63
tgcaaggaaa gcattgaaca a 21

<210> SEQ ID NO 64
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 64
gaggagtcac ctggacaatc act 23

<210> SEQ ID NO 65

<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 65
cacatgaagc agcacgactt ct 22

<210> SEQ ID NO 66
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 66
aactccagca ggaccatgtg at 22

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gcggtggttg cccaacagga 20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
acgacccgtg gtcatcttta 20

<210> SEQ ID NO 69
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 69
tagaggatca cgtaattgca gga 23

<210> SEQ ID NO 70
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 70
gttgtcaaag ctgagccttc tat 23

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
atgccagacc gtcttgatac a 21

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 72
tgacccaagt atttcagccc a 21

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 73
gaacaacggt ttcgctcttt g 21

<210> SEQ ID NO 74
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 74
gcttctacat taggccagac ttt 23

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 75
acccgcttaa cagcgtcaac a 21

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
ccaaagaggt gcgggagttt 20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
gccaatgagg gttcgagttc 20

<210> SEQ ID NO 78
<211> LENGTH: 21
<212> TYPE: DNA

```
<213> ORGANISM: Artificial Sequence
<220> FEATURE:
<223> OTHER INFORMATION: Synthetic oligonucleotide

<400> SEQUENCE: 78

aacaacatcc cgtcgttcat c                                          21


<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 79

acgaatccca gtgtgttttg g                                          21


<210> SEQ ID NO 80
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 80

tgctcaaaaa cggtatggac at                                         22


<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81

caaccaagca aatgtgagga                                            20


<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82

ggagacttgc ctggtgaaaa                                            20
```

UNITED STATES PATENT AND TRADEMARK OFFICE
CERTIFICATE OF CORRECTION

PATENT NO.        : 10,000,755 B2
APPLICATION NO.   : 15/417717
DATED             : June 19, 2018
INVENTOR(S)       : Sadovsky et al.

It is certified that error appears in the above-identified patent and that said Letters Patent is hereby corrected as shown below:

In the Specification

Column 1, Line 22, "grant numbers AI081759 and HD065893" should read –grant numbers AI081759, HD065893, and HD071707–

Signed and Sealed this
Nineteenth Day of March, 2019

Andrei Iancu
*Director of the United States Patent and Trademark Office*